United States Patent
Zhang et al.

(10) Patent No.: US 11,266,640 B2
(45) Date of Patent: Mar. 8, 2022

(54) POLYCYCLIC COMPOUND ACTING AS IDO INHIBITOR AND/OR IDO-HDAC DUAL INHIBITOR

(71) Applicant: Hangzhou Innogate Pharma Co., Ltd., Zhejiang (CN)

(72) Inventors: Hancheng Zhang, Zhejiang (CN); Xiangyang Ye, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 0 days.

(21) Appl. No.: 16/649,455

(22) PCT Filed: Sep. 20, 2018

(86) PCT No.: PCT/CN2018/106768
§ 371 (c)(1),
(2) Date: Mar. 20, 2020

(87) PCT Pub. No.: WO2019/057123
PCT Pub. Date: Mar. 28, 2019

(65) Prior Publication Data
US 2020/0276180 A1 Sep. 3, 2020

(30) Foreign Application Priority Data

Sep. 20, 2017 (CN) .......................... 201710854520.2
Dec. 21, 2017 (CN) .......................... 201711397888.7
Feb. 6, 2018 (CN) .......................... 201810119324.5

(51) Int. Cl.
| | | |
|---|---|---|
| *A61K 31/4709* | (2006.01) | |
| *A61K 31/47* | (2006.01) | |
| *A61K 31/501* | (2006.01) | |
| *A61K 31/506* | (2006.01) | |
| *A61K 31/5383* | (2006.01) | |
| *A61K 39/395* | (2006.01) | |
| *C07D 215/14* | (2006.01) | |
| *C07D 401/12* | (2006.01) | |
| *C07D 401/14* | (2006.01) | |
| *C07D 405/12* | (2006.01) | |
| *C07D 417/12* | (2006.01) | |
| *C07D 498/04* | (2006.01) | |

(52) U.S. Cl.
CPC .......... *A61K 31/4709* (2013.01); *A61K 31/47* (2013.01); *A61K 31/501* (2013.01); *A61K 31/506* (2013.01); *A61K 31/5383* (2013.01); *A61K 39/3955* (2013.01); *C07D 215/14* (2013.01); *C07D 401/12* (2013.01); *C07D 401/14* (2013.01); *C07D 405/12* (2013.01); *C07D 417/12* (2013.01); *C07D 498/04* (2013.01)

(58) Field of Classification Search
CPC .. A61K 31/4709; A61K 31/47; A61K 31/501; A61K 31/506; A61K 31/5383; A61K 39/3955; A61K 31/44; C07D 215/14; C07D 401/12; C07D 401/14; C07D 405/12; C07D 417/12; C07D 498/04; C07D 215/18; C07D 209/00; C07D 209/02; C07D 215/02; C07D 215/04; C07D 215/06; C07D 401/00; C07D 401/02; C07D 403/00; C07D 403/02
See application file for complete search history.

(56) References Cited

U.S. PATENT DOCUMENTS

2009/0192141 A1* 7/2009 Bitner .................. C07D 207/12
514/213.01

FOREIGN PATENT DOCUMENTS

| | | | | |
|---|---|---|---|---|
| CN | 106916164 A | | 7/2017 | |
| WO | WO-0181347 A2 * | 11/2001 | ............... A61P 25/08 |
| WO | WO-2014139328 A1 * | 9/2014 | ......... A61K 31/5377 |
| WO | WO-2019228170 A1 * | 12/2019 | ............... A61P 37/02 |

OTHER PUBLICATIONS

IUPAC Compendium of Chemical Terminology Gold Book 2014. p. 1429.*
WO 2019228170 (2018) WIPO English machine translation, p. 1-92.*
Topczewski et al., "Palladium-catalysed transannular C-H functionalization of alicyclic amines," Nature, vol. 531, No. (7593), Mar. 10, 2016, pp. 220-224, in particular p. 223.
International Search Report, PCT/CN2018/106768, dated Dec. 6, 2018.

* cited by examiner

*Primary Examiner* — John M Mauro
(74) *Attorney, Agent, or Firm* — Ice Miller LLP

(57) ABSTRACT

Compounds as IDO inhibitors and/or dual inhibitors of IDO-HDAC are described. Specifically, the compounds represented by the following formula (I) are described, wherein each group is defined as described in the specification. The compounds have IDO inhibitory activity or IDO-HDAC dual inhibitory activity and can be used for preventing or treating diseases associated with IDO and/or IDO-HDAC activity or expression levels. At the same time, the compounds of the present invention can be combined with an anti-tumor antibody such as PD-1 and PD-L1, and such a combination can greatly increase the anti-tumor response rate of the antibody and broaden the types of tumors to be treated.

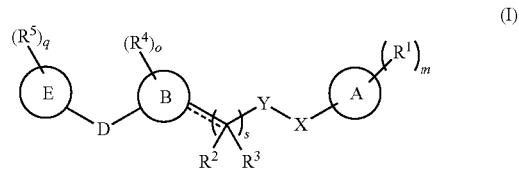

(I)

24 Claims, No Drawings

POLYCYCLIC COMPOUND ACTING AS IDO INHIBITOR AND/OR IDO-HDAC DUAL INHIBITOR

CROSS-REFERENCE TO RELATED APPLICATIONS

This application is a Section 371 of International Patent Application No. PCT/CN2018/106768, filed Sep. 20, 2018, which was published in the Chinese language on Mar. 28, 2019, under International Publication No. WO 2019/057123 A1, which claims priority under 35 U.S.C. § 119(b) to Chinese Patent Application No. 201710854520.2, filed Sep. 20, 2017, Chinese Patent Application No. 201711397888.7, filed Dec. 21, 2017, and Chinese Patent Application No. 201810119324.5, filed Feb. 6, 2018, the disclosure of all of which are incorporated herein by reference in their entireties.

TECHNICAL FIELD

This invention relates to polycyclic compounds, to processes for their preparation and to their use as IDO inhibitors.

BACKGROUND TECHNIQUE

Indoleamine 2,3-dioxygenase (IDO) is a rate-limited enzyme catalyzing the epoxidation and cleavage of indole ring of indoleamines such as tryptophan, so that it can be catabolized according to canine uric acid pathway.

IDO plays an important role in tumor immune exemption and tumorigenesis. Under normal circumstances, IDO is expressed at a low level in the body, and most tumor cells constitute a high expression of IDO, which converts L-tryptophan to N-formyl kynurenine, thus reducing the concentration of tryptophan in the cell microenvironment. The reduced tryptophan concentration makes the tryptophan-dependent T cell synthesis arrest in the G1 phase, and the T cell proliferation is inhibited, thereby inhibiting the killing effect of the body's immune system on tumor tissues. At the same time, the metabolite of tryptophan under the action of IDO is cytotoxic and can directly dissolve T cells. Therefore, inhibiting the activity of IDO can effectively prevent the degradation of tryptophan around the tumor cells, promote the proliferation of T cells, and thereby enhance the body's ability to attack tumor cells. Moreover, IDO inhibitors can also be combined with chemotherapeutic drugs to reduce the resistance of tumor cells, thereby enhancing the anti-tumor activity of conventional cytotoxic therapies. Simultaneous administration of IDO inhibitors can also increase the efficacy of therapeutic vaccines for cancer patients. In addition to its important role in tumor cell resistance, IDO is also closely associated with the pathogenesis of a variety of diseases associated with cellular immune activation. IDO has been identified as a target for major diseases such as infections, malignancies, autoimmune diseases, and AIDS associated with cellular immune activation. At the same time, inhibition of IDO is an important therapeutic strategy for patients with neurological diseases such as depression and Alzheimer's disease. Therefore, IDO inhibitors have broad clinical application prospects.

HDAC is a class of proteases that play an important role in the structural modification of chromosomes and the regulation of gene expression. HDAC deacetylates the lysine side chain at the amino terminus of histones, and histone acetylation is in a dynamic equilibrium with histone deacetylation, which is regulated by histone acetyltransferase (HAT) and histone deacetylase. The acetylation of histones reverses the acetylation of lysine residues of HAT and restores the positive charge of lysine residues, which facilitates the dissociation of DNA and histone octamers, and the relaxation of nucleosome structures, thus making various transcription factors and co-transcription factors bind specifically to the DNA binding site and activate transcription of the gene. Due to the overexpression of HDAC in tumor cells, the deacetylation of histones is enhanced. By restoring the positive charge of histones and increasing the gravitation between DNA and histones, the relaxed nucleosomes become very tight, which is not conducive to specific gene expression, including some tumor suppressor genes. HDAC inhibitors can regulate the expression and stability of apoptosis and differentiation-related proteins by increasing histone acetylation in specific regions of chromatin, induce tumor cell cycle arrest and apoptosis, promote tumor cell autophagy, and inhibit the formation of tumor angiogenesis promotes the immunogenicity of tumor cells. HDAC inhibitors not only become a targeted therapy for tumors, but also play a role in neurological diseases, inflammation, and promotion of autoimmunity. Preclinical and clinical studies have shown that HDAC inhibitors can also effectively synergistically inhibit tumor growth when combined with other anti-tumor compounds. HDAC shows significant effects to gene expression, oncoprotein stability, cell migration, protein catabolism, and cell cycle regulation by removing acetyl groups on histones.

The simultaneous suppression of IDO and HDAC by the same small molecule has not been reported. We believe that the simultaneous inhibition of these two targets is likely to improve the microenvironment of tumor cells, thereby improving immunity and producing more effective anticancer effects.

In summary, there is a lack of dual inhibitors of IDO and HDAC in the art.

SUMMARY OF THE INVENTION

The purpose of present invention is to provide a novel class of IDO inhibitors, and/or IDO-HDAC dual inhibitors, as well as methods for their preparation and use.

In the first aspect of the present invention, compounds of the following formula (I), or their optical isomers, pharmaceutically acceptable salts, prodrugs, deuterated derivatives, hydrates, or solvates thereof are provided:

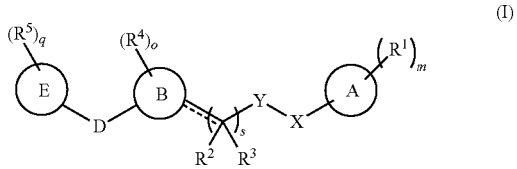

wherein:

" $=\!=\!=$ " represents single bond or double bond;

X is bond, NH, N($C_{1-4}$ alkyl), O, C(O), C(S), C(O)NH, C(O)O, or C(O)NCH$_3$;

Y is bond, NH, N($C_{1-4}$ alkyl), O, C(O), C(S), or C(O)NH;

with the proviso that the structure formed by the combination of X, Y, B and s is a stable chemical structure;

A is $C_{6-10}$ aryl, 5- to 15-membered heteroaryl, $C_{1-8}$ alkyl, $C_{2-8}$ alkenyl, $C_{2-8}$ alkynyl, $C_{3-10}$ cycloalkyl (including single ring, spiro ring, fused ring, bridged ring, etc), or 4- to 20-membered heterocyclic group (including single ring, spiro ring, fused ring, bridged ring etc. preferable 4- to 10-membered heterocyclic group);

B is $C_{3-8}$ monocycloalkyl, 4- to 8-membered monocyclic heterocyclic group containing one or more atom(s) selected from N, O or S, $C_{7-12}$ polycycloalkyl, or 5- to 12-membered polycyclic heterocyclic group containing one or more atom(s) selected from N, O or S, wherein the polycycloalkyl or polycyclic heterocyclic group refers to saturated or partially unsaturated ring structure, including spiro ring, fused ring, bridged ring; and when B is

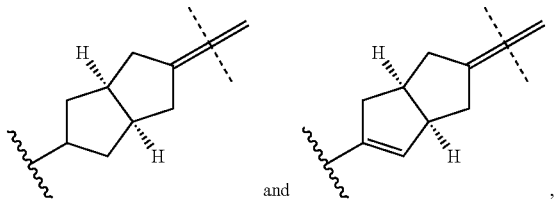

then s should be 1, meanwhile $R^3$ in $CR^2R^3$ is absent;

D is bond, oxygen, $C(R^6)_2$, $C(O)$, $C\equiv C$, $C=C$, $CH_2O$, $OCH_2$, $S(O)_2$, or $NR^7$, provided that the structure formed by connecting D, B and E is a stable chemical structure, for example, when D is oxygen or $NR^7$, the connecting point between D and B or E can not be N atom;

E is $C_{6-10}$ aryl, 5- to 10-membered heteroaryl, 5- to 10-membered heterocycle group containing 1-3 atom(s) selected from N, O or S, $(C_{4-8}$ cycloalkyl)aryl, or $(C_{4-8}$ cycloalkyl)heteroaryl, or 5- to 10-membered heterocyclic group fused to an aryl or heteroaryl (wherein the said heterocylic group contains 1-3 atom(s) selected from N, O or S));

each $R^1$ is independently selected from the group consisting of hydrogen, deuterium, halogen, $C_{1-4}$ alkyl, hydroxy, $C_{1-4}$ alkoxy, hydroxy $C_{1-4}$ alkyl, hydroxy $C_{1-4}$ alkoxy, $C_{2-4}$ alkenyl, $C_{2-4}$ alkynyl, $C_{3-10}$ cycloalkyl, 4- to 10-membered heterocyclic group (including monocyclic, spiro ring, fused ring, and bridged ring, etc), $NR^{10}R^{11}$, cyano, $C(O)R^{12}$, $C(O)NR^{10}R^{11}$, $OC(O)NR^{10}R^{11}$, $NR^{10}C(O)NR^{10}R^{11}$, $NR^{10}SO_2R^{12}$, $NR^{10}SO_2NR^{10}R^{11}$, $CO_2R^{13}$, haloalkyl $C_{1-4}$ alkyl, $C_{1-4}$ alkoxy $(C_{1-4}$ alkyl), halo $(C_{1-4}$ alkoxy), $C_{1-4}$ alkoxy $(C_{1-4}$ alkoxy), $C_{1-4}$ alkoxy $(haloC_{1-4}$ alkoxy), $C_{1-4}$ alkoxy $(C_{2-4}$ alkenyl), $C_{1-4}$ alkoxy $(C_{2-4}$ alkynyl), $S-C_{1-4}$ alkyl, $bis(C_{1-4}$ alkyl) amino $(C_{1-4}$ alkoxy), $(CR^8R^9)_n-C(O)-NHOH$, $O(CR^8R^9)_n-C(O)-NHOH$, $O(CR^8R^9)_n-C(O)-NHOH$, $NR^{10}(CR^8R^9)_n-C(O)-NHOH$,

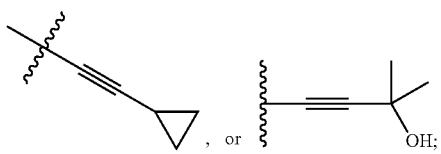

or two $R^1$ together with the carbon atom to which it is attached forms $C=O$, $C_{3-8}$ cycloalkyl, or 4- to 8 membered heterocyclic group containing 1-2 atom(s) selected from N, O or S, wherein said cycloalkyl or heterocyclic group is optionally substituted by 1-2 $R^{14}$; or when two $R^1$ are attached to two adjacent carbon atoms, the two $R^1$ together with the carbon atoms to which they attached form a $C_{3-8}$ cycloalkyl or 4- to 8-membered heterocyclyl group containing 1-2 atom(s) selected from N, O or S, wherein cycloalkyl or heterocyclic group is optionally substituted by 1-2 $R^{14}$;

herein, each $R^{14}$ is independently selected from the group consisting of hydrogen, deuterium, halogen, $C_{1-4}$ alkyl, hydroxy, $C_{1-4}$ alkoxy, CN, $NR^{10}R^{11}$, $C_{3-6}$ cycloalkyl, 4- to 8-membered heterocyclic group containing 1-2 atom(s) selected from N, O or S, $C_{6-10}$ aryl, 5- to 10-membered heteroaryl, or $=O$; with the proviso that the definition of above-described $R^1$ and A should ensure that the structure forms a stable chemical structure;

$R^2$ and $R^3$ are each independently selected from hydrogen, deuterium, $C_{1-8}$ alkyl, $C_{2-8}$ alkenyl, $C_{2-8}$ alkynyl, halo $C_{1-8}$ alkyl, $C_{3-8}$ cycloalkyl, 4- to 8-membered heterocyclyl comprising 1-2 atom(s) selected from N, O or S, $C_{6-10}$ aryl, 5- to 10-membered heteroaryl, $C_{3-6}$ cycloalkyl $(C_{1-4}$ alkyl), (4- to 8-membered heterocyclyl containing 1-2 atom(s) selected from N, O or S) $C_{1-4}$ alkyl, $(C_{6-10}$ aryl) $C_{1-4}$ alkyl, (5- to 10-membered heteroaryl) $C_{1-4}$ alkyl, fluorine, OH, CN, $CO_2H$, $C(O)NH_2$, $NR^{10}R^{11}$, $C_{1-4}$ alkoxy, $(CR^8R^9)_p-OH$, $(CR^8R^9)_p-Z-(CR^8R^9)_r-CO_2H$, $(CR^8R^9)_p-Z-(CR^8R^9)_r-C(O)NH_2$, $(CR^8R^9)_p-Z-(CR^8R^9)_r-C(O)NHR^{10}$, $(CR^8R^9)_p-Z-(CR^8R^9)_r-C(O)NR^{10}R^{11}$, $(CR^8R^9)_p-Z-(CR^8R^9)_r-C(O)NHOH$; wherein, Z is bond, $CH=CH$, $C\equiv C$, O, S, $NR^7$, $C(O)$, $C_{3-8}$ cycloalkyl, 4-to-8 membered heterocyclyl, $C_{6-10}$ aryl, 5- to 10-membered heteroaryl; or $R^3$ is absent;

or $R^2$ and $R^3$ together with the carbon atoms to which it is attached forms $C=O$, $C_{3-8}$ cycloalkyl or 4- to 8-membered heterocyclic group containing 1-2 atom(s) selected from N, O or S;

or $R^2$ and the carbon atom to which it attached to, together with one or two carbon atoms on B form $C_{3-6}$ cycloalkyl or 3- to 6-membered heterocyclic group containing 1-2 atom(s) selected from N, O or S, wherein the cyclic structure is spiro or fused ring;

and the definition of above $R^2$ and $R^3$ must ensure that they together with other groups (comprising X and Y, and B and A) form a stable chemical structure;

each $R^4$ independently is hydrogen, deuterium, halogen, $C_{1-4}$ alkyl, hydroxyl, CN, $C_{1-4}$ alkoxy, or when two $R^4$ attached to the same carbon atom, these two $R^4$ connect together with the carbon to form carbonyl group $(C=O)$, or when two $R^4$ attach to two adjacent carbon atoms, the two $R^4$ and two carbon atoms form an oxygen-containing three membered heterocyclic structure (i.e. epoxide);

each $R^5$ are independently hydrogen, deuterium, halogen, $C_{1-4}$ alkyl, $C_{2-4}$ alkenyl, $C_{2-4}$ alkynyl, $C_{3-6}$ cycloalkyl, 4- to 6-membered heterocyclic group containing 1-2 atom(s) selected from N, O or S, $C_6$ aryl, 5- to 6-membered heteroaryl, halo $C_{1-4}$ alkyl, hydroxyl, CN, halo $C_{1-4}$ alkoxy, $C(O)R^{12}$, $CO_2R^{13}$, $CONR^{10}R^{11}$, $SO_2NR^{10}R^{11}$, $NR^{10}SO_2NR^{10}R^{11}$, $NR^{10}C(O)R^{12}$, or $=O$;

each $R^6$ is independently hydrogen, deuterium, halogen, $C_{1-4}$ alkyl, hydroxy, CN, $C_{1-4}$ alkoxy;

$R^7$ is hydrogen, $C_{1-4}$ alkyl, $C_{3-6}$ cycloalkyl, 4- to 8-membered heterocyclic group, $C(O)C_{1-4}$ alkyl, $C(O)C_{3-6}$ cycloalkyl;

$R^8$ and $R^9$ are each independently selected from the group consisting of hydrogen, deuterium, halogen, $C_{1-4}$ alkyl, hydroxy, CN, $C_{1-4}$ alkoxy;

$R^{10}$ and $R^{11}$ are each independently selected from the group consisting of hydrogen, $C_{1-4}$ alkyl, $C_{3-8}$ cycloalkyl, 4- to 8-membered heterocyclic group, 6-membered aryl, 5- to 6-membered heteroaryl, $C_{1-4}$ alkoxy $(C_{1-4}$ alkyl), bis $(C_{1-4}$ alkyl) amino $(C_{1-4}$ alkyl), wherein cycloalkyl, heterocyclyl, aryl, or heteroaryl is optionally substituted by 1-3 $R^{14}$, wherein $R^{14}$ is as defined above; or $R^{10}$ and $R^{11}$ connect together with the nitrogen atom to form a 4- to 8-membered ring structure, which may additionally contain 0-2 heteroatoms selected from N, O, S, provided that the ring formed is a stable structure; and this ring structure is optionally substituted by 1-3 $R^{14}$;

$R^{12}$ is $C_{1-4}$ alkyl, $C_{2-4}$ alkenyl, $C_{2-4}$ alkynyl, $C_{3-8}$ cycloalkyl, 4- to 8-membered heterocyclic group, 6-membered aryl, 5- to 6-membered heteroaryl;

R[13] is hydrogen, $C_{1-4}$ alkyl, $C_{3-6}$ cycloalkyl, 4- to 8-membered heterocyclic group containing 1-2 atom(s) selected from N, O or S, 6-membered aryl, 5- to 6-membered heteroaryl; wherein the alkyl, cycloalkyl, heterocyclyl, aryl and heteroaryl groups may be optionally substituted by halogen, CN, or hydroxy, as long as the structure formed is a stable structure;

R[14] is hydrogen, $C_{1-4}$ alkyl, $C_{3-6}$ cycloalkyl, 4- to 8-membered heterocyclic group containing 1-2 atom(s) selected from N, O or S, 6-membered aryl, or 5- to 6-membered heteroaryl;

m is 0, 1, 2 or 3;
n is 0, 1, 2 or 3;
o is 0, 1, 2, or 3;
p is 0, 1, 2, 3 or 4;
q is 0, 1, 2, or 3;
r is 0, 1, 2, 3 or 4;
s is 0 or 1;

with the proviso that when B is $C_{3-8}$ monocyclic cycloalkyl, or 4- to 8-membered monocyclic heterocyclic group containing one or more atom(s) selected from N, O or S, and none of R[1], R[2] and R[3] contains C(O)—NH—OH group, then A is not selected from the group consisting of the following: phenyl, 5- to 6-membered heteroaryl, or $C_{5-7}$ cycloalkyl;

(wherein the statement "none of R[1], R[2] and R[3] contains C(O)—NH—OH group" refers to none of R[1], R[2] and R[3] is C(O)—NH—OH group, and none of R[1], R[2] and R[3] comprises C(O)—NH—OH structure fragment)

wherein each of the above alkyl, alkenyl, alkynyl, cycloalkyl, heterocyclyl, aryl, and heteroaryl groups is optionally and independently substituted by 1-3 substituents each independently selected from the group consisting of hydrogen, deuterium, halogen, $C_{1-4}$ alkyl, $C_{2-4}$ alkenyl, $C_{2-4}$ alkynyl, halo ($C_{1-4}$ alkyl), $C_{3-8}$ cycloalkyl, 4- to 8-membered heterocyclic group containing 1-2 atom(s) selected from N, O or S, $C_{6-10}$ aryl, 5- to 10-membered heteroaryl, OH, CN, $NO_2$, $OR^{13}$, $SR^{13}$, $N(R^7)_2$, $C(O)R^{12}$, $CO_2R^{13}$, $CONR^{10}R^{11}$, $SO_2NR^{10}R^{11}$; in the substituents, the definitions of each group are as described above.

It should be noted that the compounds claimed in formula (I) in this patent application do not include compounds disclosed in the following published patent applications: WO2015188085, WO2016073738, WO2016073770, WO2016073774, WO2017192840, WO2017192844, WO2017192845, WO20171928.

In another preferred embodiment, X is NH, N($C_{1-4}$ alkyl), O, C(O), C(O)O, C(O)NH, or C(O)NCH$_3$; Y is NH, N($C_{1-4}$ alkyl), O, C(O), or C(O)NH.

In another preferred embodiment, X is NH, C(O)NH, or C(O).

In another preferred embodiment, Y is C(O) or NH.

with the proviso that the structure formed by the combination of X and Y is a stable chemical structure.

In another preferred embodiment, the Y—X is a combination selected from the following:

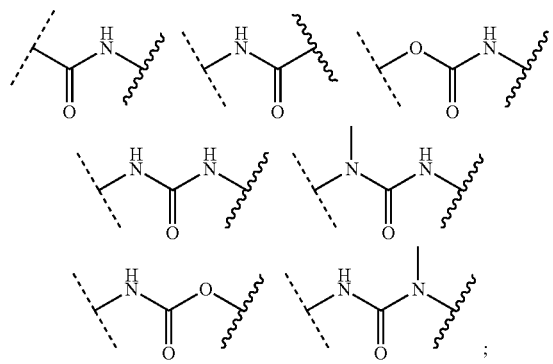

;

/ refers to the point connecting to A, / refers to the point connecting to $CR^2R^3$.

In another preferred embodiment, the Y—X is a combination selected from the following:

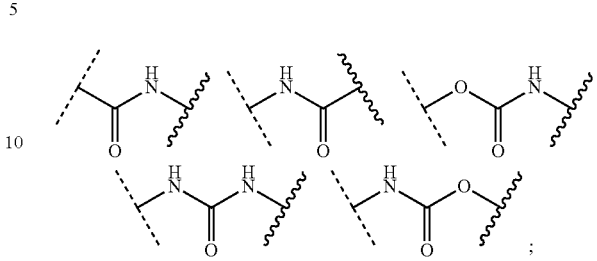

/ refers to the point connecting to A, / refers to the point connecting to $CR^2R^3$. The definitions of each group are as described above.

In another preferred embodiment, R[2] is hydrogen, deuterium or fluorine, R[3] is $C_{1-4}$ alkyl, $C_{2-4}$ alkenyl, $C_{2-4}$ alkynyl, halogenated ($C_{1-4}$ alkyl), hydroxy, $C_{1-4}$ alkoxy, $C_{3-6}$ cycloalkyl, $(CR^8R^9)_p$—Z—$(CR^8R^9)_r$—$CO_2H$, $(CR^8R^9)_p$—Z—$(CR^8R^9)_r$—C(O)NHOH.

In another preferred embodiment, R[2] and R[3] are each independently selected from the group consisting of hydrogen, deuterium, fluorine, $C_{1-4}$ alkyl, or R[2] and R[3] together with the carbon atoms to which they connected form $C_{3-6}$ cycloalkyl or C=O.

In another preferred embodiment, R[2] and R[3] are each independently selected from the group consisting of methyl, or R[2] and R[3] together with the carbon atom to which they attached to form a cyclopropyl group.

In another preferred embodiment, B is a structure selected from the following:

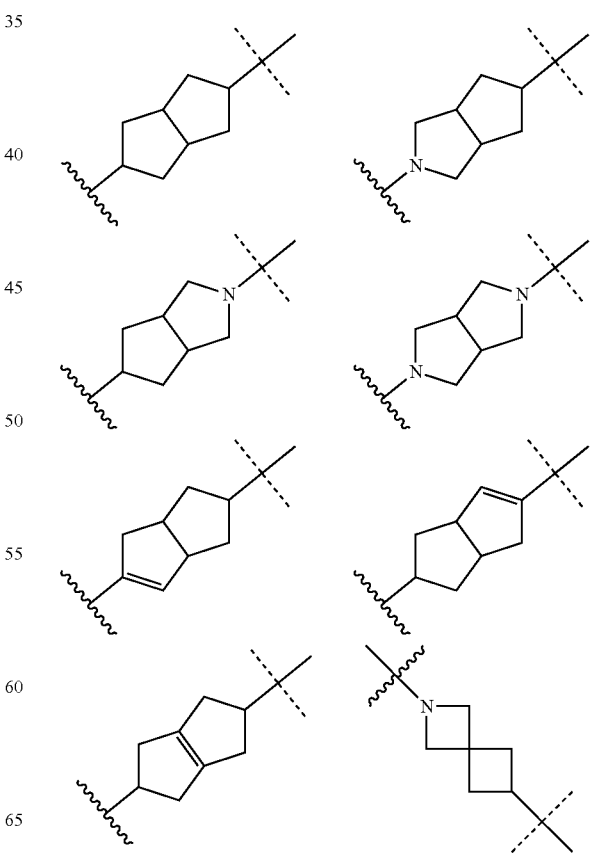

-continued

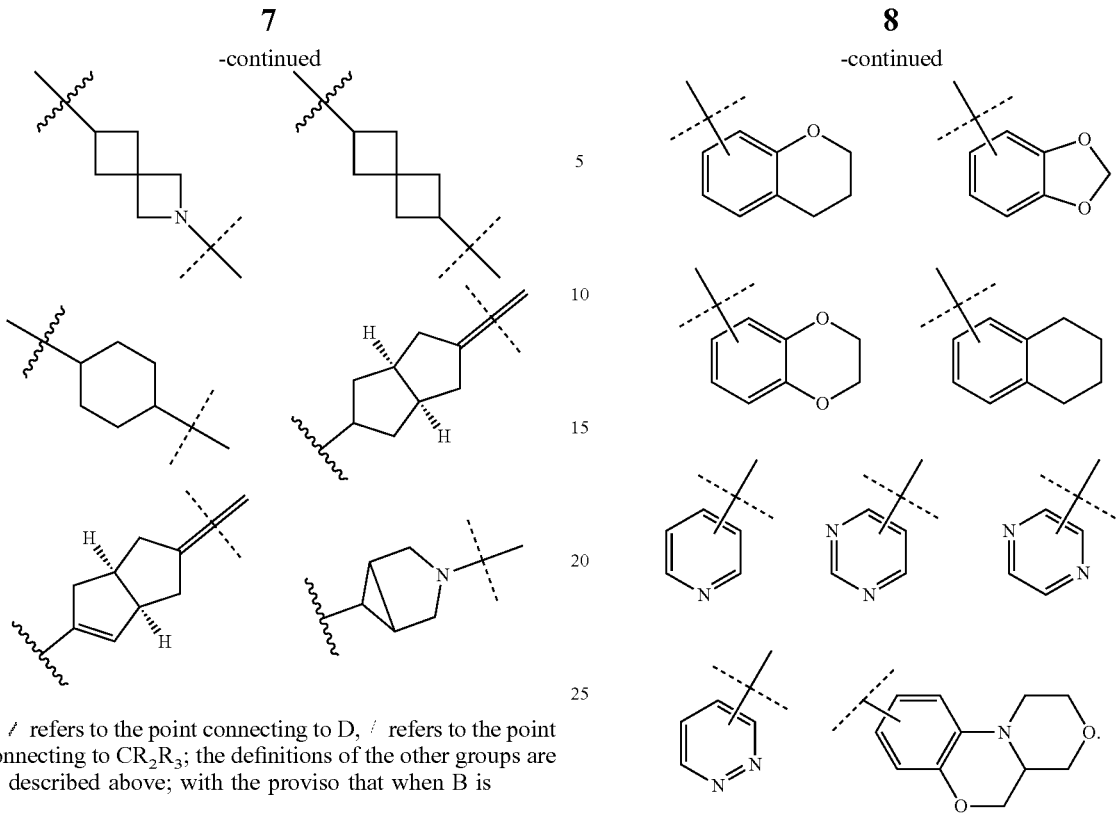

/ refers to the point connecting to D, / refers to the point connecting to $CR_2R_3$; the definitions of the other groups are as described above; with the proviso that when B is

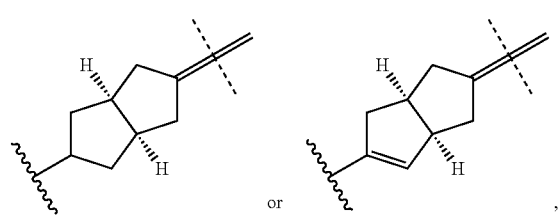

s can only be 1, and the $R^3$ in $CR^2R^3$ is absent.

In another preferred embodiment, A is $C_{6-10}$ aryl, 5- to 15-membered heteroaryl, $C_{3-10}$ cycloalkyl, 4- to 15-membered heterocyclic group, or A is as follows:

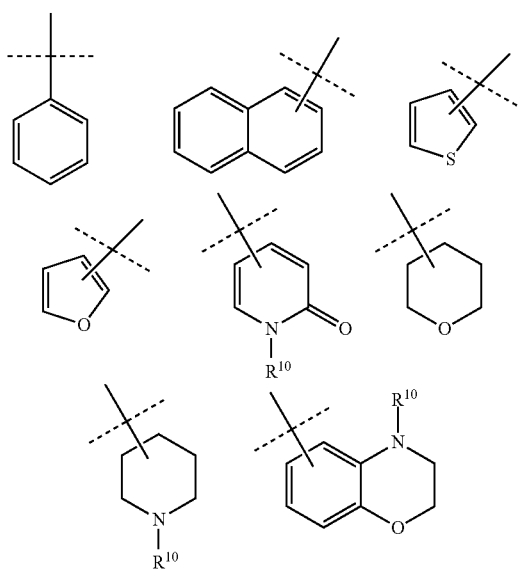

In another preferred embodiment, $R^1$ are each independently halogen, $C_{1-4}$ alkyl, $C_{1-4}$ alkoxy, $C_{2-4}$ alkenyl, $C_{2-4}$ alkynyl, cyano, $C(O)R^{12}$, $NR^{10}SO_2NR^{10}R^{11}$, $CO_2R^{13}$, $CONR^{10}R^{11}$, halo ($C_{1-4}$ alkyl), halo ($C_{1-4}$ alkoxy), $(CR^8R^9)_n$—C(O)—NHOH,

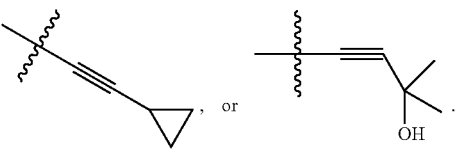

In another preferred embodiment, E is $C_{6-10}$ aryl, 5- to 10-membered heteroaryl, 5- to 10-membered heterocyclic group containing 1-3 atom(s) selected from N, O or S, or E is as follows:

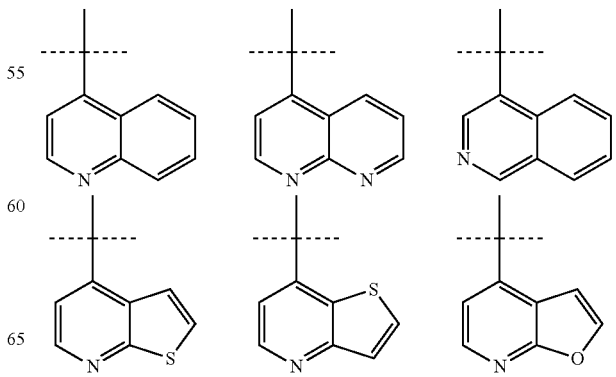

-continued
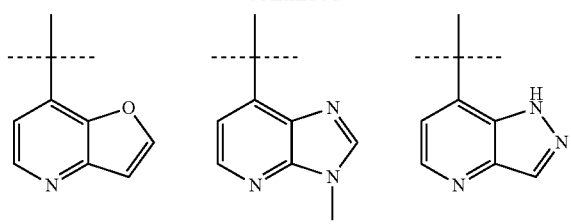
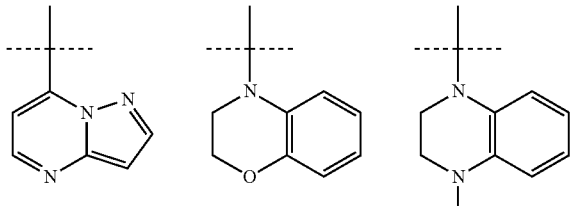
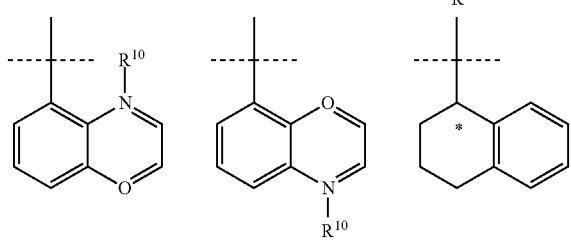
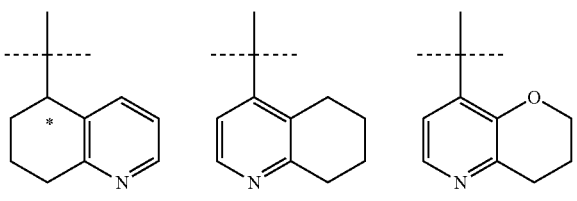
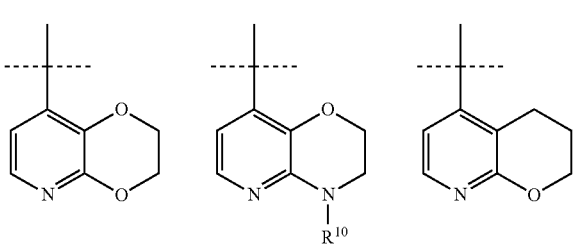
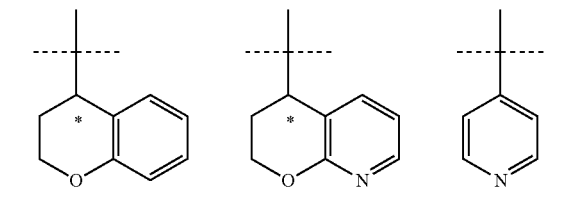
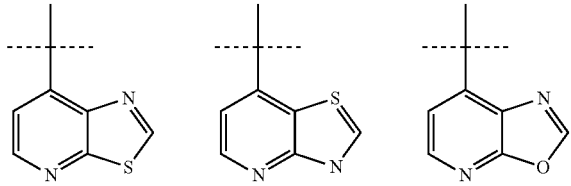
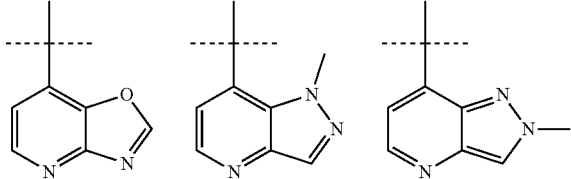
In another preferred embodiment, E is a structure selected from the following:
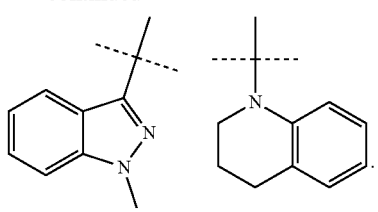
In another preferred embodiment, B is selected from the group consisting of
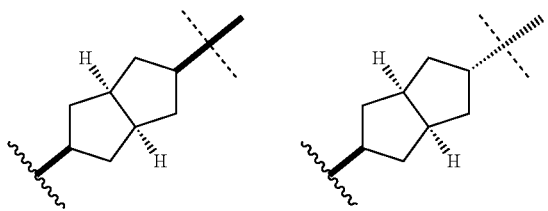

-continued

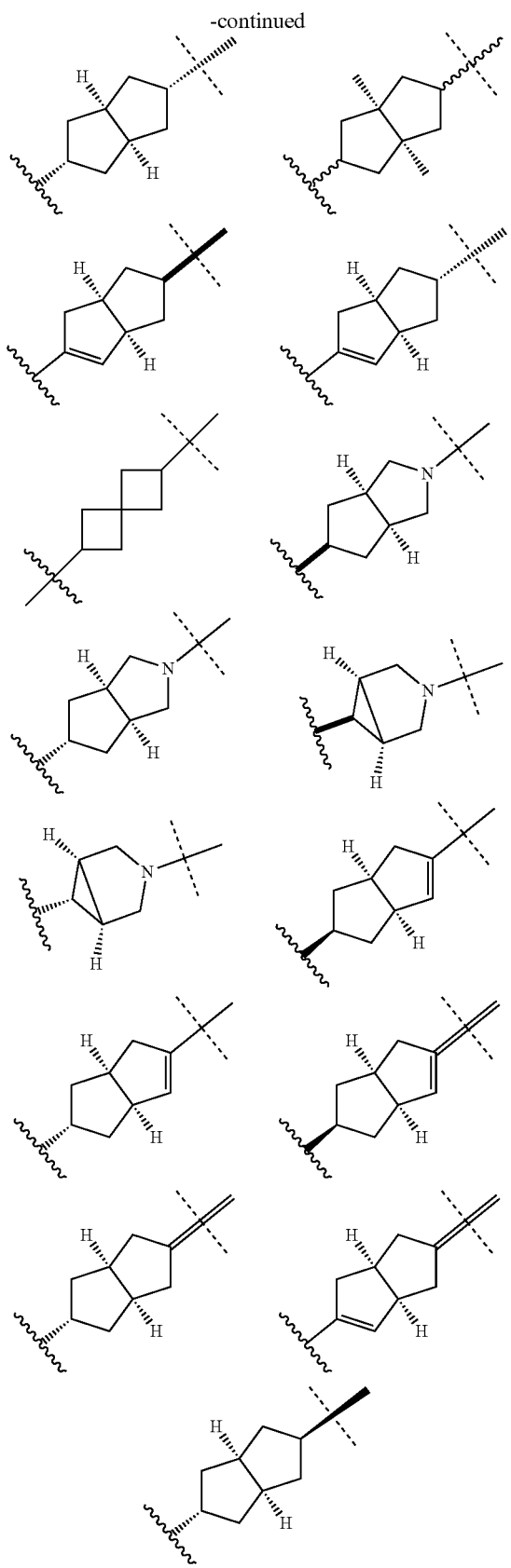

wherein ╱ refers to the point connecting to D, ╱ refers to the point connecting to CR₂R₃; provided that when B is

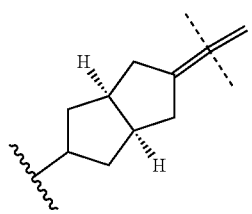 or 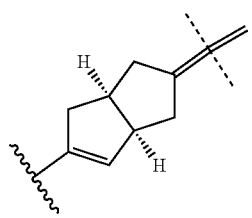, the R³ in CR²R³ is absent.

In another preferred embodiment, the compound is of the following structure:

(I-a)

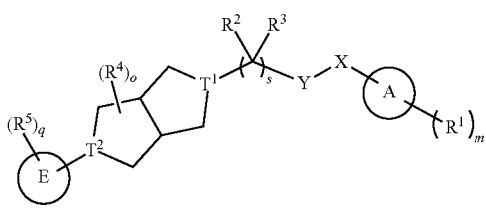

wherein T¹ and T² are each independently selected from CR¹⁵ or N, wherein R¹⁵ is H, F, or OH;

Y—X is selected from the following combinations:

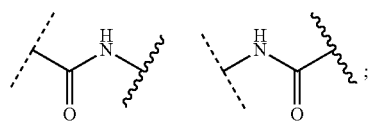

╱ refers to the point connecting to A, ╱ refers to the point connecting to CR²R³;

the definitions of each group are as described above.

In another preferred embodiment, the compound is of the following structure:

(I-aa)

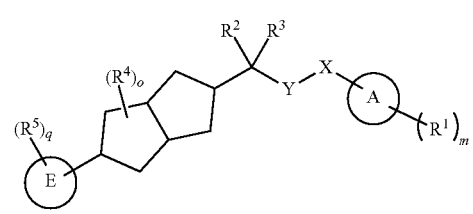

Y—X is selected from the following combinations:

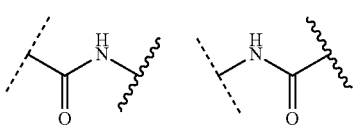

╱ refers to the point connecting to A, ╱ refers to the point connecting to CR²R³.

In another preferred embodiment, the compound is of the following structure:

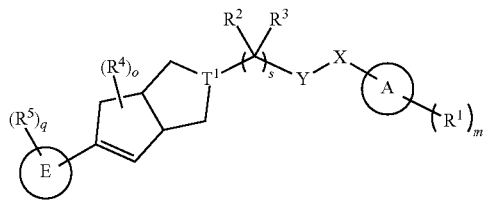
(I-b)

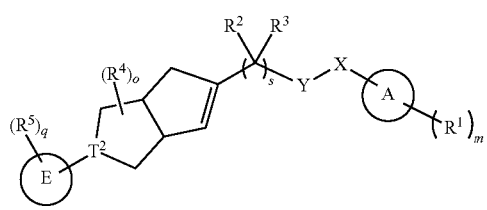
(I-c)

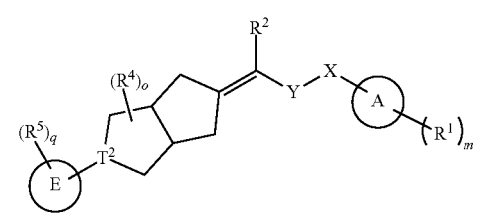
(I-d)

wherein T¹ and T² are each independently selected from $CR^{15}$ or N, wherein $R^{15}$ is H, F, or OH, Y—X is selected from the following combinations:


/ refers to the point connecting to A, / refers to the point connecting to $CR^2R^3$.

In another preferred embodiment, the compound is of the following structure:

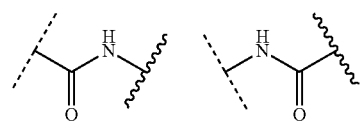
(I-ba)

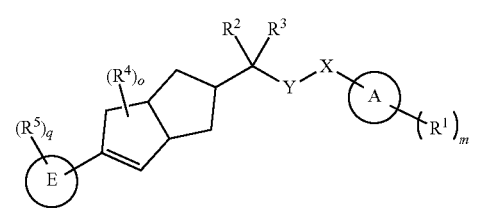
(I-ca)

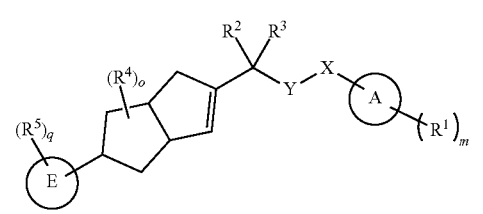
(I-da)

Y—X is selected from the following combinations:


/ refers to the point connecting to A, / refers to the point connecting to $CR^2R^3$.

In another preferred embodiment, the compound described is of the following structure:

$$G^1 \text{---} G^2$$

wherein the $G^1$ is selected from the following group:

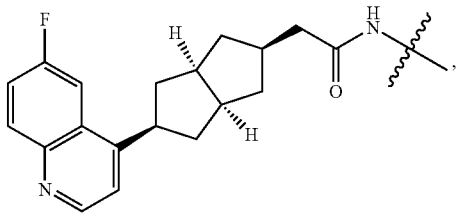

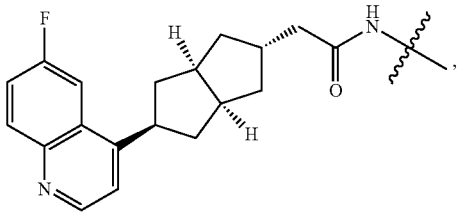

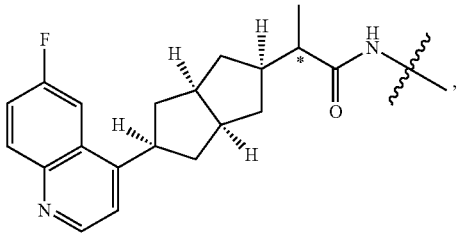

15
-continued

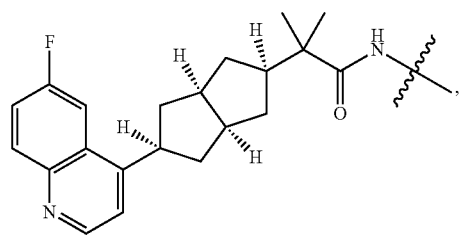
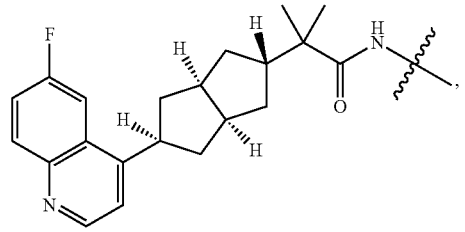
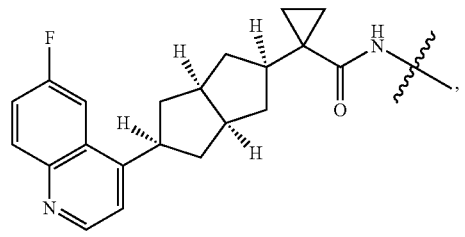
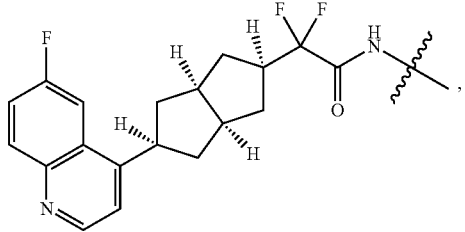
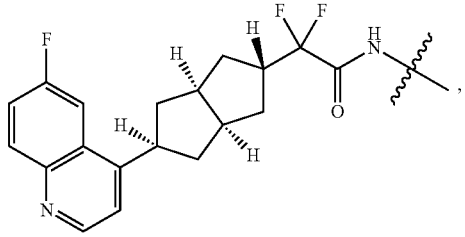
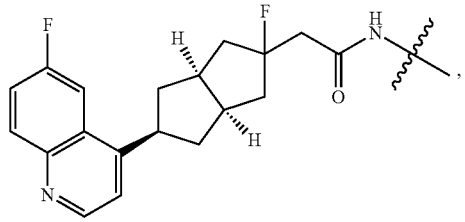
16
-continued
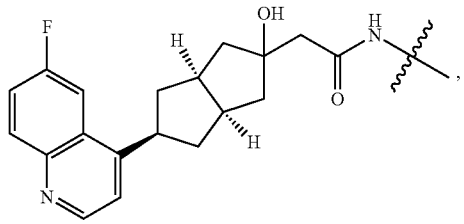
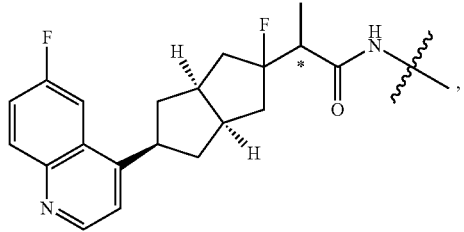
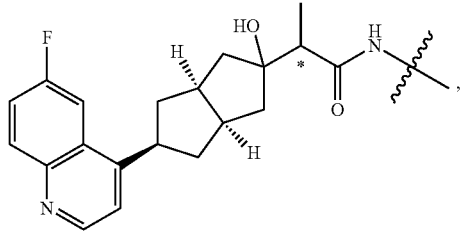
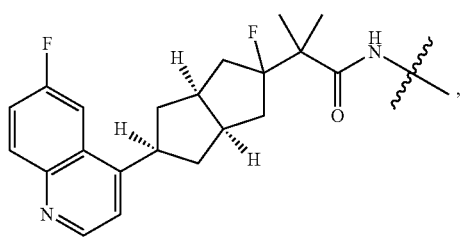
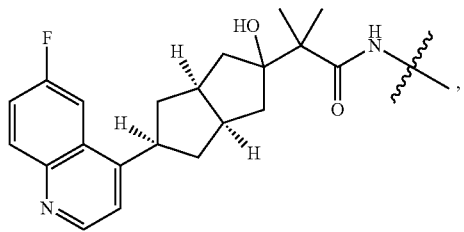
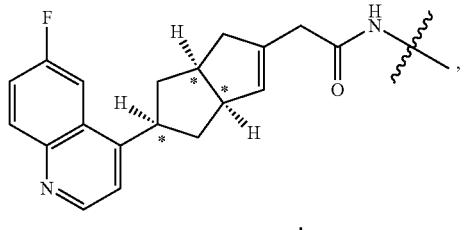
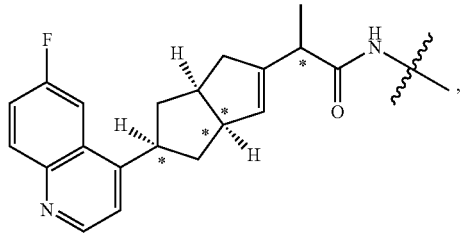

-continued
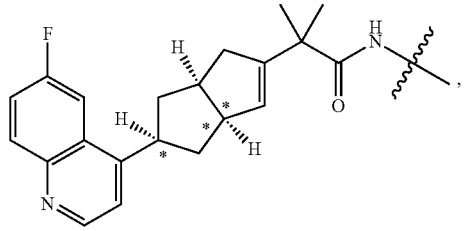
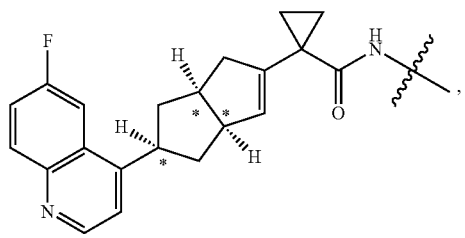
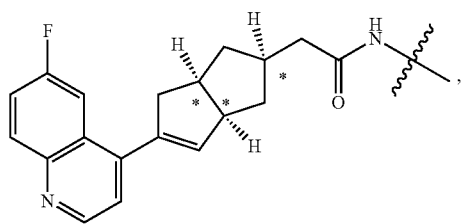
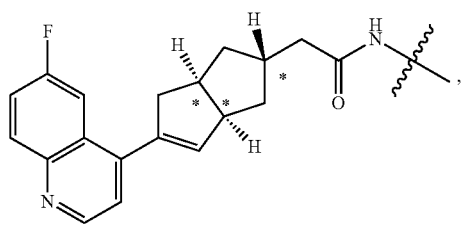
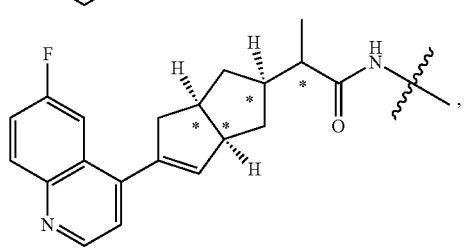
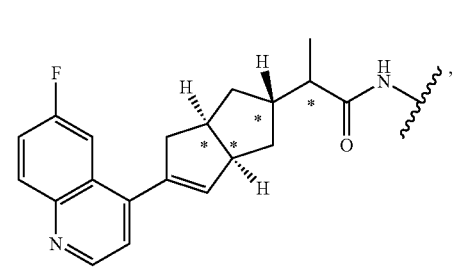
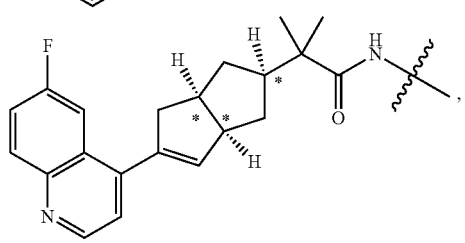
-continued
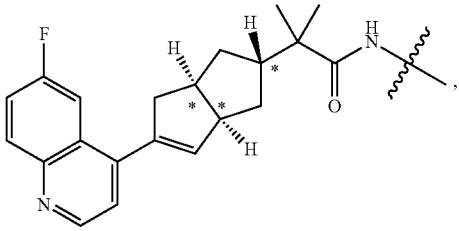
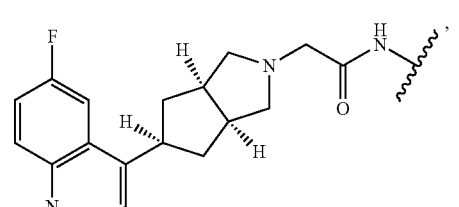
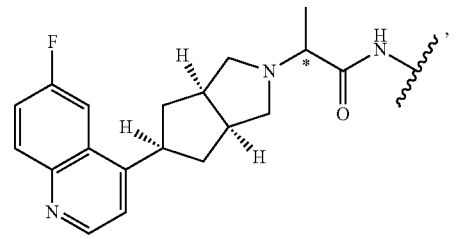
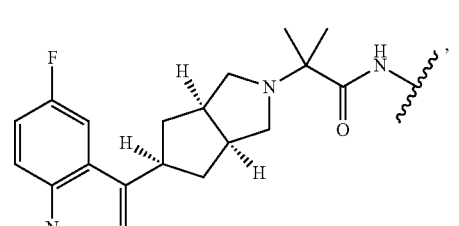
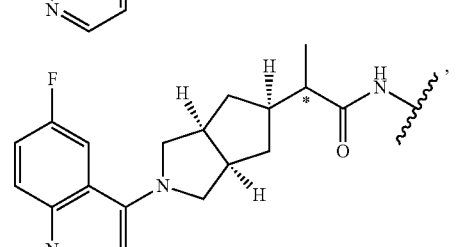
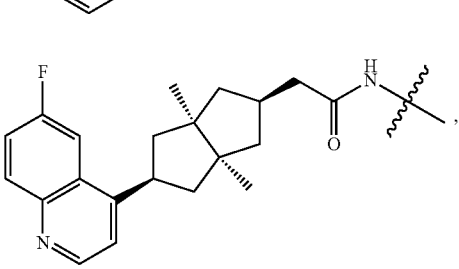
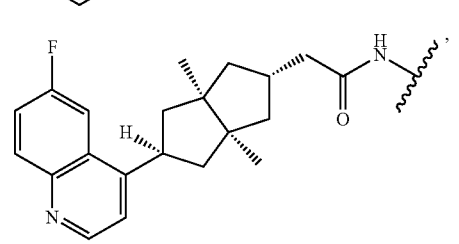

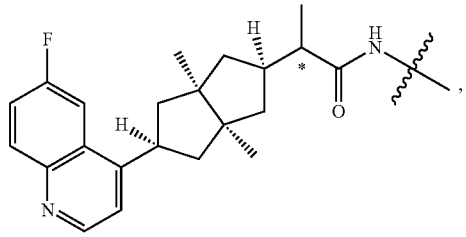
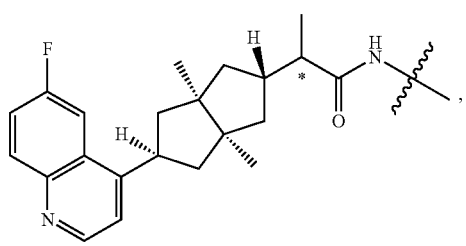
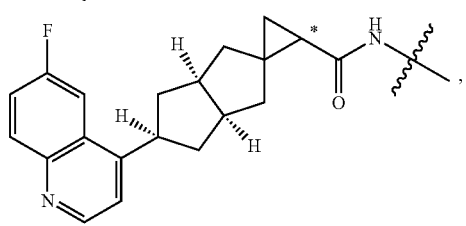
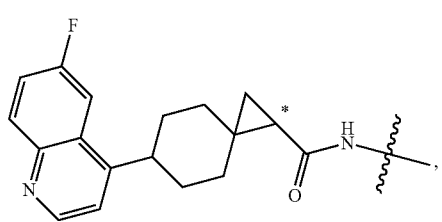
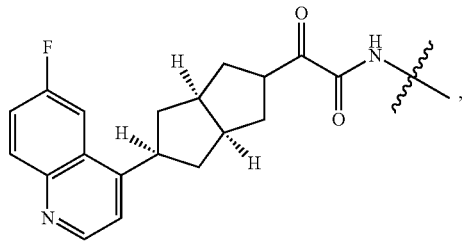
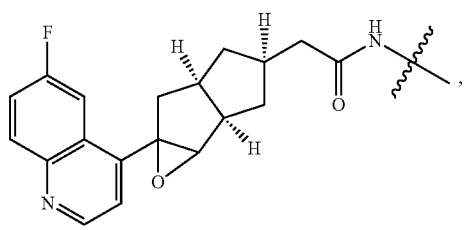
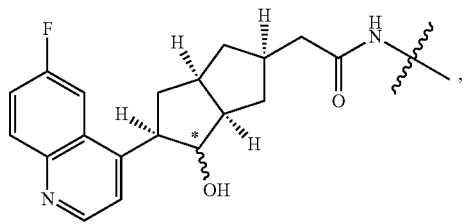
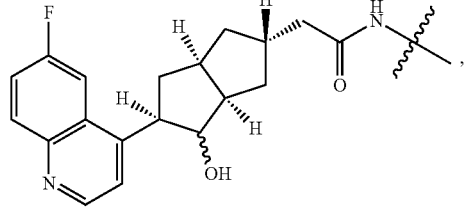
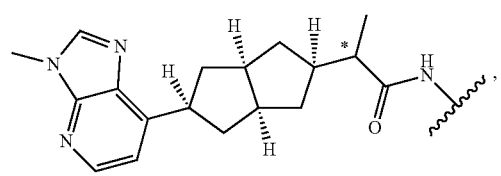
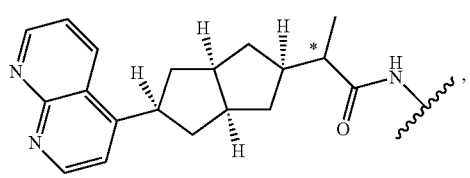
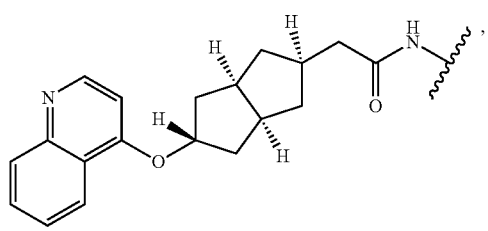
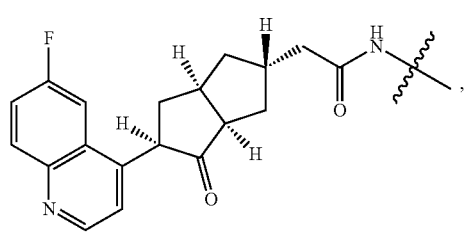
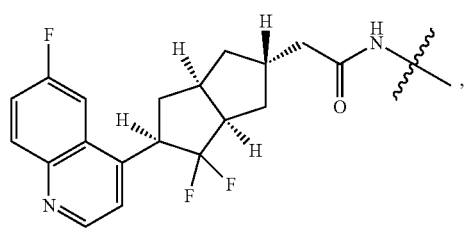
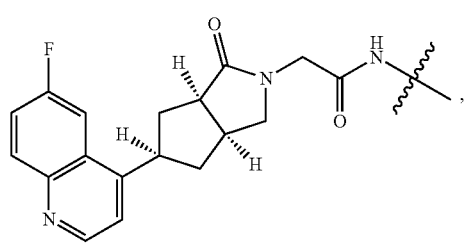

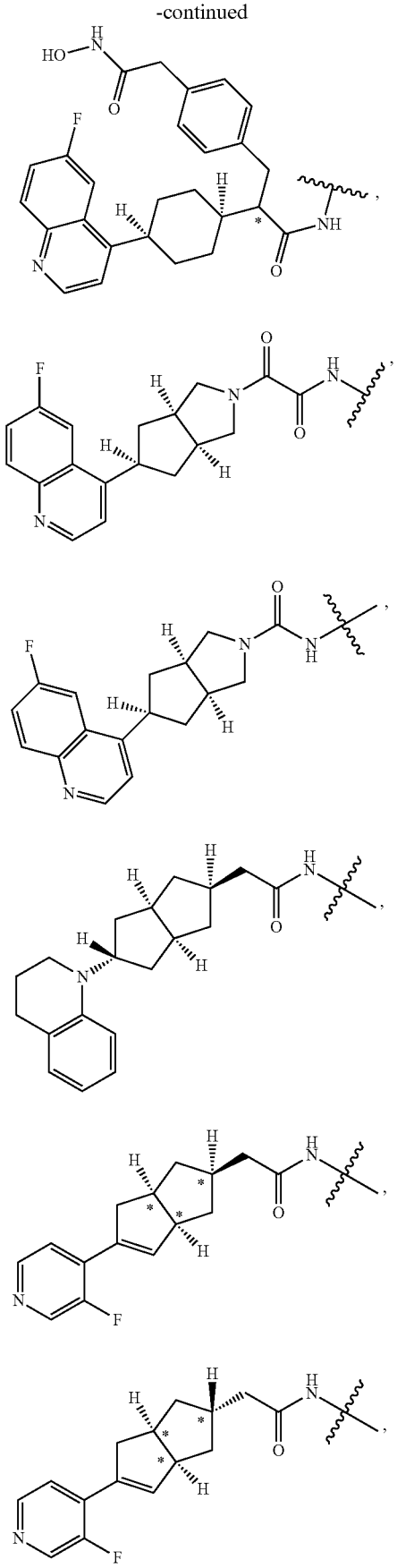
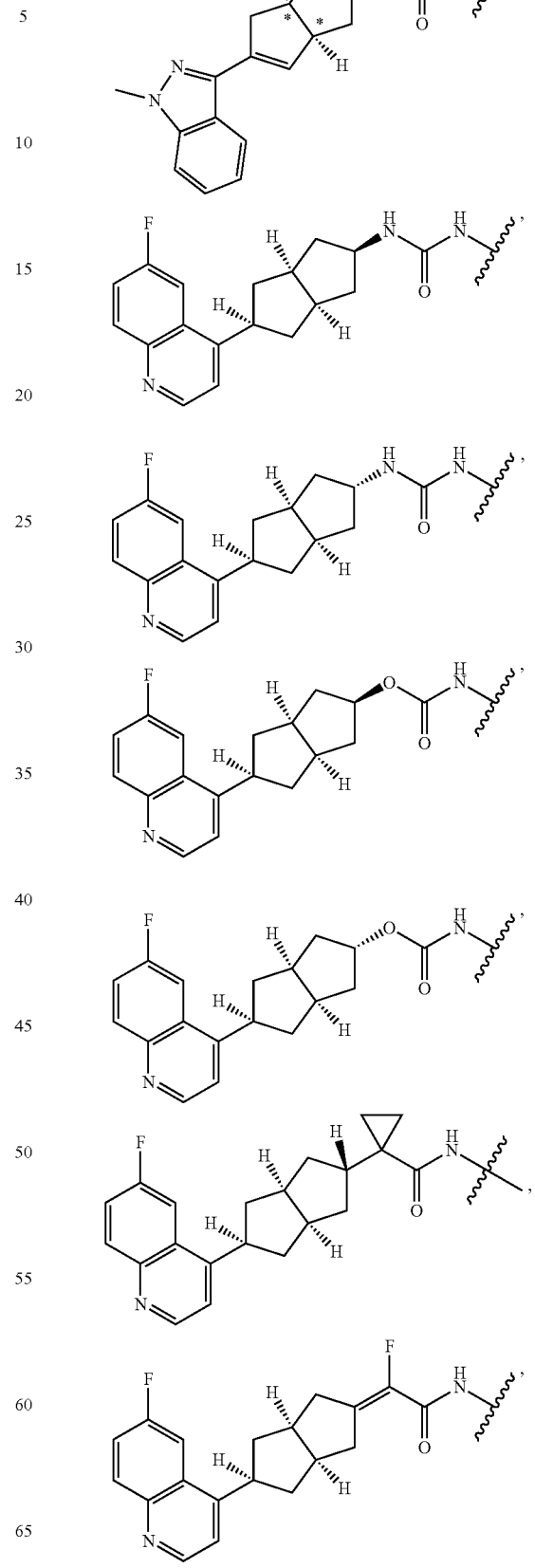

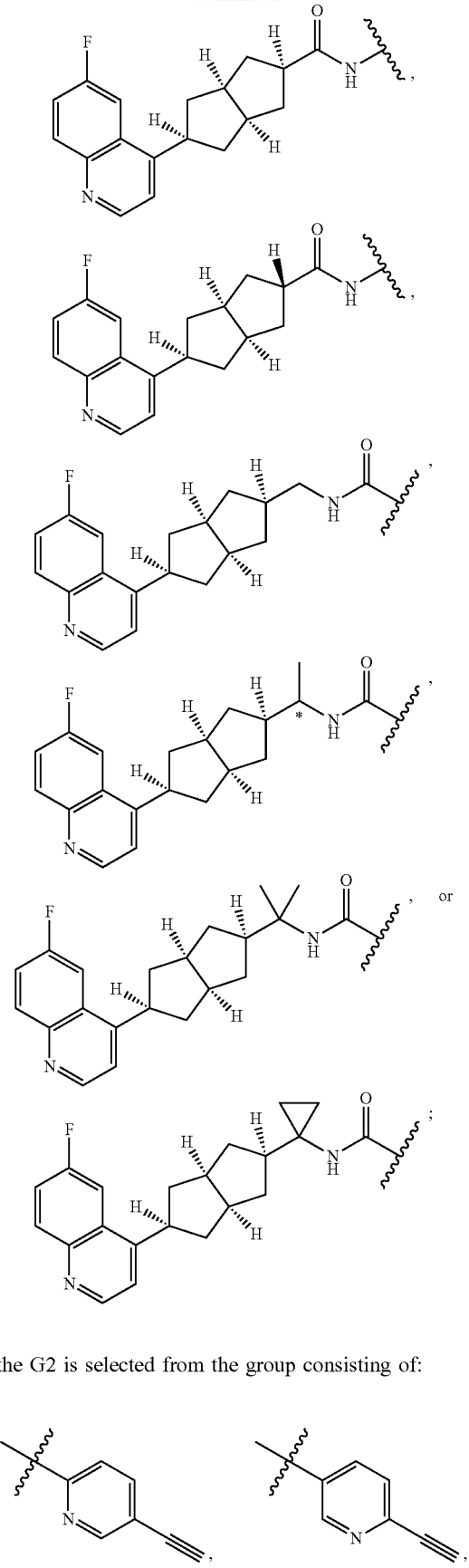
the G2 is selected from the group consisting of:
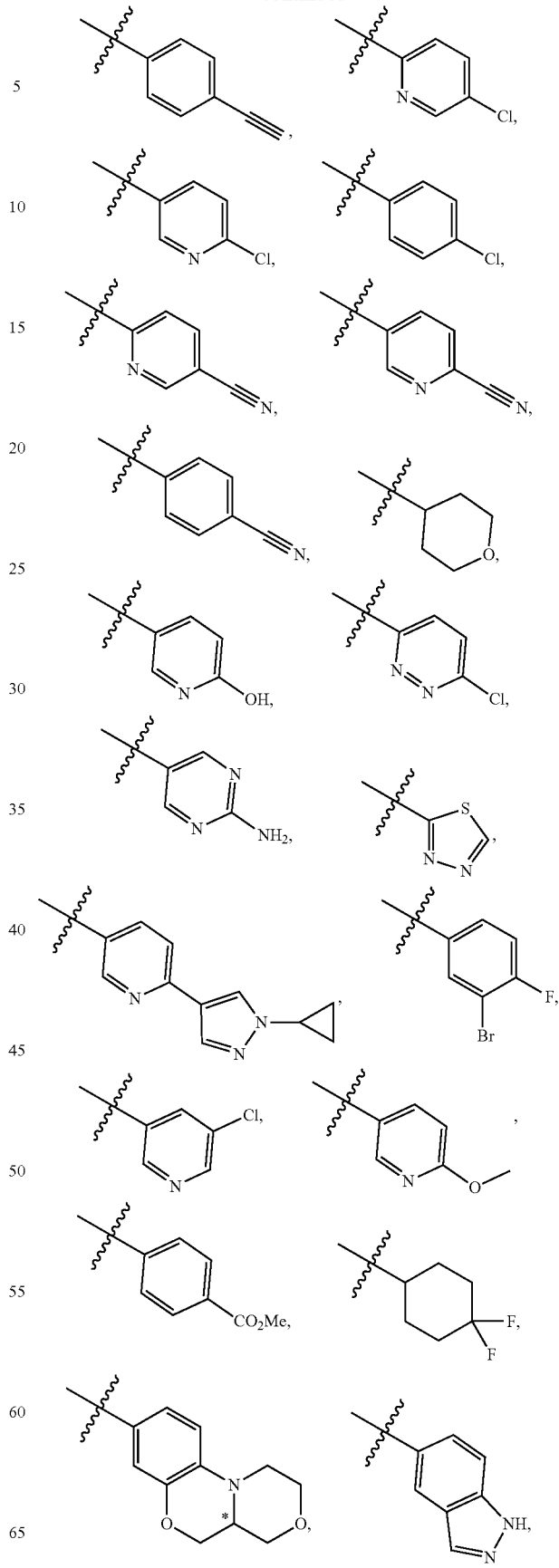

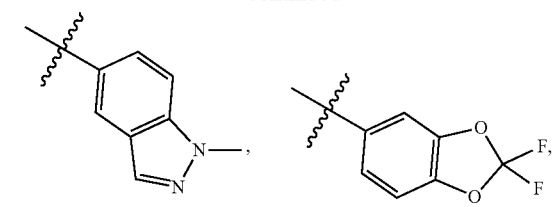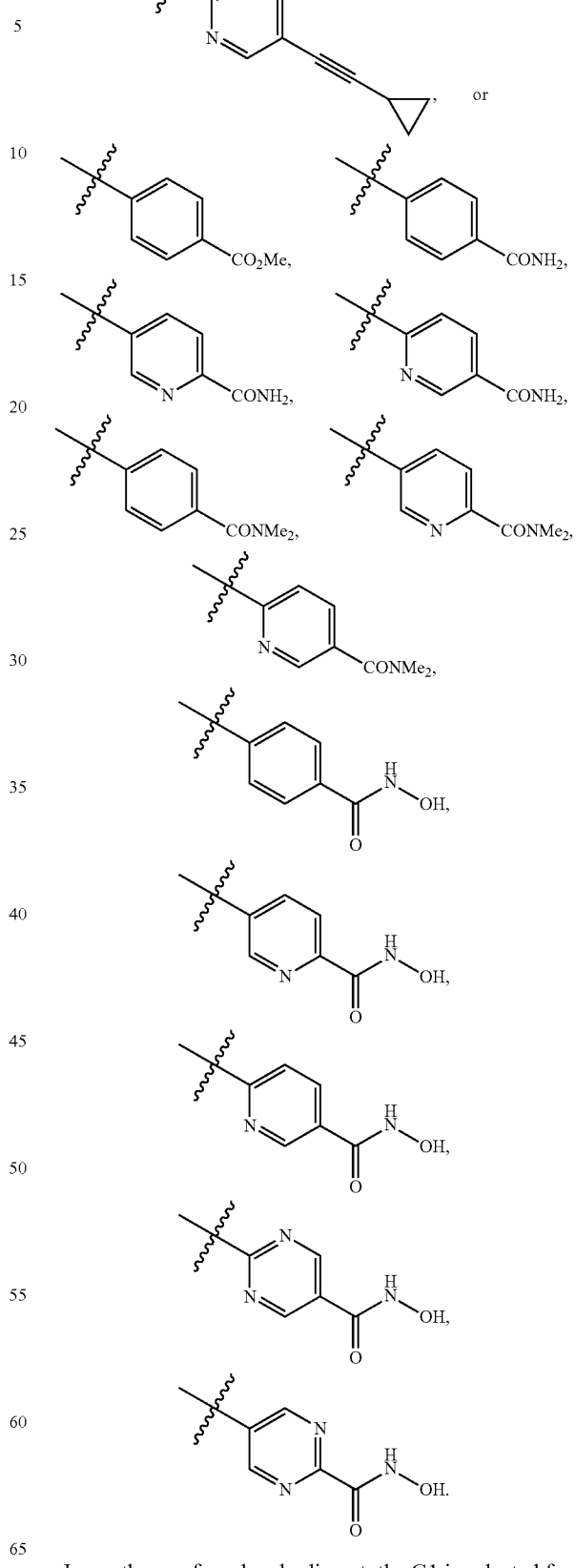
In another preferred embodiment, the G1 is selected from the group consisting of:

-continued
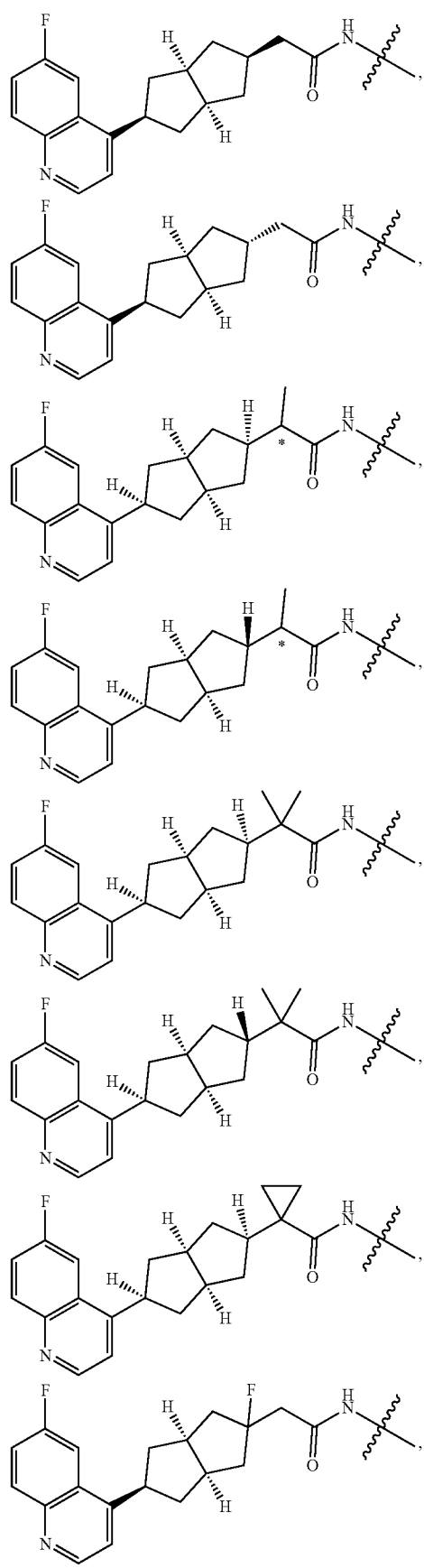
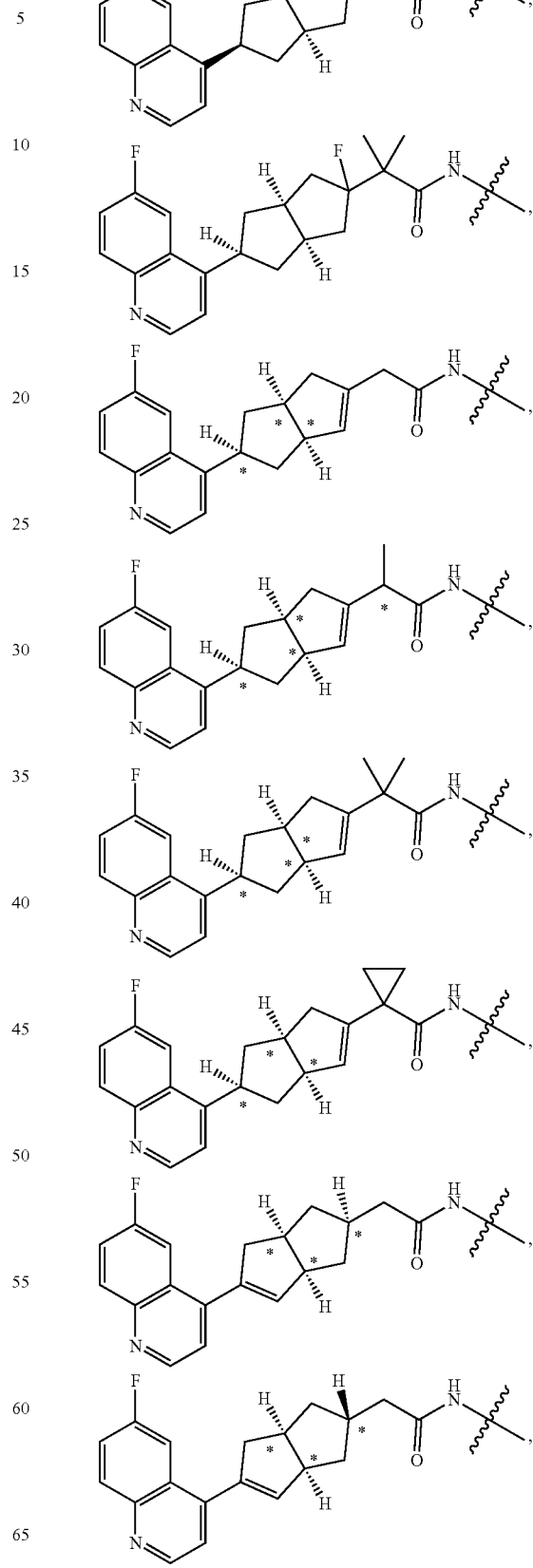

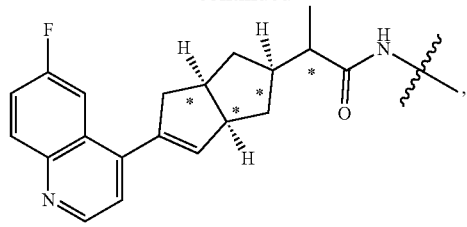
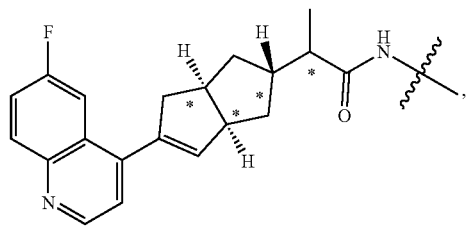
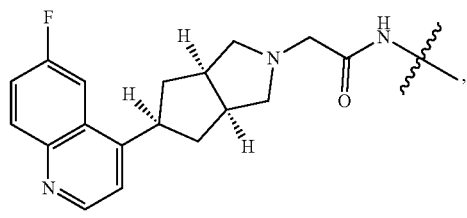
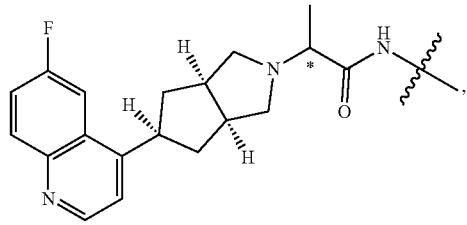
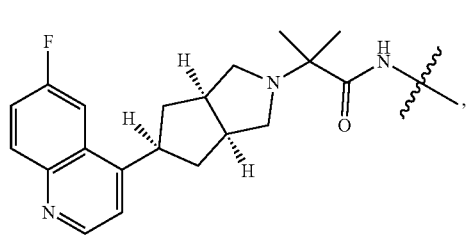
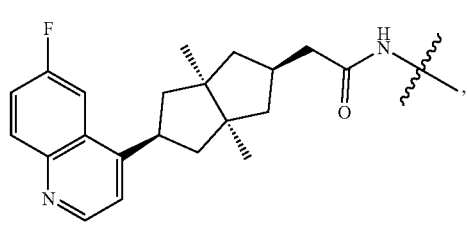
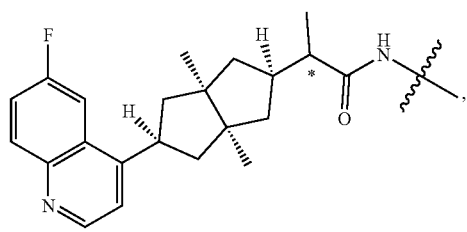
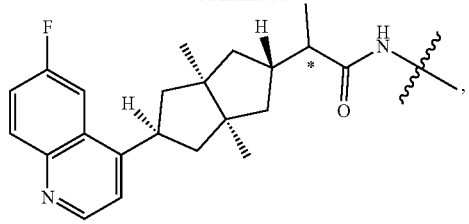
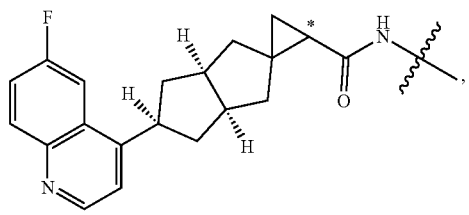
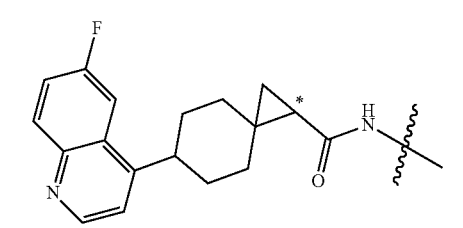
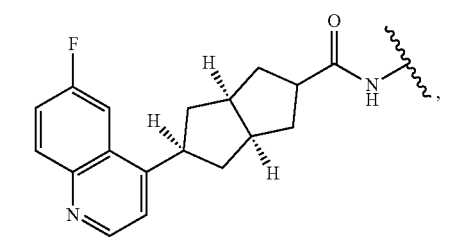
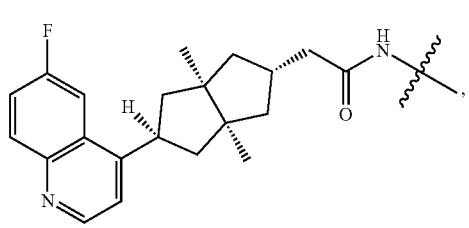
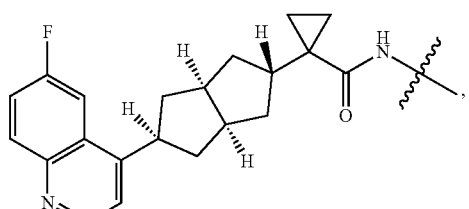
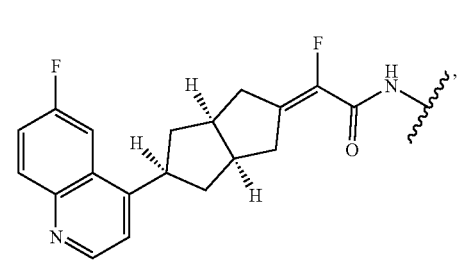

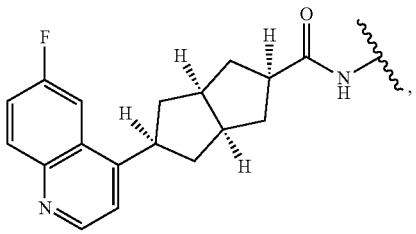
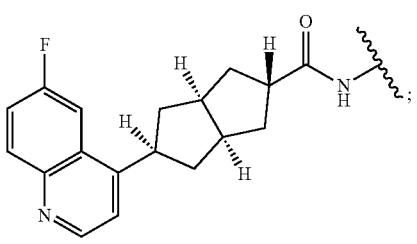
the G2 is selected from the group consisting of:
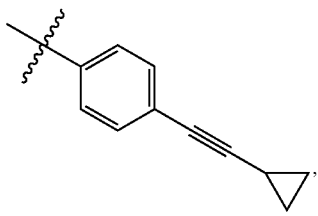
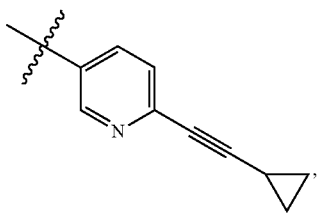

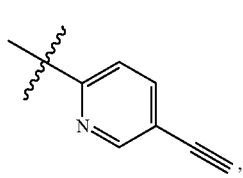 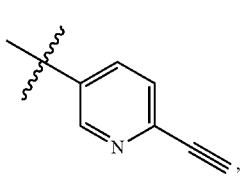
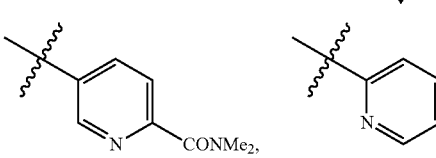
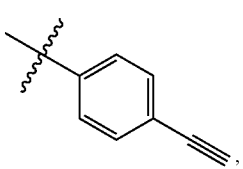 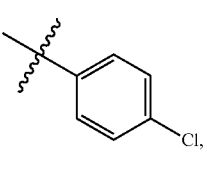
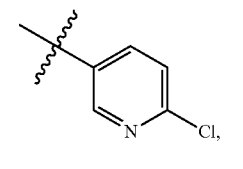 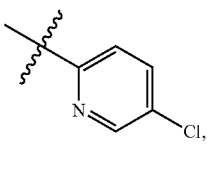
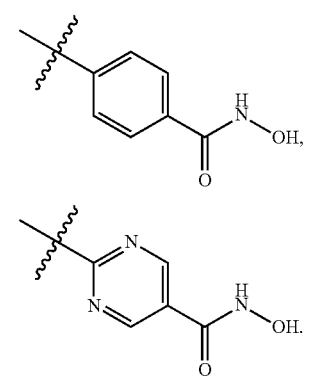 [SMILES: *c1ccc(C(=O)NO)cc1 ; *c1ncc(C(=O)NO)cn1]
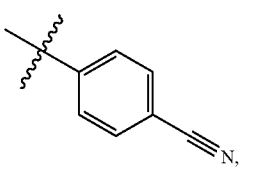 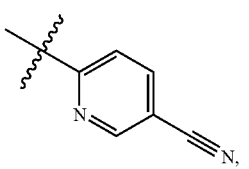
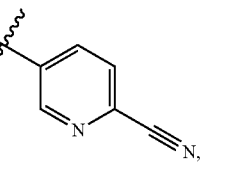 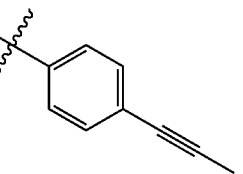
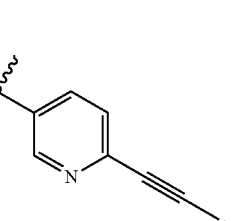 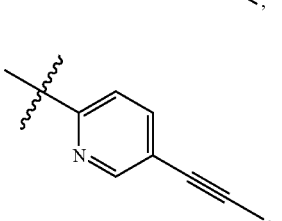
In another preferred embodiment, each group is the corresponding group of the compounds in the embodiments.
In another preferred embodiment, the compound of formula (I) is of a structure selected from the following:
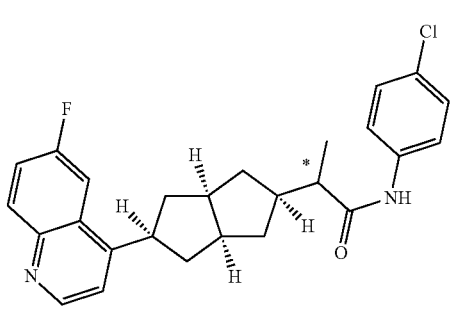

-continued
1A
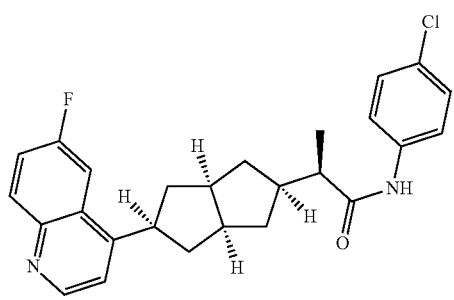
1B
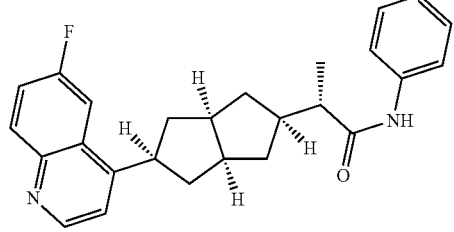
2
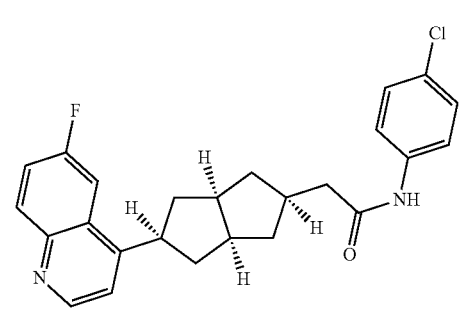
3
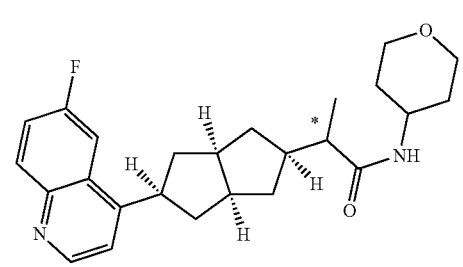
4
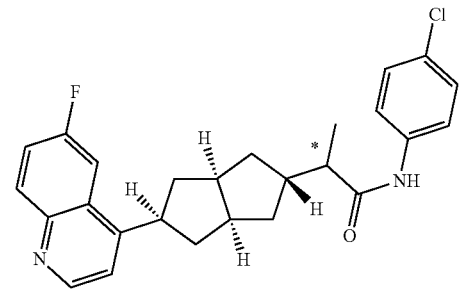
-continued
5
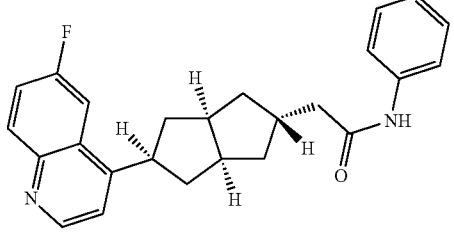
6
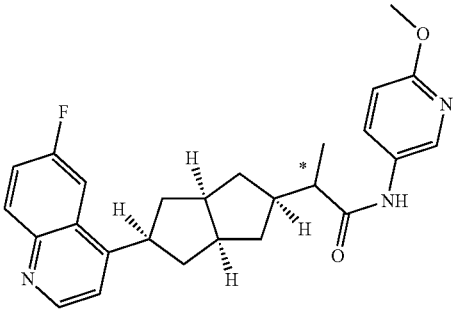
7
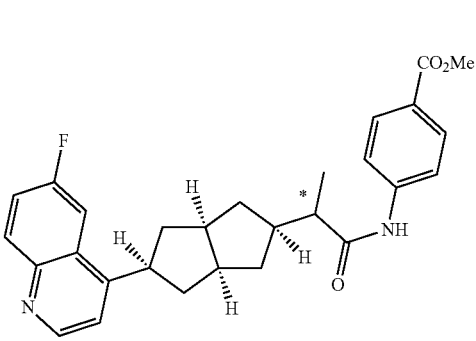
8
9
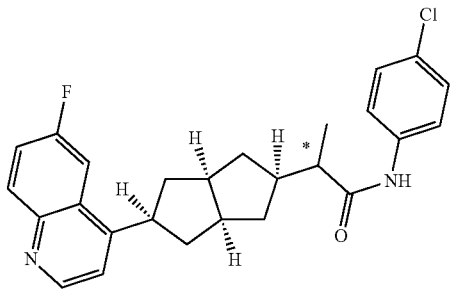

10
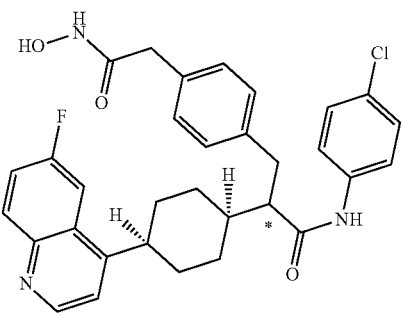
11
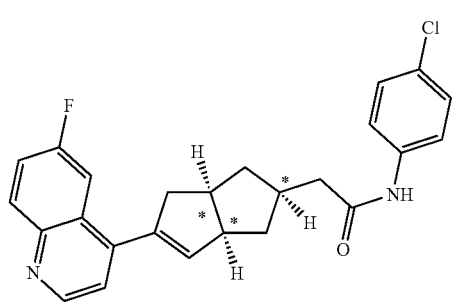
12
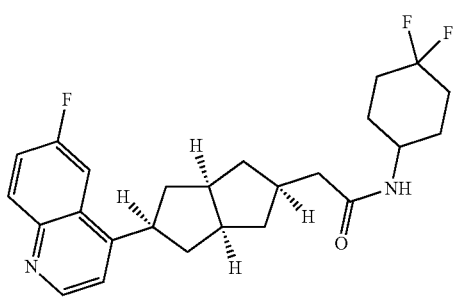
13
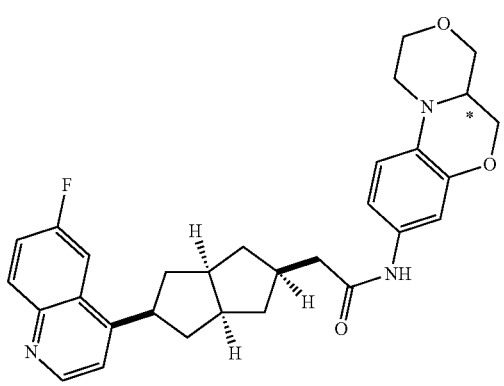
14
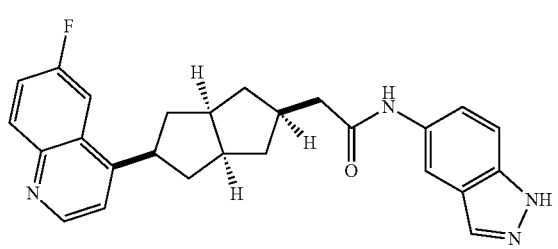
15
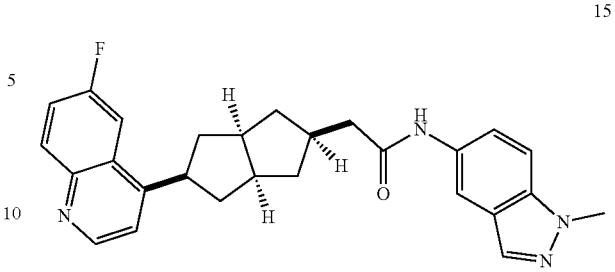
16

17

18
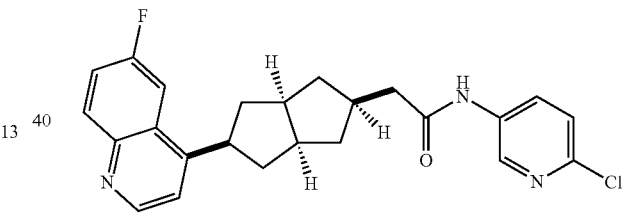
19
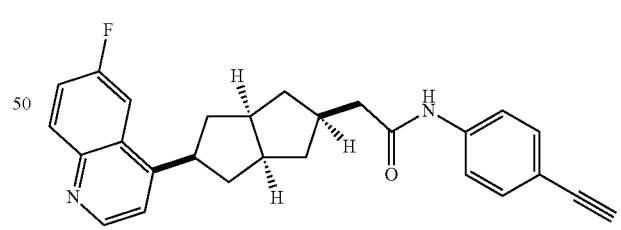
20
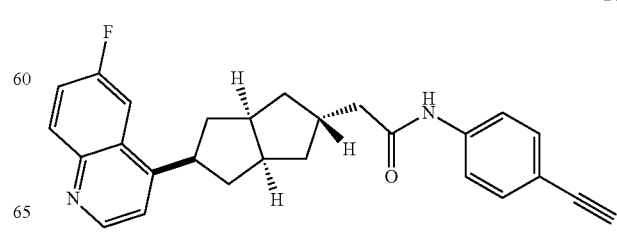

21
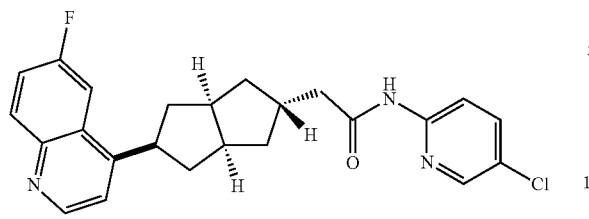
22
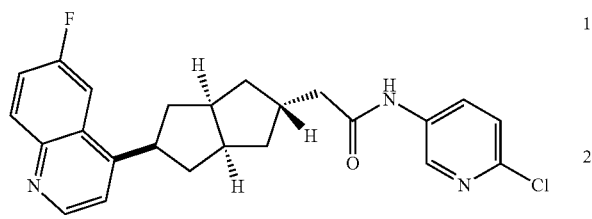
23
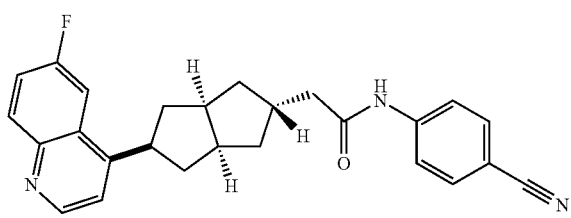
24
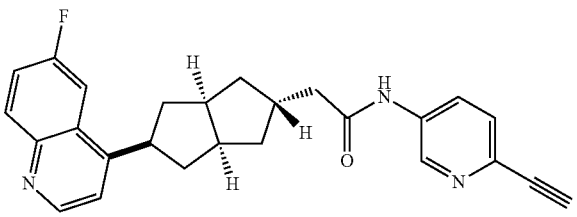
25
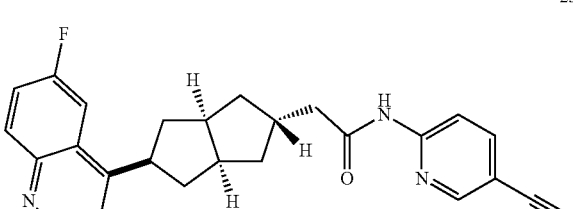
26
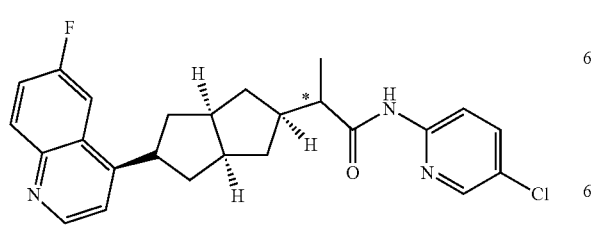
26A
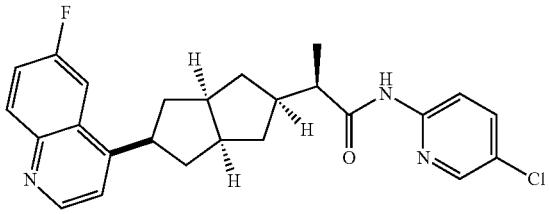
26B
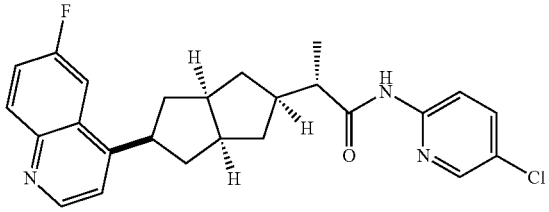
27
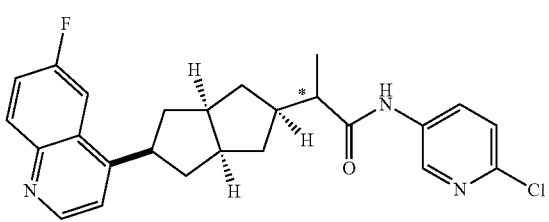
28
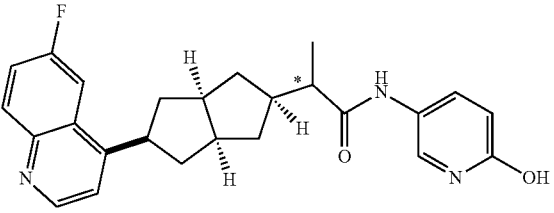
29
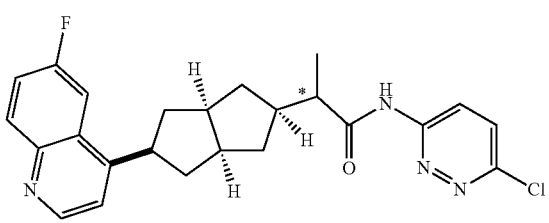
30
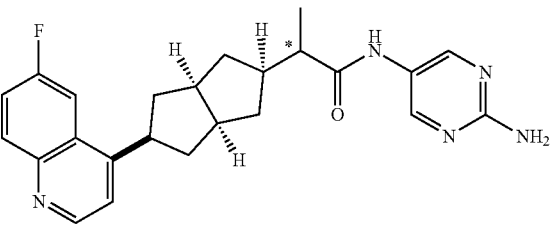

31
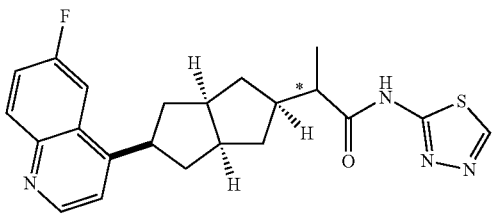
32
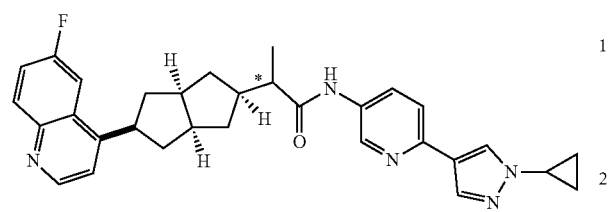
33
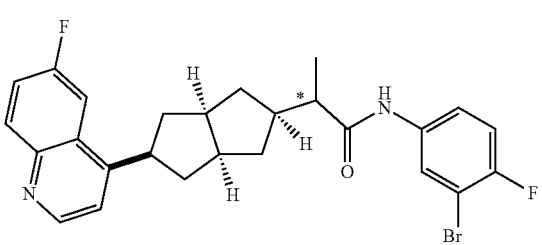
34
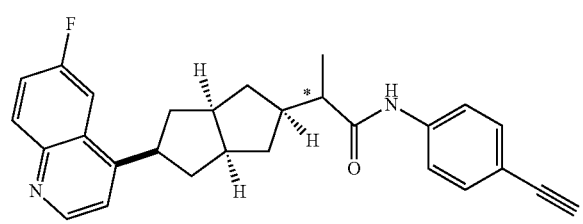
35
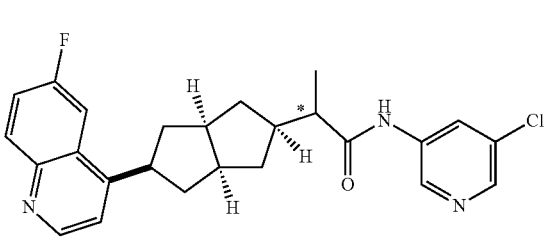
36
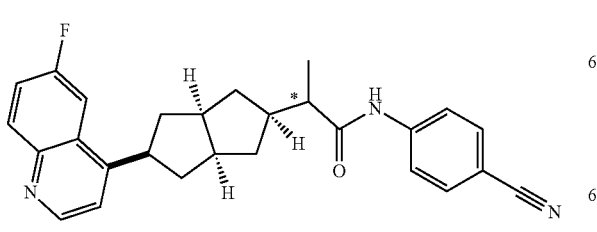
37
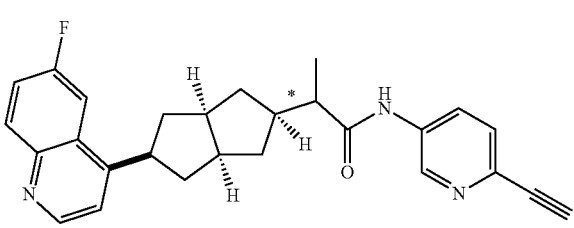
38
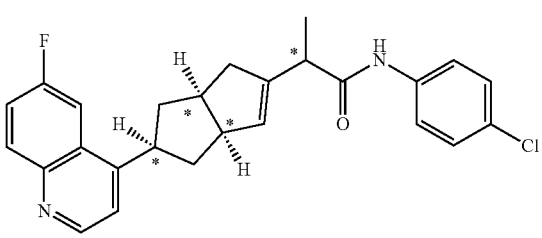
39
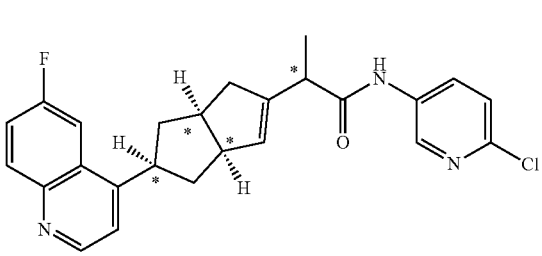
40
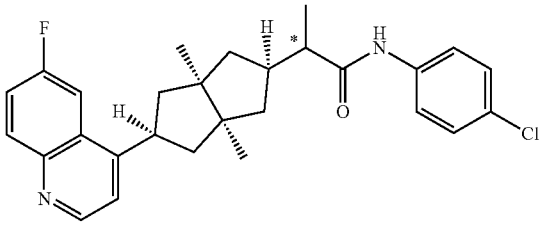
41
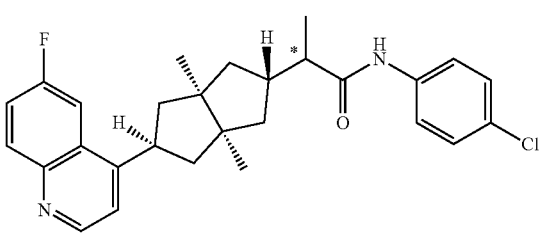
42
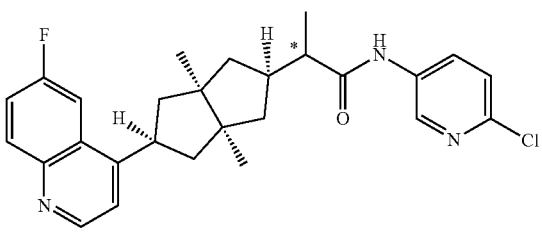

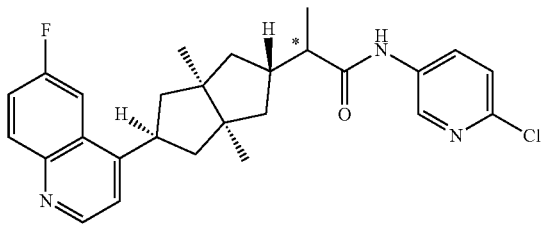
43
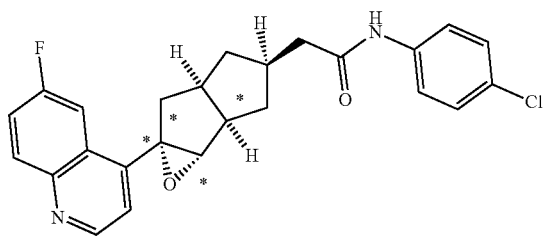
49
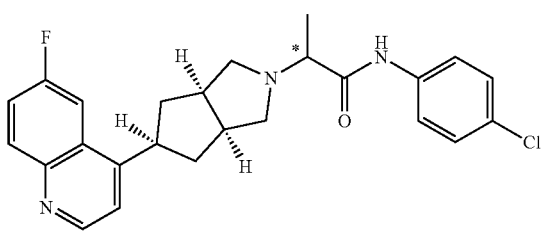
44
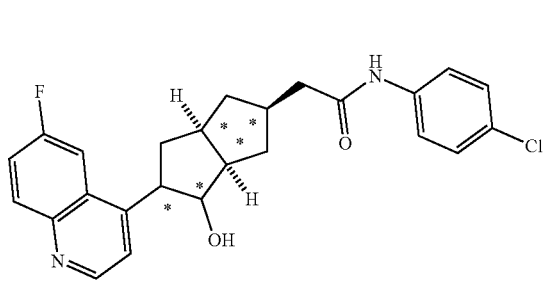
50
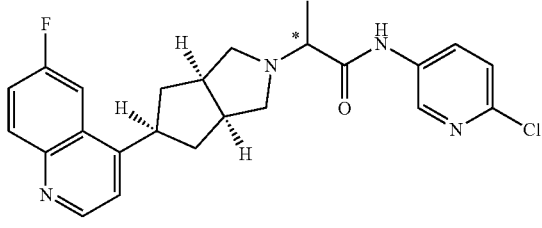
45
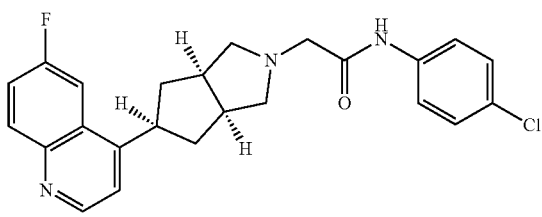
46
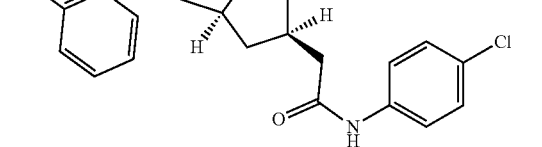
51
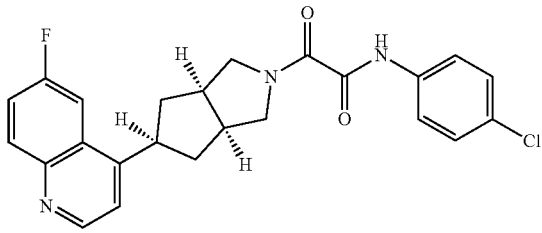
47
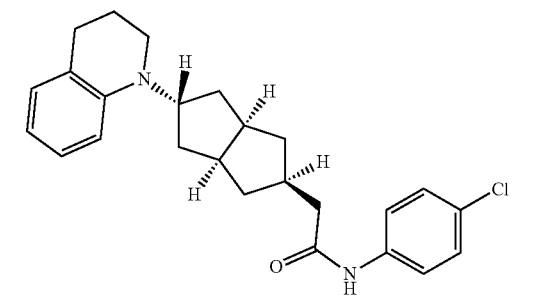
52
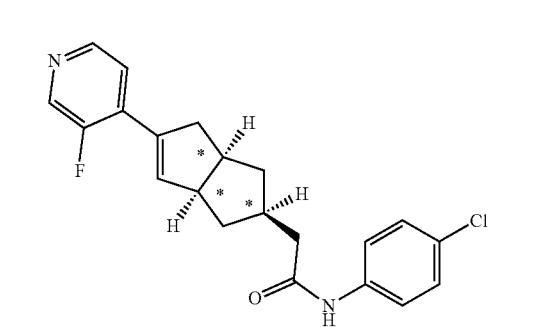
48
53

54
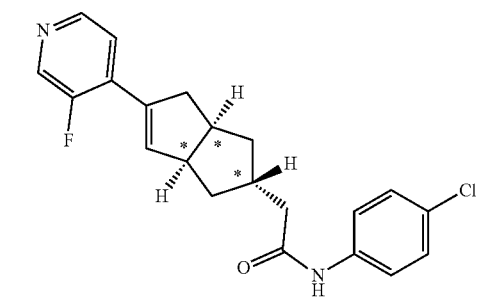
55
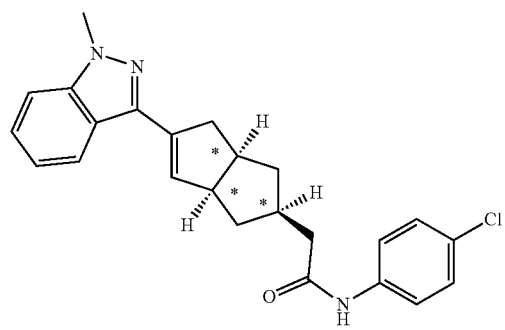
56
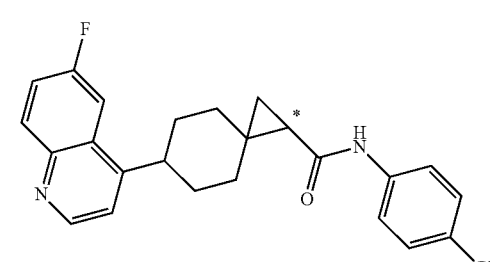
57
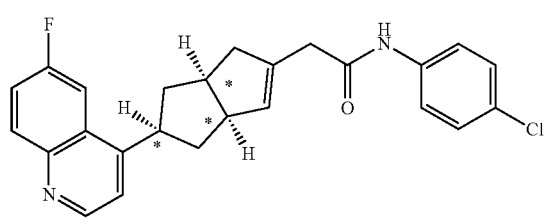
58
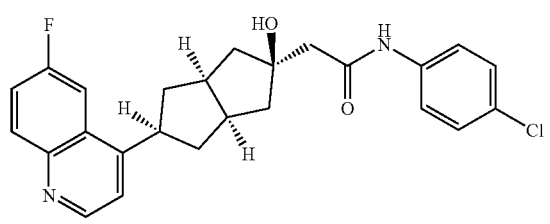
59
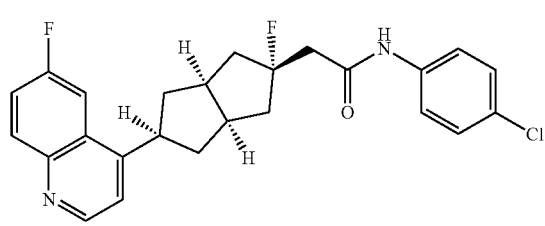
60
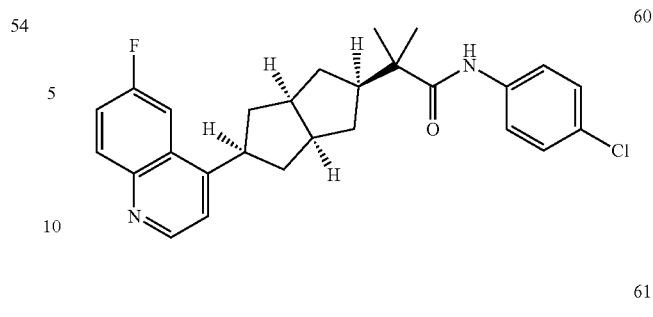
61
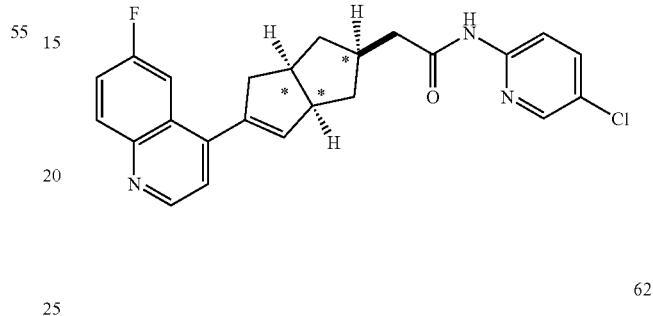
62
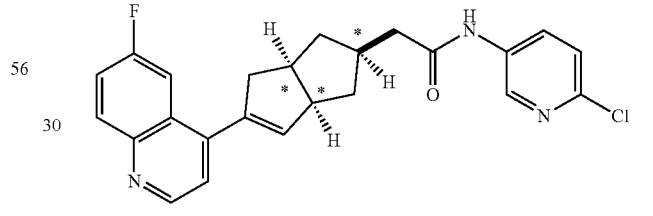
63
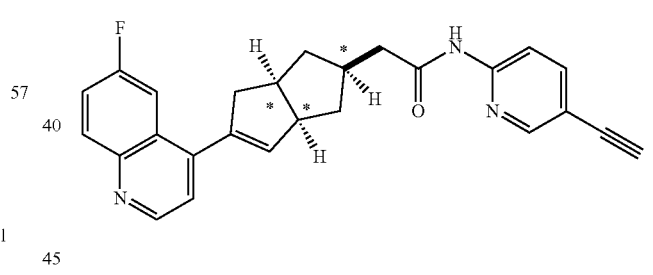
64
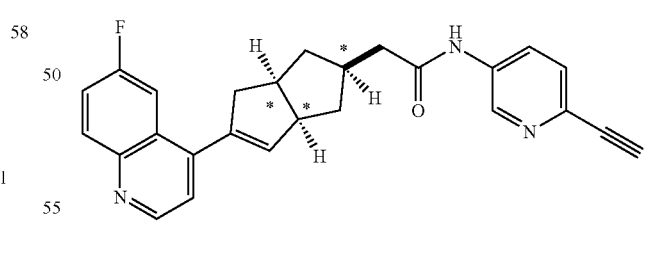
65
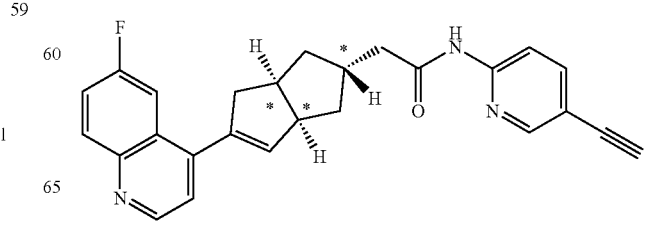

66
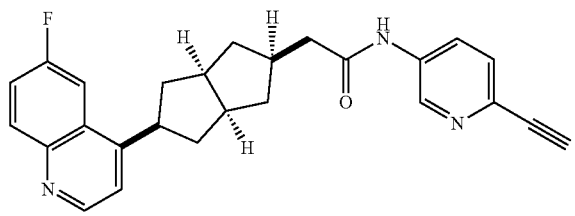
67
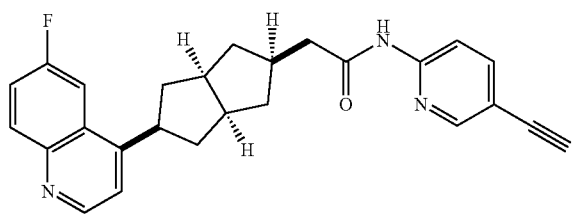
68
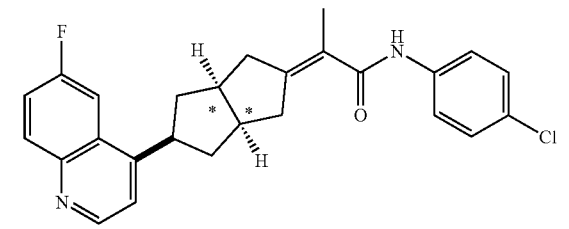
69
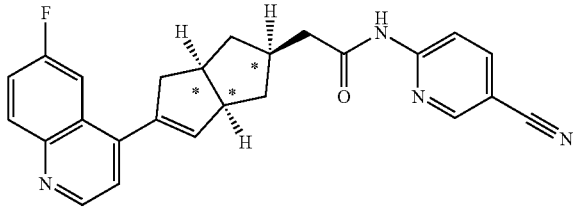
70
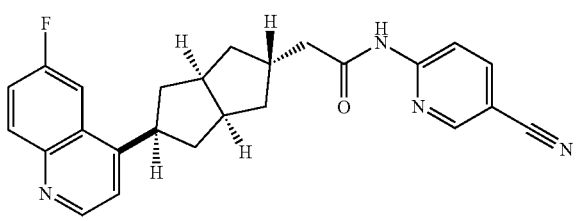
71
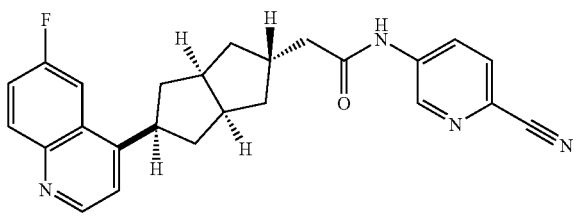
72
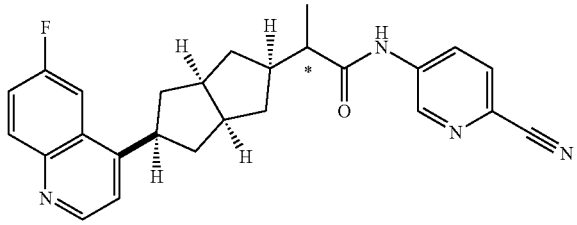
73
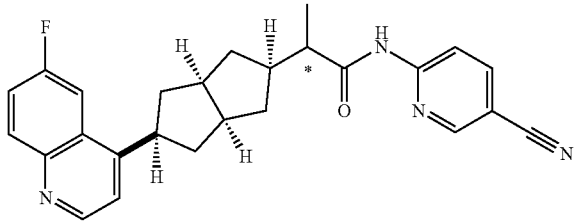
74
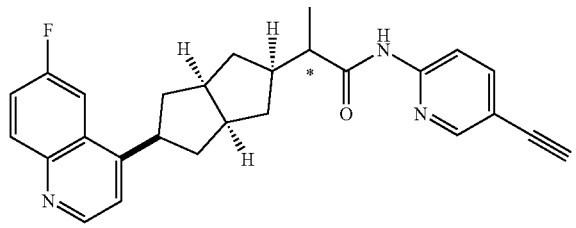
75
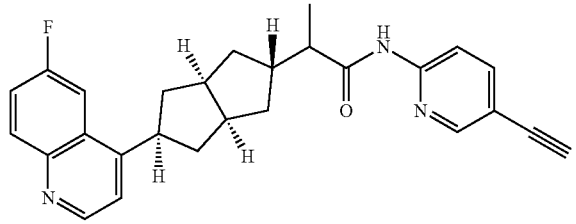
76
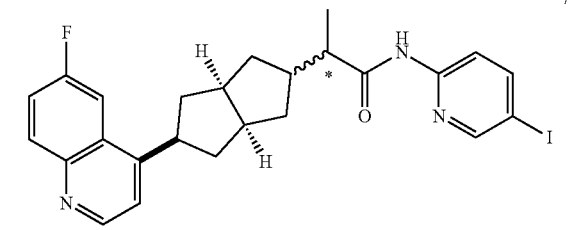
77
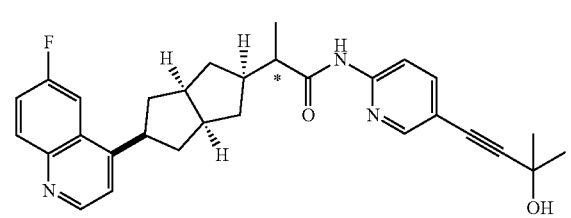

78
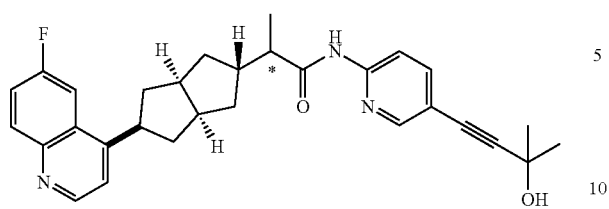
79
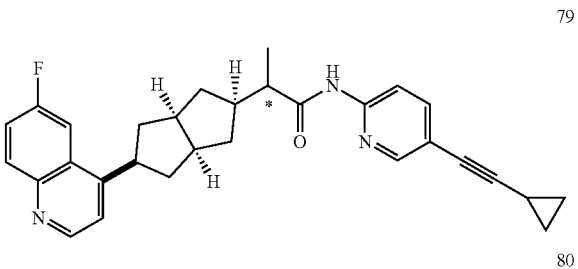
80
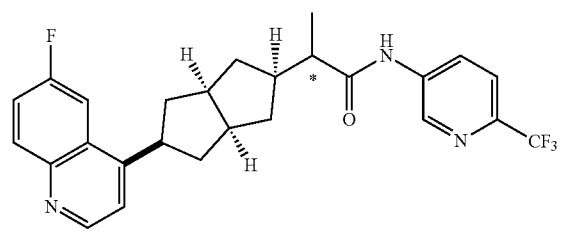
81
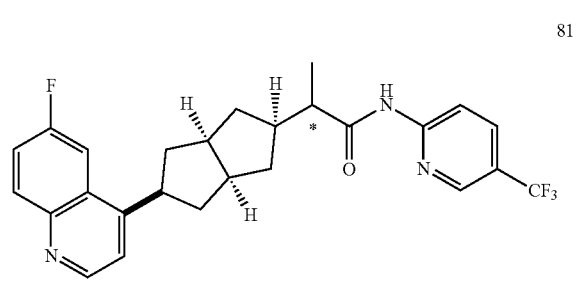
82
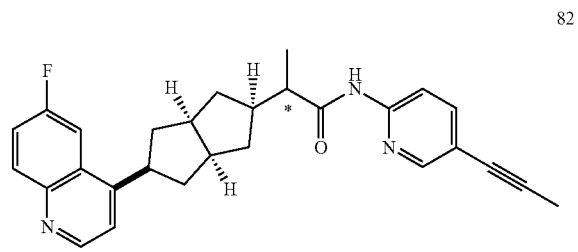
83
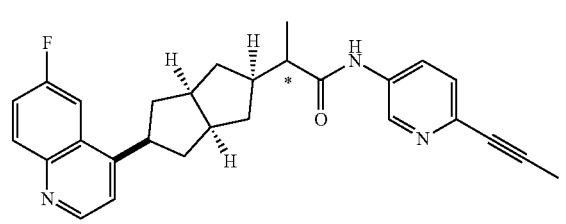
84
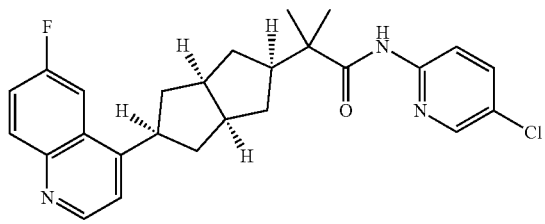
85
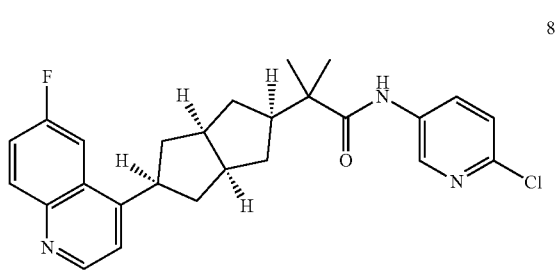
86
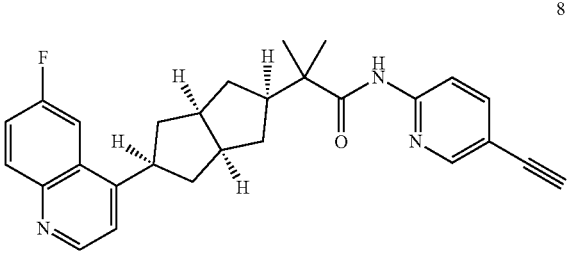
87
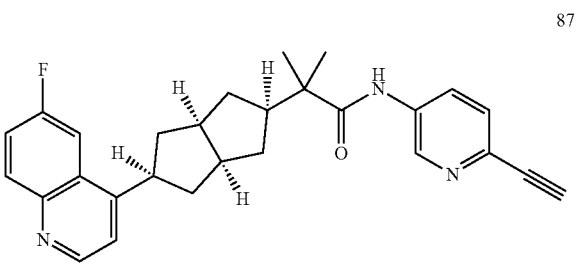
88
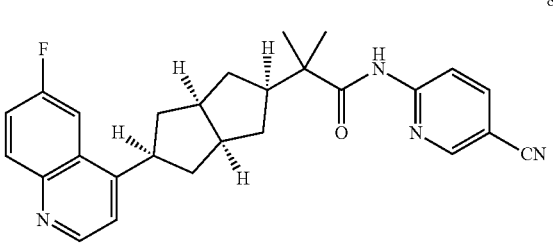
89
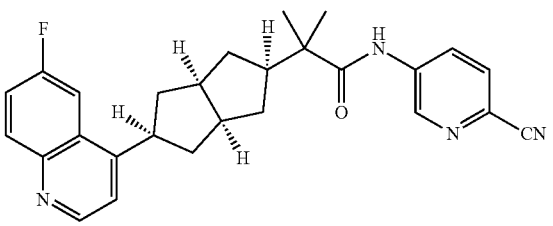

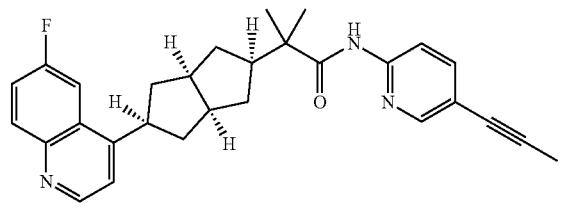
90
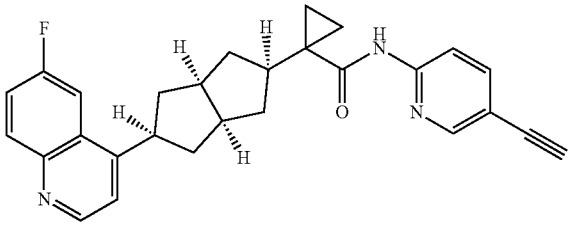
96
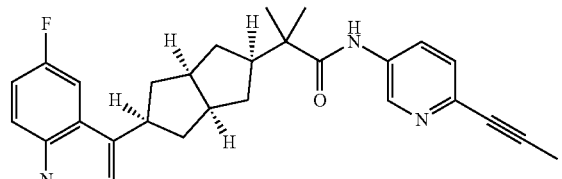
91
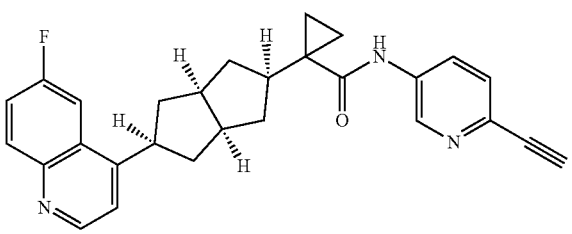
97
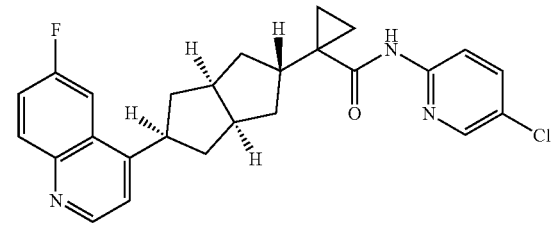
92
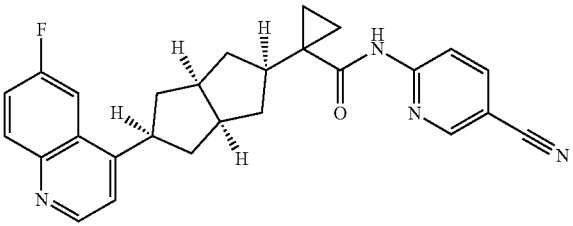
98
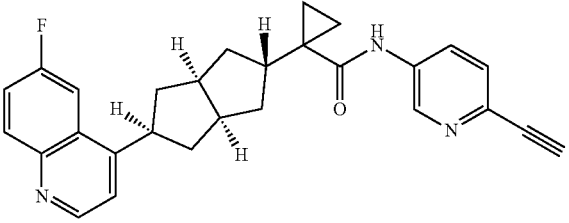
93
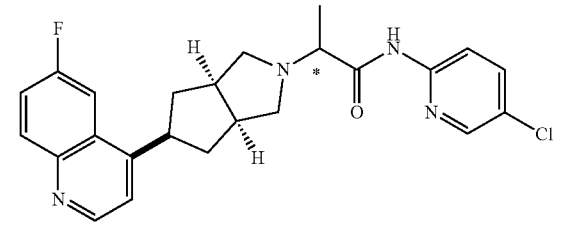
99
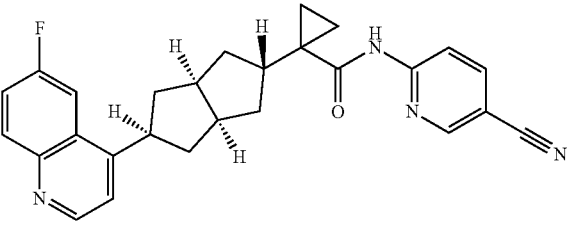
94
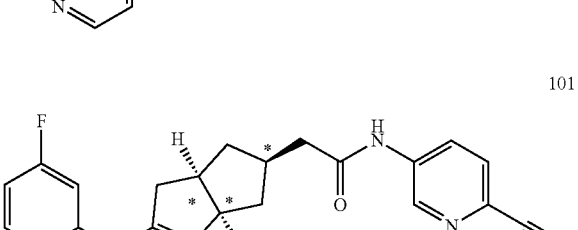
100
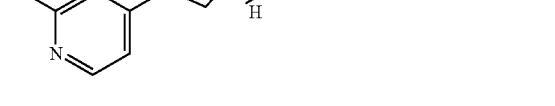
95
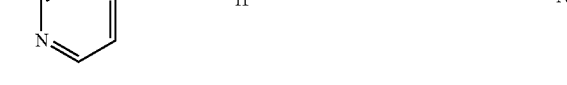
101

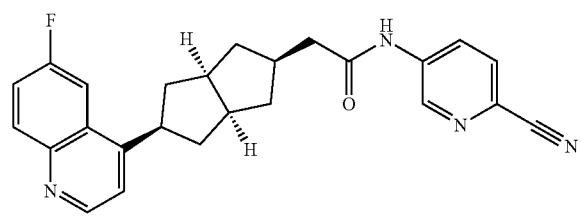
102
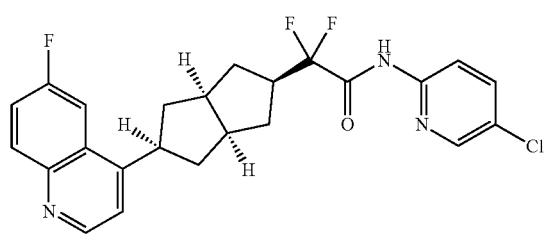
104
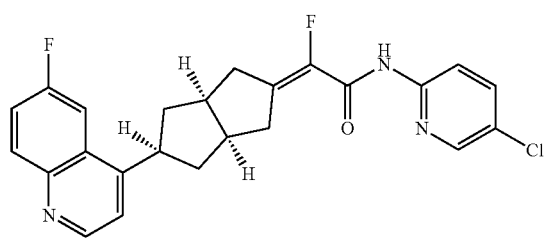
105
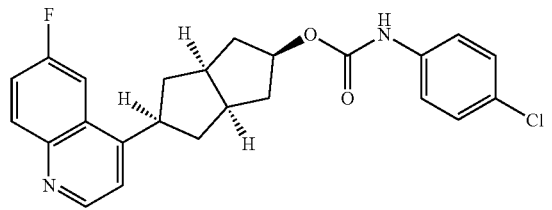
106
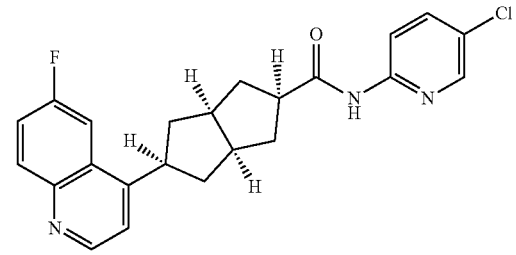
107
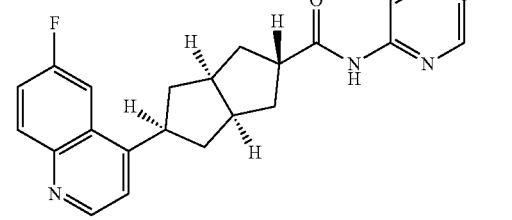
108
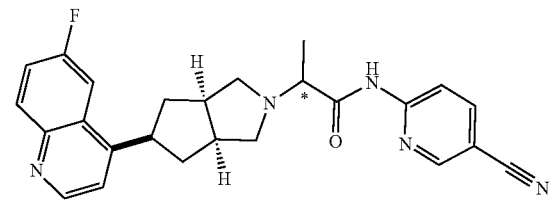
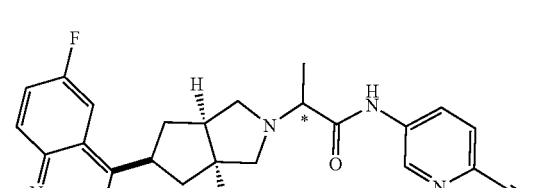
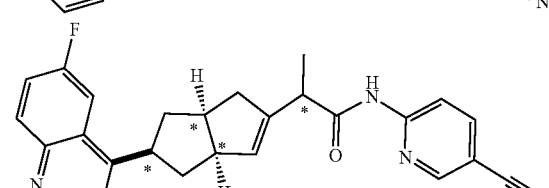
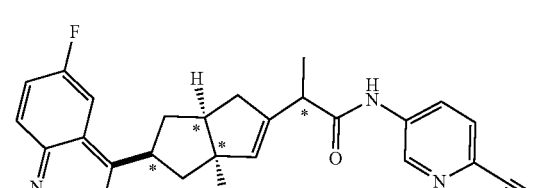
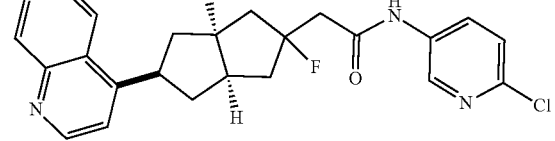
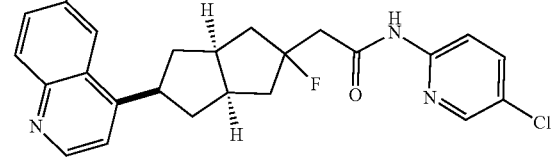
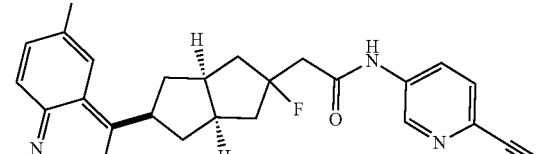
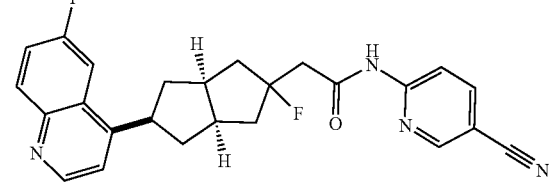

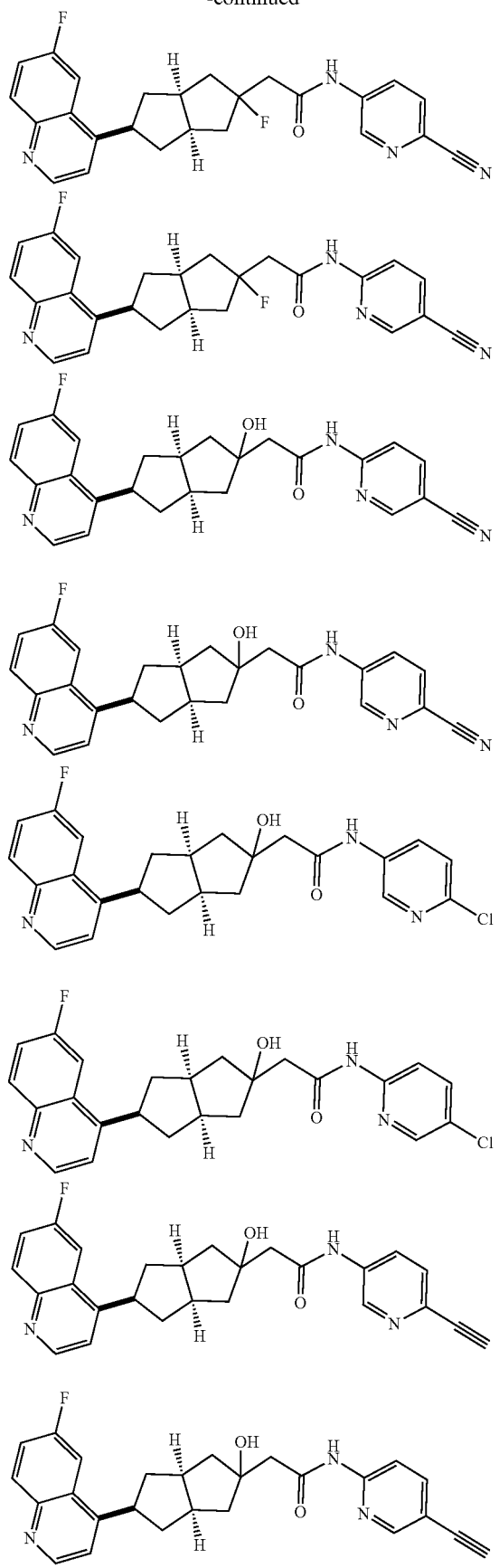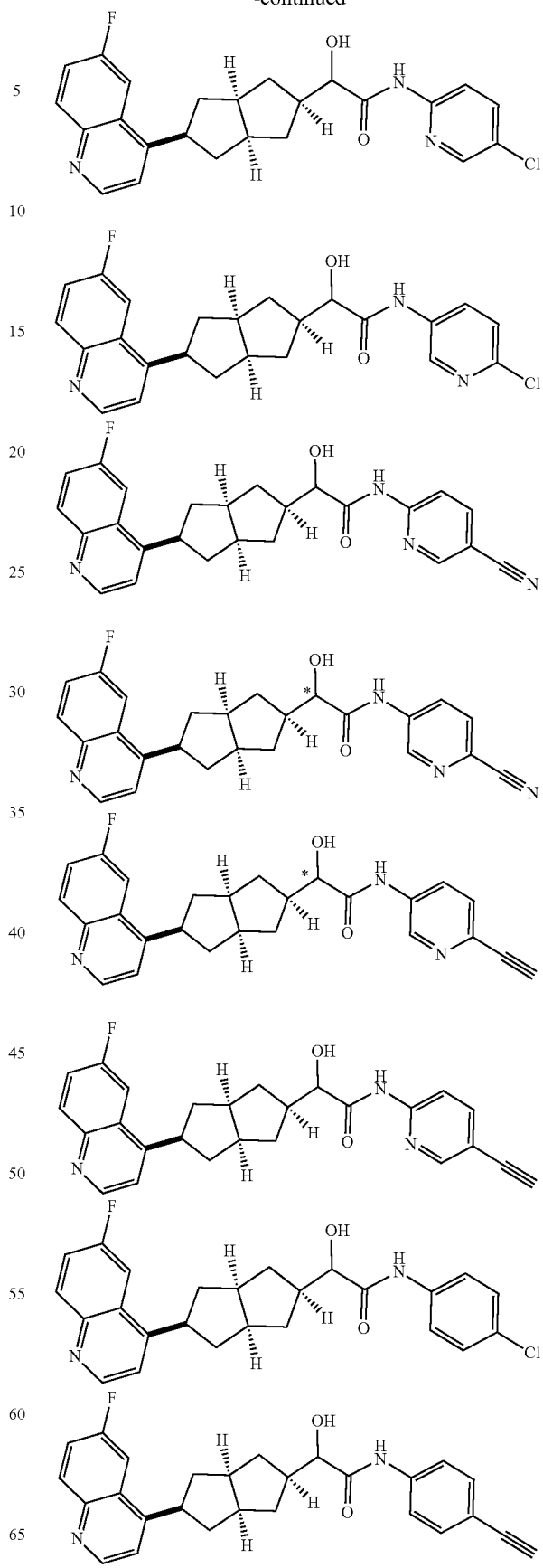

55
-continued
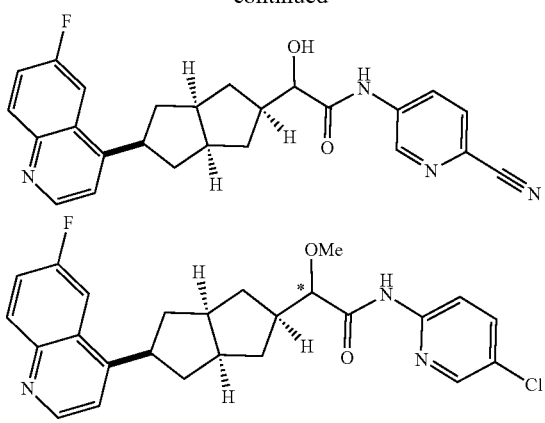
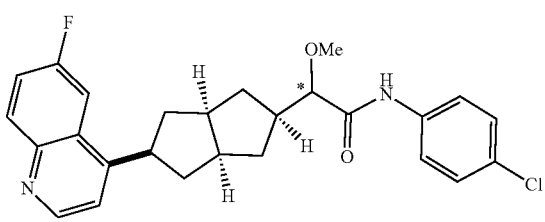
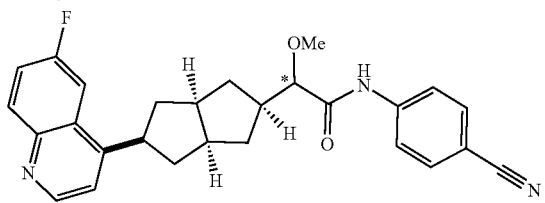
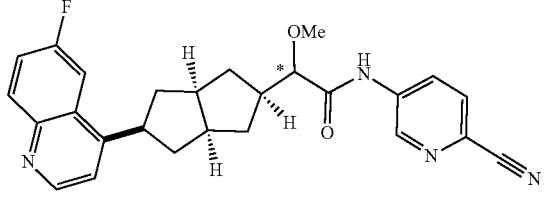
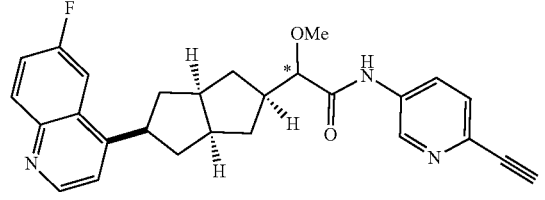
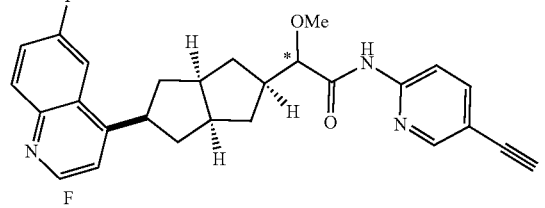
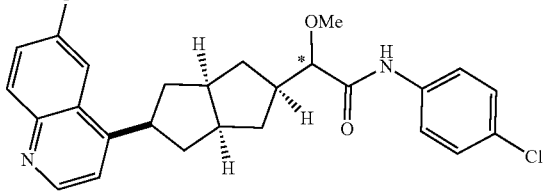
56
-continued
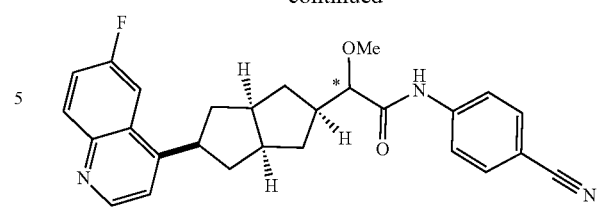
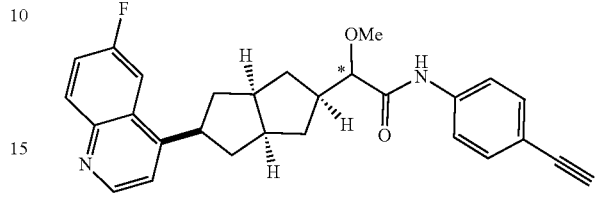
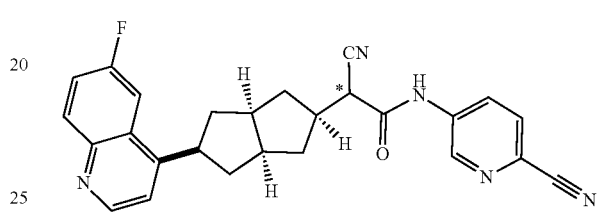
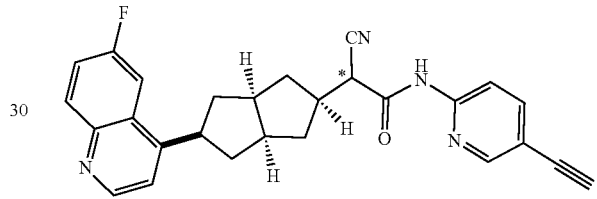
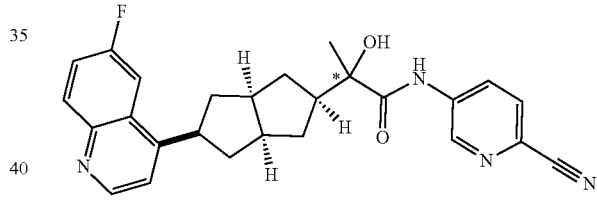
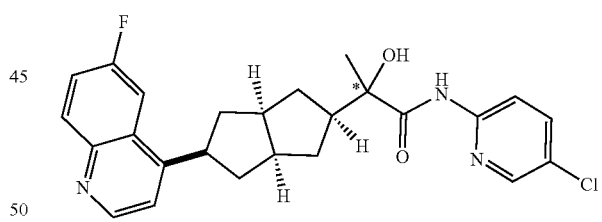
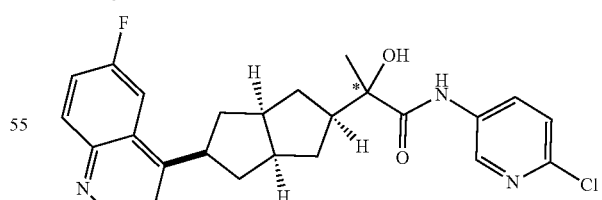
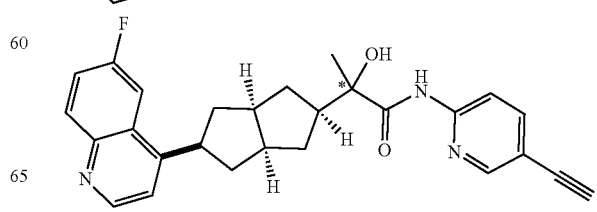

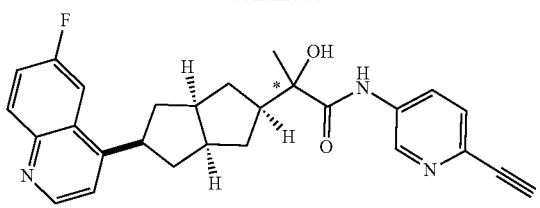
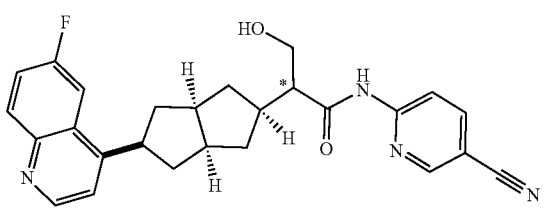
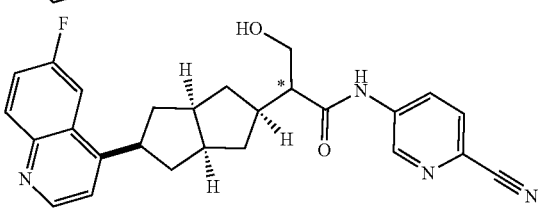
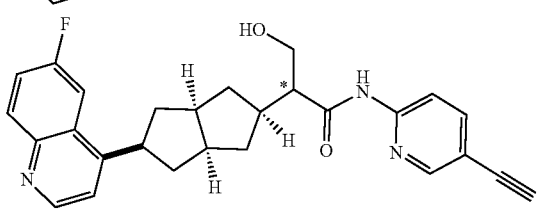
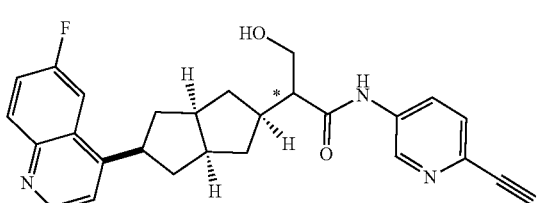
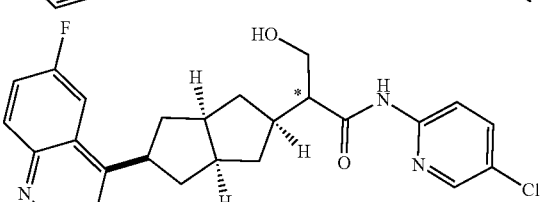
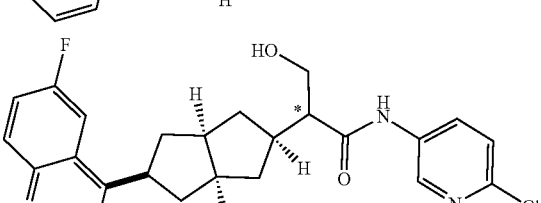
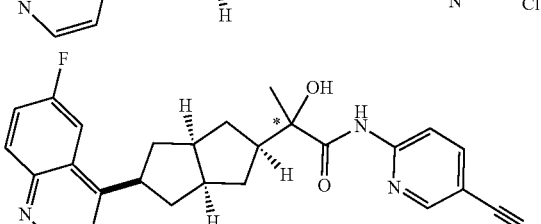
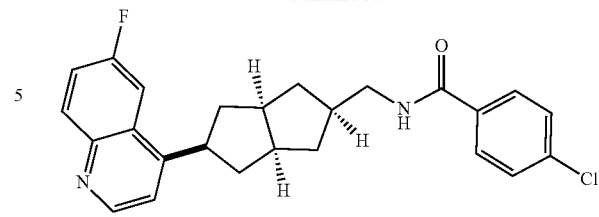
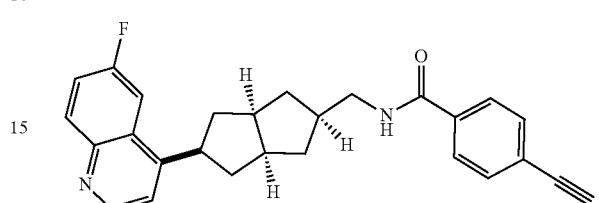
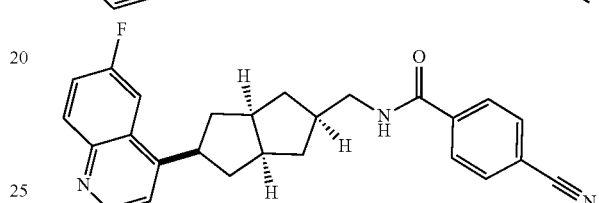
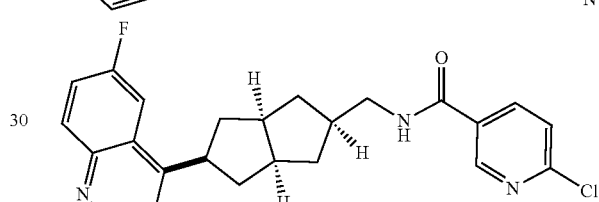
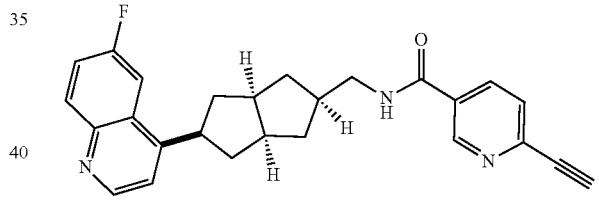
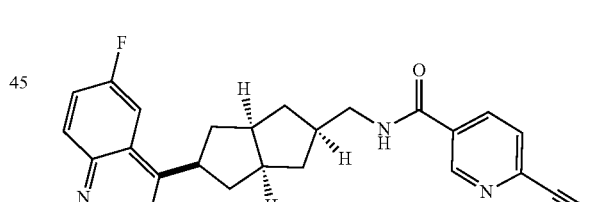
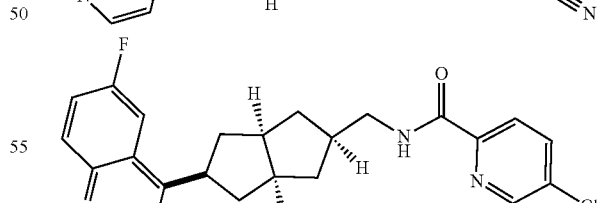
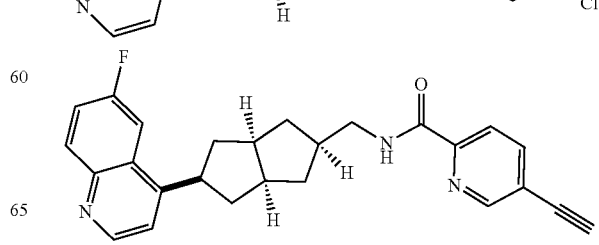

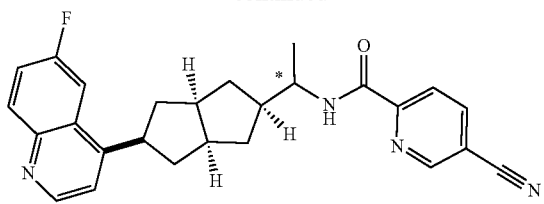
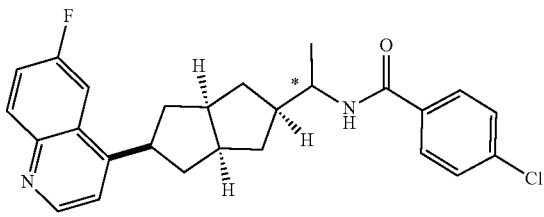

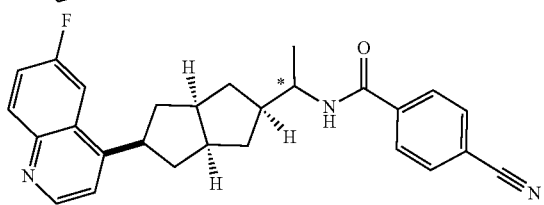

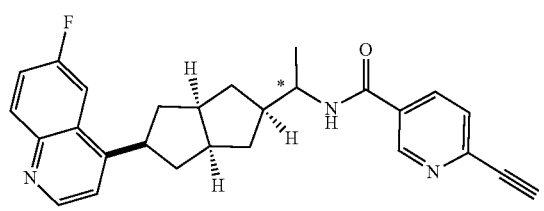

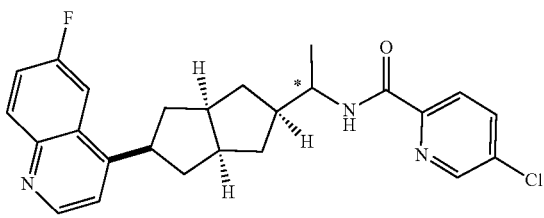
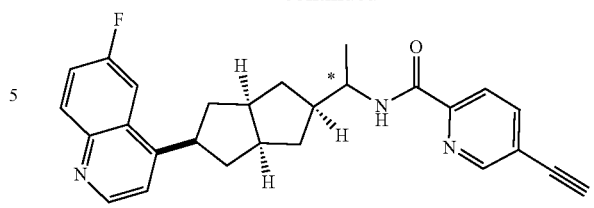
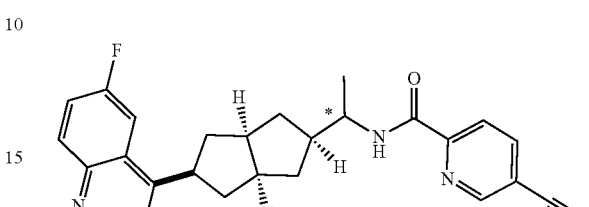

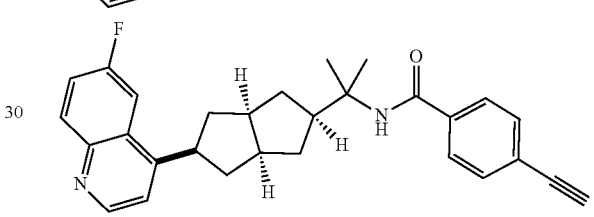

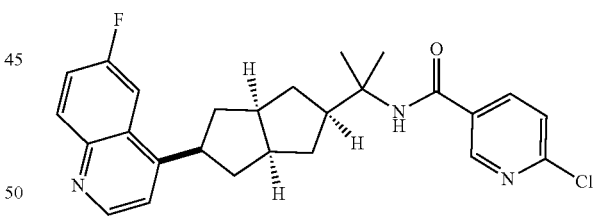

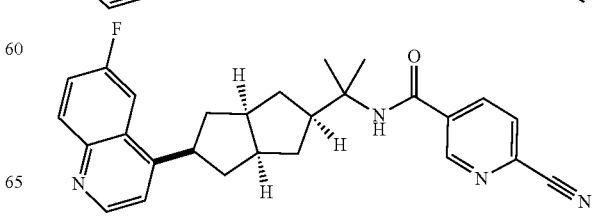

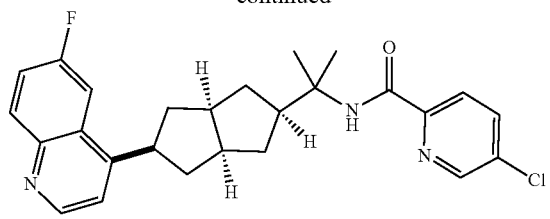

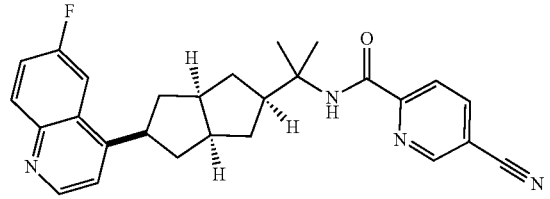
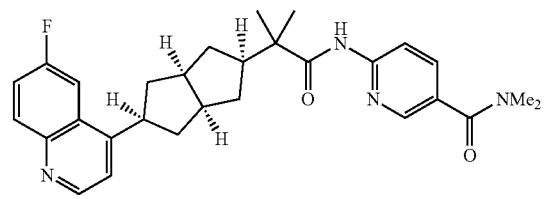
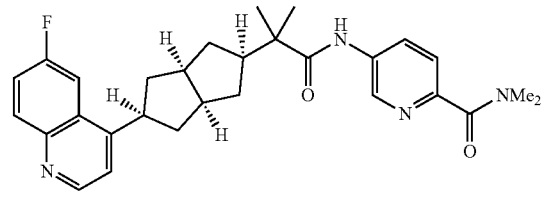
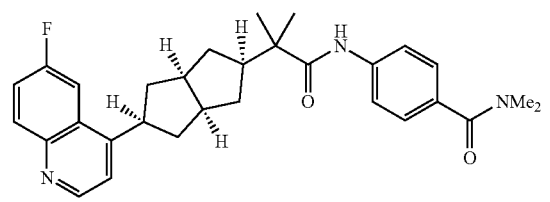
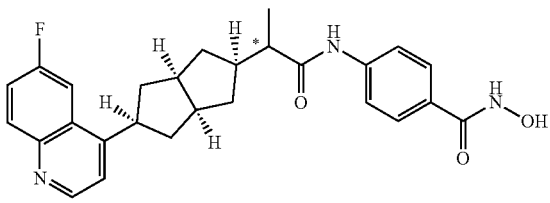
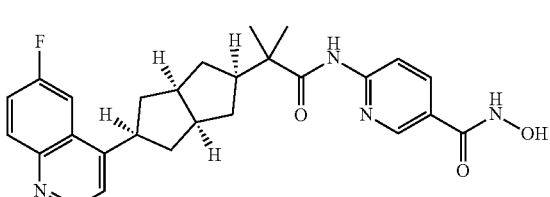
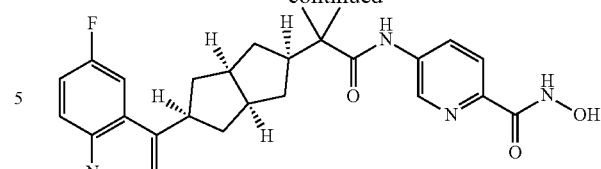
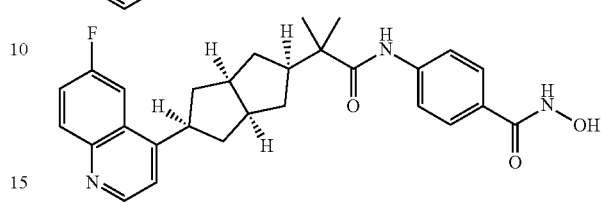
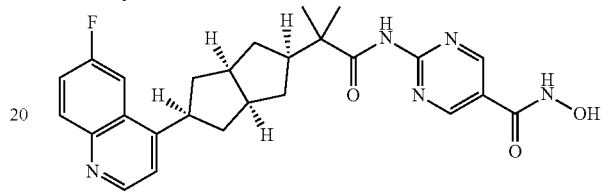
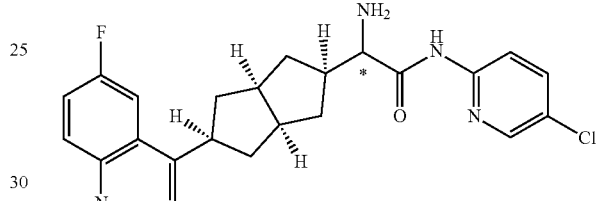
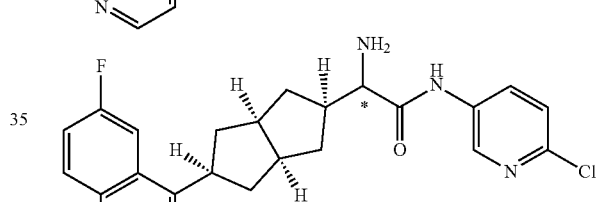

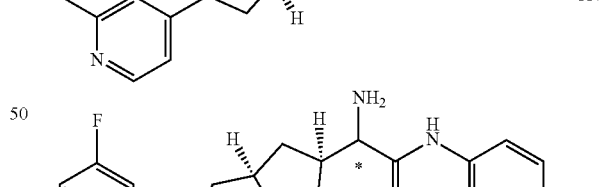
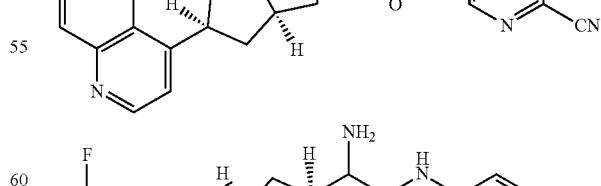
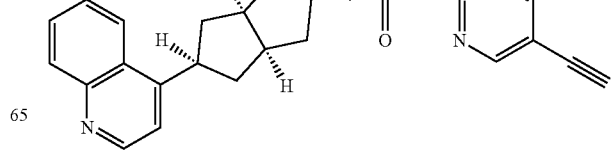

-continued

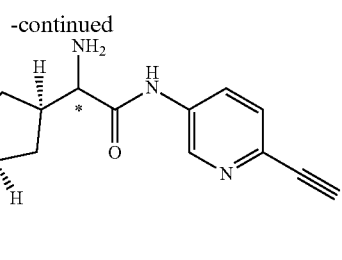

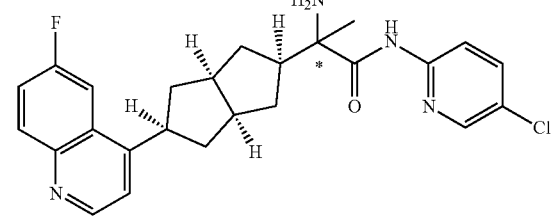

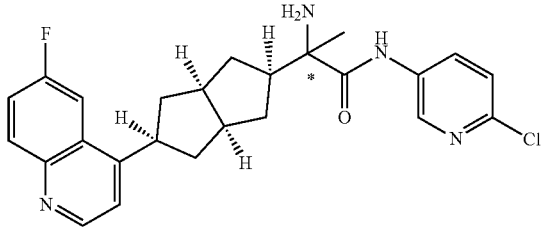

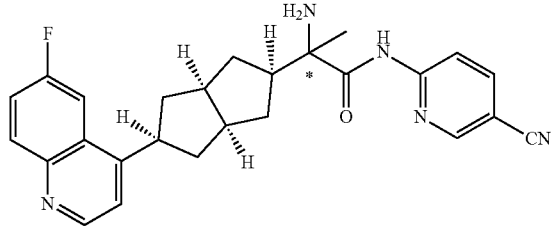

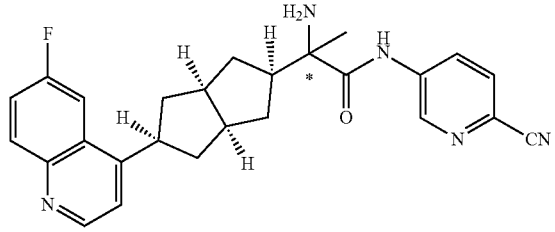

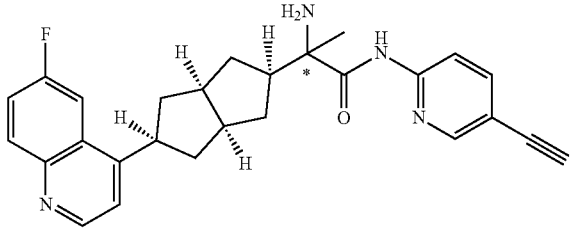

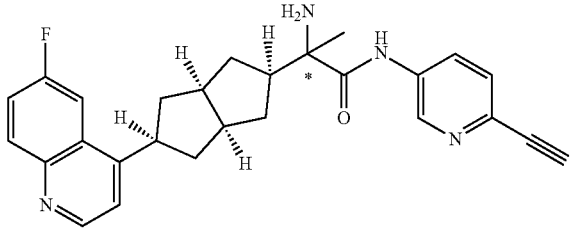

wherein "*" indicates a chiral center.

Each of the above compounds, if one or more chiral centers are involved, means that the compounds referred to in the patent of the present invention are their enantiomers, diastereomers, and/or their racemates and mixtures;

Unless specifically noted, all ethylenic bond configurations intend to include cis and trans configurations. In addition, when two substituents are both on a saturated ring (including a bicyclic ring), cis- and trans-configurations may be generated, which is also included in the scope of the invention.

In the second aspect of the present invention, a use of formula I compound of the first aspect of the present invention is provided, wherein in:

(a) the preparation of medicine for treating diseases associated with IDO activity or expression; and/or (b) the preparation of medicine for treating diseases associated with HDAC activity or expression; and/or (c) the preparation of IDO immune inhibitor; and/or (d) the preparation of IDO-HDAC dual immunization/targeting inhibitor; and/or e) in vitro non-therapeutic inhibition of IDO activity; and/or dual inhibition of IDO-HDAC activity.

In another preferred embodiment, the cancer is selected from the following: cancer, bladder cancer, breast cancer, stomach cancer, liver cancer, salivary adenosarcoma, ovarian cancer, prostate cancer, cervical cancer, epithelial cancer, multiple myeloma, pancreatic cancer, lymphoma, chronic myeloid leukemia, lymphocytic leukemia, skin T-cell lymphoma, etc.

In the third aspect of the present invention, a pharmaceutical composition is provided, which comprising: (i) therapeutically effective amount of the compound of the first aspect of the present invention or the pharmaceutically acceptable salt thereof, and (ii) pharmaceutically acceptable carrier.

In another preferred embodiment, the pharmaceutical composition also comprises effective ingredient selected from the group consisting of therapeutically effective amount of PD-1 and/or PD-L1.

In the fourth aspect of the present invention, a method of inhibiting IDO activity, or dual inhibiting IDO-HDAC activity is provided, wherein comprising administering an inhibitory effective amount of formula I compound of the first aspect of the present invention or a pharmaceutically acceptable salt thereof to an inhibition subject, or administering an inhibitory effective amount of pharmaceutical composition of the third aspect of the invention to an inhibition subject.

In another preferred embodiment, the inhibition is IDO selective inhibition.

In another preferred embodiment, the inhibition is IDO-HDAC selective inhibition.

In another preferred embodiment, the IDO activity inhibition is in vitro non-therapeutic inhibition.

In another preferred embodiment, the IDO-HDAC activity inhibition is in vitro non-therapeutic inhibition.

In the fifth aspect of the present invention, a pharmaceutical composition is provided, which comprising therapeutically effective amount of the compound of the first aspect of the present invention, or the pharmaceutically acceptable salt thereof, and optionally antibody PD-1, PD-L1, or CTLA-4.

In another preferred embodiment, the pharmaceutical composition is used for treating cancer.

In another preferred embodiment, the cancer is selected from the group consisting of breast cancer, lymphoma, leukemia, lung cancer, ovarian cancer, cervical cancer, testicular cancer, liver cancer, melanoma, colon cancer, rectal cancer, renal cell carcinoma, small intestine cancer and esophageal cancer, head and neck cancer, bladder cancer, prostate cancer, pancreatic cancer, or pharyngeal cancer.

In the sixth aspect of the present invention, a method for the preparation of compound of the first aspect of the present invention is provided, wherein the method comprises the following steps:

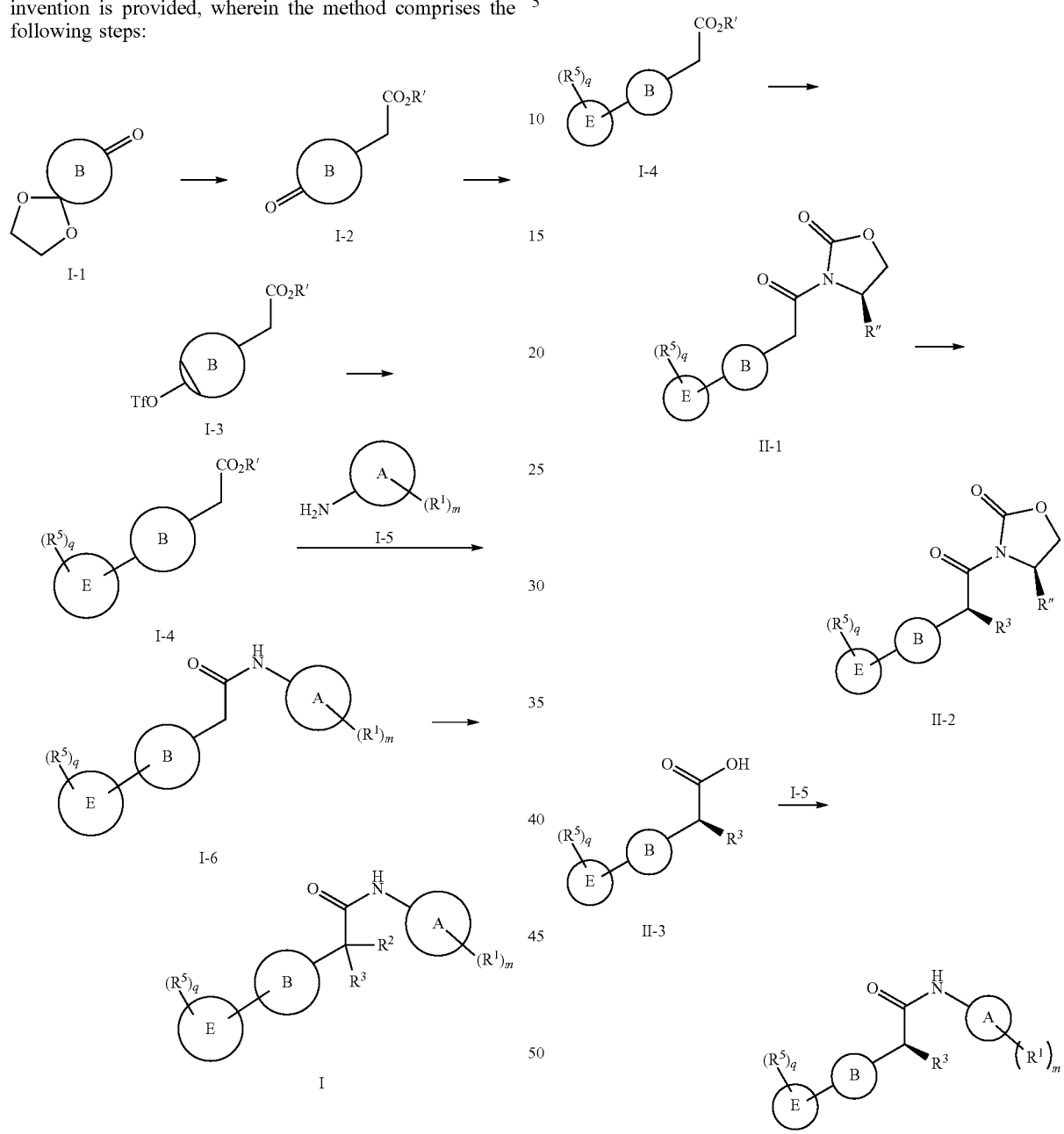

in Ⓑ, \ refers to a double bond;

(i) in an inert solvent, converting compound I-1 to I-2 by Wittig reaction followed by Pd—C catalyzed hydrogenation and deprotection of protecting group;

(ii) in an inert solvent, using a base (such as 2,6-di-tert-butylpyridine or KHMDS or LiHMDS) and Tf$_2$O (or PhNTf$_2$) to convert the compound I-2 to I-3, and then reacting with a boron compound of an corresponding aryl or heteroaryl group to obtain the coupling compound containing an ethylenic bond, and catalytically hydrogenated to obtain the compound I-4;

(iii) compound I-4 was subjected to ester hydrolysis, and the resulting acid reacted with I-5 to give compound I-6;

(iv) in an inert solvent and under a basic condition, a group was introduced into the α-position of the amide in compound I-6 to afford compound I;

(v) compound I-4 was subjected to ester hydrolysis, and the resulting acid reacted with Evans chiral reagent (usually R″ is phenyl or benzyl) to obtain II-1, which facilitated the introduction of a chiral R$^3$ group at the α-position of the amide, to afford compound II-2;

(vi) compound II-2 was hydrolyzed to give acid II-3, which then reacted with I-5 to give the compound II;

(vii) when the Evans chiral reagent used in (v) is in opposite configuration, the above (v) and (vi) steps can be used to prepare the compound IIa, which is the enantiomer of the compound II;

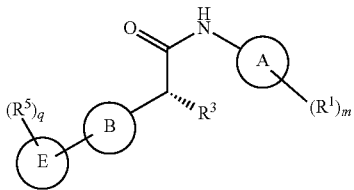

(viii) starting from compound I-1, α-ketoester III-4 was prepared via multi-step reaction. Then compound III-4 was converted to α,β-unsaturated ester III-5 by Wittig reaction. and the compound III-5 was used for double bond cyclopropanation reaction to give compound III-6. Finally ester hydrolysis and amidation reaction gave compound III;

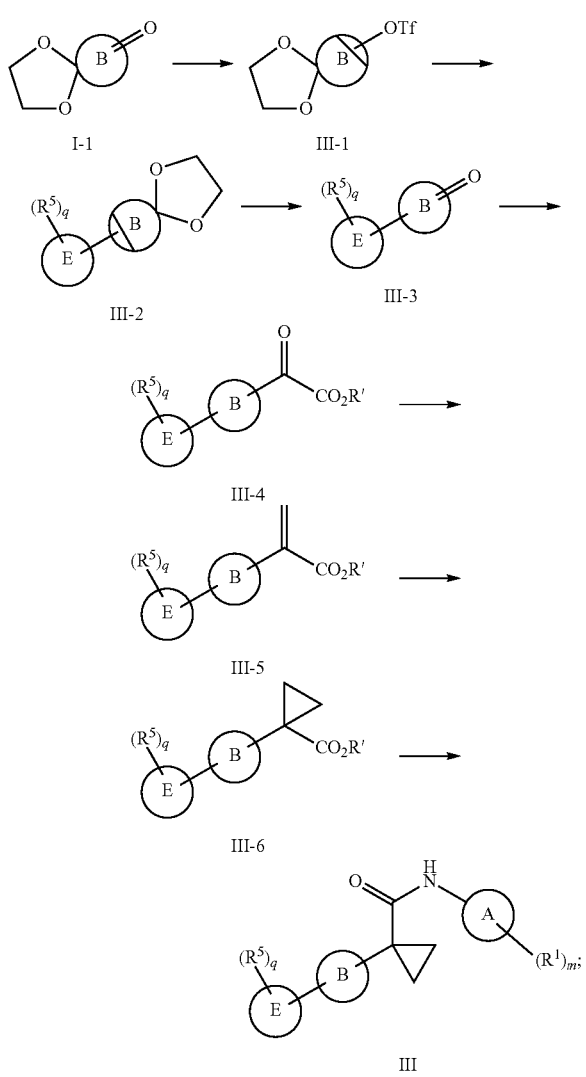

in

\ indicates a double bond.

It is to be understood that within the scope of the present invention, the various technical features of the present invention and the technical features specifically described hereinafter (as in the embodiments) may be combined with each other to constitute a new or preferred technical solution. Due to space limitations, we will not repeat them here.

DETAILED DESCRIPTION

After long-term and intensive research, the present inventors have unexpectedly discovered a class of polycyclic compounds having IDO inhibitory activity and/or dual inhibitory activity of IDO-HDAC, and thus can be used for the preparation of pharmaceutical composition for treatment of diseases related to IDO and/or HDAC activities or expression levels. Based on the above findings, the inventors completed the present invention.

Terminology

Unless otherwise stated, "or" as used herein has the same meaning as "and/or" (refers to "or" and "and").

Unless otherwise specified, among all compounds of the present invention, each chiral carbon atom (chiral center) may optionally be in the R configuration or the S configuration, or a mixture of the R configuration and the S configuration.

As used herein, the term "alkyl", alone or as part of another substituent, refers to a straight (ie, unbranched) or branched saturated hydrocarbon group containing only carbon atoms, or a combination of straight and branched chains. When the alkyl group has a carbon number limitation (e.g., $C_{1-10}$), it means that the alkyl group has 1 to 10 carbon atoms. For example, $C_{1-8}$ alkyl refers to an alkyl group containing from 1 to 8 carbon atoms, including methyl, ethyl, propyl, isopropyl, butyl, isobutyl, sec-butyl, tert-butyl, or the like.

As used herein, the term "alkenyl", when used alone or as part of another substituent, refers to a straight or branched, carbon chain group having at least one carbon-carbon double bond. Alkenyl groups can be substituted or unsubstituted. When the alkenyl group has a carbon number limit (e.g., $C_{2-8}$), it means that the alkenyl group has 2-8 carbon atoms. For example, $C_{2-8}$ alkenyl refers to alkenyl groups having 2-8 carbon atoms, including ethenyl, propenyl, 1,2-butenyl, 2,3-butenyl, butadienyl, or the like.

As used herein, the term "alkynyl", when used alone or as part of another substituent, refers to an aliphatic hydrocarbon group having at least one carbon-carbon triple bond. The alkynyl group can be straight or branched, or a combination thereof. When the alkynyl group has a carbon number limitation (e.g., $C_{2-8}$ alkynyl group), it means that the alkynyl group has 2 to 8 carbon atoms. For example, the term "$C_{2-8}$ alkynyl" refers to a straight or branched alkynyl group having 2-8 carbon atoms, including ethynyl, propynyl, isopropynyl, butynyl, isobutynyl, secondary butynyl, tert-butynyl, or the like.

As used herein, either used alone or as part of another substituent, the term "cycloalkyl" refers to a unit ring having a saturated or partially saturated ring, a bicyclic or polycyclic (fused ring, bridged or spiro) ring system. When a certain cycloalkyl group has a carbon number limitation (e.g., $C_{3-10}$), it means that the cycloalkyl group has 3 to 10 carbon atoms. In some preferred embodiments, the term "$C_{3-8}$ cycloalkyl" refers to a saturated or partially saturated monocyclic or bicyclic alkyl group having from 3 to 8 carbon atoms, including cyclopropyl, cyclobutyl, cyclopentyl, cycloheptyl, or the like. "Spirocycloalkyl" refers to a bicyclic or polycyclic group that shares a carbon atom (called a spiro atom) between the monocyclic rings. These may contain one or more double bonds, but none of the rings have fully conjugated π-electron system. "Fused cycloalkyl" refers to an all-carbon bi-cyclic or polycyclic group in which each ring share two neighboring carbon atoms with other ring(s), which may contain one or more double bonds, but none of the rings have a fully conjugated π-electron system "Bridge cycloalkyl" refers to an all-carbon polycyclic group in which two rings share two carbon atoms that are not directly bonded, which may contain one or more double bonds, but none of the rings have a fully conjugated π-electron system. The atoms contained in the cycloalkyl group are all carbon atoms. Some examples of cycloalkyl groups are as follows, and the present invention is not limited to the following cycloalkyl groups.

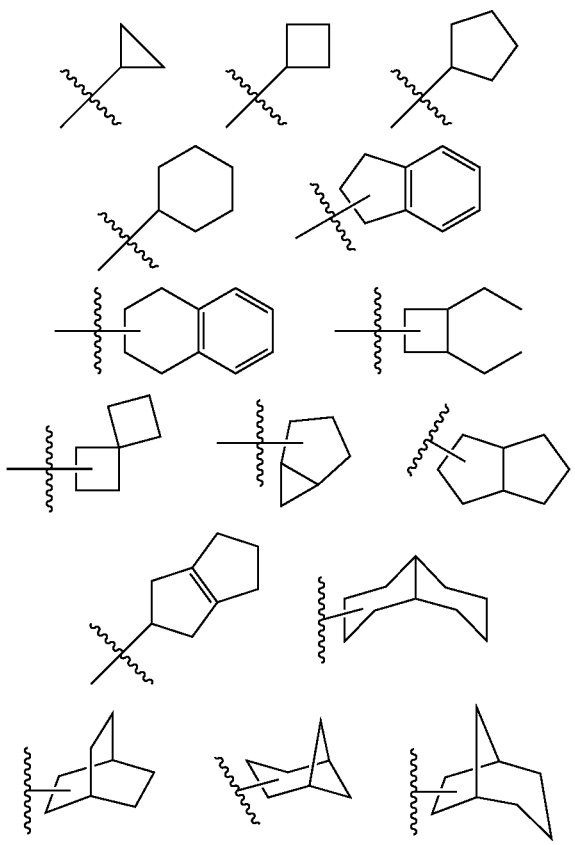

Unless otherwise stated, the following terms used in the instructions and claims have the following meanings. "Aryl" means an all-carbon monocyclic or fused polycyclic (ie, a ring that shares a pair of adjacent carbon atoms) groups having a conjugated π-electron system, such as phenyl and naphthyl. The aryl ring may be fused to other cyclic groups (including saturated and unsaturated rings), but may not contain heteroatoms such as nitrogen, oxygen, or sulfur, while the point of attachment to the parent must be on the carbon atoms of a ring in a conjugated π-electron system. The aryl group can be substituted or unsubstituted. The following are some examples of aryl groups, and the present invention is not limited to the aryl groups described below.

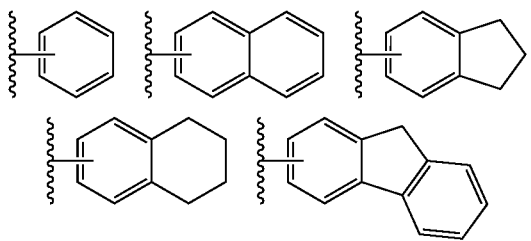

"Heteroaryl" refers to a heteroaromatic group containing one to more heteroatoms. The heteroatoms referred to herein include oxygen, sulfur, and nitrogen. For example, furyl, thienyl, pyridyl, pyrazolyl, pyrrolyl, N-alkylpyrrolyl, pyrimidinyl, pyrazinyl, imidazolyl, tetrazolyl, and the like. The heteroaryl ring may be fused to an aryl, heterocyclic or cycloalkyl ring wherein the ring to which the parent structure is attached is a heteroaryl ring. The heteroaryl group can be optionally substituted or unsubstituted. The following are some examples of heteroaryl groups, and the present invention is not limited to the following heteroaryl groups. Among them, the last three heteroaryl groups are tricyclic heteroaryl groups, which are the focus of the present invention.

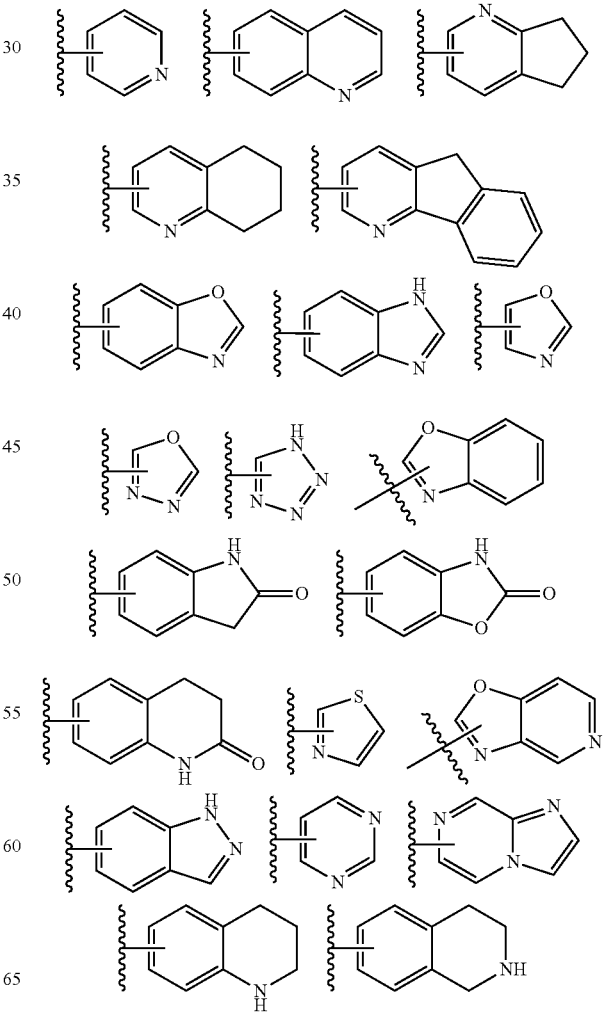

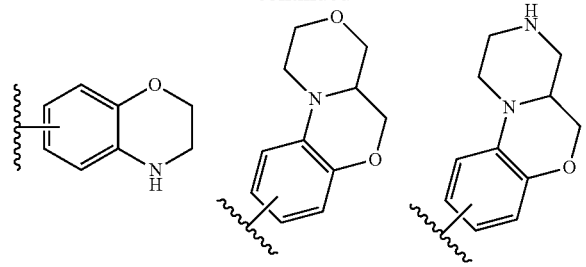

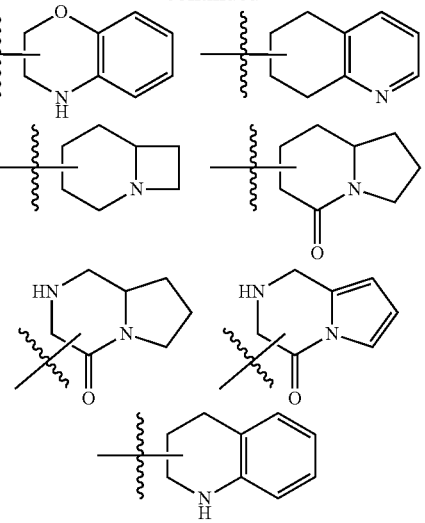

"Heterocyclyl" means a saturated or partially unsaturated monocyclic or polycyclic cyclic hydrocarbon substituent wherein one or more of the ring atoms are selected from nitrogen, oxygen or sulfur and the remaining ring atoms are carbon. Non-limiting examples of monocyclic heterocyclic groups include pyrrolidinyl, piperidinyl, piperazinyl, morpholinyl, thiomorpholinyl, homopiperazinyl. Polycyclic heterocyclic group refers to a heterocyclic group including a spiro ring, a fused ring, and a bridged ring. "Spirocyclic heterocyclyl" refers to a polycyclic heterocyclic group in which each ring of the system shares an atom (referred to as a spiro atom) with other rings in the system, wherein one or more of the ring atoms is selected from the group consisting of nitrogen, oxygen or sulfur, the remaining ring atoms are carbon. "Fused ring heterocyclyl" refers to a polycyclic heterocyclic group in which each ring of the system shares an adjacent pair of atoms with other rings in the system, and one or more rings may contain one or more double bonds, but none one ring has a fully conjugated π-electron system, and wherein one or more ring atoms are selected from nitrogen, oxygen or sulfur, and the remaining ring atoms are carbon. "Bridged heterocyclyl" refers to a polycyclic heterocyclic group in which any two rings share two atoms which are not directly bonded, these may contain one or more double bonds, but none of the rings have a fully conjugated π-electron system and wherein one or more of the ring atoms are selected from nitrogen, oxygen or sulfur, and the remaining ring atoms are carbon. If a heterocyclic group has both a saturated ring and an aromatic ring (for example, the saturated ring and the aromatic ring are fused together), the point attached to the parent must be on the saturated ring. Note: When the point attached to the parent is on the aromatic ring, it is called a heteroaryl group and is not called a heterocyclic group. Some examples of the heterocyclic group are as follows, and the present invention is not limited to the following heterocyclic group.

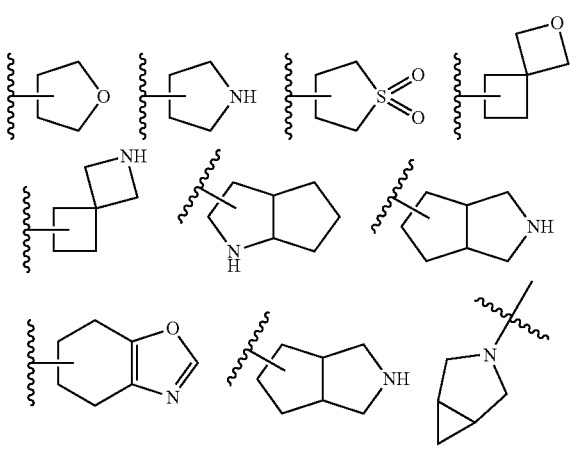

As used herein, the term "halogen", when used alone or as part of another substituent, refers to F, Cl, Br, and I.

As used herein, the term "substituted" (when with or without "optionally") means that one or more hydrogen atoms on a particular group are replaced by a particular substituent. Particular substituents are the substituents described above in the corresponding paragraphs, or the substituents which appear in the examples. Unless otherwise stated, an optionally substituted group may have a substituent selected from a particular group at any substitutable position of the group, and the substituents may be the same or different at each position. A cyclic substituent, such as a heterocyclic group, may be attached to another ring, such as a cycloalkyl group, to form a spirobicyclic ring system, i.e., the two rings have a common carbon atom. Those skilled in the art will appreciate that the combinations of substituents contemplated by the present invention are those that are stable or chemically achievable. The substituents are, for example but not limited to, $C_{1-8}$ alkyl, $C_{2-8}$ alkenyl, $C_{2-8}$ alkynyl, $C_{3-8}$ cycloalkyl, 3- to 12-membered heterocyclic, aryl, heteroaryl, halogen, hydroxy, carboxy (—COOH), $C_{1-8}$ aldehyde, $C_{2-10}$ acyl, $C_{2-10}$ ester group, amino.

For convenience and in accordance with conventional understanding, the term "optionally substituted" or "optionally substituted" applies only to sites which are capable of being substituted by a substituent, and does not include those which are not chemically achievable.

As used herein, unless otherwise specified, the term "pharmaceutically acceptable salt" refers to a salt that is suitable for contact with the tissue of a subject (eg, a human) without causing unpleasant side effects. In some embodiments, a pharmaceutically acceptable salt of a compound of the invention includes a salt (eg, a potassium salt, a sodium salt, a magnesium salt, a calcium salt) of a compound of the invention having an acidic group or is basic a salt of a compound of the invention (e.g., a sulfate, a hydrochloride, a phosphate, a nitrate, a carbonate).

General Synthetic Method for Compounds

The compound of the formula I of the present invention can be synthesized by the following method, however, the conditions of the method, such as the reactant, the solvent, the base, the amount of the compound used, the reaction temperature, the time required for the reaction, and the like are not limited to the following explanations. The compounds of the present invention may also be conveniently prepared by combining various synthetic methods described in the specification or known in the art, and such combinations are readily made by those skilled in the art to which the present invention pertains.

In the production method of the present invention, each reaction is usually carried out in an inert solvent at a reaction temperature of −78° C. to 150° C. (preferably 20 to 120° C.). The reaction time in each step is usually from 0.5 to 48 h, preferably from 2 to 12 h.

Scheme A-1 describes a general synthetic method for compound A11:

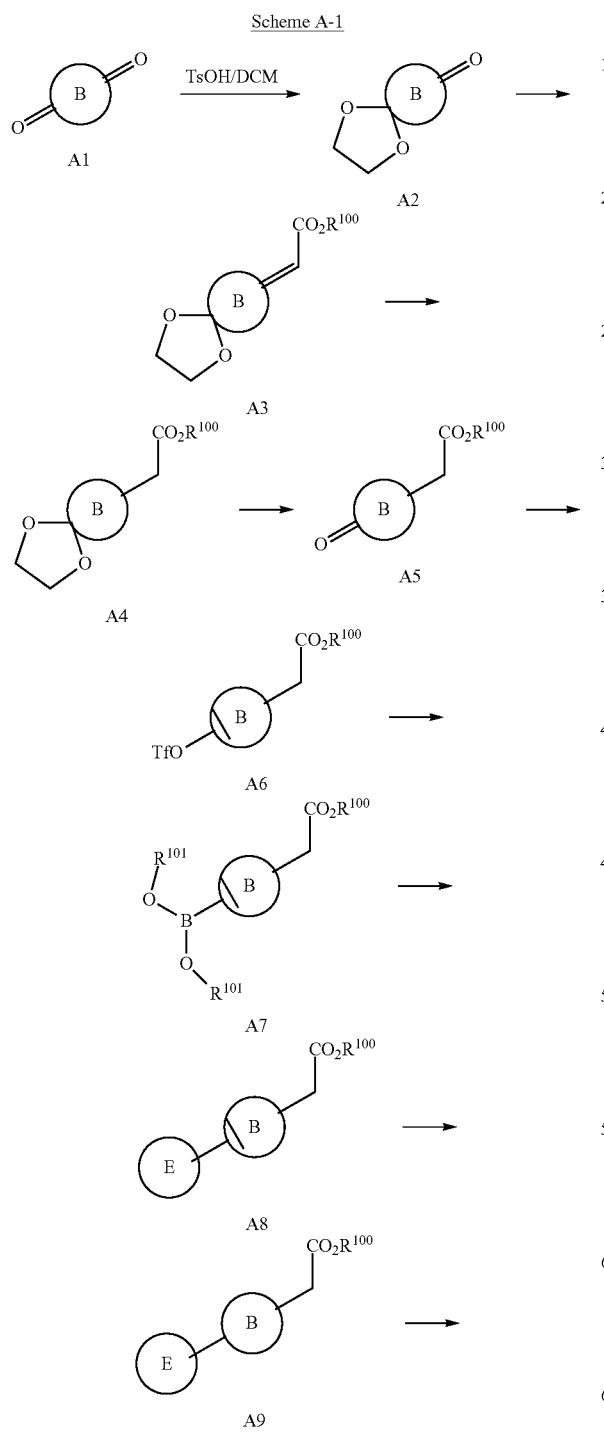

Scheme A-2 describes a general synthetic method for compound A13:

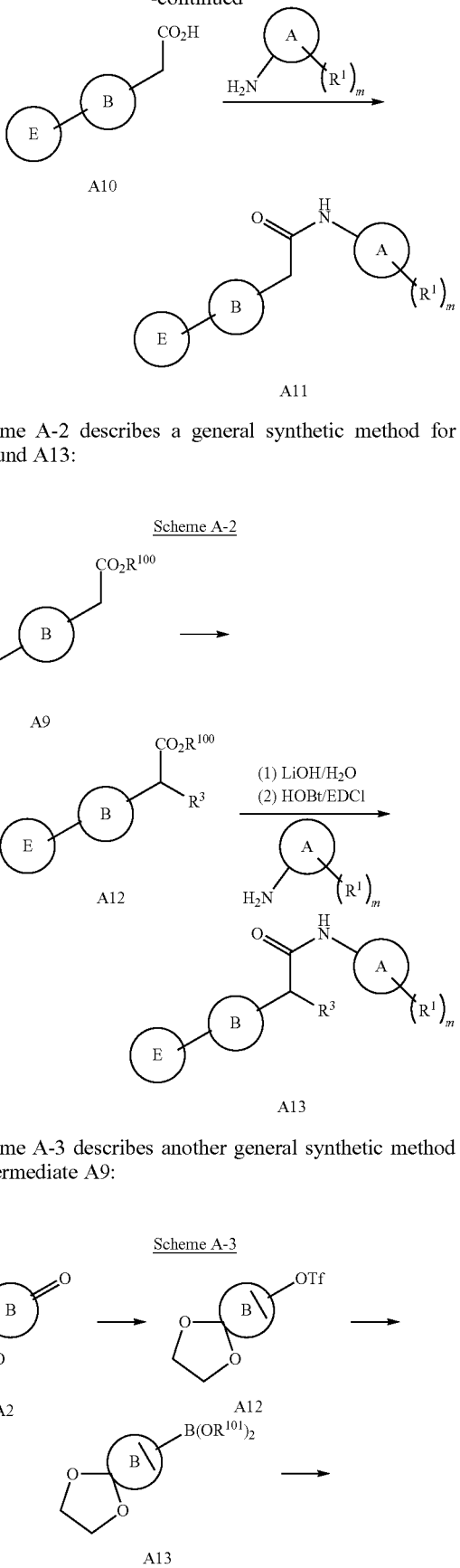

Scheme A-3 describes another general synthetic method for Intermediate A9:

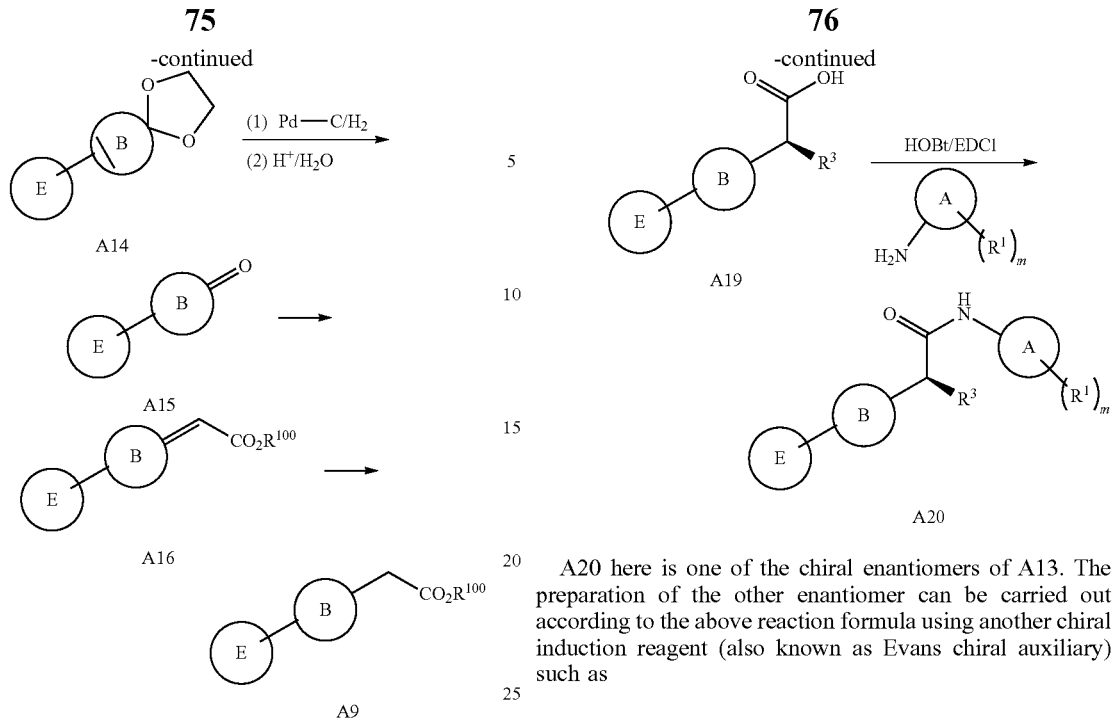

A20 here is one of the chiral enantiomers of A13. The preparation of the other enantiomer can be carried out according to the above reaction formula using another chiral induction reagent (also known as Evans chiral auxiliary) such as

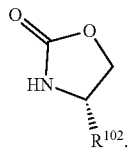

Here, $R^{102}$ is usually a phenyl group or a benzyl group.

Intermediate A9 is a key intermediate, it can be used to prepare compounds A11 and A13 (see Schemes A-1 and A-2). It should be mentioned that the compound A13 obtained by the above method is a racemate.

Scheme A-4 describes a general chiral synthesis method for compound A20:

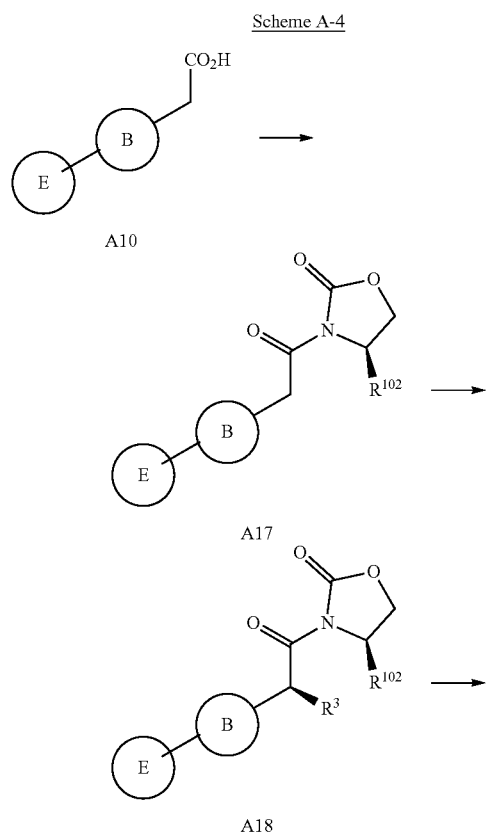

Scheme B-1 describes a general synthetic method for Compound B7:

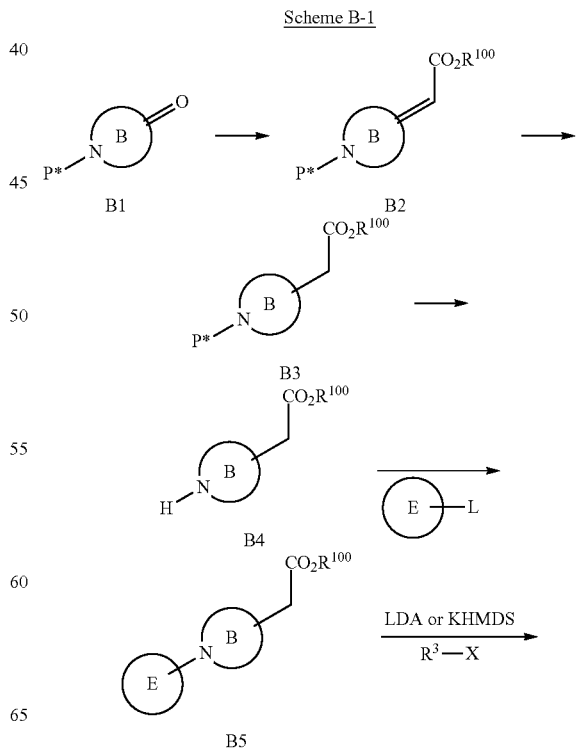

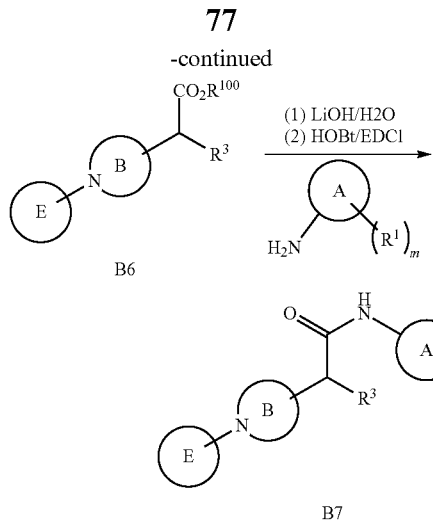

The compound B7 here is a racemate. The two optically pure single enantiomers of B7 can be prepared by the method of Scheme A-4.

Scheme B-2 describes a general synthetic method for compound B14:

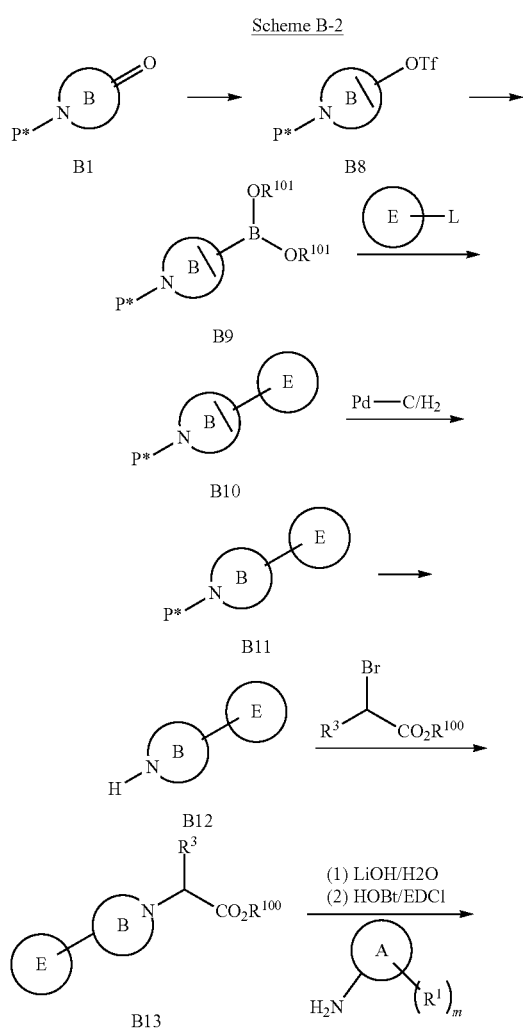

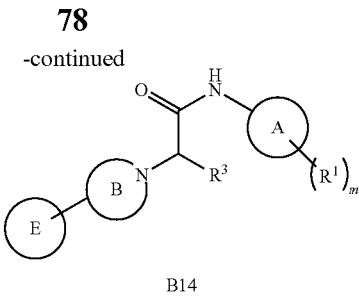

Wherein L is a leaving group. Compound B14 obtained here is a racemate. Two single optically pure enantiomers of B14 can be isolated by chiral preparative HPLC.

Further, BI14 can also be obtained by directly performing a substitution reaction with the intermediates B12 and B15.

Scheme C-1 describes a general synthetic method for compound C6:

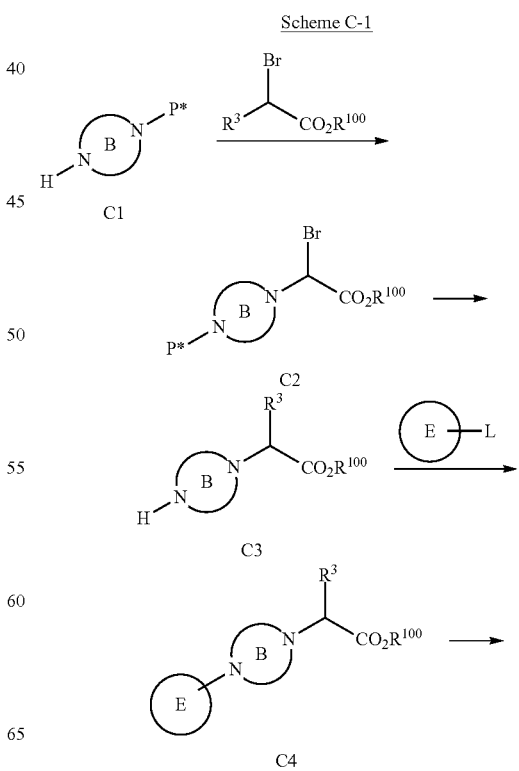

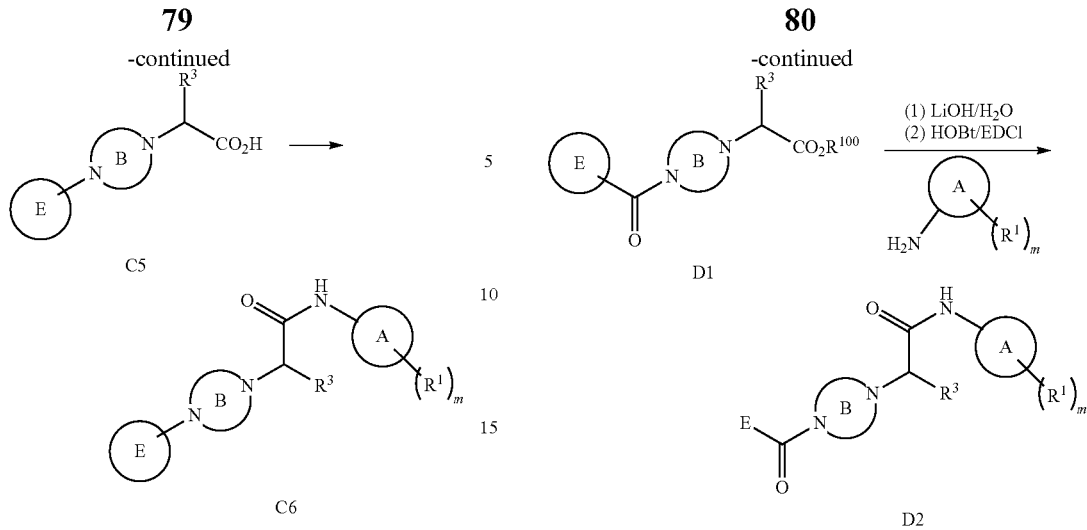

Wherein L is a leaving group.

Scheme C-2 describes another general synthetic method for intermediate C4. Intermediate C4 is the key raw material for the preparation of compound C6:

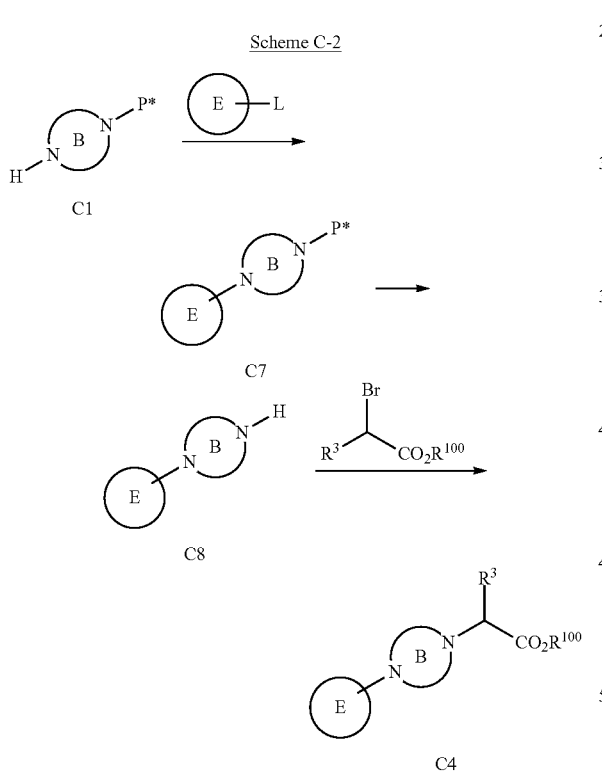

Wherein L is a leaving group.

Scheme D-1 describes a general synthetic method for compound D2:

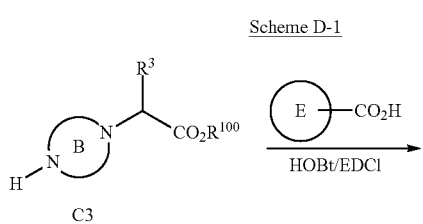

Scheme D-2 describes a general synthetic method for compound D6:

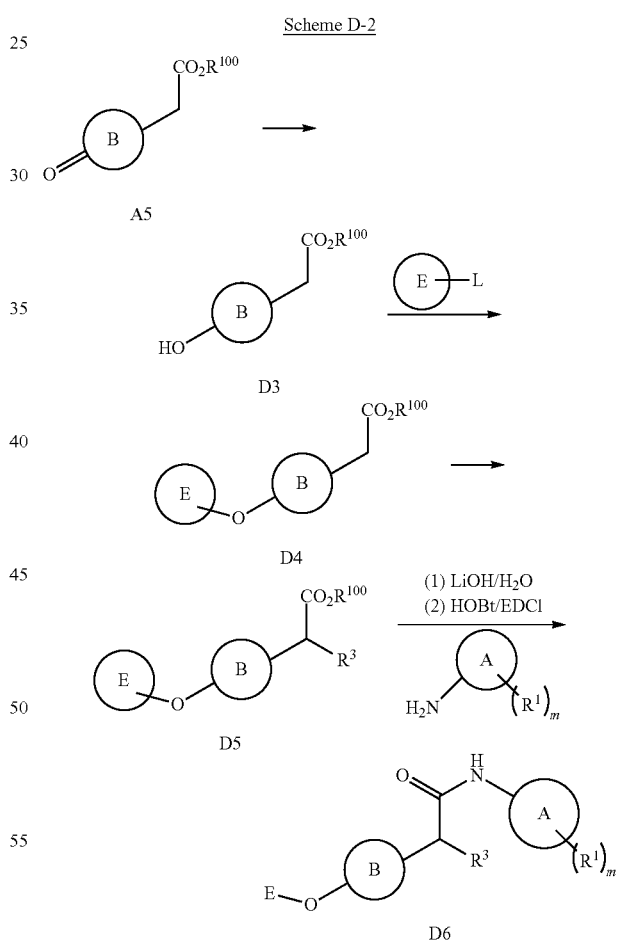

Wherein L is a leaving group.

The compounds D2 and D6 herein are racemates. Their respective two optically pure, single enantiomers can be separated by chiral preparative HPLC.

The following compounds D7, D8, D9, and D10 can be prepared by combining the above-exemplified reaction schemes:

D7
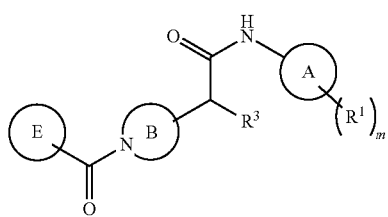
D8
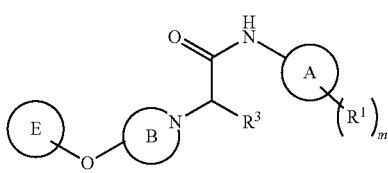
D9
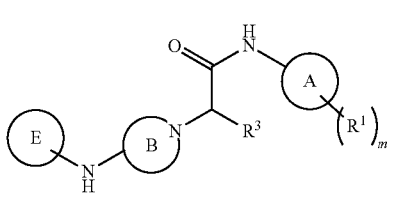
D10
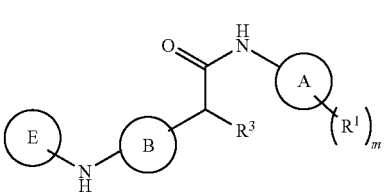
Scheme E-1 describes a general synthetic method for compound E10:
Scheme E-1
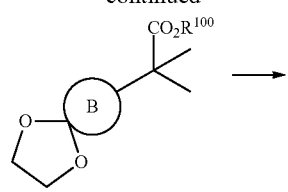
A2
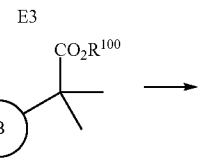
E1
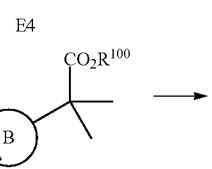
E2
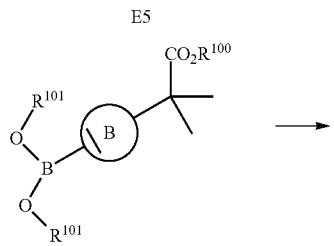
E3
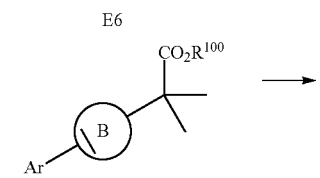
E4
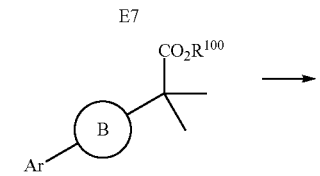
E5
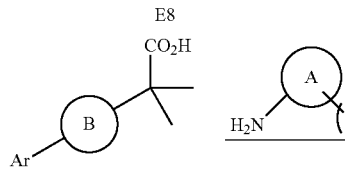
E6
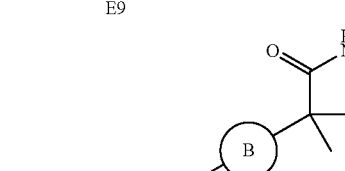
E7
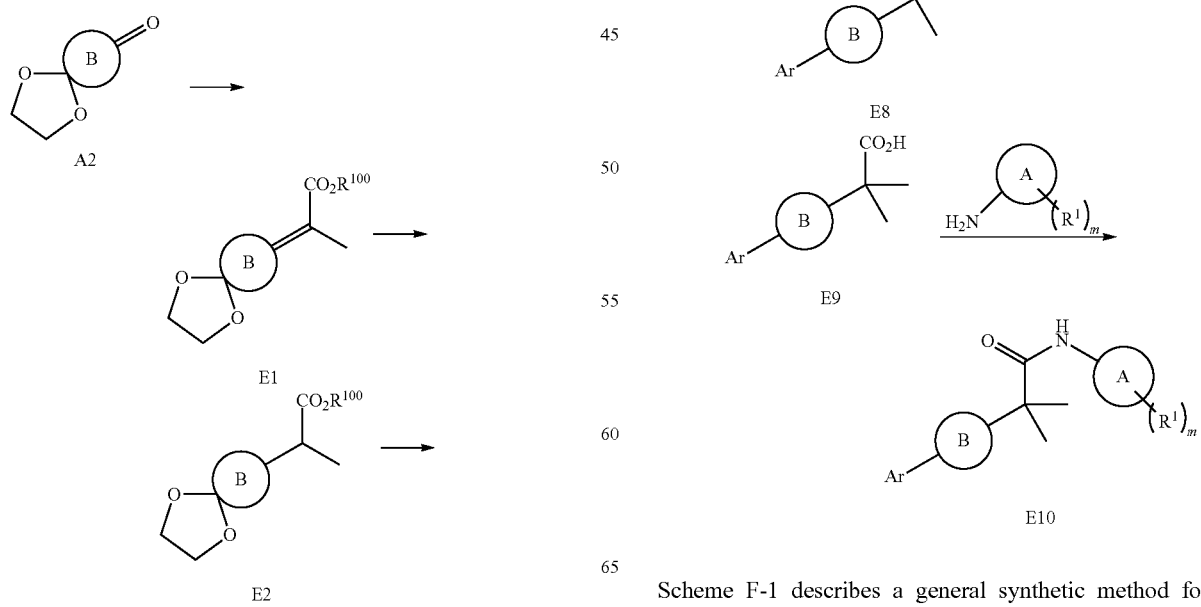
Scheme F-1 describes a general synthetic method for compound F7:

Scheme F-1

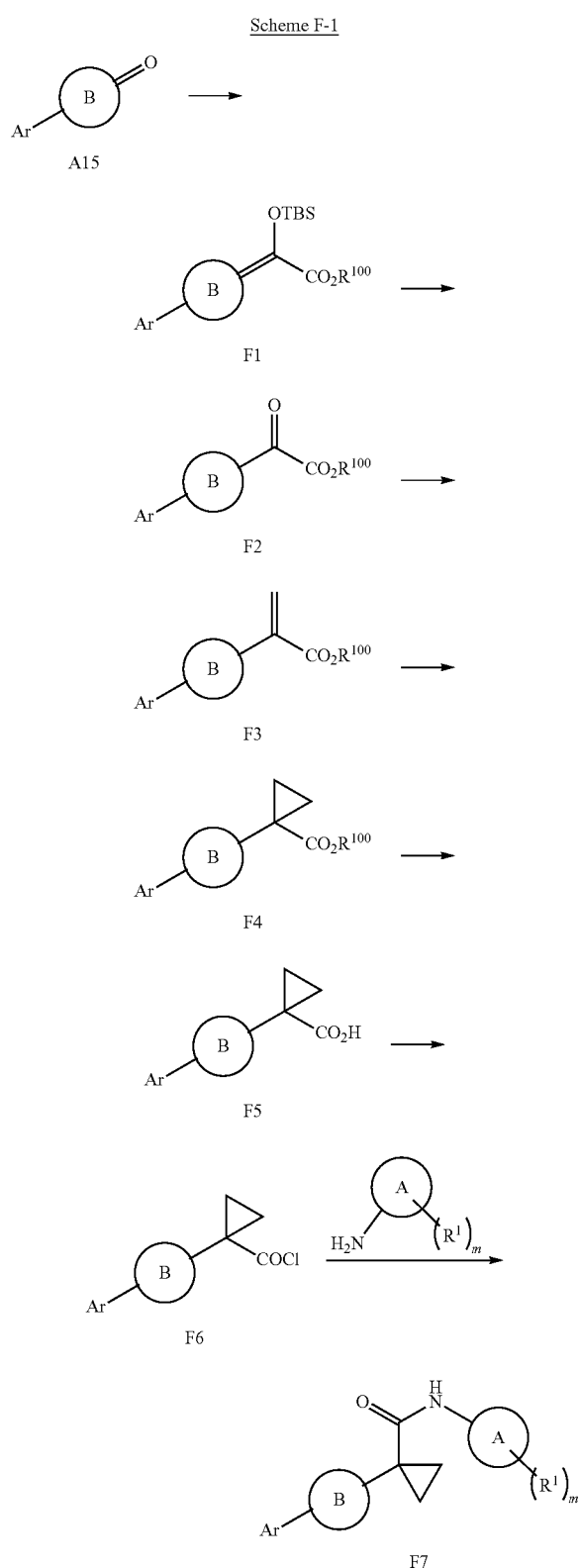

It should be noted that the above various reaction formulas are intended to exemplify the synthesis of the compounds A11, A13, A20, B7, B14, C6, D2, D6, D7, D8, D9, D10, E10 and F7 using the routes in the general synthetic schemes. Our actual synthetic route is not limited to the above routes.

Other relevant synthetic routes should be obvious to organic chemists and pharmaceutical chemists with expertise. We will not elaborate here. Compounds A11, A13, A20, B7, B14, C6, D2, D6, D7, D8, D9, D10, E10 and F7 are part of the formula (I). Other molecules of formula (I) not listed may be obtained by designed synthesis according to the above Schemes.

Pharmaceutically Acceptable Salts, Solvates, Stereoisomers, Tautomers

The term "pharmaceutically acceptable salt" as used herein refers to a salt of a compound of the invention and a pharmaceutically acceptable inorganic and organic acid, wherein preferred inorganic acids include, but are not limited to, hydrochloric acid, hydrogen bromic acid, phosphoric acid, nitric acid, sulfuric acid; preferred organic acids include, but are not limited to: formic acid, acetic acid, propionic acid, succinic acid, naphthalene disulfonic acid (1,5), arsonic acid, oxalic acid, tartaric acid, lactic acid, salicylic acid, benzoic acid, valeric acid, diethyl acetic acid, malonic acid, succinic acid, fumaric acid, pimelic acid, adipic acid, maleic acid, malic acid, sulfamic acid, phenylpropionic acid, gluconic acid, ascorbic acid, nicotinic acid, isonicotinic acid, methanesulfonic acid, p-toluenesulfonic acid, citric acid, and amino acids.

The term "pharmaceutically acceptable solvate" as used herein refers to a compound of the invention that forms a solvate with a pharmaceutically acceptable solvent, wherein the pharmaceutically acceptable solvent includes, but is not limited to, water, ethanol, methanol, isopropanol, tetrahydrofuran, dichloromethane.

The term "pharmaceutically acceptable stereoisomer" as used herein means that the chiral carbon atom to which the compound of the invention relates may be in the R configuration, in the S configuration, or a combination thereof.

Pharmaceutical Composition and Method of Administration

Since the compound of the present invention has excellent inhibitory activity against IDO, the compound of the present invention and various crystal forms thereof, a pharmaceutically acceptable inorganic or organic salt, hydrate or solvate, and a pharmaceutical composition containing a compound in the present invention as main active ingredients can be used to treat, prevent, and alleviate diseases associated with IDO activity or expression levels. According to the prior art, the compounds of the present invention are useful for treating (but not limited to) various diseases such as lung cancer, bladder cancer, breast cancer, gastric cancer, liver cancer, salivary gland sarcoma, ovarian cancer, prostate cancer, cervical cancer, epithelial cell carcinoma, multiple myeloma, pancreatic cancer, lymphoma, chronic myelogenous leukemia, lymphocytic leukemia, cutaneous T-cell lymphoma, etc.; bone-related diseases such as bone dysplasia, dyschondroplasia, dwarfism, Kruzong syndrome, etc.; T cell-mediated inflammation and autoimmune diseases such as rheumatoid arthritis, collagen II arthritis, multiple sclerosis, systemic lupus erythematosus, psoriasis, juvenile diabetes, Sjogren's syndrome, thyroid disease, sarcoidosis, inflammatory bowel disease, celiac disease and so on. The pharmaceutical compositions of the present invention comprise a safe or effective amount of a compound of the present invention, or a pharmaceutically acceptable salt thereof, and a pharmaceutically acceptable excipient or carrier. By "safe and effective amount" it is meant that the amount of the compound is sufficient to significantly improve the condition without causing serious side effects. In general, the pharmaceutical compositions contain from 1 to 2000 mg of the compound of the invention per agent, more preferably from 5 to 200 mg of the compound of the invention per agent. Preferably, the "one dose" is a capsule or tablet.

"Pharmaceutically acceptable carrier" means: one or more compatible solid or liquid fillers or gel materials which are suitable for human use and which must be of sufficient purity and of sufficiently low toxicity. By "compatibility" it is meant herein that the components of the composition are capable of intermingling with the compounds of the invention and with each other without significantly reducing the efficacy of the compound. Examples of pharmaceutically acceptable carriers are cellulose and its derivatives (such as sodium carboxymethylcellulose, sodium ethylcellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween®), run Wet agents (such as sodium lauryl sulfate), colorants, flavoring agents, stabilizers, antioxidants, preservatives, pyrogen-free water, and the like.

The mode of administration of the compound or pharmaceutical composition of the present invention is not particularly limited, and representative modes of administration include, but are not limited to, oral, intratumoral, rectal, parenteral (intravenous, intramuscular or subcutaneous), and topical administration.

Solid dosage forms for oral administration include capsules, tablets, pills, powders, and granules. In these solid dosage forms, the active compound is mixed with at least one conventional inert excipient (or carrier), such as sodium citrate or dicalcium phosphate, or mixed with: (a) a filler or compatibilizer, for example, starch, lactose, sucrose, glucose, mannitol and silicic acid; (b) binders such as hydroxymethylcellulose, alginates, gelatin, polyvinylpyrrolidone, sucrose and acacia; (c) humectants, for example, glycerin; (d) a disintegrant such as agar, calcium carbonate, potato starch or tapioca starch, alginic acid, certain complex silicates, and sodium carbonate; (e) a slow solvent such as paraffin; (f) absorbing accelerators, for example, quaternary amine compounds; (g) wetting agents, such as cetyl alcohol and glyceryl monostearate; (h) adsorbents, for example, kaolin; and (i) lubricants, for example, talc, calcium stearate, magnesium stearate, solid polyethylene glycol, sodium lauryl sulfate, or a mixture thereof. In capsules, tablets and pills, the dosage form may also contain a buffer.

Solid dosage forms such as tablets, dragees, capsules, pills, and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric and waxy materials. If necessary, the active compound may also be in microencapsulated form with one or more of the above-mentioned excipients.

Liquid dosage forms for oral administration include pharmaceutically acceptable emulsions, solutions, suspensions, syrups or elixirs. In addition to the active compound, the liquid dosage form may contain inert diluents conventionally employed in the art, such as water or other solvents, solubilizers and emulsifiers, for example, ethanol, isopropanol, ethyl carbonate, ethyl acetate, propylene glycol, 1, 3-butanediol, dimethylformamide and oils, especially cottonseed oil, peanut oil, corn germ oil, olive oil, castor oil and sesame oil or a mixture of these substances.

In addition to these inert diluents, the compositions may contain adjuvants such as wetting agents, emulsifying and suspending agents, sweetening agents, flavoring agents and perfumes.

In addition to the active compound, the suspension may contain suspending agents, for example, ethoxylated isostearyl alcohol, polyoxyethylene sorbitol and sorbitan esters, microcrystalline cellulose, aluminum methoxide and agar or mixtures of these and the like.

Compositions for parenteral injection may comprise a physiologically acceptable sterile aqueous or nonaqueous solution, dispersion, suspension or emulsion, and a sterile powder for reconstitution into a sterile injectable solution or dispersion. Suitable aqueous and nonaqueous vehicles, diluents, solvents or vehicles include water, ethanol, polyols, and suitable mixtures thereof.

Dosage forms for the compounds of the invention for topical administration include ointments, powders, patches, propellants and inhalants. The active ingredient is admixed under sterile conditions with a physiologically acceptable carrier and any preservatives, buffers, or, if necessary, propellants.

The compounds of the invention may be administered alone or in combination with other pharmaceutically acceptable compounds.

When a pharmaceutical composition is used, a safe and effective amount of a compound of the invention is administered to a mammal (e.g., a human) in need of treatment wherein the dosage is a pharmaceutically effective effective dosage, for a 60 kg body weight, The daily dose is usually from 1 to 2000 mg, preferably from 5 to 500 mg. Of course, specific doses should also consider factors such as the route of administration, the health of the patient, etc., which are within the skill of the skilled physician.

The Main Advantages of the Invention Include:
1. Provided a compound of formula I.
2. A novel structure of IDO inhibitors and/or IDO-HDAC dual inhibitors, which inhibit the activity of IDO at very low concentrations, and their preparation and use are provided.
3. A class of pharmaceutical compositions for treating diseases associated with IDO and/or IDO-HDAC activity is provided.

The invention is further illustrated below in conjunction with specific embodiments. It is to be understood that the examples are not intended to limit the scope of the invention. The experimental methods in the following examples which do not specify the specific conditions are usually in accordance with conventional conditions or according to the conditions recommended by the manufacturer. Percentages and parts are by weight unless otherwise stated.

Example 1. Preparation of Compound 1

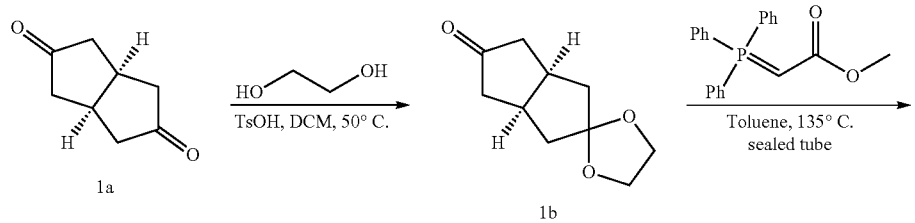

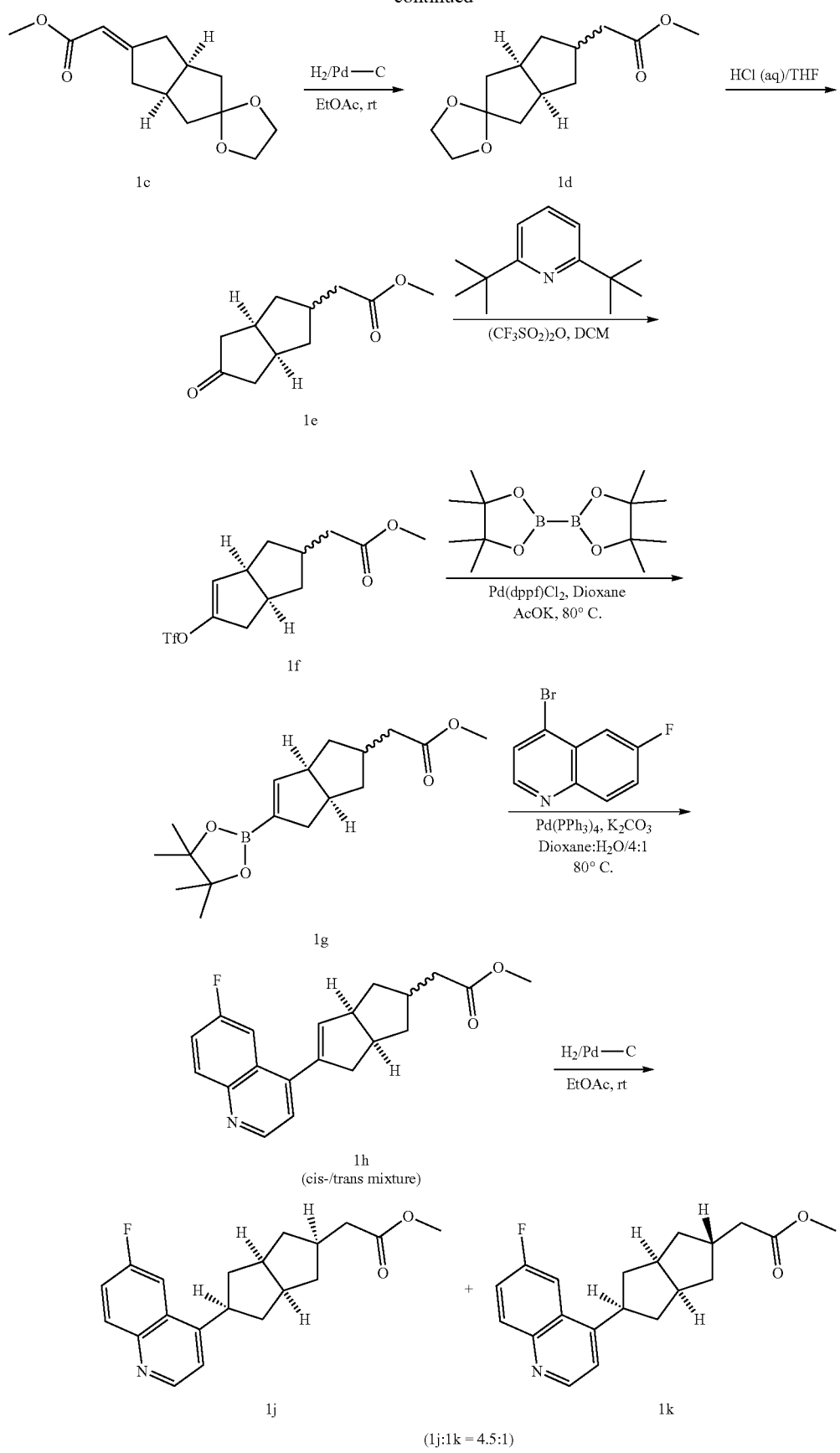

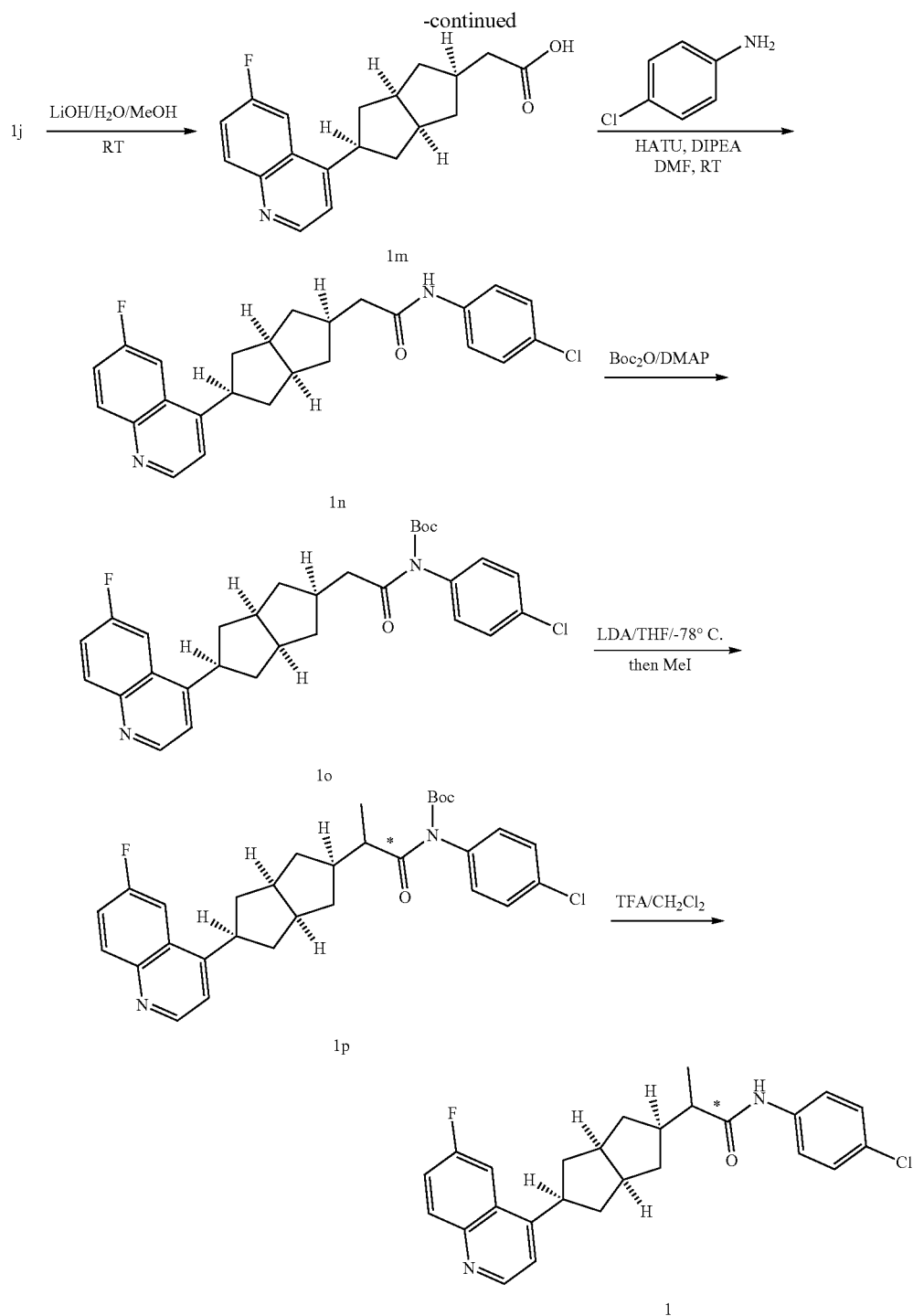

Compound 1a (10 g, 72.4 mmol), ethylene glycol (4.1 mL), and p-toluenesulfonic acid (1.4 g, 0.73 mmol) were dissolved in $CH_2Cl_2$ (200 mL), the reaction mixture was stirred at 50° C. overnight. The reaction mixture was washed by water (100 mL), the organic phase was collected, dried over $Na_2SO_4$, and filtered. The filtrate was concentrated in vacuo, the residue was purified via column chromatography (EtOAc/petroleum ether=0-20%) to afford colorless oil 1b (6.5 g, yield 49%). $^1$H NMR (500 MHz, $CDCl_3$) δ 3.87 (s, 4H), 2.83-2.81 (m, 2H), 2.48-2.43 (m, 2H), 2.22-2.12 (m, 4H), 1.70 (dd, J=13.8, 5.3 Hz, 2H).

Compound 1b (6.5 g, 35.7 mmol) was dissolved in toluene (50 mL), then methyl (triphenylphosphoranylidene) acetate (17.9 g, 53.5 mmol) was added. The reaction was stirred for 48 hours at 135° C. in sealed tube. The reaction solution was diluted by EtOAc (50 mL), washed by brine (15 mL). The organic phase was dried over $Na_2SO_4$, and filtered. The filtrate was concentrated in vacuo, the crude product was purified via column chromatography (EtOAc/petroleum ether=0-10%) to afford gray solid compound 1c (6.8 g, yield 80%). $^1$H NMR (500 MHz, $CDCl_3$) δ 5.77 (s, 1H), 3.88 (s, 4H), 3.68 (s, 3H), 3.00 (dd, J=19.3, 9.2 Hz, 1H), 2.82-277 (m, 1H), 2.872-2.67 (m, 2H), 2.62-2.57 (m, 1H), 2.40 (J=17.3, 4.8 Hz, 1H), 2.10-2.01 (m, 2H), 1.67-1.59 (m, 2H).

Compound 1c (6.8 g, 28.5 mmol) was dissolved in EtOAc (50 mL), and was added 10% Pd/C (0.6 g), then was stirred overnight at room temperature and H$_2$ atmosphere. Pd/C was removed by filtrated through celite pie, the filtrate was concentrated in vacuo to afford colorless oil 1d (6.2 g, yield 91%). The ratio of cis to trans is about 4.5:1.

Compound 1d (3.2 g, 13.3 mmol) was dissolved in THF (50 mL), under the cooling of an ice-water bath, HCl (1 N, 20 mL) was added slowly, then the mixture was warmed to room temperature and stirred overnight. The reaction was extracted with EtOAc (3×30 mL), the combined organic phase was dried over Na$_2$SO$_4$, and filtered. The filtrate was concentrated in vacuo, the crude product was purified via column chromatography (EtOAc/petroleum ether=0-20%) to afford colorless oil 1e (1.9 g, yield 73%).

Compound 1e (1.9 g, 9.7 mmol) was dissolved in CH$_2$Cl$_2$ (40 mL), at 0° C. 2,6-di-t-butyl-4-methyl-pyridine (2.98 g, 14.5 mmol) was added slowly. After stirred for 1 hour, the mixture was cooled to 0° C., trifluoromethanesulfonic anhydride (5.5 g, 19.5 mmol) was added slowly, the mixture was warmed to room temperature gradually, and stirred overnight. At 0° C., the reaction mixture was poured into saturated aqueous Na$_2$CO$_3$ solution (30 mL), and the organic layer was separate, the aqueous layer was extracted with CH$_2$Cl$_2$ (2×40 mL). The combined organic layers were washed with brine (20 mL), dried over Na$_2$SO$_4$, filtered, and concentrated under reduced pressure. The crude product was purified via column chromatography (EtOAc/petroleum ether=0-10%) to afford compound 1f (2.1 g, yield 60%) as a colorless oil.

Compound 1f (2.1 g, 6.4 mmol), bis(pinacolato)diboron (1.95 g, 7.68 mmol), potassium acetate (1.59 g, 16.2 mmol), Pd(dppf)$_2$Cl$_2$ (145 mg, 19.8 mmol) were dissolved in 1,4-dioxane (40 mL), and the mixture was stirred at 80° C. under nitrogen atmosphere overnight. The reaction mixture was concentrated under reduced pressure, then EtOAc (40 mL) was added. The mixture was washed with water, extracted with EtOAc (2×40 mL). The combined organic layer was washed by brine (1×15 mL), dried over Na$_2$SO$_4$, filtered, and concentrated under reduced pressure. The crude product was purified via column chromatography (EtOAc/petroleum ether=0-10%) to afford compound 1g (1.3 g, yield 66%) as an colorless oil.

Compound 1g (620 mg, 2 mmol), 4-bromo-6-fluoroquinoline (570 mg, 2.4 mmol), potassium carbonate (840 mg, 6.1 mmol), Pd(PPh$_3$)$_4$ (240 mg, 0.21 mmol) were dissolved in 1,4-dioxane (20 mL) and water (5 mL), and stirred for 4 hours at 80° C. under the protection of N$_2$. The reaction solution was concentrated in vacuo, and added EtOAc (20 mL), washed by water, extracted with EtOAc (2×40 mL), the combined organic phase was washed by brine, dried over Na$_2$SO$_4$, and filtered. The filtrate was concentrated in vacuo, the crude product was purified via column chromatography (EtOAc/petroleum ether=0-25%) to afford colorless oil compound 1h (510 mg, yield 77%). Compound 1h is a mixture of two stereoisomers, ratio is 1:0.7.

Compound 1h (510 mg, 1.57 mmol) was dissolved in ethyl acetate (20 mL), and was added 10% Pd/C (50 mg), the reaction was stirred for 2 hours at room temperature and H$_2$ atmosphere. The reaction solution filtrated through a celite pad to removed Pd/C, the filtrate was concentrated in vacuo to afford crude product. The crude product was purified via column chromatography (EtOAc/petroleum ether=0-20%) to afford colorless oil compound 1j (391.9 mg, yield 82%) and 1k (87.1 mg, yield 18%).

Compound 1j (84 mg, 0.255 mmol) was dissolved in MeOH (2 mL), and was added saturated LiOH aqueous solution (1 mL), TLC results indicated the reaction was completed. The reaction mixture was added HCl solution (1N), adjusted its pH value to almost 6, extracted with EtOAc (3×5 mL), the combined organic phase was washed by brine, dried over Na$_2$SO$_4$, and filtered. The filtrate was concentrated in vacuo to afford white solid compound 1m (72 mg, yield 91%).

Compound 1m (72 mg, 0.228 mmol), 4-chlorophenyamine (43.8 mg, 0.342 mmol), HATU (105 mg, 0.276 mmol), DIPEA (93 mg, 0.72 mmol) were dissolved in DMF (5 mL), and were stirred for 0.5 hours at N$_2$ protection. The reaction was quenched by adding water, extracted with EtOAc (3×10 mL); the combined organic phase was washed by brine, dried over Na$_2$SO$_4$, and filtered. The filtrate was concentrated in vacuo, the crude product was purified via column chromatography (EtOAc/petroleum ether=0-25%) to afford white solid compound 1n (50 mg, yield 53%).

Compound 1n (50 mg, 0.12 mmol), DMAP (38.7 mg, 0.18 mmol) and BOC anhydride (21.67 mg, 0.18 mmol) were dissolved in CH$_3$CN (1 mL), the mixture was heated to 50° C. and stirred for 5 minutes. The reaction solution was concentrated in vacuo, the obtained crude product was purified via preparative TLC (30%, EtOAc: petroleum ether) to afford white solid compound 1o (35 mg, yield 57%).

Compound 1o (32 mg, 0.061 mmol) was dissolved in THF (0.5 mL) and was cooled to −20° C. under N$_2$ protection, then was slowly added LDA (0.085 mL, 0.18 mmol), and warmed to 0° C. and stirred for 20 minutes, then was cooled to −20° C. and MeI (26 mg, 0.18 mmol) was added to the above solution, which was stirred for 20 minutes at 0° C. The reaction mixture was added saturated NH$_4$Cl aqueous solution (5 mL), extracted with EtOAc (3×10 mL); the combined organic phase was washed by brine (3×10 mL), dried over Na$_2$SO$_4$, and filtered. The filtrate was concentrated in vacuo, the crude product was purified via preparative TLC (30%, EtOAc: petroleum ether) to afford pale yellow solid compound 1p (6.0 mg, yield 18%).

At 0° C., to a solution of compound 1p (6 mg, 0.009 mmol) in CH$_2$Cl$_2$ (0.5 mL) was added HCl (0.004 mL, 4 M dioxane solution), the mixture was stirred for 20 minutes at 0° C., then aqueous NaHCO$_3$ (5 mL) was added, extracted with EtOAc (3×4 mL); the combined organic phase was washed with brine (3×4 mL), dried over Na$_2$SO$_4$, and filtered. The filtrate was concentrated in vacuo, the crude product was purified via preparative TLC (50%, EtOAc: petroleum ether) to afford compound 1 (3.0 mg, yield 61%) as a pale yellow solid. $^1$H NMR (500 MHz, CDCl$_3$) δ 8.79 (d, J=5.0 Hz, 1H), 8.11-8.08 (m, 1H), 7.69-7.67 (m, 1H), 7.50-7.44 (m, 3H), 7.35-7.34 (m, 1H), 7.29-7.27 (m, 2H), 7.22 (s, 1H), 3.73-3.71 (m, 1H), 2.72-2.69 (m, 2H), 2.45-2.37 (m, 2H), 2.32-2.21 (m, 2H), 2.20-2.16 (m, 2H), 1.50-1.48 (m, 2H), 1.27 (d, J=5.0 Hz, 3H), 1.14-1.05 (m, 2H). LCMS m/z 437.3 [M+H]$^+$.

Compound 1 can be prepared by another synthetic route, detailed scheme is shown as below:

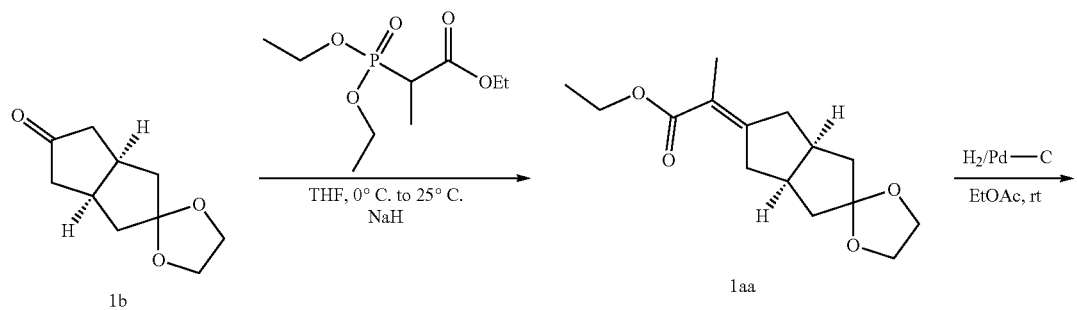
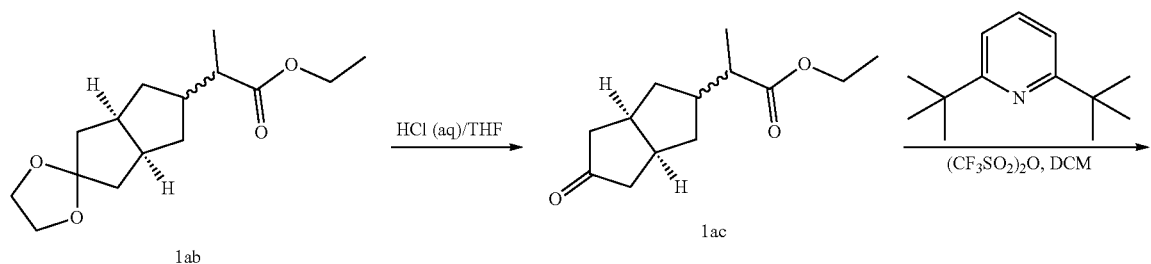
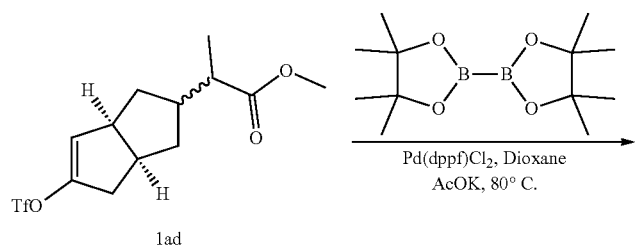
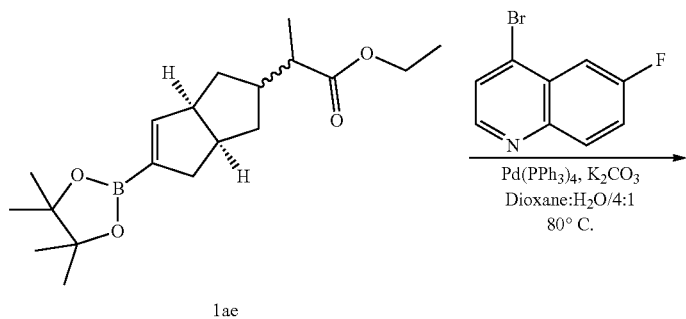
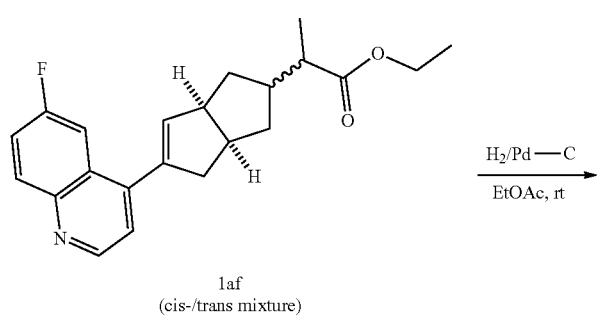

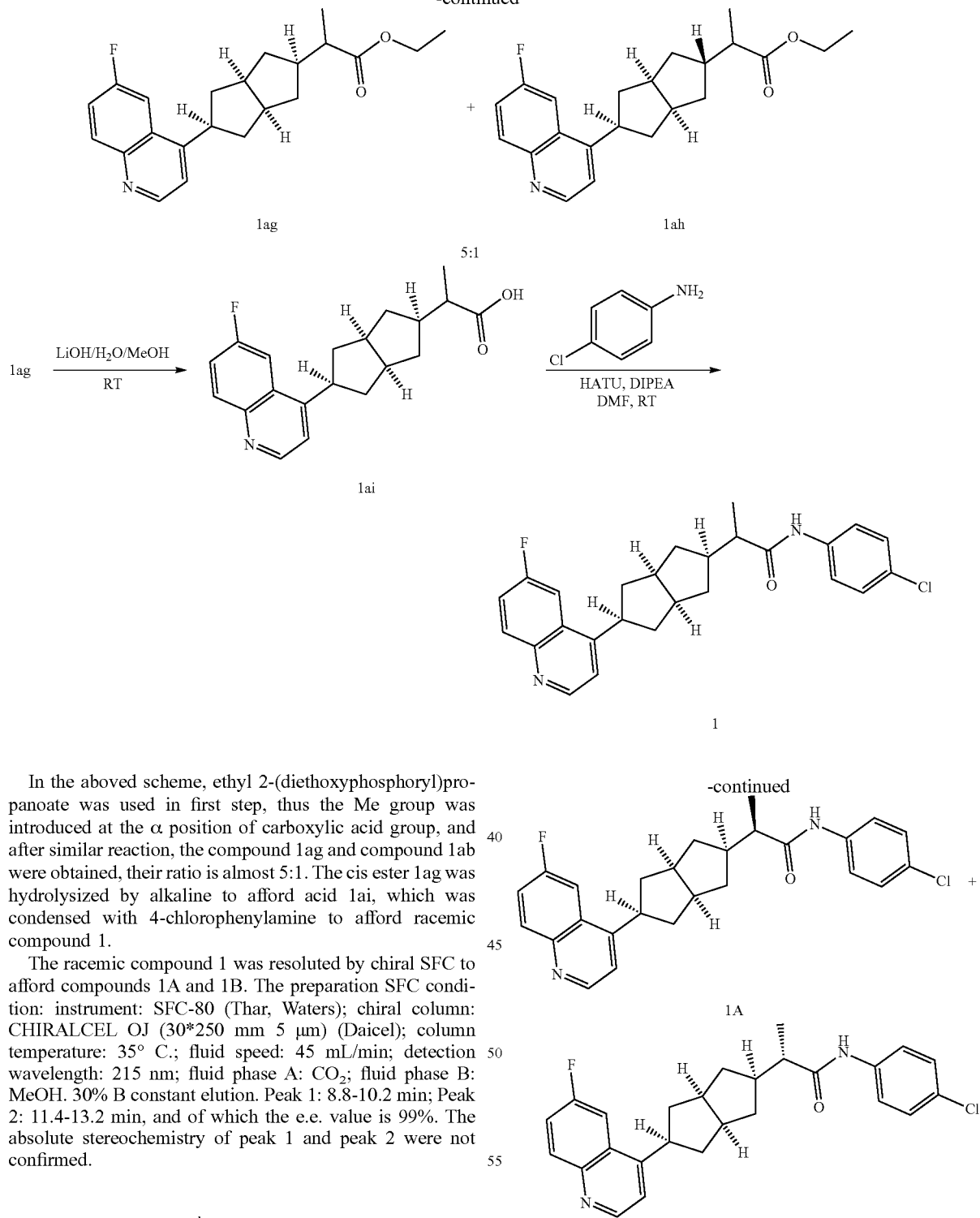

In the aboved scheme, ethyl 2-(diethoxyphosphoryl)propanoate was used in first step, thus the Me group was introduced at the α position of carboxylic acid group, and after similar reaction, the compound 1ag and compound 1ab were obtained, their ratio is almost 5:1. The cis ester 1ag was hydrolysized by alkaline to afford acid 1ai, which was condensed with 4-chlorophenylamine to afford racemic compound 1.

The racemic compound 1 was resolved by chiral SFC to afford compounds 1A and 1B. The preparation SFC condition: instrument: SFC-80 (Thar, Waters); chiral column: CHIRALCEL OJ (30*250 mm 5 μm) (Daicel); column temperature: 35° C.; fluid speed: 45 mL/min; detection wavelength: 215 nm; fluid phase A: $CO_2$; fluid phase B: MeOH. 30% B constant elution. Peak 1: 8.8-10.2 min; Peak 2: 11.4-13.2 min, and of which the e.e. value is 99%. The absolute stereochemistry of peak 1 and peak 2 were not confirmed.

Peak 1 compound: $^1$H NMR (500 MHz, $CDCl_3$) δ 8.80 (d, J=4.6 Hz, 1H), 8.11 (dd, J=9.2, 5.7 Hz, 1H), 7.69 (dd, J=10.5, 2.7 Hz, 1H), 7.50 (d, J=8.7 Hz, 2H), 7.49-7.44 (m, 1H), 7.36 (d, J=4.6 Hz, 1H), 7.30 (d, J=8.8 Hz, 2H), 7.11 (s, 1H), 3.77-3.71 (m, 1H), 2.74-2.70 (m, 2H), 2.47-2.38 (m, 2H), 2.36-2.25 (m, 2H), 2.22-2.15 (m, 2H), 1.54-1.48 (m, 2H), 1.28 (d, J=6.8 Hz, 3H), 1.16-1.02 (m, 2H). LCMS m/z 437.3 [M+H]$^+$. e.e. value 99.0%.

Peak 2 compound: ¹H NMR (500 MHz, CDCl₃) δ 8.80 (d, J=4.6 Hz, 1H), 8.11 (dd, J=9.2, 5.7 Hz, 1H), 7.68 (dd, J=10.5, 2.7 Hz, 1H), 7.50 (d, J=8.8 Hz, 2H), 7.50-7.45 (m, 1H), 7.36 (d, J=4.6 Hz, 1H), 7.29 (d, J=8.8 Hz, 2H), 7.19 (s, 1H), 3.77-3.70 (m, 1H), 2.73-2.66 (m, 2H), 2.49-2.37 (m, 2H), 2.37-2.24 (m, 2H), 2.21-2.18 (m, 2H), 1.53-1.47 (m, 2H), 1.28 (d, J=6.8 Hz, 3H), 1.17-1.02 (m, 2H). LCMS m/z 437.3 [M+H]⁺. e.e. value 99.0%.

Example 2. Preparation of Compound 1A

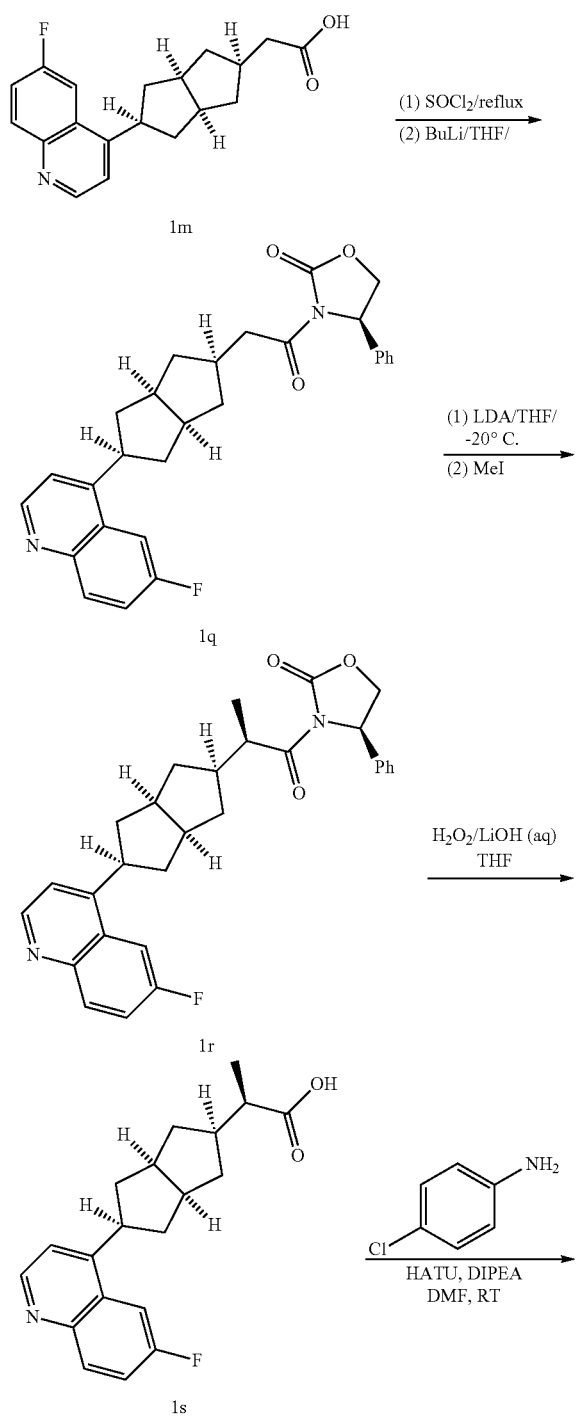

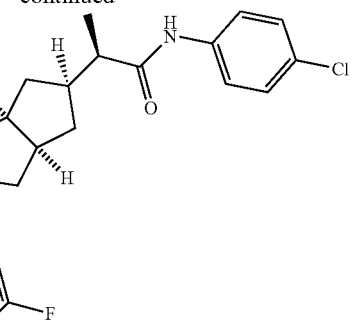

Compound 1m (35 mg, 0.11 mmol) was refluxed in SOCl₂ for 1 hour. The remaining SOCl₂ was removed via distillation under reduced pressure. The crude product acyl chloride was used for next step directly. In a dry round flask, (R)-4-phenyl-2-oxazolidinone (34 mg, 0.11 mmol) was dissolved in THF (1 mL), and was cooled to −65° C. under N₂ protection, then LDA (0.1 mL, 0.21 mmol) was added slowly, and was stirred 15 minutes at this temperature. The THF (2 mL) solution of crude acyl chloride was added into the above reaction mixture, which was stirred for 1 hour at this temperature. Saturated aq. NH₄Cl (6 mL) was added to the reaction, followed by extraction with EtOAc (3×5 mL). The combined organic layers were washed with brine (3×5 mL), dried over Na₂SO₄, filtered, and concentrated in vacuo. The crude product was purified via preparative TLC (50%, EtOAc: petroleum ether) to afford compound 1q (15 mg, yield 31%) as a white solid. LCMS m/z 459.2 [M+H]⁺.

Compound 1A was prepared from compound 1q, the detailed procedure refer to the patents WO2016073774 and WO2016073770.

Example 3. Preparation of Compound 2

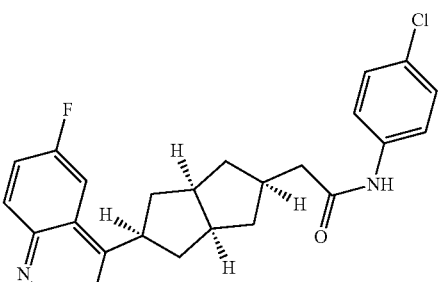

Compound 2 was prepared by following the preparation of compound 1, wherein compound 2 is compound 1n in above scheme. ¹H NMR (500 MHz, CDCl₃) δ 8.80 (d, J=4.2 Hz, 1H), 8.10 (dd, J=9.3, 6.0 Hz, 1H), 7.68 (d, J=10.4 Hz, 1H), 7.48 (d, J=8.4 Hz, 2H), 7.36 (d, J=4.5 Hz, 1H), 7.28 (d, J=8.4 Hz, 3H), 7.15 (s, 1H), 3.74-3.73 (m, 1H), 3.61-3.57 (m, 1H), 2.75-2.73 (m, 2H), 2.57-2.50 (m, 1H), 2.45-2.38 (m, 3H), 2.28-2.26 (m, 2H), 1.48-1.44 (m, 2H), 11.13-1.12 (m, 2H). LCMS m/z 423.1 [M+H]⁺.

Example 4. Preparation of Compound 3

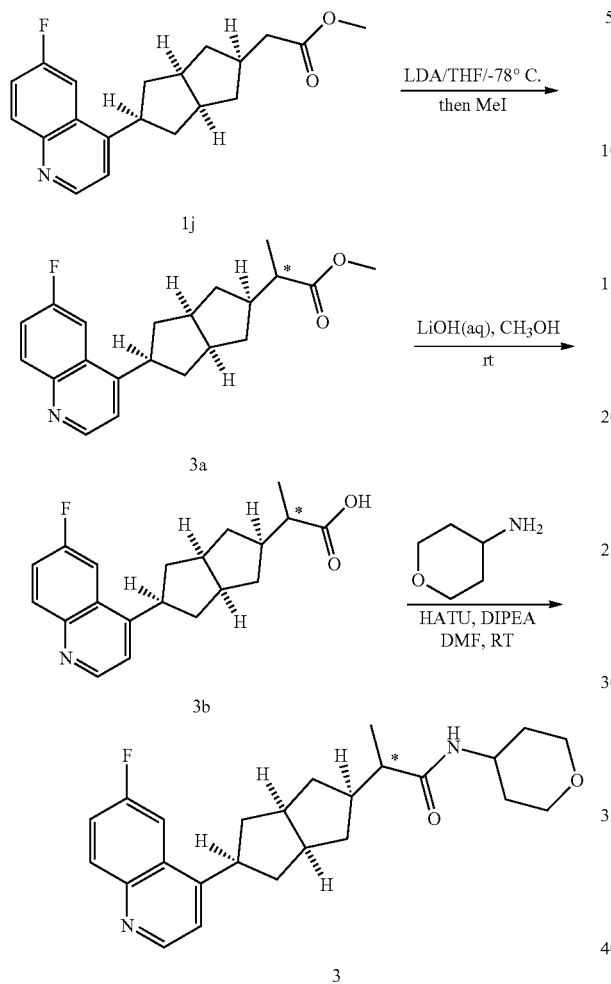

THF (0.5 mL) and LDA (2.0 M THF solution, 1.22 mL, 2.44 mmol) were put in a dry round bottom flask, cooled to −78° C. under N₂ protection, and added 1,3-Dimethyl-3,4,5,6-tetrahydro-2(1H)-pyrimidinone (118 mg, 0.92 mmol) and the solution 1j (0.2 g, 0.61 mmol) in THF (0.5 mL), the reaction was stirred for 1 hour at −20° C. then the reaction was added MeI (0.35 g, 2.44 mmol), and was stirred for another 1 hour. The reaction was added saturated aq. NH₄Cl (5 mL), extracted with EtOAc (3×5 mL); the combined organic phase was washed by brine (3×4 mL), dried over Na₂SO₄, and filtered. The filtrate was concentrated in vacuo, the crude product was purified via preparative TLC (20%, EtOAc: petroleum ether) to afford pale yellow solid compound (120 mg, yield 58%).

Compound 3a (120 mg, 0.35 mmol) was dissolved in MeOH (2 mL) and water (0.4 mL), then was added KOH (197 mg, 3.5 mmol), the mixture was stirred for 30 minutes at 50° C. TLC results indicated the reaction was complete. The reaction was cooled to 0° C., added HCl solution (3N), adjusted its pH=6, extracted with EtOAc (3×10 mL), the combined organic phase was washed by brine (3×5 mL), dried over Na₂SO₄, and filtered. The filtrate was concentrated in vacuo to afford pale brown solid compound 3b (100 mg, yield 87%).

3b (14 mg, 0.043 mmol), HOBT (8.67 mg, 0.064 mmol), EDCI (12.3 mg, 0.064 mmol) and DIPEA (16.58 mg, 0.13 mmol) were dissolved in DMF (0.5 mL), and was added 4-aminotetrahydropyran (6.5 mg, 0.064 mmol), the reaction was stirred for 2 hours at 50° C., which was concentrated in vacuo to afford crude product, and the crude product was purified via preparative TLC (20%, EtOAc: petroleum ether) to afford white solid compound 3 (2 mg, yield 5%). ¹H NMR (500 MHz, CDCl₃) δ 8.80 (d, J=4.5 Hz, 1H), 8.11 (dd, J=9.0, 5.7 Hz, 1H), 7.69 (dd, J=10.4, 2.4 Hz, 1H), 7.51-7.43 (m, 1H), 7.36 (d, J=4.4 Hz, 1H), 5.30 (d, J=8.0 Hz, 1H), 4.08-3.91 (m, 3H), 3.72 (m, 1H), 3.49 (t, J=11.5 Hz, 2H), 2.72 (m, 2H), 2.41 (m, 2H), 2.27-2.14 (m, 2H), 2.08 (m, 1H), 2.02-1.82 (m, 3H), 1.55-1.38 (m, 4H), 1.17 (d, J=8.4 Hz, 3H), 1.03 (m, 2H). LCMS m/z 411.2 [M+H]⁺.

Example 5. Preparation of Compound 4

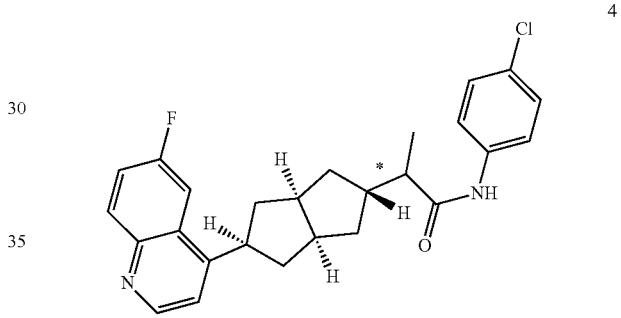

Compound 4 was prepared from compound 3b and 4-chloroaniline according the preparation method of compound 3. ¹H NMR (500 MHz, CDCl₃) δ 8.80 (d, J=4.5 Hz, 1H), 8.11 (dd, J=9.1, 5.7 Hz, 1H), 7.68 (d, J=10.5, 1H), 7.51 (d, J=8.7 Hz, 2H), 7.48 (t, J=8.3 Hz, 1H), 7.30 (d, J=8.7 Hz, 2H), 7.28 (s, 1H), 7.21 (s, 1H), 3.59-3.57 (m, 1H), 3.14 (t, J=12.0 Hz, 1H), 2.19 (t, J=7.2 Hz, 1H), 2.16-2.08 (m, 1H), 2.07-2.03 (m, 1H), 1.84-1.60 (m, 6H), 1.47-1.39 (m, 2H), 1.30 (d, J=6.7 Hz, 3H). LCMS m/z 437.1 [M+H]⁺.

Example 6. Preparation of Compound 5

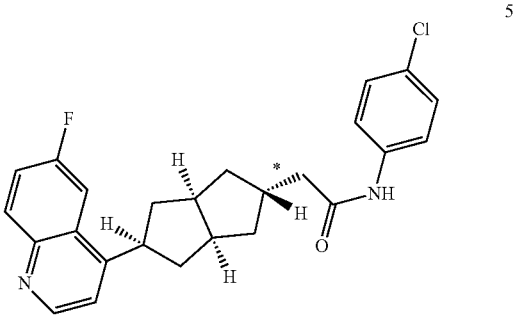 [SMILES: O=C(C[C@H]1C[C@@H]2C[C@H](c3ccnc4ccc(F)cc34)C[C@@H]2C1)Nc1ccc(Cl)cc1]

Compound 5 was prepared from compound 1k and 4-chloroaniline according the preparation method of compound 2. $^1$H NMR (500 MHz, CDCl$_3$) δ 8.79 (d, J=4.6 Hz, 1H), 8.10 (dd, J=9.2, 5.7 Hz, 1H), 7.68 (dd, J=10.5, 2.8 Hz, 1H), 7.48 (d, J=8.8 Hz, 2H), 7.47-7.44 (m, 1H), −7.34 (m, J=4.6 Hz, 1H), 7.32 (s, 1H), 7.28 (d, J=8.8 Hz, 2H), 3.48-3.40 (m, 1H), 2.81-2.75 (m, 2H), 2.57-2.54 (m, 1H), 2.41 (d, J=7.1 Hz, 2H), 2.40-2.35 (m, 2H), 1.78 (dd, J=12.8, 5.7 Hz, 2H), 1.46-1.37 (m, 4H). LCMS m/z 423.1 [M+H]$^+$.

Example 7. Preparation of Compound 6

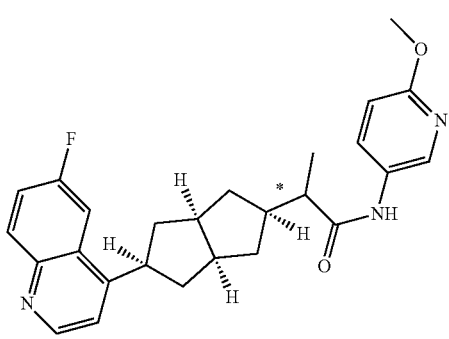

Compound 6 was prepared from compound 3b and 2-methoxy-5-amino pyridine according the preparation method of compound 3. $^1$H NMR (500 MHz, CDCl$_3$) δ 8.79 (d, J=4.5 Hz, 1H), 8.15 (d, J=2.7 Hz, 1H), 8.10 (dd, J=9.1, 5.7 Hz, 1H), 7.96 (dd, J=8.9, 2.1 Hz, 1H), 7.68 (dd, J=10.4, 2.6 Hz, 1H), 7.49-7.44 (m, 1H), 7.35 (d, J=4.5 Hz, 1H), 7.28 (s, 1H), 6.73 (d, J=8.9 Hz, 1H), 3.91 (s, 3H), 3.74-3.69 (m, 1H), 2.73-2.69 (m, 2H), 2.44-2.36 (m, 2H), 2.33-2.17 (m, 4H), 1.49 (dd, J=20.2, 12.0 Hz, 2H), 1.28 (d, J=6.7 Hz, 3H), 1.17-1.02 (m, 2H). LCMS m/z 434.2 [M+H]$^+$.

Example 8. Preparation of Compound 7

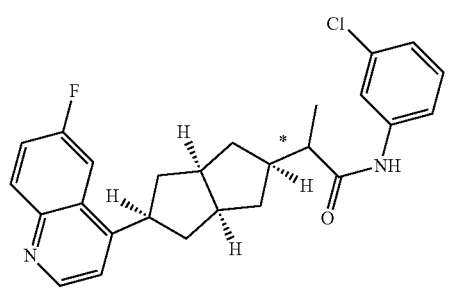

Compound 7 was prepared from compound 3b and 3-chloroaniline according the preparation method of compound 3. $^1$H NMR (500 MHz, CDCl$_3$) δ 8.80 (d, J=4.5 Hz, 1H), 8.11 (dd, J=9.2, 5.7 Hz, 1H), 7.54 (dd, J=5.8, 3.3 Hz, 2H), 7.50-7.44 (m, 1H), 7.38 (s, 1H), 7.36 (d, J=4.7 Hz, 1H), 7.24 (d, J=8.1 Hz, 1H), 7.16 (s, 1H), 7.09 (d, J=8.0 Hz, 1H), 3.80-3.68 (m, 1H), 2.78-2.66 (m, 2H), 2.46-2.16 (m, 6H), 1.54-1.41 (m, 2H), 1.28 (d, J=6.8 Hz, 3H), 1.17-1.04 (m, 2H). LCMS m/z 437.1 [M+H]$^+$.

Example 9. Preparation of Compound 8

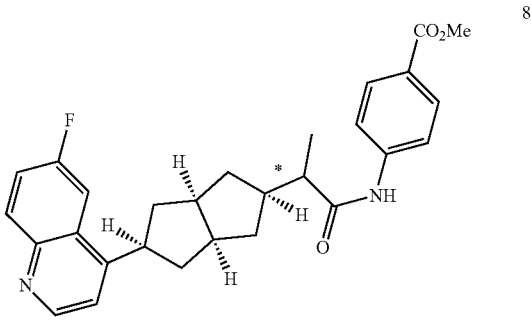 [SMILES: COC(=O)c1ccc(NC(=O)C(C)[C@H]2C[C@H]3C[C@@H](c4ccnc5ccc(F)cc45)C[C@H]3C2)cc1]

Compound 8 was prepared from compound 3b and methyl 4-aminobenzoate according the preparation method of compound 3. $^1$H NMR (500 MHz, CDCl$_3$) δ 8.79 (d, J=4.6 Hz, 1H), 8.10 (dd, J=9.2, 5.7 Hz, 1H), 8.01 (d, J=8.7 Hz, 2H), 7.68 (dd, J=10.5, 2.7 Hz, 1H), 7.63 (d, J=8.7 Hz, 2H), 7.49-7.44 (m, 1H), 7.35 (d, J=4.6 Hz, 1H), 7.33 (s, 1H), 3.90 (s, 3H), 3.77-3.69 (m, 1H), 2.73-2.67 (m, 2H), 2.45-2.20 (m, 7H), 2.03-1.98 (m, 1H), 1.29 (d, J=6.7 Hz, 3H), 1.17-1.04 (m, 2H). LCMS m/z 461.2 [M+H]$^+$.

Example 10. Preparation of Compound 9

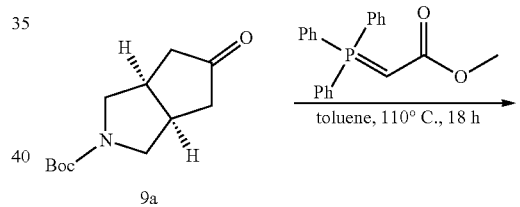

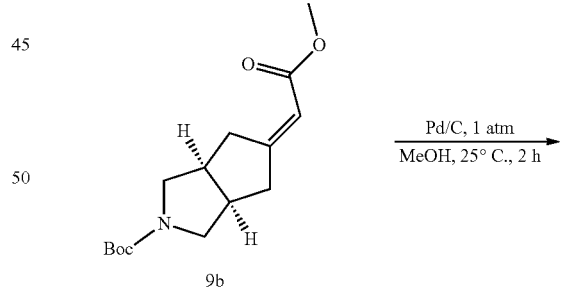

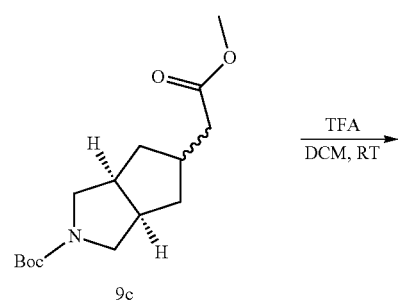

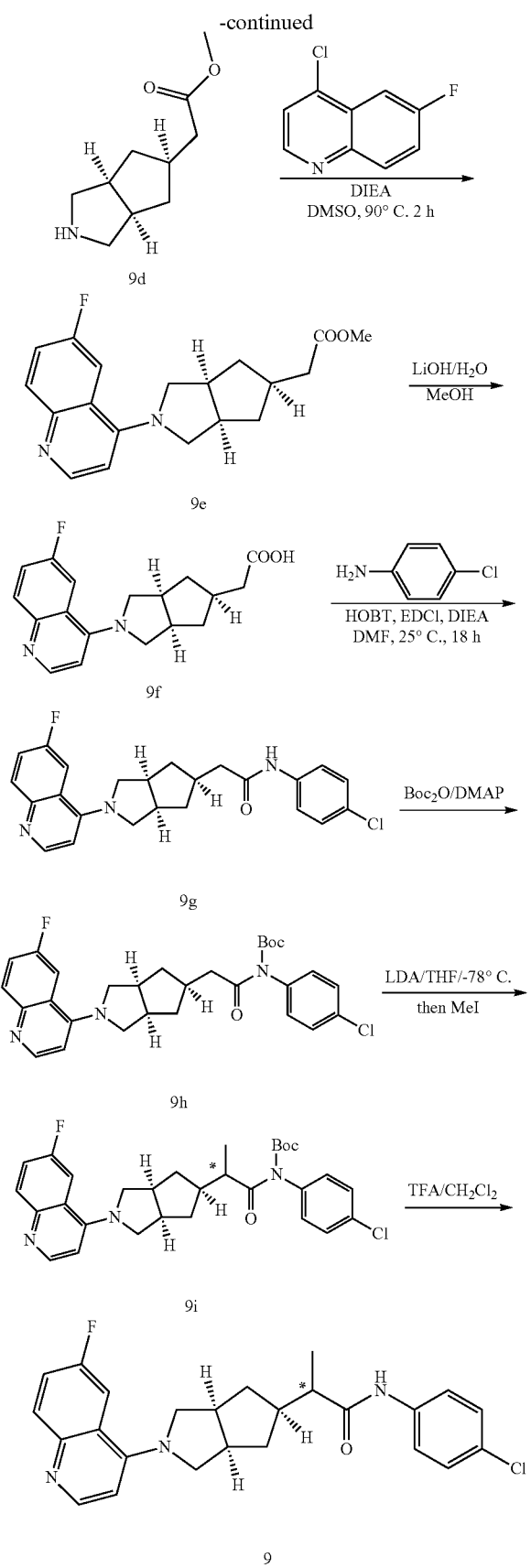

Compound 9a (1.0 g, 4.44 mmol) was dissolved in toluene (10 mL), and added Methyl (triphenylphosphoranylidene) acetate (2.23 g, 6.66 mmol). The reaction mixture was stirred for 18 hours at 110° C. in sealed tube. The reaction solution was diluted with EtOAc (50 mL), washed by brine (15 mL), the organic phase dried over $Na_2SO_4$, and filtered. The filtrate was concentrated in vacuo, the crude product was purified via column chromatography (EtOAc/petroleum ether=0-15%) to afford gray solid compound 9b (0.69 g, yield 55%).

Compound 9b (0.69 g, 2.45 mmol) was dissolved in EtOH (5 mL), then added 10% Pd/C (261 mg), the mixture was stirred overnight at 1 atm $H_2$ atmosphere, was filtrated through a celite pad to remove the Pd/C, concentrated in vacuo to afford colorless oil 9c (0.65 g, yield 94%).

Trifluoroacetic acid (1.46 mL, 23.10 mmol) was added slowly into a solution of compound 9c (0.65 g, 2.31 mmol) in $CH_2Cl_2$ (2 mL), the mixture was stirred for 30 minutes at room temperature. When the reaction was finished, it was concentrated in vacuo to afford light yellow oil 9d (0.3 g, yield 71%), the crude product was used for next step directly without further purification.

Compound 9d (0.3 g, 1.64 mmol), 4-chloro-6-fluoroquinoline (357 mg, 1.96 mmol), DIPEA (0.634 g, 4.91 mmol) were dissolved in DMSO (3 mL). The reaction mixture was heated to 90° C. in nitrogen atmosphere, and stirred for 18 hours. The reaction was concentrated in vacuo, the crude product was purified via column chromatography (EtOAc/petroleum ether=0-50%) to afford light yellow oil compound 9e (0.44 g, yield 81%). $^1H$ NMR shown that the ratio of cis/trans is almost 5:1.

LiOH (36.46 mg, 1.5 mmol) was added into a solution of 9e (50 mg, 0.15 mmol) in MeOH (2 mL)/water (0.4 mL), the mixture was stirred for 30 minutes at room temperature. TLC results indicated the reaction was complete. The reaction was added HCl solution (3N), adjusted its pH=6, extracted with EtOAc (3×5 mL), dried over $Na_2SO_4$, and filtered. The filtrate was concentrated in vacuo to afford light yellow solid compound 9f (45 mg, yield 94%). The crude product was used for next step without further purification.

Compound 9f (45 mg, 0.14 mmol), HOBT (29.4 mg, 0.21 mmol), EDCI (41.2 mg, 0.24 mmol) were dissolved in DMF (1 mL), then DIPEA (55.5 mg, 0.43 mmol) was added, the reaction mixture was stirred for 2 hours at 50° C. After concentrated in vacuo, the crude product was purified via preparative TLC (50%, EtOAc: petroleum ether) to afford compound 9g (25 mg, yield 41%).

Compound 9g (25 mg, 0.059 mmol), 4-dimethylaminopyridine (10.8 mg, 0.088 mmol), di-tert-butyl dicarbonate (19.3 mg, 0.088 mmol) were dissolved in MeCN (1 mL), and was stirred for 5 minutes at 50° C. the reaction mixture was distilled in reduce pressure. The crude product was purified via preparative TLC to afford compound 9h.

Compound 9h (15 mg, 0.028 mmol) was dissolved in THF (0.5 mL), was cooled to −20° C. at $N_2$ protection, and was added LDA (0.085 mL, 0.086 mmol) slowly. The reaction was stirred for 20 minutes at 0° C., then was cooled to −20° C., was added MeI (12 mg, 0.085 mmol), and was stirred for 20 minutes at this temperature. The reaction mixture was added saturated aq. $NH_4Cl$ (4 mL), extracted with EtOAc (3×5 mL); the combined organic phase was washed by brine (3×5 mL), dried over $Na_2SO_4$, and filtered. The filtrate was concentrated in vacuo, the crude product was purified via preparative TLC (50%, EtOAc: petroleum ether) to afford light yellow solid 9i (5 mg, yield 32%).

Compound 9i (5 mg, 9.0 mol) was dissolved in $CH_2Cl_2$ (0.5 mL), and was added HCl (4 mL, 4M dioxane solution). After stirring 20 minute, the TLC result shown the reaction finished. The reaction mixture was added saturated aq.

NaHCO$_3$ (4 mL), extracted with EtOAc (3×3 mL); the combined organic phase was dried and filtered. The filtrate was concentrated in vacuo, the resulted crude product was purified via preparative TLC (50%, EtOAc: CH$_2$Cl$_2$) to afford white solid compound 9 (0.74 mg, yield 18%). $^1$H NMR (500 MHz, CD$_3$OD) δ 8.43 (d, J=5.6 Hz, 1H), 7.93 (dd, J=5.5, 3.5 Hz, 1H), 7.90 (d, J=3.1 Hz, 1H), 7.63-7.53 (m, 2H), 7.51 (dd, J=11.8, 5.4 Hz, 1H), 7.32-7.21 (m, 2H), 6.79 (d, J=5.6 Hz, 1H), 3.69-3.46 (m, 5H), 2.93-2.77 (m, 2H), 2.45-2.10 (m, 4H), 1.47-1.38 (m, 1H), 1.25 (d, J=6.8 Hz, 3H). LCMS m/z 437.99 [M+H]$^+$.

Example 11. Preparation of Compound 10

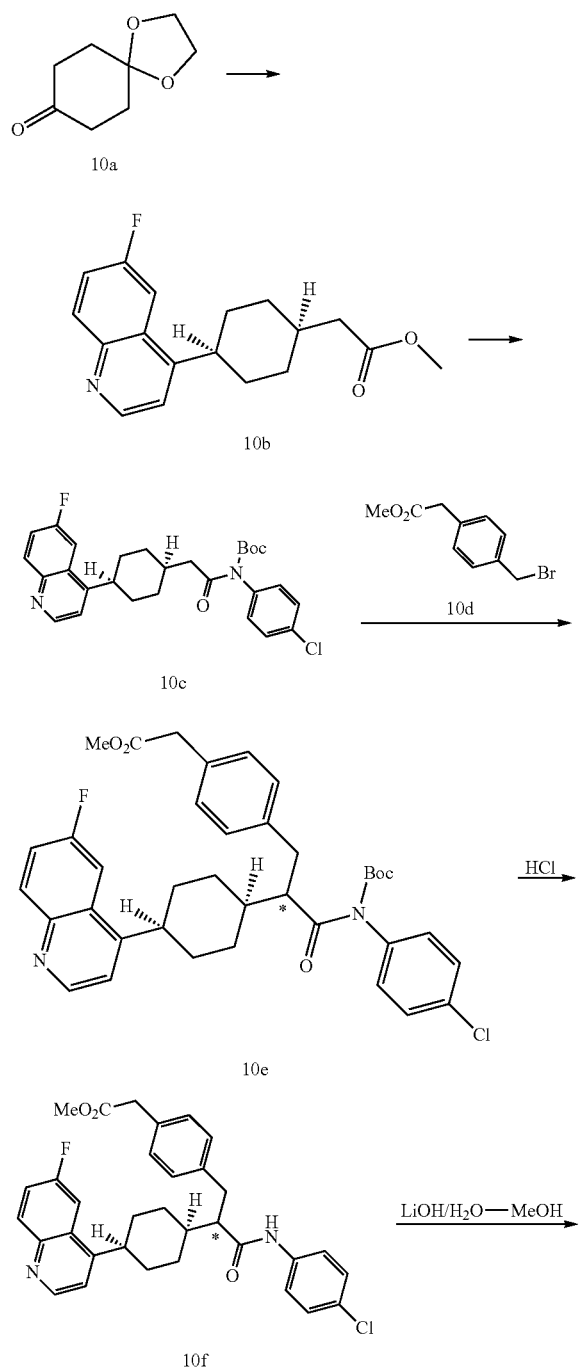

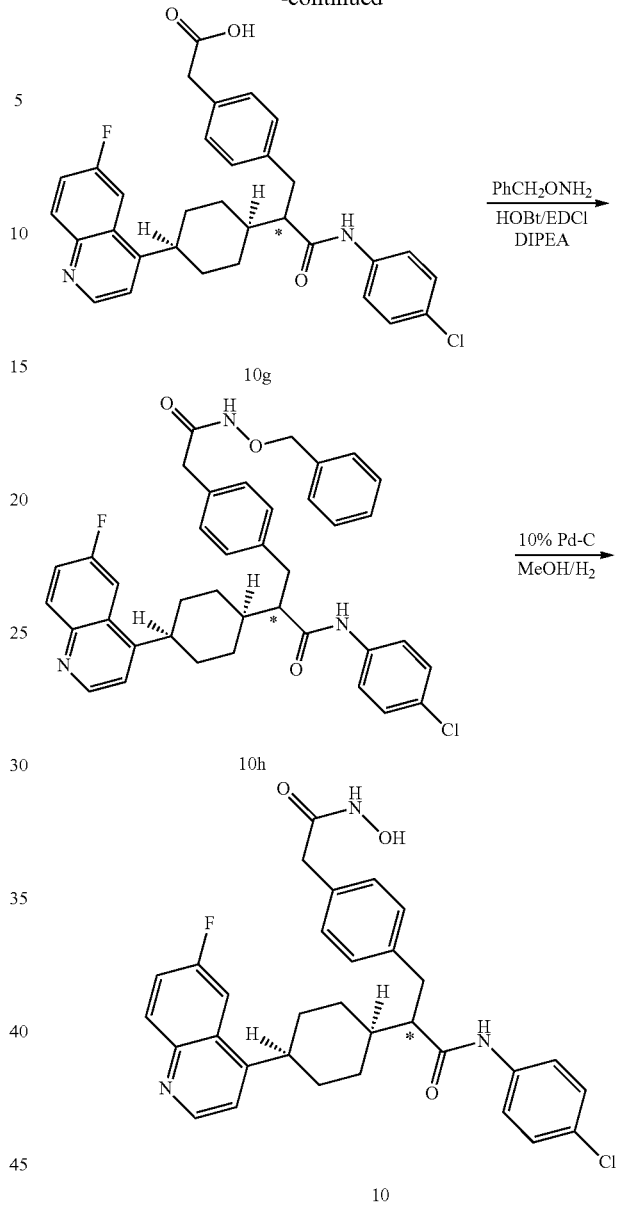

Compund 10b was prepared from compound 10a according the procedure of patent WO2016073774 and WO2016073770. Compound 10c was prepared from compound 10b (detailed procedure refer to the preparation of 1o).

Compound 10c (120 mg, 0.24 mmol) was dissolved in THF (0.5 mL), cooled to −20° C., and added LDA (0.42 mL, 0.85 mmol) slowly, and warmed to 0° C. and stirred 20 minutes, then cooled to −20° C., 10d (205 mg, 0.85 mmol) was added into the above solution, and stirred for 20 minutes at 0° C. The reaction mixture was added saturated aq. NH$_4$Cl (5 mL), extracted with EtOAc (3×10 mL); the combined organic phase was washed by brine (3×10 mL), dried over Na$_2$SO$_4$, and filtered. The filtrate was concentrated in vacuo, the resulted crude product was purified via preparative TLC (30%, EtOAc: petroleum ether) to afford light yellow solid compound 10e (76 mg, yield 40%).

Compound 10f was prepared from compound 10e (detailed procedure refer to the preparation of 1).

Compound 10g was prepared from compound 10f (detailed procedure refer to the preparation of 1m).

Compound 10g (7.8 mg, 14.31 μmol), HOBt (2.90 mg, 21.47 μmol), EDCI (4.12 mg, 21.47 μmol) and DIPEA (5.55 mg, 42.39 μmol) were dissolved in DMF (0.5 mL), then was added O-benzylhydroxylamine (2.64 mg, 21.47 mmol), and was stirred for 2 hours at room temperature. The reaction solution was concentrated in reduced pressure, the crude product was purified via preparative TLC (10%, MeOH: CH$_2$Cl$_2$) to afford colorless oil compound 10h (4.1 mg, yield 44%). LCMS m/z 650.2 [M+H]$^+$.

Compound 10h (4.1 mg, 6.31 μmol) was dissolved in MeOH (0.5 mL), added 10% Pd/C (6.71 mg, 63.06 μmol), the reaction was stirred for 10 minutes at H$_2$ atmosphere (1 atm). The TLC result shown the reaction finished. Pd/C was removed by filtration, the filtrate was concentrated in reduced pressure, the crude product was purified via preparative TLC (10%, MeOH: CH$_2$Cl$_2$) to afford compound 10 (0.51 mg, yield 14%). LCMS m/z 560.2 [M+H]$^+$.

Example 12. Preparation of Compound 11

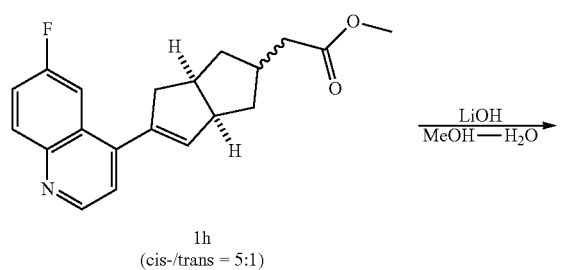

1h
(cis-/trans = 5:1)

LiOH
MeOH—H$_2$O

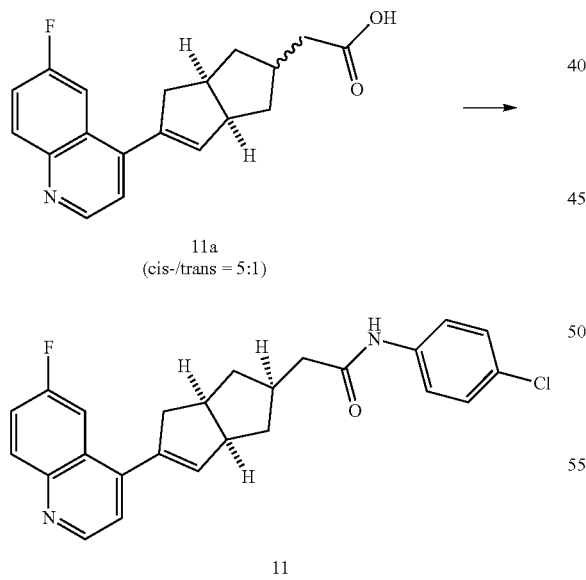

11a
(cis-/trans = 5:1)

11

Compound 11 was prepared from compound 1h, which was hydrolysis, the resulting acid 11a was condenzed with 4-chloroaniline to afford the main product, compound 11. $^1$H NMR (500 MHz, CD$_3$OD) δ 8.75 (d, J=4.6 Hz, 1H), 8.08 (dd, J=9.3, 5.5 Hz, 1H), 7.85 (dd, J=10.3, 2.8 Hz, 1H), 7.67-7.50 (m, 3H), 7.42 (d, J=4.6 Hz, 1H), 7.35-7.23 (m, 2H), 6.08 (d, J=1.6 Hz, 1H), 3.56-3.49 (m, 1H), 3.19-3.11 (m, 1H), 2.96-2.87 (m, 1H), 2.59 (d, J=16.7 Hz, 1H), 2.47 (d, J=6.5 Hz, 2H), 2.36 (dd, J=14.8, 8.2 Hz, 2H), 2.26 (dd, J=12.1, 7.0 Hz, 1H), 1.32-1.17 (m, 2H). LCMS m/z 421.2 [M+H]$^+$.

Example 13. Preparation of Compound 12

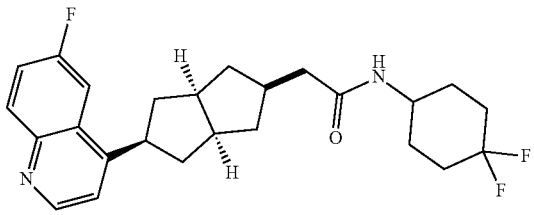

12

Compound 12 was prepared from the carbamate condensation of intermediate 1m with 4,4-difluorocyclohexamine. $^1$H NMR (500 MHz, CDCl$_3$) δ 8.79 (d, J=4.6 Hz, 1H), 8.10 (dd, J=9.2, 5.7 Hz, 1H), 7.68 (dd, J=10.4, 2.7 Hz, 1H), 7.54-7.44 (m, 1H), 7.35 (d, J=4.5 Hz, 1H), 5.29 (d, J=7.6 Hz, 1H), 3.92-3.89 (m, 1H), 3.76-3.69 (m, 1H), 2.73-2.68 (m, 2H), 2.45-2.38 (m, 3H), 2.24 (d, J=7.2 Hz, 2H), 2.21-2.16 (m, 2H), 2.10-2.08 (m, 2H), 2.02-1.97 (m, 2H), 1.93-1.79 (m, 2H), 1.54-1.46 (m, 4H), 1.08-1.01 (m, 2H). LCMS m/z 431.4 [M+H]$^+$.

Example 14. Preparation of Compound 13

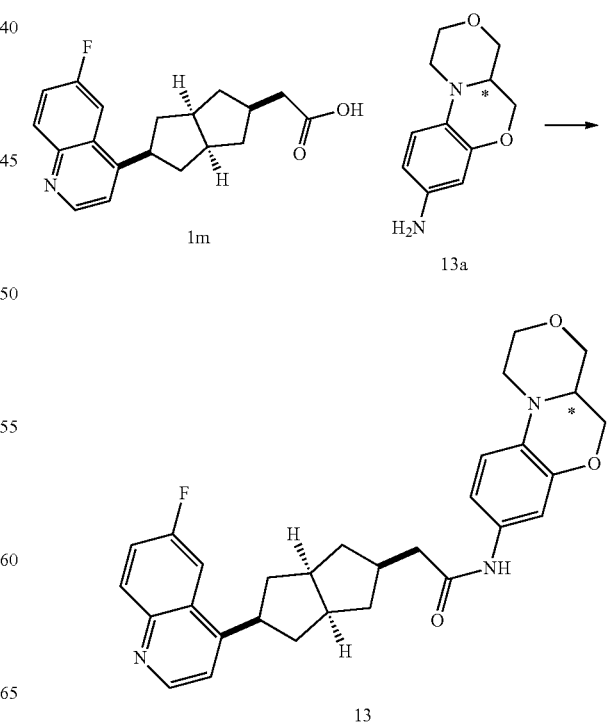

13

Compound 13 was prepared from the carbamate condensation of intermediate 1m with compound 13a. $^1$H NMR (500 MHz, CDCl$_3$) δ 8.78 (d, J=4.5 Hz, 1H), 8.11-8.08 (m, 1H), 7.67 (d, J=10.0 Hz, 1H), 7.45-7.44 (m, 1H), 7.35 (d, J=4.4 Hz, 1H), 7.09 (s, 1H), 7.02 (d, J=8.4 Hz, 1H), 6.96 (s, 1H), 6.70-6.67 (m, 1H), 4.12 (t, J=6.9 Hz, 1H), 4.03-4.02 (m, 1H), 3.95-3.91 (m, 1H), 3.85-3.84 (m, 1H), 3.75-3.70 (m, 2H), 3.49-3.44 (m, 1H), 3.28-3.24 (m, 1H), 3.18-3.17 (m, 1H), 2.84-2.80 (m, 1H), 2.76-2.66 (m, 2H), 2.54-2.48 (m, 1H), 2.41-2.38 (m, 4H), 2.25-2.23 (m, 2H), 1.52-1.46 (m, 2H), 1.12-1.06 (m, 2H). LCMS m/z 502.3 [M+H]$^+$.

Example 15. Preparation of Compound 14

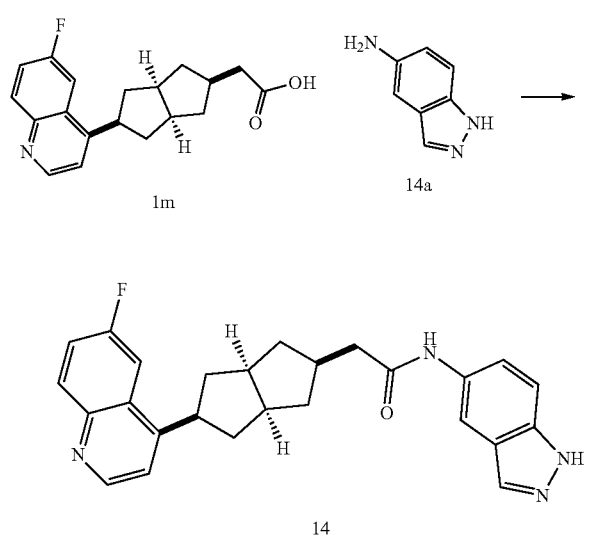

Compound 14 was prepared from the carbamate condensation of intermediate 1m with compound 14a. $^1$H NMR (500 MHz, DMSO-d$_6$) δ 12.95 (s, 1H), 9.85 (s, 1H), 8.80 (d, J=4.5 Hz, 1H), 8.11 (s, 1H), 8.07 (dd, J=9.1, 5.8 Hz, 1H), 8.00-7.97 (m, 2H), 7.67-7.64 (m, 1H), 7.53 (d, J=4.4 Hz, 1H), 7.47-7.41 (m, 2H), 3.87-3.82 (m, 1H), 2.72-2.64 (m, 3H), 2.42 (d, J=16.4 Hz, 2H), 2.33-2.32 (m, 2H), 2.12-2.09 (m, 2H), 1.51-1.45 (m, 2H), 1.15-1.09 (m, 2H). LCMS m/z 429.4 [M+H]$^+$.

Example 16. Preparation of Compound 15

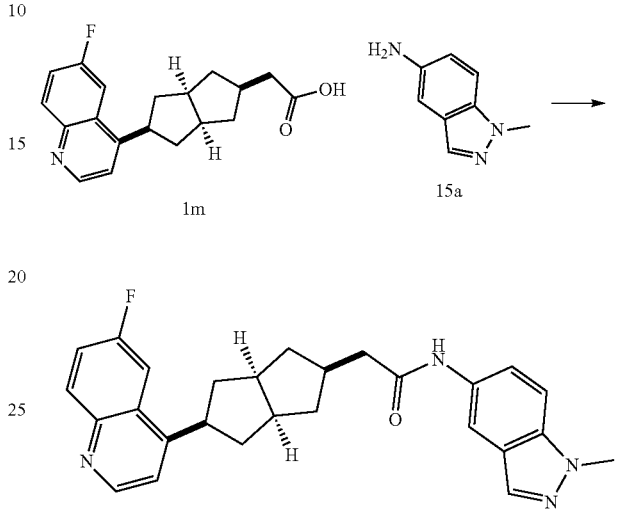

Compound 15 was prepared from the carbamate condensation of intermediate 1m with compound 15a. $^1$H NMR (500 MHz, CDCl$_3$) δ 8.79 (d, J=4.6 Hz, 1H), 8.10 (dd, J=9.2, 5.7 Hz, 1H), 7.99 (d, J=1.3 Hz, 1H), 7.91 (s, 1H), 7.68 (dd, J=10.4, 2.7 Hz, 1H), 7.48-7.31 (m, 5H), 4.05 (s, 3H), 3.77-3.69 (m, 1H), 2.74-2.70 (m, 2H), 2.58-2.55 (m, 1H), 2.47 (d, J=7.2 Hz, 2H), 2.44-2.39 (m, 2H) 2.31-2.26 (m, 2H), 1.54-1.48 (m, 2H), 1.16-1.10 (m, 2H). LCMS m/z 443.4 [M+H]$^+$.

Example 17. Preparation of Compound 16

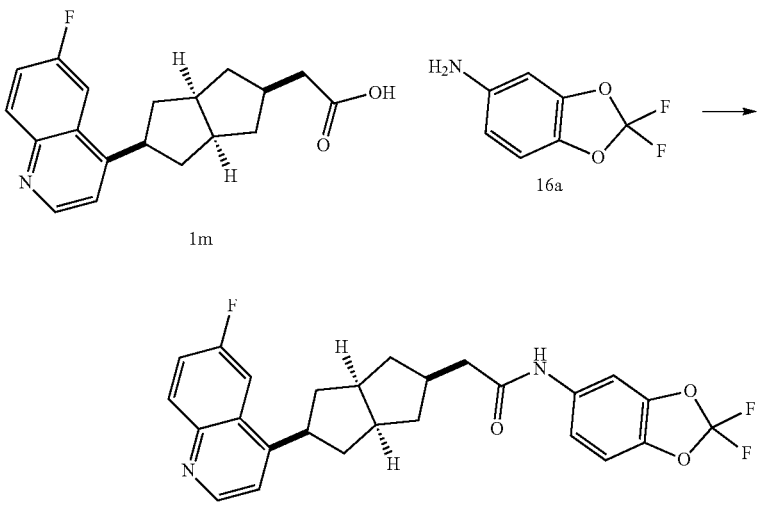

Compound 16 was prepared from the carbamate condensation of intermediate 1m with compound 16a. $^1$H NMR (500 MHz, DMSO-d$_6$) δ 10.11 (s, 1H), 8.80 (d, J=4.5 Hz, 1H), 8.07 (dd, J=9.2, 5.8 Hz, 1H), 7.98 (dd, J=10.9, 2.7 Hz, 1H), 7.78 (d, J=1.9 Hz, 1H), 7.67-7.63 (m, 1H), 7.53 (d, J=4.5 Hz, 1H), 7.33-7.32 (m, 1H), 7.24 (dd, J=8.8, 2.0 Hz, 1H), 3.87-3.80 (m, 1H), 2.66-2.64 (m, 2H), 2.39-2.31 (m, 5H), 2.10-2.07 (m, 2H), 1.50-1.44 (m, 2H), 1.10-1.06 (m, 2H). LCMS m/z 469.3 [M+H]$^+$.

Example 18. Preparation of Compound 17

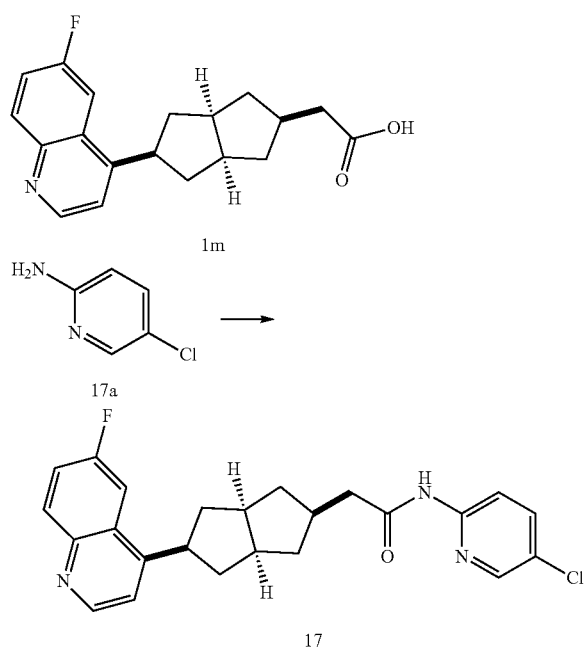

Compound 17 was prepared from the carbamate condensation of intermediate 1m with compound 17a. $^1$H NMR (500 MHz, CDCl$_3$) δ 8.81 (d, J=4.6 Hz, 1H), 8.22-8.21 (m, 2H), 8.12 (dd, J=9.2, 5.7 Hz, 1H), 7.89 (s, 1H), 7.70-7.66 (m, 2H), 7.49-7.45 (m, 1H), 7.38 (d, J=4.5 Hz, 1H), 3.77-3.70 (m, 1H), 2.76-2.71 (m, 2H), 2.57-2.51 (m, 1H), 2.49 (d, J=7.2 Hz, 2H), 2.45-2.40 (m, 2H), 2.29-2.24 (m, 2H), 1.59-1.49 (m, 2H), 1.16-1.09 (m, 2H). LCMS m/z 424.22 [M+H]$^+$.

Example 19. Preparation of Compound 18

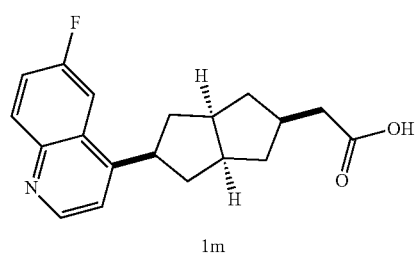

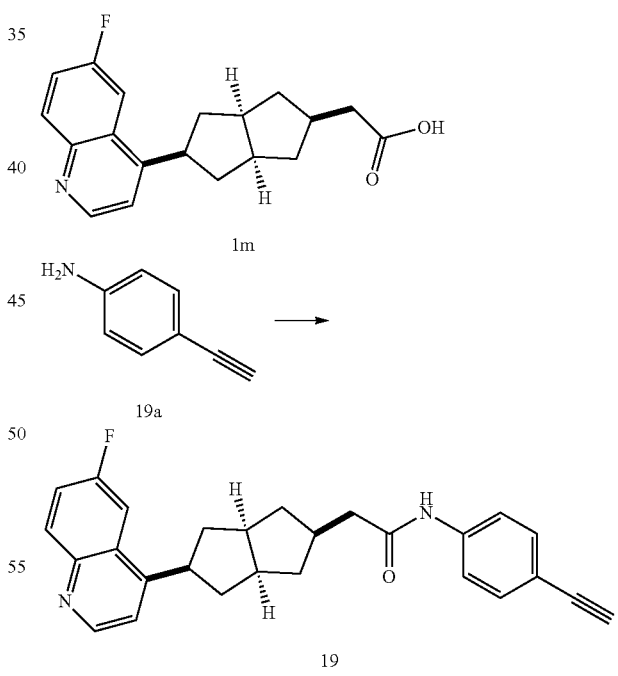

Compound 18 was prepared from the carbamate condensation of intermediate 1m with compound 18a. $^1$H NMR (500 MHz, CDCl$_3$) δ 8.81 (s, 1H), 8.36 (d, J=2.2 Hz, 1H), 8.22-8.18 (m, 2H), 7.71 (dd, J=10.1, 2.2 Hz, 1H), 7.53-7.49 (m, 1H), 7.43 (s, 1H), 7.30 (d, J=8.7 Hz, 1H), 3.80-3.73 (m, 1H), 2.78-2.73 (m, 2H), 2.55-2.50 (m, 1H), 2.49 (d, J=6.9 Hz, 2H), 2.44 (dt, J=12.4, 6.2 Hz, 2H), 2.30-2.25 (m, 2H), 1.53 (dd, J=20.0, 12.1 Hz, 2H), 1.13 (dd, J=19.3, 11.4 Hz, 2H). LCMS m/z 424.21 [M+H]$^+$.

Example 20. Preparation of Compound 19

Compound 19 was prepared from the carbamate condensation of intermediate 1m with compound 19a. $^1$H NMR (500 MHz, CDCl$_3$) δ 8.79 (d, J=4.5 Hz, 1H), 8.11 (dd, J=9.2, 5.7 Hz, 1H), 7.68 (dd, J=10.4, 2.6 Hz, 1H), 7.51 (d, J=8.4 Hz, 2H), 7.49-7.44 (m, 3H), 7.36 (d, J=4.7 Hz, 2H), 3.76-3.49 (m, 1H), 3.04 (s, 1H), 2.77-2.67 (m, 2H), 2.56-2.52 (m, 1H), 2.45 (d, J=7.1 Hz, 2H), 2.43-2.37 (m, 2H), 2.28-2.23 (m, 2H), 1.53-1.48 (m, 2H), 1.13-1.07 (m, 2H). LCMS m/z 413.29 [M+H]⁺.

Example 21. Preparation of Compound 20

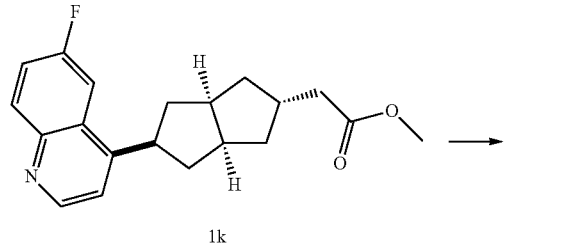

1k

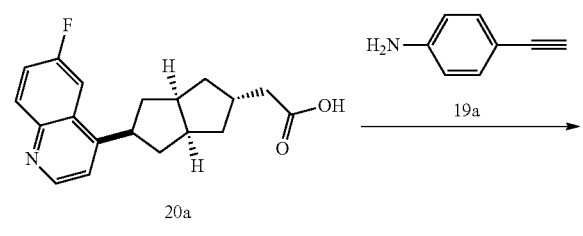

20a

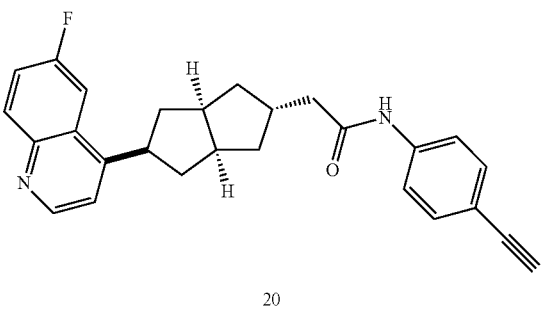

20

Compound 20 was prepared by carbamate condensation reaction of compound 19a and compound 20a which was obtained by hydrolysis of compound 1k. ¹H NMR (500 MHz, CDCl₃) δ 8.79 (d, J=4.5 Hz, 1H), 8.11 (dd, J=9.2, 5.7 Hz, 1H), 7.69 (dd, J=10.5, 2.7 Hz, 1H), 7.52 (d, J=8.5 Hz, 2H), 7.48-7.45 (m, 3H), 7.35 (d, J=4.6 Hz, 1H), 7.33 (s, 1H), 3.48-3.41 (m, 1H), 3.05 (s, 1H), 2.82-2.74 (m, 2H), 2.62-2.52 (m, 1H), 2.43 (d, J=7.1 Hz, 2H), 2.41-2.35 (m, 2H), 1.79 (dd, J=12.8, 5.7 Hz, 2H), 1.47-1.37 (m, 4H). LCMS m/z 413.30 [M+H]⁺.

Example 22. Preparation of Compound 21

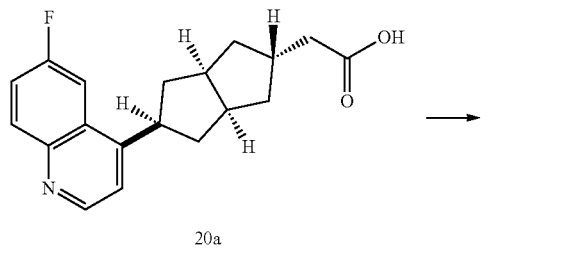

20a

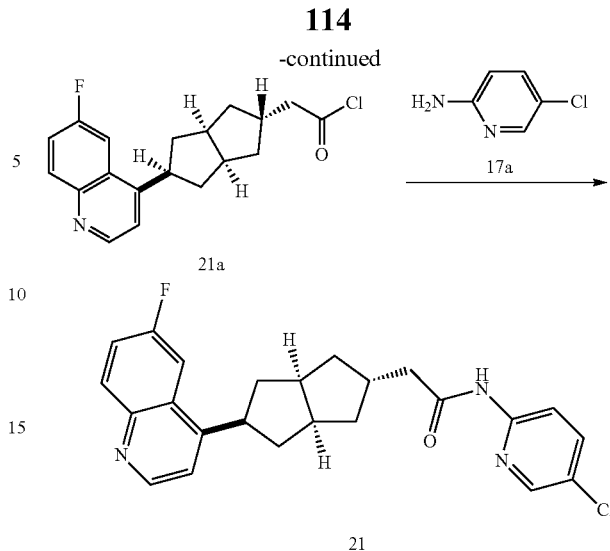

Compound 20a (150 mg, 0.479 mmol) was dissolved in SOCl₂ (5 mL), and the reaction was heated to 50° C. and stirred for 30 minutes. The reaction was concentrated in reduced pressure to afford white solid compound 21a (150 mg, yield 94.3%). The crude product was used directly for next step without further purification.

2-amino-5-chloropyridine (17a, 15 mg, 0.117 mmol) was dissolved in THF (1.0 mL), and was slowly added NaH (60%, 4.7 mg, 0.117 mmol) in ice-water batch, the reaction was slowly warmed to room temperature and stirred for 1 hour, then was added the THF solution (1 mL) of compound 20b (38.71 mg, 0.117 mmol) slowly, heated to 60° C. and stirred for 6 hours. The reaction solution was poured into saturated aq. NaHCO₃, extracted with EtOAc (3×2 mL), the combined organic phase was washed by brine (15 mL), dried over Na₂SO₄ and filtered. The filtrate was concentrated in vacuo, the residue was purified via column chromatography (EtOAc/petroleum ether=0-5%) to afford white solid compound 21 (9.87 mg, yield 20%). ¹H NMR (500 MHz, CDCl₃) δ 8.81 (d, J=4.6 Hz, 1H), 8.24-8.19 (m, 3H), 7.96 (s, 1H), 7.72 (dd, J=10.3, 1.7 Hz, 1H), 7.68 (dd, J=8.9, 2.4 Hz, 1H), 7.52-7.48 (m, 1H), 7.41 (s, 1H), 3.51-3.44 (m, 1H), 2.84-2.76 (m, 2H), 2.61-2.52 (m, 1H), 2.47 (d, J=7.1 Hz, 2H), 2.42-2.36 (m, 2H), 1.80 (dd, J=12.8, 5.7 Hz, 2H), 1.44 (dt, J=19.9, 12.8 Hz, 4H). LCMS m/z 424.20 [M+H]⁺.

Example 23. Preparation of Compound 22

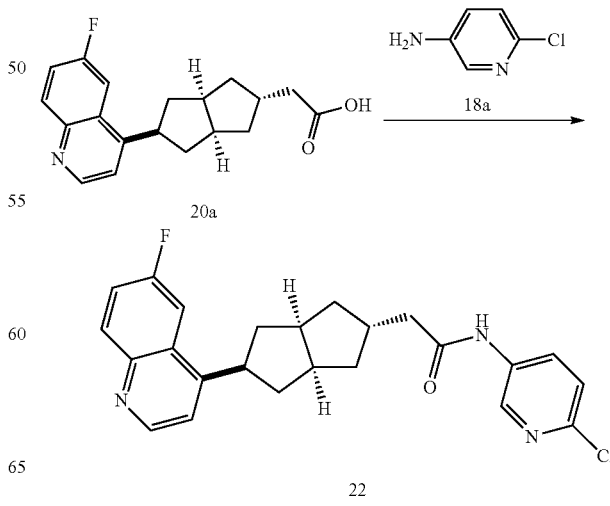

Compound 22 was prepared from the carbamate condensation of intermediate 20a with compound 18a. $^1$H NMR (500 MHz, CDCl$_3$) δ 8.79 (d, J=4.5 Hz, 1H), 8.36 (d, J=2.7 Hz, 1H), 8.19 (dd, J=8.6, 2.5 Hz, 1H), 8.12 (dd, J=9.1, 5.7 Hz, 1H), 7.69 (dd, J=10.4, 2.6 Hz, 1H), 7.48 (dd, J=8.6, 2.0 Hz, 1H), 7.40 (s, 1H), 7.36 (d, J=4.5 Hz, 1H), 7.30 (d, J=8.7 Hz, 1H), 3.49-3.42 (m, 1H), 2.84-2.73 (m, 2H), 2.62-2.50 (m, 1H), 2.46 (d, J=7.0 Hz, 2H), 2.42-2.38 (m, 2H), 1.79 (dd, J=12.7, 5.7 Hz, 2H), 1.49-1.35 (m, 4H). LCMS m/z 424.26 [M+H]$^+$.

Example 24. Preparation of Compound 23

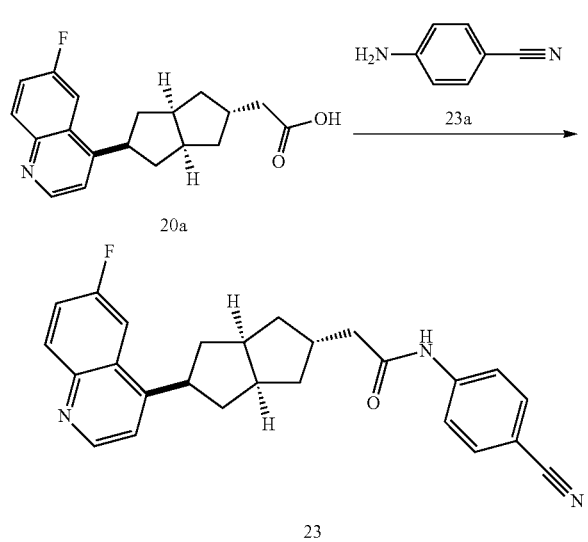

23

Compound 23 was prepared from the carbamate condensation of intermediate 20a with compound 23a. $^1$H NMR (500 MHz, CDCl$_3$) δ 8.78 (d, J=4.3 Hz, 1H), 8.14 (s, 1H), 7.70-7.68 (m, 3H), 7.63-7.57 (m, 2H), 7.51-7.43 (m, 1H), 7.37 (d, J=4.0 Hz, 1H), 7.32 (s, 1H), 3.50-3.41 (m, 1H), 2.83-2.74 (m, 2H), 2.60-2.52 (m, 1H), 2.45 (d, J=7.1 Hz, 2H), 2.42-2.35 (m, 2H), 1.79 (dd, J=12.8, 5.7 Hz, 2H), 1.46-1.38 (m, 4H). LCMS m/z 414.24 [M+H]$^+$.

Example 25. Preparation of Compound 24

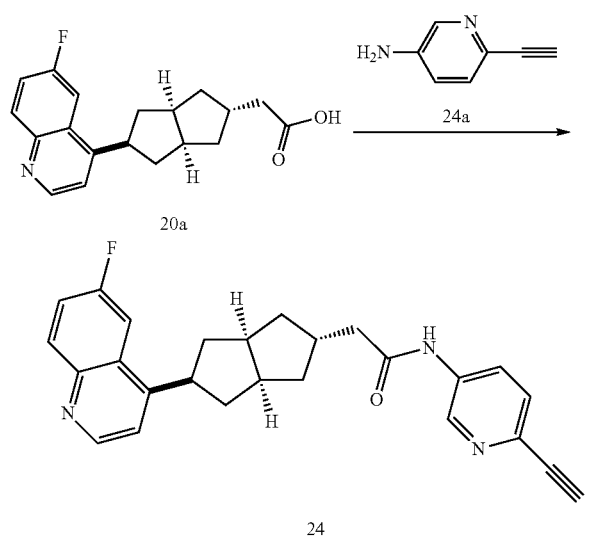

24

Compound 24 was prepared from the carbamate condensation of intermediate 20a with compound 24a. $^1$H NMR (500 MHz, CDCl$_3$) δ 8.78 (d, J=4.6 Hz, 1H), 8.49 (d, J=2.4 Hz, 1H), 8.24 (dd, J=8.5, 2.2 Hz, 1H), 8.16 (s, 1H), 7.69 (dd, J=10.4, 2.7 Hz, 1H), 7.50-7.44 (m, 2H), 7.38 (d, J=4.3 Hz, 1H), 7.30 (s, 1H), 3.50-3.41 (m, 1H), 3.11 (s, 1H), 2.78 (dd, J=12.9, 7.2 Hz, 2H), 2.60-2.52 (m, 1H), 2.46 (d, J=7.0 Hz, 2H), 2.42-2.35 (m, 2H), 1.79 (dd, J=12.8, 5.7 Hz, 2H), 1.46-1.38 (m, 4H). LCMS m/z 207.78 [½M+H]$^+$.

Example 26. Preparation of Compound 25

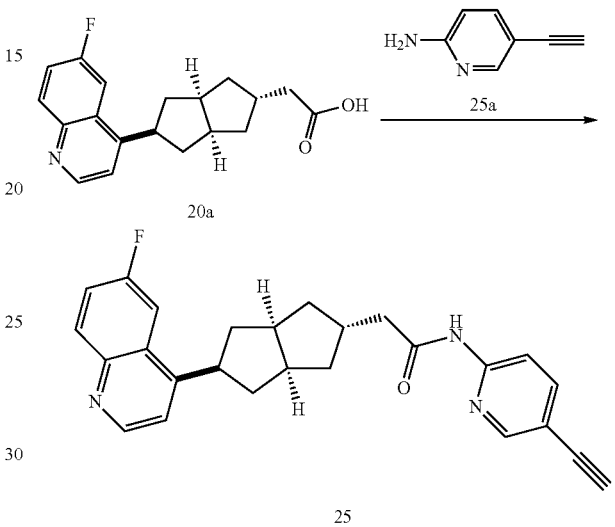

25

Compound 25 was prepared from the carbamate condensation of intermediate 20a with compound 25a. $^1$H NMR (500 MHz, CDCl$_3$) δ 8.72 (d, J=4.6 Hz, 1H), 8.31 (d, J=1.6 Hz, 1H), 8.14 (d, J=8.7 Hz, 1H), 8.06 (dd, J=8.7, 5.8 Hz, 1H), 7.85 (s, 1H), 7.72 (dd, J=8.6, 2.1 Hz, 1H), 7.62 (dd, J=10.4, 2.7 Hz, 1H), 7.45-7.37 (m, 1H), 7.30 (d, J=4.5 Hz, 1H), 3.42-3.35 (m, 1H), 3.09 (s, 1H), 2.76-2.67 (m, 2H), 2.53-2.46 (m, 1H), 2.40 (d, J=7.1 Hz, 2H), 2.32 (dd, J=11.8, 6.5 Hz, 2H), 1.72 (dd, J=12.8, 5.7 Hz, 2H), 1.41-1.29 (m, 4H). LCMS m/z 414.28 [M+H]$^+$.

Example 27. Preparation of Compound 26

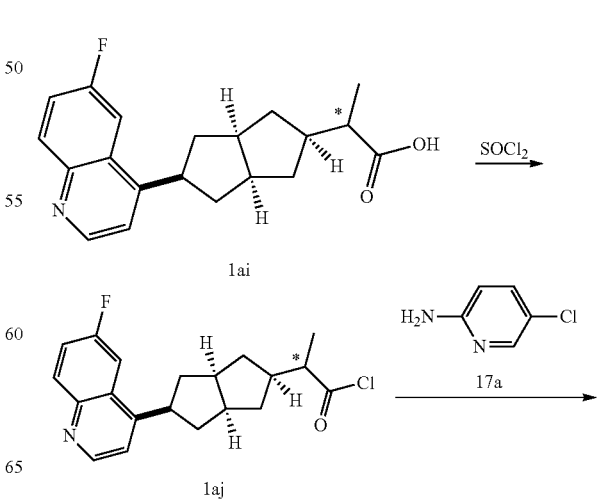

-continued

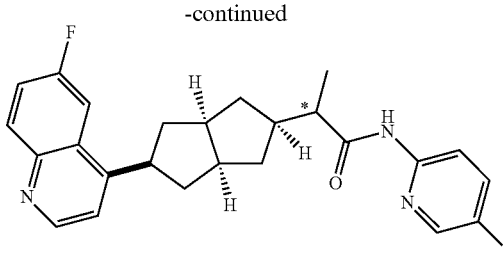

26

Compound 1ai (300 mg, 0.92 mmol) was dissolved in SOCl$_2$ (5 mL), and the reaction was heated to 50° C. and stirred for 30 minutes. The reaction was concentrated in reduced pressure to afford white solid compound 1aj (300 mg, yield 95%), the crude product was used directly for next step without further purification.

2-Amino-5-chloropyridine (17a, 45 mg, 0.35 mmol) was dissolved in THF (3 mL), and was added NaH (60%, 14 mg, 0.35 mmol) slowly in ice-water batch, the reaction was slowly warmed to room temperature and stirred for 1 hour, then was added the THF solution (2 mL) of compound 1aj (100 mg, 0.29 mmol) slowly, heated to 60° C. and stirred for 6 hours. The reaction solution was poured into saturated aq. NaHCO$_3$, extracted with EtOAc (3×5 mL), the combined organic phase was dried over Na$_2$SO$_4$ and filtered. The filtrate was concentrated in vacuo, the residue was purified via column chromatography (EtOAc/petroleum ether=0-5%) to afford white solid compound 26 (54 mg, yield 43%). $^1$H NMR (500 MHz, CD$_3$OD) δ 8.72 (d, J=4.7 Hz, 1H), 8.26 (d, J=2.6 Hz, 1H), 8.13 (d, J=8.9 Hz, 1H), 8.05 (dd, J=9.2, 5.6 Hz, 1H), 7.88 (dd, J=10.6, 2.7 Hz, 1H), 7.77 (dd, J=8.9, 2.5 Hz, 1H), 7.59-7.54 (m, 2H), 3.94-3.83 (m, 1H), 2.77-2.71 (m, 2H), 2.49-2.37 (m, 3H), 2.31-2.24 (m, 2H), 2.06-2.02 (m, 1H), 1.60-1.51 (m, 2H), 1.22 (d, J=6.8 Hz, 3H), 1.18-1.09 (m, 2H). LCMS m/z 438.26 [M+H]$^+$.

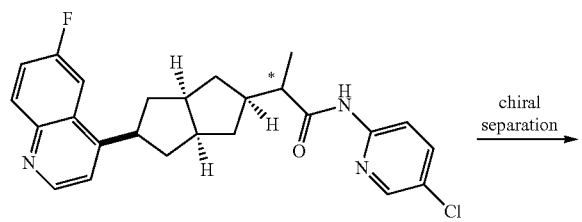

26 chiral separation

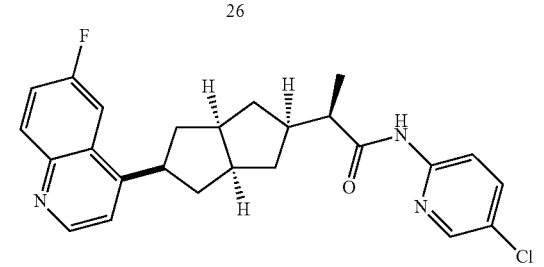

26A

+

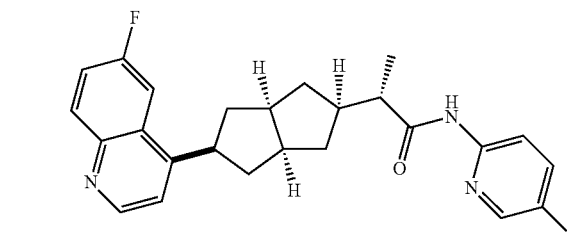

26B

The racemic compound 26 was resoluted by chiral SFC to afford 26A and 26B. The preparation SFC condition: instrument: SFC-80 (Thar, Waters); chiral column: CHIRALCEL AS-3 (30*250 mm 5 μm) (Daicel); column temperature: 35° C.; fluid speed: 45 mL/min; detection wavelength: 215 nm; fluid phase A: CO$_2$; fluid phase B: MeOH. 20% B constant elution. Peak 1: 15-17.5 min; Peak 2: 20-23 min. The absolute stereochemistry of peak 1 and peak 2 were not confirmed.

Peak 1 compound: $^1$H NMR (500 MHz, CD$_3$OD) δ 8.74 (d, J=4.7 Hz, 1H), 8.27 (d, J=2.6 Hz, 1H), 8.15 (d, J=8.9 Hz, 1H), 8.06 (dd, J=9.2, 5.6 Hz, 1H), 7.89 (dd, J=10.6, 2.7 Hz, 1H), 7.78 (dd, J=8.9, 2.6 Hz, 1H), 7.61-7.57 (m, 1H), 7.55 (d, J=4.8 Hz, 1H), 3.91-3.84 (m, 1H), 2.82-2.64 (m, 2H), 2.53-2.36 (m, 3H), 2.33-2.20 (m, 2H), 2.13-2.01 (m, 1H), 1.62-1.48 (m, 2H), 1.23 (d, J=6.8 Hz, 3H), 1.17-1.08 (m, 1H). LCMS m/z 438.1 [M+H]$^+$. e.e. value 99.8%.

Peak 2 compound: $^1$H NMR (500 MHz, CD$_3$OD) δ 8.75 (d, J=4.7 Hz, 1H), 8.29 (d, J=2.6 Hz, 1H), 8.16 (d, J=8.9 Hz, 1H), 8.07 (dd, J=9.2, 5.6 Hz, 1H), 7.91 (dd, J=10.6, 2.8 Hz, 1H), 7.79 (dd, J=8.9, 2.6 Hz, 1H), 7.62-7.58 (m, 1H), 7.57 (d, J=4.9 Hz, 1H), 3.93-3.86 (m, 1H), 2.83-2.70 (m, 2H), 2.55-2.38 (m, 3H), 2.33-2.21 (m, 2H), 2.12-2.04 (m, 1H), 1.62-1.54 (m, 2H), 1.25 (d, J=6.8 Hz, 3H), 1.16-1.09 (m, 1H). LCMS m/z 438.1 [M+H]$^+$. e.e. value 99.0%.

Example 28. Preparation of Compound 27

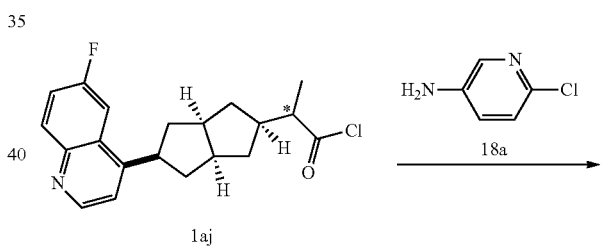

1aj

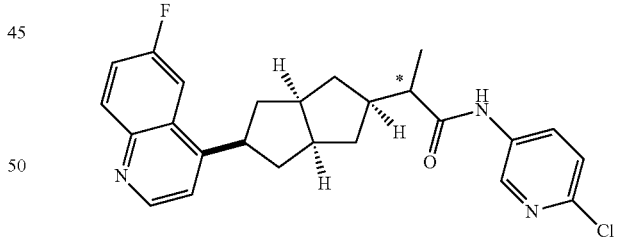

27

Compound 27 was prepared from the carbamate condensation of intermediate 1aj with compound 18a. $^1$H NMR (500 MHz, CDCl$_3$) δ 8.80 (d, J=4.5 Hz, 1H), 8.36 (d, J=2.7 Hz, 1H), 8.21 (d, J=8.7 Hz, 1H), 8.10 (dd, J=9.2, 5.7 Hz, 1H), 7.68 (dd, J=10.4, 2.6 Hz, 1H), 7.49-7.45 (m, 1H), 7.35-7.34 (m, 1H), 7.31-7.29 (m, 1H), 7.22 (s, 1H), 3.78-3.69 (m, 1H), 2.76-2.67 (m, 2H), 2.45-2.40 (m, 2H), 2.30-2.22 (m, 3H), 2.17-2.15 (m, 1H), 1.51-1.50 (m, 2H), 1.28 (d, J=9.0 Hz, 3H), 1.14-1.06 (m, 2H). LCMS m/z 438.28 [M+H]$^+$.

Example 29. Preparation of Compound 28

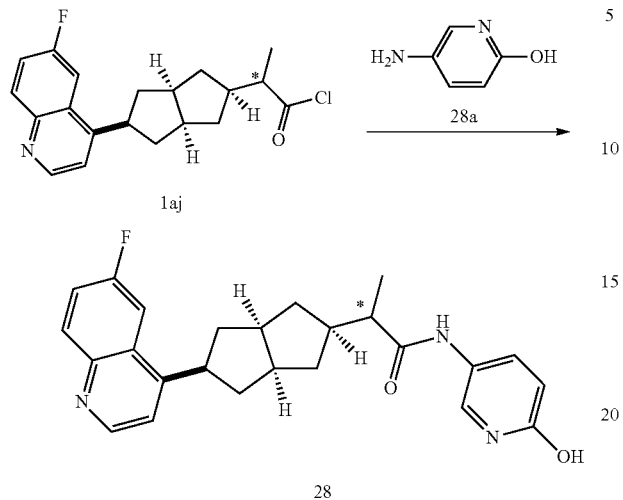

Compound 28 was prepared from the carbamate condensation of intermediate 1aj with compound 28a. $^1$H NMR (500 MHz, CD$_3$OD) δ 8.76 (d, J=4.7 Hz, 1H), 8.08 (dd, J=9.3, 5.5 Hz, 1H), 8.03-8.01 (m, 1H), 7.92 (dd, J=10.6, 2.7 Hz, 1H), 7.62-7.27 (m, 3H), 6.57 (d, J=9.8 Hz, 1H), 3.93-3.88 (m, 1H), 2.85-2.74 (m, 2H), 2.47-2.43 (m, 2H), 2.36-2.25 (m, 3H), 2.11-2.07 (m, 1H), 1.62-1.55 (m, 2H), 1.24 (d, J=6.7 Hz, 3H), 1.21-1.12 (m, 2H). LCMS m/z 420.30 [M+H]$^+$.

Example 30. Preparation of Compound 29

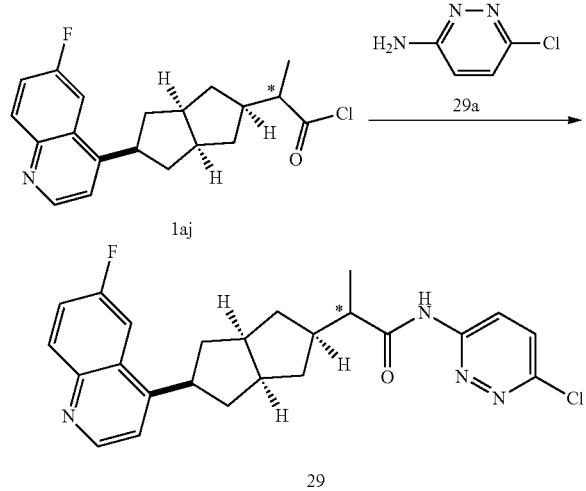

Compound 29 was prepared from the carbamate condensation of intermediate 1aj with compound 29a. $^1$H NMR (500 MHz, CDCl$_3$) δ 8.80 (d, J=4.6 Hz, 1H), 8.65 (s, 1H), 8.55 (d, J=9.3 Hz, 1H), 8.10 (dd, J=9.2, 5.7 Hz, 1H), 7.67 (dd, J=10.4, 2.7 Hz, 1H), 7.52 (d, J=9.4 Hz, 1H), 7.48-7.44 (m, 1H), 7.36 (d, J=4.5 Hz, 1H), 3.75-3.71 (m, 1H), 2.72-2.70 (m, 2H), 2.44-2.38 (m, 2H), 2.35-2.20 (m, 3H), 2.16-2.13 (m, 1H), 1.52-1.50 (m, 2H), 1.30 (d, J=8.9 Hz, 3H), 1.18-1.19 (m, 2H). LCMS m/z 439.26 [M+H]$^+$.

Example 31. Preparation of Compound 30

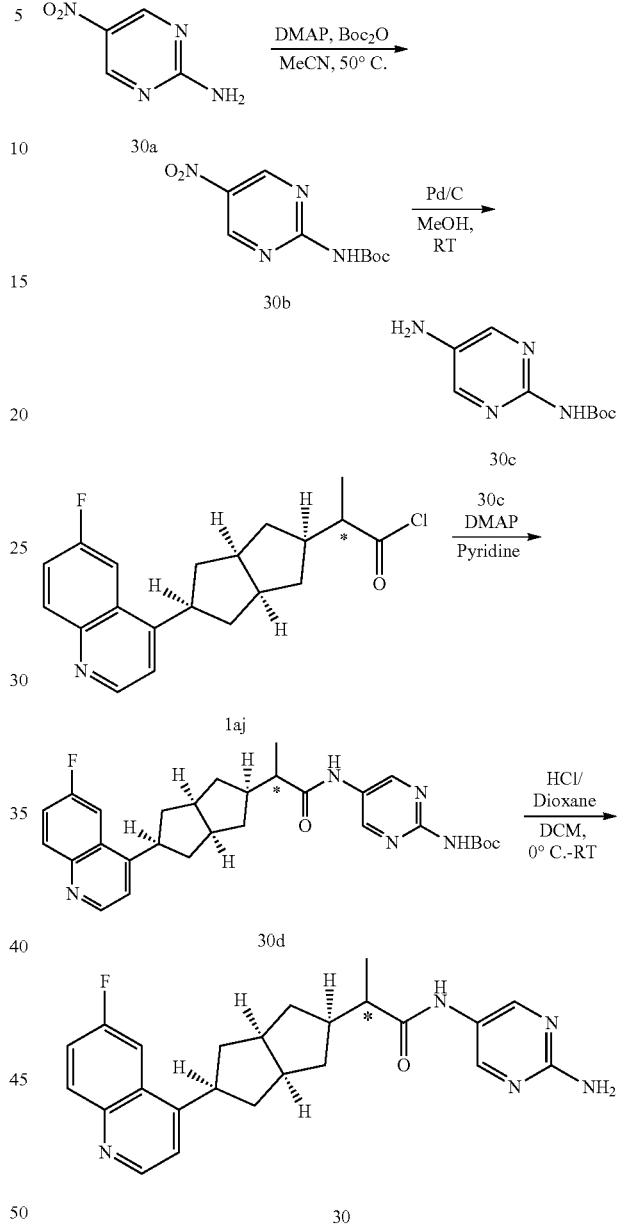

Compound 30a (300 mg, 2.14 mmol) and 4-dimethylaminopyridine (314 mg, 2.57 mmol) were dissolved in MeCN (2 mL), and was added di-tert-butyl dicarbonate (19.3 mg, 0.088 mmol) at room temperature. The reaction was heated to 50° C. and stirred for 30 minutes. The reaction solution was concentrated in reduced pressure, and purified via column chromatography (EtOAc/petroleum ether=0-20%) to afford yellow solid compound 30b (120 mg, yield 24%).

Compound 30b (120 mg, 0.5 mmol) was dissolved in MeOH (2 mL), and added 10% Pd/C (10 mg, 0.1 mmol), the reaction was stirred for 3 hours at H$_2$ atmosphere. The reaction was filtrated, concentrated in reduced pressure, and purified via preparative TLC (20%, EtOAc/petroleum ether) to afford yellow solid compound 30c (87 mg, yield 83%).

Compound 1aj (20 mg, 0.062 mmol), compound 30c (16 mg, 0.073 mmol), 4-dimethylaminopyridine (8 mg, 0.0062 mmol) were dissolved pyridine (2 mL), and stirred for 18 hours at 100° C. The reaction was concentrated in reduced pressure, crude product was purified via preparative TLC (50%, EtOAc/petroleum ether) to afford white solid compound 30d (2 mg, yield 6%).

Compound 30d (4 mg, 0.0039 mmol) was dissolved in CH₂Cl₂ (0.5 mL), and slowly added HCl (0.5 mL, 4N dioxane solution) in ice-water batch. The reaction was adjusted its pH value to almost 7 by using saturated aq. NaHCO₃, extracted with EtOAc (3×5 mL), the combined organic phase was dried over Na₂SO₄, and filtered. The filtrate was concentrated in vacuo, and purified via preparative TLC (50%, EtOAc/petroleum ether) to afford white solid compound 30 (0.99 mg, yield 61%). ¹H NMR (500 MHz, CDCl₃) δ 8.81 (s, 1H), 8.79 (d, J=4.6 Hz, 1H), 8.10 (dd, J=9.2, 5.7 Hz, 1H), 7.68 (dd, J=10.4, 2.7 Hz, 1H), 7.48-7.44 (m, 2H), 7.35 (d, J=4.6 Hz, 1H), 7.25 (s, 2H), 3.78-3.69 (m, 1H), 2.74-2.68 (m, 2H), 2.46-2.14 (m, 6H), 1.50-1.46 (m, 2H), 1.28 (d, J=7.1 Hz, 3H), 1.16-1.05 (m, 2H). LCMS m/z 420.32 [M+H]⁺.

Example 32. Preparation of Compound 31

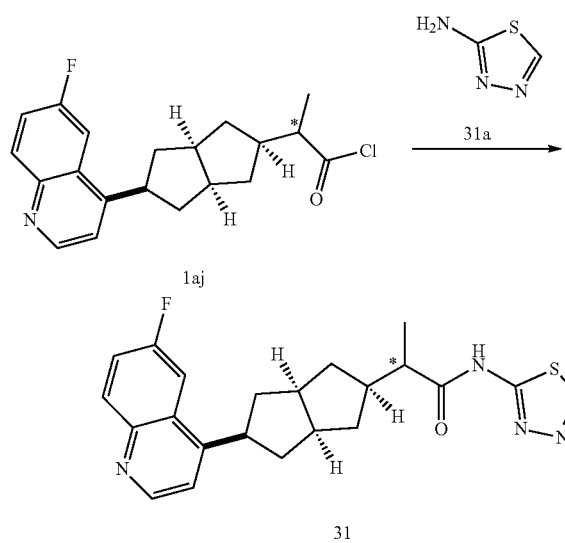

Intermediate 1aj and compound 31a reacted to afford compound 31b, which was de-protected in acid condition to obtain compound 31. ¹H NMR (500 MHz, CDCl₃) δ 13.12 (s, 1H), 8.80 (s, 1H), 8.77 (d, J=4.5 Hz, 1H), 8.09 (dd, J=9.2, 5.7 Hz, 1H), 7.66 (dd, J=10.4, 2.5 Hz, 1H), 7.47-7.43 (m, 1H), 7.31 (d, J=4.5 Hz, 1H), 3.73-3.68 (m, 1H), 2.99-2.93 (m, 1H), 2.73-2.63 (m, 2H), 2.44-2.39 (m, 2H), 2.34-2.28 (m, 2H), 2.10-2.05 (m, 1H), 1.58-1.42 (m, 2H), 1.35 (d, J=6.8 Hz, 3H), 1.27-1.22 (m, 2H). LCMS m/z 411.30 [M+H]⁺.

Example 33. Preparation of Compound 32

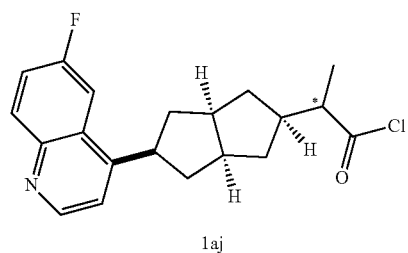

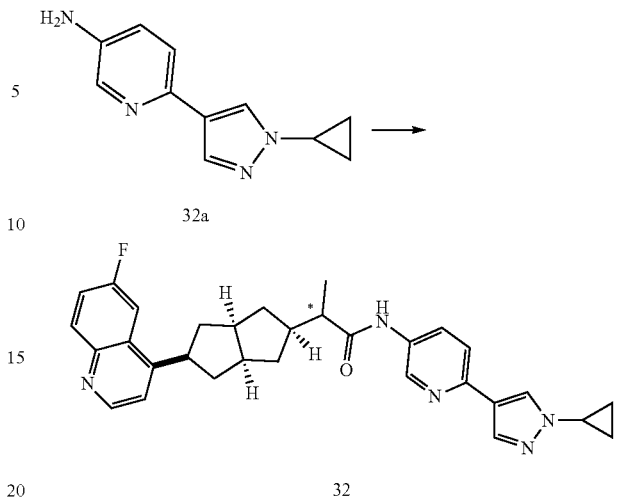

Compound 32a was prepared according to WO2017/024996A1. Pyrazole-4-boronic acid pinacol ester (100 mg, 0.42 mmol), 5-amino-2-bromopyridine (62 mg, 0.36 mmol), Pd(dppf)₂Cl₂ (26 mg, 0.036 mmol) and K₂CO₃ (60 mg, 0.42 mmol) were dissolved in dioxane (2 mL), the reaction solution was heated to 100° C. and stirred for 2 hours under the N₂ protection. The reaction solution was extracted with EtOAc (3×10 mL), the combined organic phase was dried over Na₂SO₄, and filtered. The filtrate was concentrated in vacuo, and purified via column chromatography (EtOAc/petroleum ether=0-30%) to afford yellow solid compound 32a (50 mg, yield 70%).

Intermediate 1aj and compound 32a reacted to afford compound 32. ¹H NMR (500 MHz, CDCl₃) δ 8.80 (d, J=4.4 Hz, 1H), 8.54 (s, 1H), 8.31 (s, 1H), 8.14-8.11 (m, 1H), 8.05 (s, 1H), 7.92 (s, 1H), 7.68 (dd, J=10.4, 1.9 Hz, 1H), 7.48-7.46 (m, 2H), 7.37 (d, J=4.6 Hz, 1H), 3.75-3.71 (m, 1H), 3.65-3.64 (m, 1H), 2.75-2.69 (m, 2H), 2.44-2.40 (m, 2H), 2.36-2.16 (m, 4H), 1.53-1.49 (m, 2H), 1.30 (d, J=6.1 Hz, 3H), 1.22-1.17 (m, 3H), 1.13-1.05 (m, 3H). LCMS m/z 510.31 [M+H]⁺.

Example 34. Preparation of Compound 33

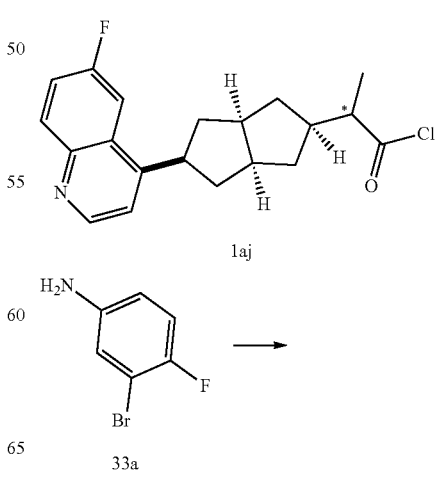

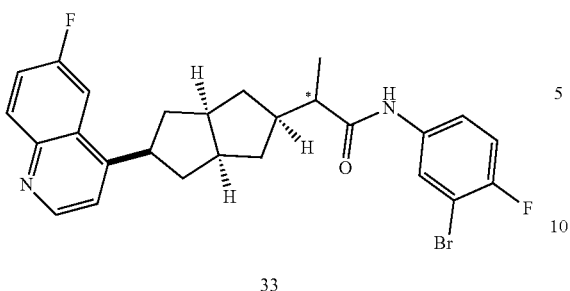

33

Intermediate 1aj and compound 33a reacted to afford compound 33. $^1$H NMR (500 MHz, CDCl$_3$) δ 8.80 (d, J=4.5 Hz, 1H), 8.13 (dd, J=9.1, 5.7 Hz, 1H), 7.89 (dd, J=5.7, 2.2 Hz, 1H), 7.69 (dd, J=10.3, 2.5 Hz, 1H), 7.50-7.37 (m, 3H), 7.17 (s, 1H), 7.09-7.06 (m, 1H), 3.78-3.71 (m, 1H), 2.74-2.71 (m, 2H), 2.48-2.16 (m, 6H), 1.54-1.48 (m, 2H), 1.28 (d, J=6.7 Hz, 3H), 1.17-1.04 (m, 2H). LCMS m/z 501.15 [M+H]$^+$.

Example 35. Preparation of Compound 34

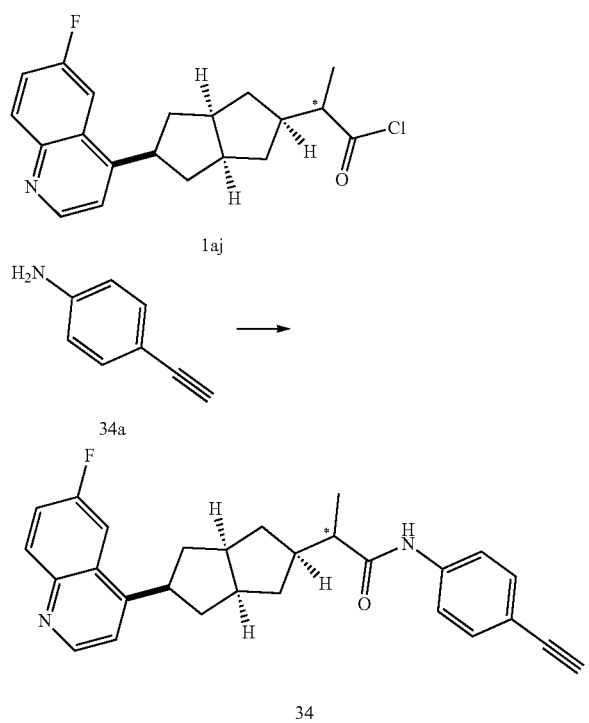

34

Intermediate 1aj and compound 34a reacted to afford compound 34. $^1$H NMR (500 MHz, CD$_3$OD) δ 8.72 (d, J=4.7 Hz, 1H), 8.05 (dd, J=9.2, 5.6 Hz, 1H), 7.89 (dd, J=10.6, 2.7 Hz, 1H), 7.59-7.53 (m, 4H), 7.40-7.39 (m, 2H), 3.90-3.83 (m, 1H), 3.40 (s, 1H), 2.77-2.69 (m, 2H), 2.45-2.34 (m, 3H), 2.29-2.22 (m, 2H), 2.09-2.06 (m, 1H), 1.59-1.50 (m, 2H), 1.21 (d, J=6.7 Hz, 3H), 1.16-1.08 (m, 2H). LCMS m/z 427.32 [M+H]$^+$.

Example 36. Preparation of Compound 35

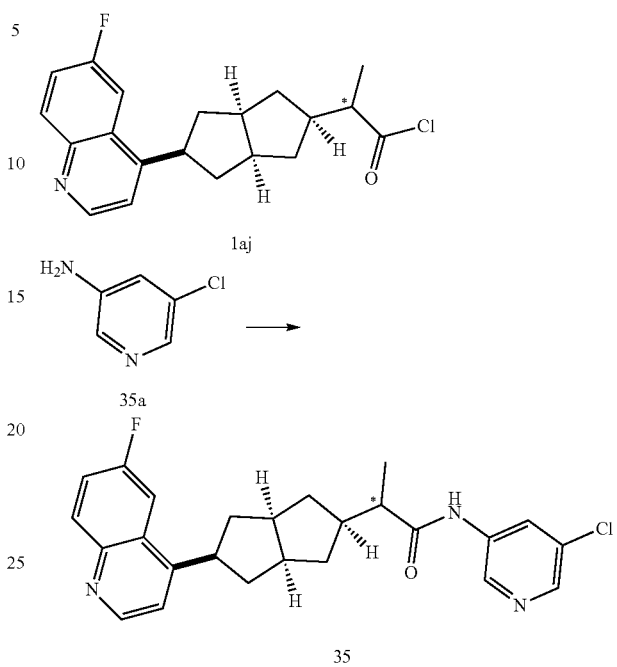

35

Intermediate 1aj and compound 35a reacted to afford compound 35. $^1$H NMR (500 MHz, CDCl$_3$) δ 11.0 (s, 1H), 8.83 (s, 1H), 8.42-8.29 (m, 2H), 8.21 (dd, J=8.8, 5.7 Hz, 1H), 7.08 (s, 1H), 7.71 (dd, J=10.3, 2.6 Hz, 1H), 7.53-7.43 (m, 2H), 3.76-3.73 (m, 1H), 3.68-3.64 (m, 1H), 3.11-3.08 (m, 1H), 3.71 (t, J=7.6 Hz, 3H), 2.43-2.14 (m, 7H), 1.27 (d, J=6.5 Hz, 3H). LCMS m/z 438.25 [M+H]$^+$.

Example 37. Preparation of Compound 36

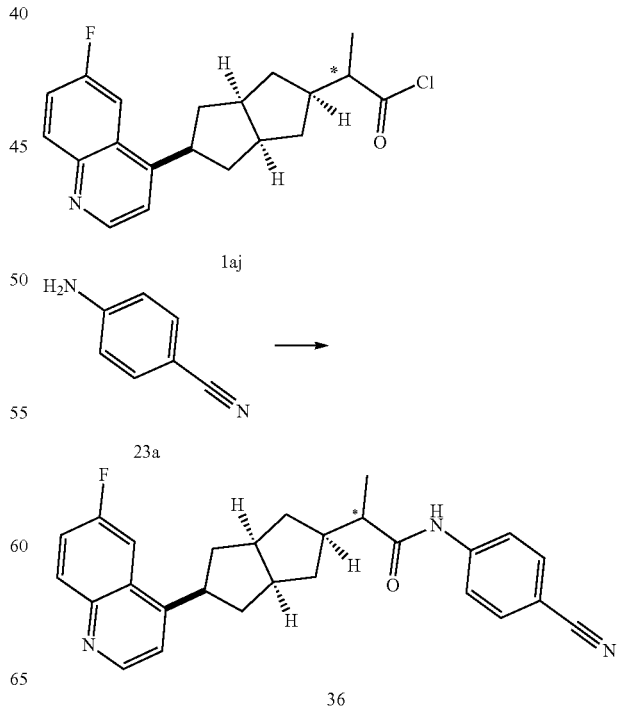

36

Intermediate 1aj and compound 23a reacted to afford compound 36. ¹H NMR (500 MHz, CD₃OD) δ 8.72 (d, J=4.7 Hz, 1H), 8.04 (d, J=5.5 Hz, 1H), 7.89 (dd, J=10.6, 2.7 Hz, 1H), 7.79-7.78 (m, 2H), 7.67-7.65 (m, 2H), 7.59-7.53 (m, 2H), 3.91-3.84 (m, 1H), 2.79-2.69 (m, 2H), 2.43-2.38 (m, 3H), 2.31-2.22 (m, 2H), 2.09-2.00 (m, 1H), 1.59-1.50 (m, 2H), 1.23 (d, J=6.8 Hz, 3H), 1.19-1.06 (m, 2H). LCMS m/z 428.3 [M+H]⁺.

Example 38. Preparation of Compound 37

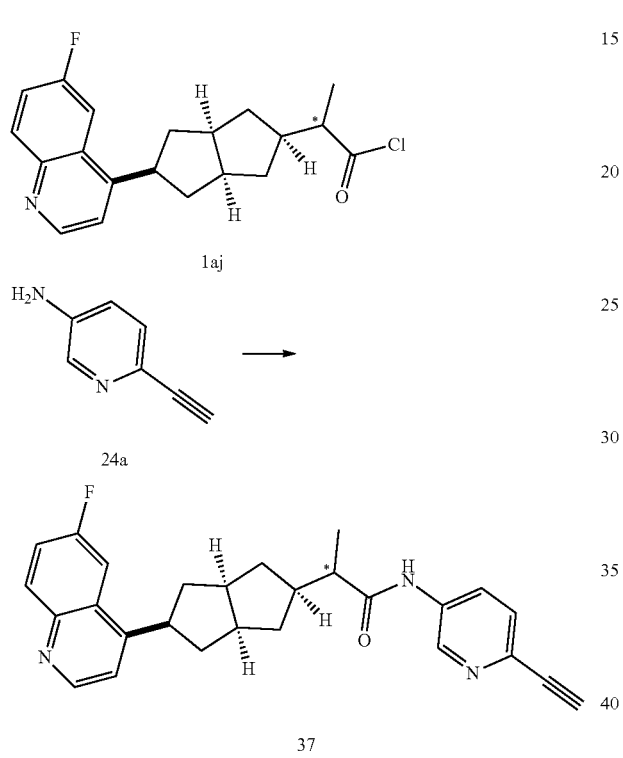

Intermediate 1aj and compound 24a reacted to afford compound 37. ¹H NMR (500 MHz, CD₃OD) δ 8.73 (d, J=4.5 Hz, 1H), 8.70 (d, J=2.2 Hz, 1H), 8.15 (dd, J=8.6, 2.5 Hz, 1H), 8.05 (dd, J=9.2, 5.6 Hz, 1H), 7.89 (dd, J=10.6, 2.7 Hz, 1H), 7.59-7.52 (m, 3H), 3.91-3.84 (m, 1H), 3.68 (s, 1H), 2.80-2.72 (m, 2H), 2.45-2.39 (m, 3H), 2.28-2.25 (m, 2H), 2.09-2.06 (m, 1H), 1.60-1.51 (m, 2H), 1.23 (d, J=7.2 Hz, 3H), 1.20-1.09 (m, 2H). LCMS m/z 428.26 [M+H]⁺.

Example 39. Preparation of Compound 38

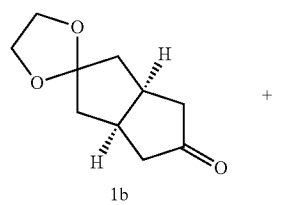

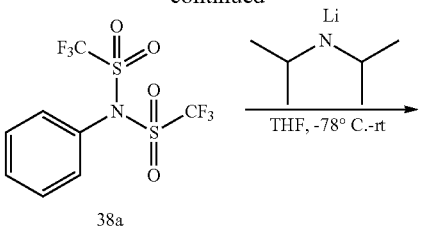

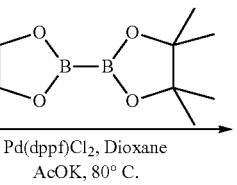

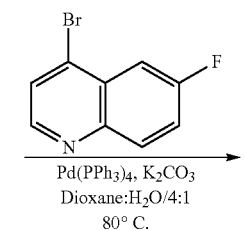

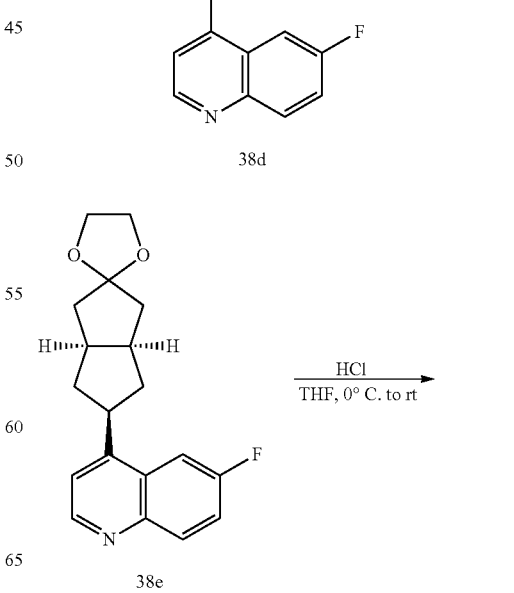

-continued

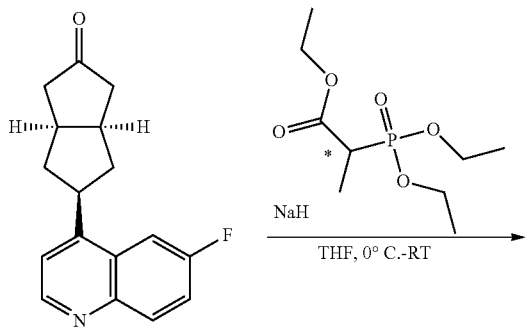

38f

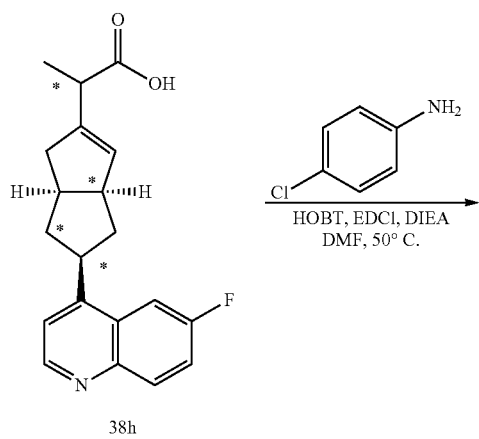

38g

38h

Compound 1b (200 mg, 1.1 mmol) was dissolved in dry THF (3 mL), added LDA (235 mg, 2.2 mmol) at −78° C., and after stirring for 1 hour at this temperature, N,N-bis(trifluoromethylsulfonyl)aniline 38a (588 mg, 1.65 mmol) was added, the reaction was slowly warmed to room temperature and stirred for 1 hour, and added saturated aqueous NH$_4$Cl (2 mL) to quench the reaction, extracted with EtOAc (3×10 mL), the combined organic phase was dried over Na$_2$SO$_4$, and filtered. The filtrate was concentrated in vacuo, and purified via column chromatography (EtOAc/petroleum ether=0-20%) to afford colorless oil 38b (200 mg, yield 57%).

Compound 38 was prepared from compound 38b by multistep reactions, detailed procedures refer to the synthetic procedure of compound 1.

Compound 38d: $^1$H NMR (500 MHz, CD$_3$OD) δ 8.82 (d, J=4.5 Hz, 1H), 8.13 (dd, J=9.2, 5.6 Hz, 1H), 7.96 (dd, J=10.5, 2.8 Hz, 1H), 7.51-7.50 (m, 1H), 7.25 (d, J=4.4 Hz, 1H), 5.93 (dd, J=3.8, 1.9 Hz, 1H), 4.06-3.94 (m, 4H), 3.61-3.54 (m, 1H), 3.18-3.16 (m, 1H), 3.17-3.14 (m, 1H), 3.11-3.02 (m, 1H), 2.70-2.63 (m, 1H), 2.25-2.14 (m, 2H), 1.95-1.88 (m, 1H), 1.86-1.79 (m, 1H).

Compound 38e: $^1$H NMR (500 MHz, CD$_3$OD) δ 8.79 (d, J=4.5 Hz, 1H), 8.10 (dd, J=9.2, 5.6 Hz, 1H), 7.71 (dd, J=10.5, 2.7 Hz, 1H), 7.47-7.45 (m, 1H), 7.40 (d, J=4.6 Hz, 1H), 4.00-3.87 (m, 4H), 3.62-3.50 (m, 1H), 2.83-2.72 (m, 2H), 2.38-2.31 (m, 2H), 2.07 (dd, J=13.5, 9.0 Hz, 2H), 1.80-1.68 (m, 4H). The stereo configuration of compound 38e was determined by 2D NMR (COSY and NOESY). The two bridgehead hydrogens on quinoline and parallel ring were trans-position.

Compound 38: $^1$H NMR (500 MHz, CD$_3$OD) δ 8.61-8.56 (m, 1H), 7.97-7.93 (m, 1H), 7.82-7.79 (m, 1H), 7.49-7.43 (m, 3H), 7.41-7.32 (m, 1H), 7.21-7.19 (m, 2H), 3.61-3.59 (m, 1H), 3.31 (s, 1H), 3.22-3.21 (m, 2H), 2.87-2.83 (m, 1H), 2.59-2.52 (m, 1H), 2.45-2.41 (m, 1H), 2.25 (d, J=4.6 Hz, 1H), 2.15-2.11 (m, 1H), 1.48-1.34 (m, 2H), 1.25 (d, J=6.8 Hz, 3H). LCMS m/z 435.26 [M+H]$^+$.

Example 40. Preparation of Compound 39

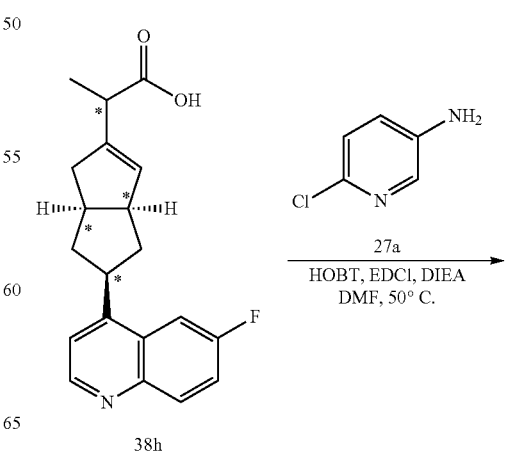

38

38h

-continued
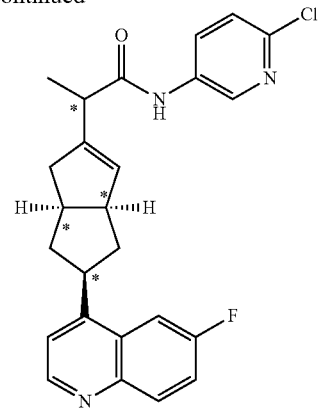
39
Compound 39 was prepared from the reaction of compound 38h with compound 27a. ¹H NMR (500 MHz, CD₃OD) δ 8.72 (dd, J=13.5, 4.7 Hz, 1H), 8.60 (t, J=2.7 Hz, 1H), 8.13 (dd, J=8.7, 2.7 Hz, 1H), 8.09-8.06 (m, 1H), 7.93 (dd, J=10.6, 2.6 Hz, 1H), 7.62-7.58 (m, 1H), 7.53 (d, J=4.7 Hz, 1H), 7.45 (dd, J=15.9, 6.7 Hz, 1H), 5.65 (s, 1H), 3.77-3.70 (m, 1H), 3.46-3.38 (m, 3H), 3.01-2.95 (m, 1H), 2.67 (dd, J=16.1, 8.8 Hz, 1H), 2.56 (dt, J=20.7, 7.5 Hz, 1H), 2.40-2.36 (m, 1H), 2.28-2.23 (m, 1H), 1.60-1.48 (m, 2H), 1.39 (d, J=6.7 Hz, 3H). LCMS m/z 436.2 [M+H]⁺.
Example 41 and 42. Preparation of Compound 40 and 41
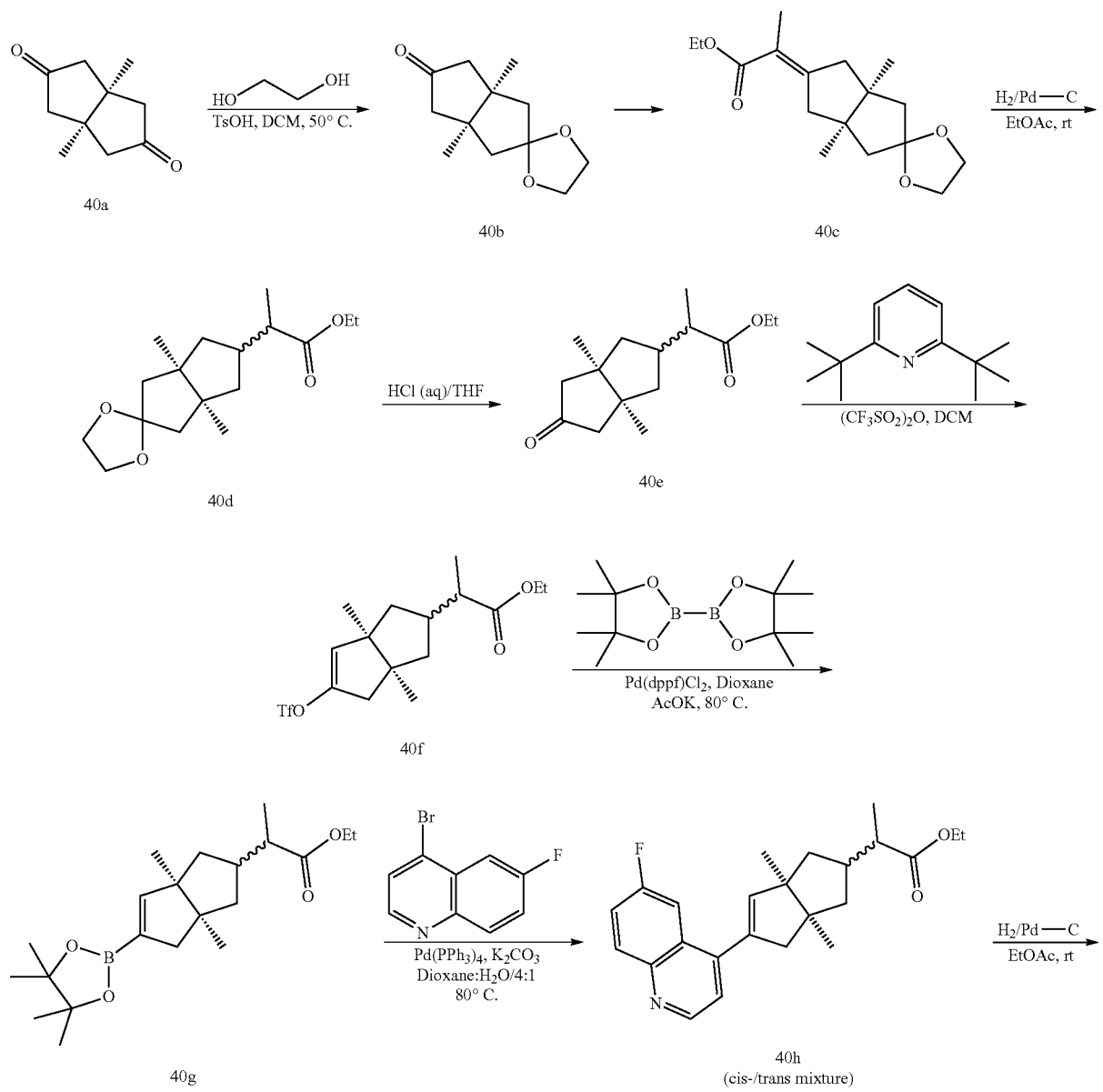

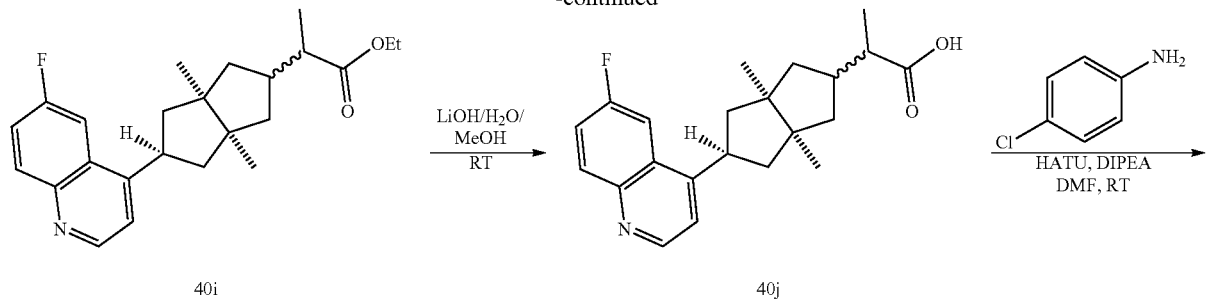

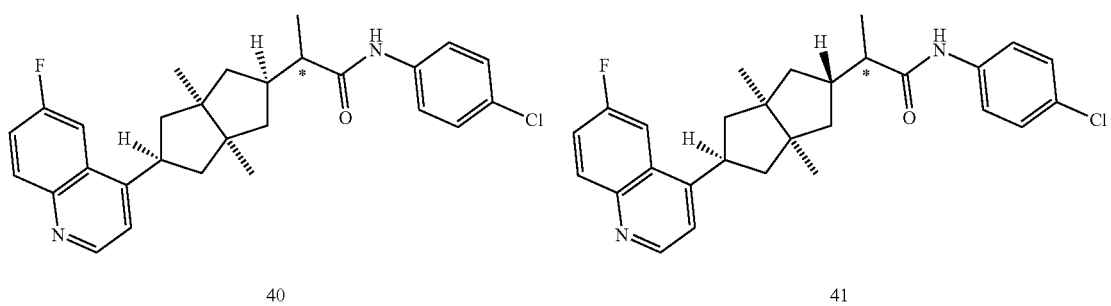

Starting from compound 40a, according the synthetic procedure of compound 1 and 38, Compound 40 and 41 was prepared by using multistep reaction and purified via preparative TLC, their ratio is 1.5:1. Compound 40: $^1$H NMR (500 MHz, CDCl$_3$) δ 8.79 (d, J=4.5 Hz, 1H), 8.12-8.09 (m, 1H), 7.65 (dd, J=10.4, 2.7 Hz, 1H), 7.50 (d, J=8.8 Hz, 2H), 7.49-7.44 (m, 1H), 7.33 (d, J=4.5 Hz, 1H), 7.30-7.27 (m, 3H), 3.61-3.53 (m, 1H), 2.36-2.23 (m, 1H), 2.10-2.06 (m, 1H), 2.05-2.00 (m, 1H), 1.97-1.77 (m, 7H), 1.26 (d, J=6.7 Hz, 3H), 1.19 (s, 3H), 1.16 (s, 3H). LCMS m/z 465.3 [M+H]$^+$. Compound 41: $^1$H NMR (500 MHz, CDCl$_3$) δ 8.70 (d, J=4.3 Hz, 1H), 8.05-8.02 (m, 1H), 7.58-7.56 (m, 1H), 7.43-7.38 (m, 3H), 7.31 (s, 1H), 7.27 (d, J=4.3 Hz, 1H), 7.20 (d, J=8.5 Hz, 2H), 3.90-3.82 (m, 1H), 2.42-2.37 (m, 1H), 2.12-1.99 (m, 3H), 1.92-1.78 (m, 4H), 1.58-1.53 (m, 1H), 1.50-1.45 (m, 1H), 1.18-1.15 (m, 3H), 1.09 (s, 3H), 1.07 (s, 3H). LCMS m/z 465.25 [M+H]$^+$.

Example 43 and 44. Preparation of Compound 42 and 43

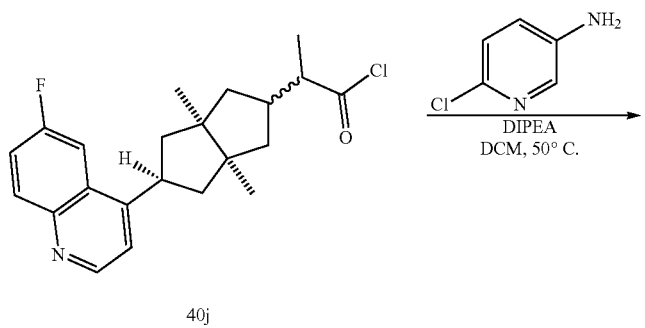

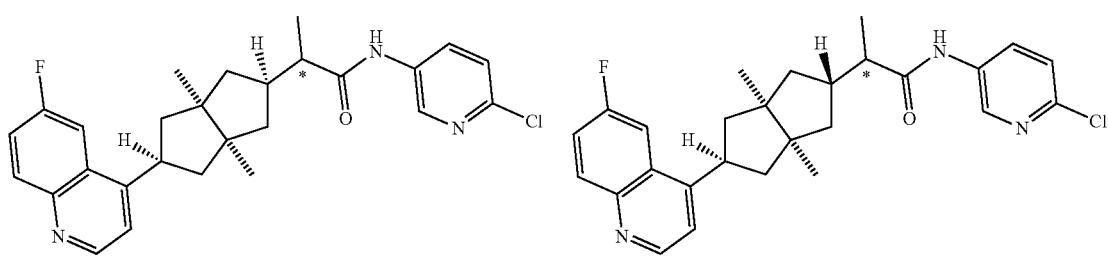

Compound 42 and 43 was prepared by following the preparation of compound 40 and 41. Compound 42: $^1$H NMR (500 MHz, CD$_3$OD) δ 8.64 (d, J=4.7 Hz, 1H), 8.48 (d, J=2.7 Hz, 1H), 8.01 (dd, J=8.7, 2.8 Hz, 1H), 7.97 (dd, J=9.2, 5.6 Hz, 1H), 7.72 (dd, J=10.4, 2.7 Hz, 1H), 7.51-7.45 (m, 2H), 7.31 (d, J=8.7 Hz, 1H), 3.37-3.60 (m, 1H), 2.23-2.18 (m, 2H), 1.97-1.65 (m, 8H), 1.14 (s, 3H), 1.12 (d, J=6.8 Hz, 3H), 1.11 (s, 3H). LCMS m/z 466.2 [M+H]$^+$.

Compound 43: $^1$H NMR (500 MHz, CD$_3$OD) δ 8.73 (d, J=4.7 Hz, 1H), 8.58 (d, J=2.7 Hz, 1H), 8.11-8.07 (m, 2H), 7.85 (dd, J=10.5, 2.8 Hz, 1H), 7.63-7.57 (m, 2H), 7.41 (d, J=8.7 Hz, 1H), 4.10-4.07 (m, 1H), 2.52-2.36 (m, 2H), 2.23-2.13 (m, 2H), 2.07-2.05 (m, 1H), 1.95-1.91 (m, 1H), 1.80-1.64 (m, 4H), 1.23 (s, 3H), 1.22 (d, J=6.8 Hz, 3H), 1.20 (s, 3H). LCMS m/z 466.2 [M+H]$^+$.

Example 45. Preparation of Compound 44

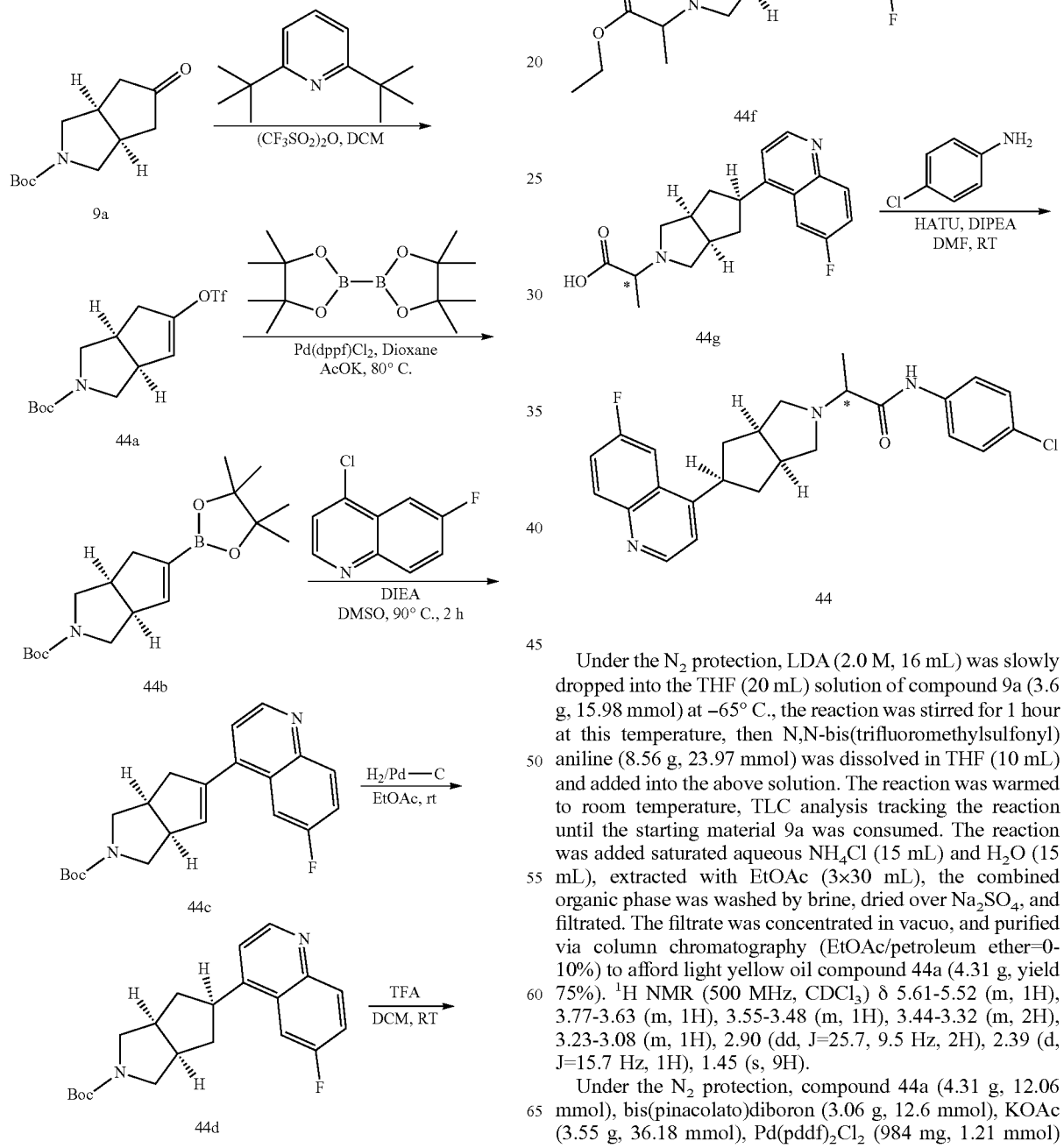

Under the N$_2$ protection, LDA (2.0 M, 16 mL) was slowly dropped into the THF (20 mL) solution of compound 9a (3.6 g, 15.98 mmol) at −65° C., the reaction was stirred for 1 hour at this temperature, then N,N-bis(trifluoromethylsulfonyl) aniline (8.56 g, 23.97 mmol) was dissolved in THF (10 mL) and added into the above solution. The reaction was warmed to room temperature, TLC analysis tracking the reaction until the starting material 9a was consumed. The reaction was added saturated aqueous NH$_4$Cl (15 mL) and H$_2$O (15 mL), extracted with EtOAc (3×30 mL), the combined organic phase was washed by brine, dried over Na$_2$SO$_4$, and filtrated. The filtrate was concentrated in vacuo, and purified via column chromatography (EtOAc/petroleum ether=0-10%) to afford light yellow oil compound 44a (4.31 g, yield 75%). $^1$H NMR (500 MHz, CDCl$_3$) δ 5.61-5.52 (m, 1H), 3.77-3.63 (m, 1H), 3.55-3.48 (m, 1H), 3.44-3.32 (m, 2H), 3.23-3.08 (m, 1H), 2.90 (dd, J=25.7, 9.5 Hz, 2H), 2.39 (d, J=15.7 Hz, 1H), 1.45 (s, 9H).

Under the N$_2$ protection, compound 44a (4.31 g, 12.06 mmol), bis(pinacolato)diboron (3.06 g, 12.6 mmol), KOAc (3.55 g, 36.18 mmol), Pd(pddf)$_2$Cl$_2$ (984 mg, 1.21 mmol) were added into dioxane (25 mL), and heated to 80° C. and reacted overnight. TLC analysis tracking the reaction until the starting material 44a was consumed. The reaction was added H$_2$O, extracted with EtOAc (3×30 mL), the combined organic phase was washed by brine, dried and filtered. The filtrate was concentrated in vacuo, and purified via column chromatography (EtOAc/petroleum ether=0-10%) to afford gray oil compound 44b (3.13 g, yield 77%). $^1$H NMR (500 MHz, DMSO-d$_6$) δ 6.23-6.16 (m, 1H), 3.43 (d, J=10.8 Hz, 1H), 2.80-2.70 (m, 2H), 2.16 (d, J=16.5 Hz, 1H), 1.31 (s, 9H), 1.24 (d, J=2.2 Hz, 1H), 1.14 (s, 12H), 1.12-1.08 (m, 3H).

Under the N$_2$ protection, compound 44b (3.13 g, 9.34 mmol), 4-chloro-6-fluoroquinoline (1.70 g, 9.34 mmol), K$_2$CO$_3$ (3.87 g, 28.01 mmol), Pd(PPh$_3$)$_4$ (1.08 g, 0.93 mmol) were added into dioxane (36 mL) and water (9 mL), then were heated to 80° C. and reacted for 5 hours, TLC analysis tracking the reaction until the starting material 44b was consumed. The reaction solution was cooled to room temperature; added H$_2$O, extracted with EtOAc (3×30 mL), the combined organic phase was washed by brine, dried over Na$_2$SO$_4$, and filtered. The filtrate was concentrated in vacuo, and purified via column chromatography (EtOAc/petroleum ether=0-20%) to afford light yellow oil compound 44c (2.12 g, yield 64%). $^1$H NMR (500 MHz, DMSO-d$_6$) δ 8.81 (dd, J=4.5, 1.8 Hz, 1H), 8.15-8.09 (m, 1H), 7.71 (d, J=10.3 Hz, 1H), 7.49 (m, 1H), 7.24 (d, J=4.5 Hz, 1H), 6.01-5.96 (m, 1H), 3.80-3.76 (m, 1H), 3.66-3.64 (m, 4H), 3.19-3.08 (m, 2H), 2.66-2.63 (m, 1H), 1.49 (s, 9H).

Compound 44c (1.90 g, 5.36 mmol) was dissolved in EtOAc (25 mL), added 10% Pd/C (200 mg), and reacted 1 hour at H$_2$ atmosphere. TLC analysis tracking the reaction until the starting material 44c was consumed. The reaction solution was cooled to room temperature, filtered, and concentrated in vacuo, the resulting crude product was purified via column chromatography (EtOAc/petroleum ether=0-20%) to afford gray-white solid compound 44d (1.67 g, yield 87%).

HCl (2M dioxane solution, 10 mL) was droped slowly into the CH$_2$Cl$_2$ (10 mL) solution of compound 44d (1.67 g, 4.69 mmol), then was stirred and reacted for 1 hour at room temperature. TLC analysis tracking the reaction until the starting material 44d was consumed. The reaction solution concentrated in vacuo to afford white solid 44e (1.71 g, yield 100%). The crude product was used for next step directly without further purification.

Compound 44e (156 mg, 0.61 mmol), ethyl 2-bromopropionate (193 mg, 1.22 mmol), K$_2$CO$_3$ (252 mg, 1.83 mmol) were dissolved in CH$_3$CN (8 mL), then was heated to 80° C. and reacted overnight. TLC analysis tracking the reaction until the starting material 44e was consumed. The reaction was concentrated and added H$_2$O, extracted with EtOAc (3×10 mL), the combined organic phase was washed by brine, dried over Na$_2$SO$_4$, and filtered. The filtrate was concentrated in vacuo, and purified via column chromatography (EtOAc/petroleum ether=0-20%) to afford colorless oil compound 44f (142 mg, yield 78%). $^1$H NMR (500 MHz, CDCl$_3$) δ 8.82 (d, J=4.5 Hz, 1H), 8.12 (dd, J=9.2, 5.7 Hz, 1H), 7.72 (dd, J=10.5, 2.7 Hz, 1H), 7.50-7.40 (m, 2H), 4.24-4.18 (m, 2H), 3.58-3.50 (m, 1H), 3.30-3.27 (m, 1H), 2.83-2.59 (m, 6H), 2.41 (m, 2H), 1.70 (d, J=7.1 Hz, 2H), 1.38 (d, J=6.5 Hz, 3H), 1.31 (t, J=7.1 Hz, 3H).

Compound 44f (142 mg, 0.40 mmol) was dissolved in MeOH (5 mL), and added LiOH solution (10 M, 5 mL), stirred for 1 hour at room temperature. TLC analysis tracking the reaction until the starting material 44f was consumed. The reaction was concentrated, adjusted the pH value to 5-6 by using diluted HCl (3N), extracted with EtOAc three times, the combined organic phase was dried over Na$_2$SO$_4$, and filtered. The filtrate was concentrated in vacuo to afford white solid crude product 44g (98 mg, yield 75%).

Compound 44g (15 mg, 0.05 mmol), HATU (28 mg, 0.08 mmol), DIPEA (20 mg, 0.15 mmol), 4-chloroaniline (10 mg, 0.08 mmol) were dissolved in DMF (1 mL), and stirred overnight at room temperature, LCMS detecting till the reaction was finished. The reaction was concentrated to romve the solvent, and added H$_2$O, extracted with EtOAc (3×5 mL), the combined organic phase was washed by brine, dried over Na$_2$SO$_4$, and filtered. The filtrate was concentrated in vacuo, and the crude product was purified via column chromatography (50%, EtOAc/petroleum ether) to afford white solid compound 44 (6.2 mg, yield 16%). $^1$H NMR (500 MHz, CDCl$_3$) δ 9.13 (s, 1H), 8.86 (d, J=4.4 Hz, 1H), 8.15 (dd, J=9.0, 5.8 Hz, 1H), 7.72 (d, J=10.3 Hz, 1H), 7.51 (dd, J=11.6, 5.5 Hz, 1H), 7.48-7.39 (m, 3H), 7.26 (d, J=1.8 Hz, 1H), 3.64-3.53 (m, 1H), 3.14 (q, J=6.6 Hz, 1H), 2.86 (s, 2H), 2.79 (d, J=9.2 Hz, 2H), 2.62-2.48 (m, 4H), 1.60 (d, J=8.6 Hz, 2H), 1.40 (d, J=6.9 Hz, 3H). LCMS m/z 438.23 [M+H]$^+$.

Example 46. Preparation of Compound 45

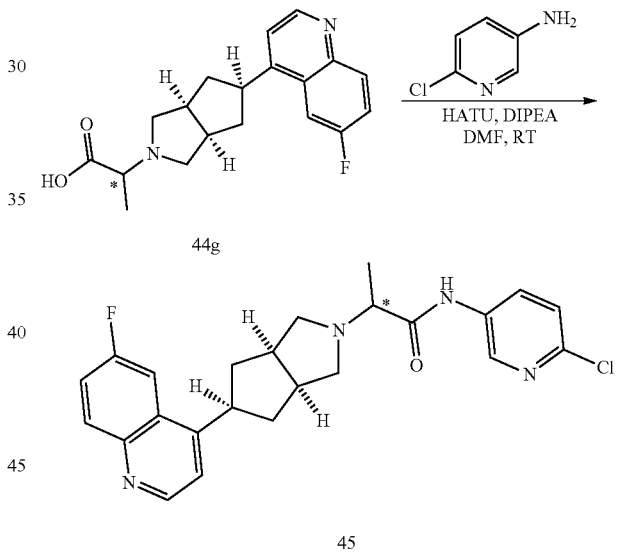

Compound 45 was synthesized according the synthetic method of compound 44. LCMS m/z 220.2 [½M+H]$^+$.

Example 47. Preparation of Compound 46

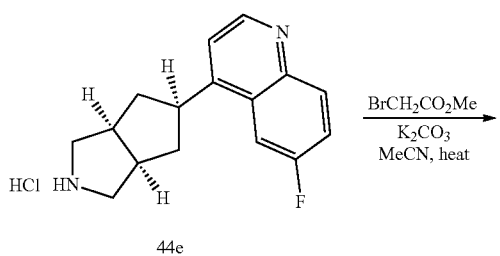

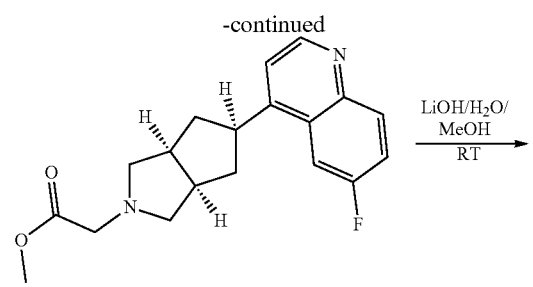

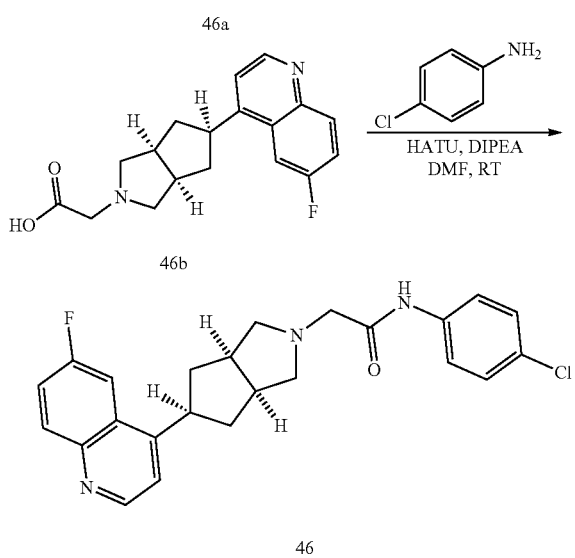

Compound 44e (60 mg, 0.21 mmol), methyl bromoacetate (38 mg, 0.25 mmol), K$_2$CO$_3$ (85 mg, 0.63 mmol) were dissolved in MeCN (5 mL), and heated to 50° C. and reacted overnight. TLC analysis tracking the reaction until the starting material 44e was consumed. The reaction was concentrated and added H$_2$O, extracted with EtOAc (3×10 mL), the combined organic phase was washed by brine, dried over Na$_2$SO$_4$, and filtered. The filtrate was concentrated in vacuo to afford crude product, which was purified via column chromatography (10-50%, EtOAc/petroleum ether) to afford light yellow oil compound 46a (43 mg, yield 64%).

Compound 46a (43 mg, 0.13 mmol) was dissolved in MeOH (5 mL), and was dropped LiOH solution (10 M, 5 mL), and stirred for 1 hour at room temperature, TLC analysis tracking the reaction until the starting material 46a was consumed. The reaction solution was concentrated, adjusted the pH value to 5-6 by using diluted HCl (3N), extracted with EtOAc (3×10 mL), dried over Na$_2$SO$_4$, and filtered. The filtrate was concentrated in vacuo to afford white solid compound 46b (21 mg, yield 51%).

Compound 46b (21 mg, 0.07 mmol), 4-chloroaniline (17 mg, 0.14 mmol), HATU (32 mg, 0.08 mmol), DIPEA (27 mg, 0.21 mmol) were dissolved in DMF (2 mL), and stirred overnight at room temperature. LCMS detecting it until the reaction was finished. The reaction was concentrated to remove the solvent, and added H$_2$O, extracted with EtOAc (3×5 mL), the combined organic phase was washed by brine, dried over Na$_2$SO$_4$, and filtered. The filtrate was concentrated in vacuo, the resulting crude product was purified preparative TLC (50%, EtOAc/petroleum ether) to afford white solid compound 46 (9.10 mg, yield 32%). $^1$H NMR (500 MHz, CDCl$_3$) δ 9.14 (s, 1H), 8.79 (d, J=4.5 Hz, 1H), 8.08 (dd, J=9.2, 5.7 Hz, 1H), 7.63 (dd, J=10.4, 2.8 Hz, 1H), 7.46-7.41 (m, 3H), 7.38-7.34 (m, 1H), 7.20 (d, J=8.8 Hz, 2H), 3.52 (m, 1H), 3.27 (s, 2H), 2.85-2.66 (m, 4H), 2.62-2.43 (m, 4H), 1.63-1.59 (m, 2H). LCMS m/z 424.11 [M+H]$^+$.

Example 48. Preparation of Compound 47

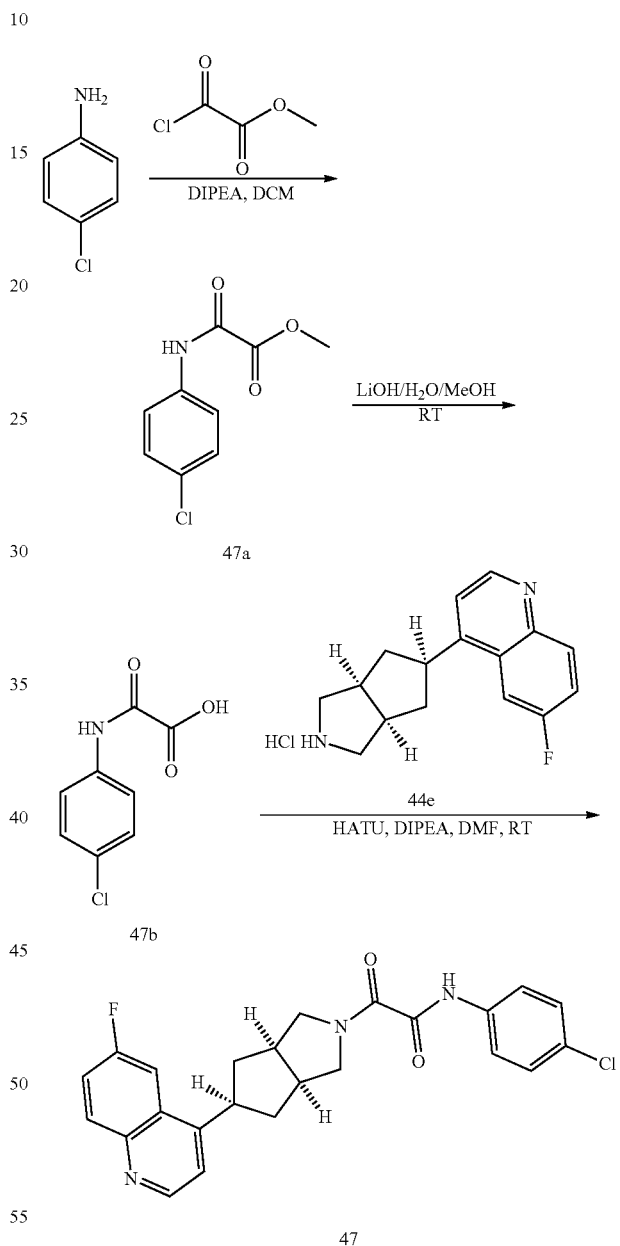

Methyl oxalyl chloride (576 mg, 4.70 mmol) was dropped into the CH$_2$Cl$_2$ solution of 4-chloroaniline (300 mg, 2.35 mmol), DIPEA (909 mg, 7.05 mmol), then was warmed to room temperature and reacted overnight, TLC analysis tracking the reaction was finished. The reaction solution was poured into saturated aqueous NaHCO$_3$, extracted with EtOAc (3×30 mL), the combined organic phase was washed by brine, dried over Na$_2$SO$_4$, and filtered. The filtrate was concentrated in vacuo to afford crude product, which was purified via column chromatography (0-10%, EtOAc/petroleum ether) to afford light yellow oil compound 47a (418 mg, yield 83%).

Compound 47a (418 mg, 1.96 mmol) was dissolved in MeOH (5 mL), and dropped LiOH aqueous solution (10 M, 5 mL), stirred for 1 hour at room temperature, TLC analysis tracking the reaction was finished. The reaction was concentrated, adjusted the pH value to 5-6 by using diluted HCl (3N), extracted with EtOAc (3×10 mL), the combined organic phase was dried over $Na_2SO_4$, and filtered. The filtrate was concentrated in vacuo to afford white solid 47b (327 mg, yield 84%).

Compound 44e (10 mg, 0.03 mmol), 47b (10 mg, 0.05 mmol), HATU (14 mg, 0.04 mmol), DIPEA (12 mg, 0.09 mmol) were dissolved in DMF (1 mL), stirred overnight at room temperature, LCMS tracking the reaction was finished. The reaction was concentrated, added water, extracted with EtOAc (3×5 mL), the combined organic phase was washed by brine, dried over $Na_2SO_4$, and filtered. The filtrate was concentrated in vacuo, the resulting crude product was purified via column chromatography (50%, EtOAc/petroleum ether) to afford white solid compound 47 (6.10 mg, yield 41)%. $^1$H NMR (500 MHz, $CDCl_3$) δ 9.46 (s, 1H), 8.80 (d, J=4.5 Hz, 1H), 8.14 (dd, J=9.2, 5.6 Hz, 1H), 7.65 (dd, J=10.3, 2.7 Hz, 1H), 7.60-7.54 (m, 2H), 7.48 (m, 1H), 7.35 (d, J=4.6 Hz, 1H), 7.32 (d, J=2.2 Hz, 1H), 7.31 (d, J=2.1 Hz, 1H), 4.32-4.19 (m, 2H), 3.84-3.75 (m, 2H), 3.07-3.05 (m, 1H), 2.94-2.90 (m, 1H), 2.55-2.52 (m, 2H), 1.75-1.70 (m, 1H), 1.70-1.64 (m, 2H). LCMS m/z 438.23 [M+H]$^+$.

Example 49. Preparation of Compound 48

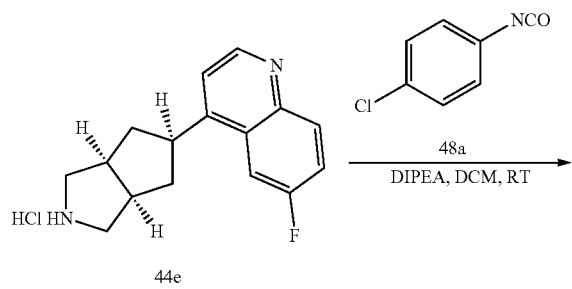

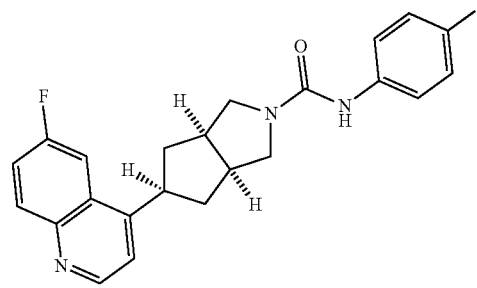

48

Compound 48a (24 mg, 0.15 mmol) was dissolved in $CH_2Cl_2$ (1 mL), and was slowly dropped into $CH_2Cl_2$ (2 mL) solution of compound 44e (30 mg, 0.10 mmol), DIPEA (39 mg, 0.30 mmol). After dropping, the reaction was stirred overnight at room temperature, LCMS tracking the reaction was finished. The reaction was added with water, extracted with EtOAc (3×10 mL), the combined organic phase was washed by brine, dried over $Na_2SO_4$, and filtered. The filtrate was concentrated in vacuo, the resulting crude product was purified via preparative TLC (50%, EtOAc/petroleum ether) to afford white solid compound 48 (16.5 mg, yield 39%). $^1$H NMR (500 MHz, $CDCl_3$) δ 8.80 (d, J=4.6 Hz, 1H), 8.13 (dd, J=9.3, 5.7 Hz, 1H), 7.65 (dd, J=10.4, 2.8 Hz, 1H), 7.50-7.46 (m, 1H), 7.39-7.34 (m, 3H), 7.24-7.21 (m, 2H), 6.22 (s, 1H), 3.76 (m, 1H), 3.69 (dd, J=10.3, 7.5 Hz, 2H), 3.51-3.46 (m, 2H), 3.04-2.94 (m, 2H), 2.60-2.48 (m, 2H), 1.73-1.70 (m, 2H). LCMS m/z 410.25 [M+H]$^+$.

Example 50. Preparation of Compound 49

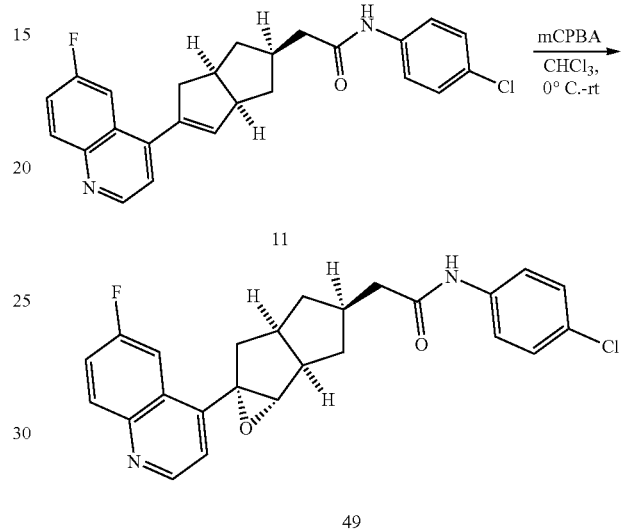

Compound 11 (180 mg, 0.427 mmol) was dissolved in $CHCl_3$ (1 mL), and was added mCPBA at 0° C., the reaction was stirred for 0.5 hour at 0° C., then slowly warmed to room temperature, TLC analysis tracking the reaction was finished, the reaction was quenched by adding saturated aqueous $NaHSO_4$, extracted with $CH_2Cl_2$ (3×10 mL), the combined organic phase was washed by saturated aqueous $Na_2CO_3$ and brine respectively, dried over $Na_2SO_4$, and filtered. the resulting crude product was purified via column chromatography (EtOAc/petroleum ether=0-100%) to afford light yellow solid compound 49 (85 mg, yield 45%). $^1$H NMR (500 MHz, $CD_3OD$) δ 8.76 (dd, J=9.5, 5.3 Hz, 1H), 8.57 (d, J=6.3 Hz, 1H), 7.98-7.96 (m, 1H), 7.76-7.72 (m, 1H), 7.56 (d, J=8.7 Hz, 2H), 7.45 (d, J=6.3 Hz, 1H), 7.29 (d, J=8.7 Hz, 2H), 6.15 (s, 1H), 3.52 (d, J=7.7 Hz, 1H), 3.15 (dd, J=16.2, 8.7 Hz, 1H), 2.95-2.88 (m, 1H), 2.60 (d, J=16.2 Hz, 1H), 2.47-2.45 (m, 2H), 2.37-2.34 (m, 2H), 2.27-2.23 (m, 1H), 1.34-1.33 (m, 2H). LCMS m/z 437.3 [M+H]$^+$.

Example 51. Preparation of Compound 50

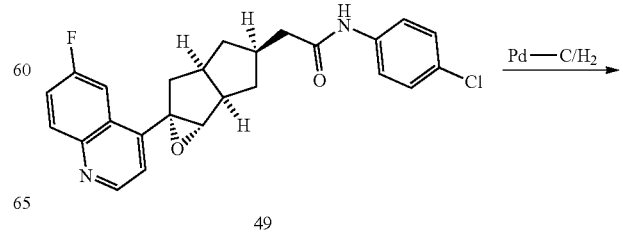

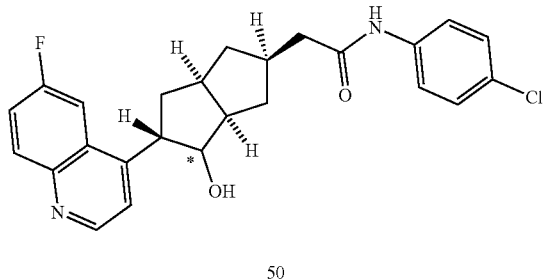

50

Compound 49 (10 mg, 0.023 mmol) was dissolved in EtOAc (3 mL), was added 10% Pd/C (3 mg), and was stirred for 1 hour at 0° C. under the H$_2$ atmosphere. TLC analysis tracking the reaction was finished. Pd/C was removed by filtrating through the celite pad, the filtrate was concentrated in vacuo. The crude product was purified via column chromatography (CH$_2$Cl$_2$/MeOH=0-10%) to afford white solid compound 50 (3 mg, yield 30%). $^1$H NMR (500 MHz, CDCl$_3$) δ 8.86-8.83 (m, 1H), 8.43 (d, J=6.3 Hz, 1H), 7.69 (dd, J=9.9, 2.5 Hz, 1H), 7.53-7.47 (m, 3H), 7.34 (s, 1H), 7.28 (d, J=8.8 Hz, 2H), 7.25 (s, 1H), 3.67-3.60 (m, 1H), 2.73-2.69 (m, 2H), 2.54-2.50 (m, 1H), 2.43-2.39 (m, 3H), 2.32-2.20 (m, 2H), 1.49-1.43 (m 2H), 1.10-1.07 (m, 2H). LCMS m/z 439.23 [M+H]$^+$.

Example 52. Preparation of Compound 51

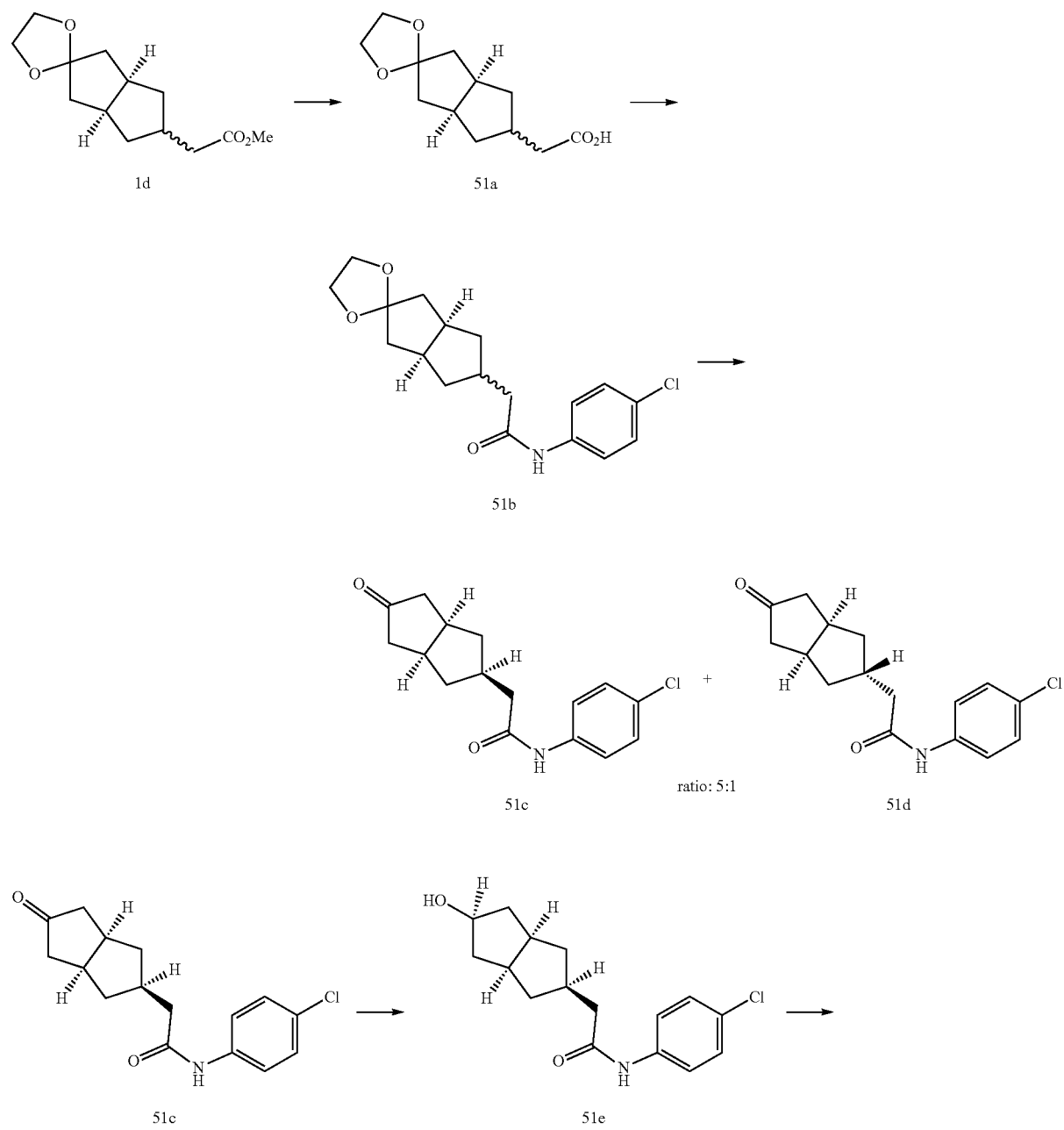

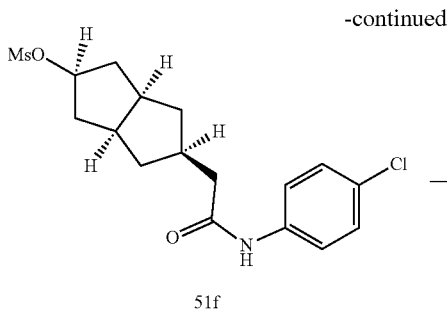

51f

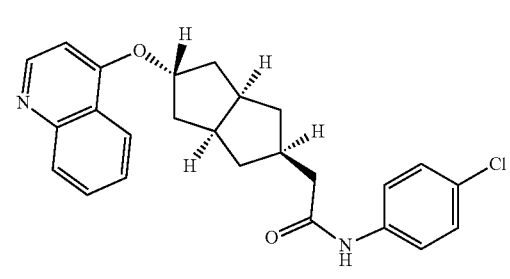

51

Compound 1d (1.20 g, 5.0 mmol) was dissolved in MeOH (10 mL), added NaOH (0.80 g, 20.0 mmol)/H$_2$O (2 mL) solution, and stirred overnight at room temperature, TLC analysis tracking the reaction was finished. The reaction was concentrated to remove MeOH, added H$_2$O (10 mL), adjusted the pH value to 5 by using diluted HCl (0.5 N) in ice-water bath, extracted with EtOAc (3×10 mL), the combined organic was dried and concentrated to afford crude product 51a (1.04 g, 92%).

Compound 51a (600 mg, 2.65 mmol) was dissolved in DMF (15 mL), added HATU (1.20 g, 3.18 mmol), DIPEA (1.03 g, 7.95 mmol), then added 4-chloroaniline (0.51 g, 3.98 mmol), the reaction was stirred for 1 hour at room temperature under the N$_2$ protection. The reaction was quenched by adding water (10 mL), extracted with EtOAc (3×20 mL), the combined organic phase was washed by brine, dried and filtered to afford crude product, which was purified via column chromatography (EtOAc/petroleum ether=0-20%) to afford mixture 51b (1.02 g, 114%). $^1$H NMR (500 MHz, CDCl$_3$) δ 7.46 (d, J=7.6 Hz, 2H), 7.31 (s, 1H), 7.27-7.25 (m, 2H), 3.91-3.87 (m, 4H), 2.54 (d, J=3.6 Hz, 2H), 2.38 (d, J=7.2 Hz, 2H), 2.29-2.24 (m, 1H), 2.15-2.11 (m, 2H), 1.98-1.96 (m, 2H), 1.59 (dd, J=13.3, 2.8 Hz, 2H), 1.13 (dd, J=20.1, 11.5 Hz, 2H).

Compound 51b (1.02 g, 3.04 mmol) was dissolved in THF (20 mL), and was slowly dropped HCl (12.5 mL, 1 N), stirred for 1.0 hour at room temperature. The reaction was concentrated in vacuo, and extracted the water phase with EtOAc (3×20 mL), the combined organic phase was washed by brine, dried and concentrated, the crude product was purified via column chromatography (EtOAc/petroleum ether=0-33%) to afford compound 51c (560 mg) and compound 51d (120 mg). 51c: $^1$H NMR (500 MHz, CDCl$_3$) δ 7.58 (s, 1H), 7.47 (d, J=8.6 Hz, 2H), 7.27 (d, J=7.8 Hz, 2H), 2.74-2.71 (m, 2H), 2.54-2.50 (m, 2H), 2.40 (d, J=7.1 Hz, 2H), 2.35-2.28 (m, 2H), 2.05 (d, J=7.2 Hz, 1H), 2.01 (d, J=6.8 Hz, 1H), 1.08-1.02 (m, 1H). 51d: $^1$H NMR (500 MHz, CDCl$_3$) δ 7.46 (d, J=8.8 Hz, 2H), 7.28 (d, J=8.9 Hz, 2H), 7.15 (s, 1H), 2.90-2.85 (m, 1H), 2.60-2.40 (m, 3H), 2.39 (d, J=7.3 Hz, 2H), 2.09-2.06 (m, 2H), 1.80-1.65 (m, 4H), 0.89-0.84 (m, 1H).

Compound 51c (140 mg, 0.48 mmol) was dissolved in THF (10 mL), added NaBH$_4$ (90 mg, 2.40 mmol), the reaction was stirred 2.0 hour at ice-water bath. The reaction was quenched by saturated aqueous NH$_4$Cl solution, extracted with EtOAc (2×10 mL), the combined organic phase was washed by brine, dried and concentrated to afford compound 51e (100 mg, 71%).

Compound 51e (90 mg, 0.31 mmol) was dissolved in CH$_2$Cl$_2$ (5 mL), was added Et$_3$N (78 mg, 0.78 mmol), and was slowly dropped methanesulfonyl chloride (53 mg, 0.46 mmol) in ice-water bath. The mixture was reacted for 2.0 hours at room temperature. The reaction solution was washed by saturated aqueous NaHCO$_3$ solution, extracted with CH$_2$Cl$_2$ (2×10 mL), the combined organic phase was washed by brine, dried and concentrated. The resulting crude product was purified via column chromatography (EtOAc/petroleum ether=0~1/3) to afford compound 51f (103 mg, yield 88%).

4-Hydroxyquinoline (20 mg, 0.068 mmol) was dissolved in dry THF (5 mL), was added NaH (8.3 mg, 0.21 mmol, 60%) at 0° C., was stirred for 0.5 hours at room temperature, was added compound 51f (20 mg, 0.068 mmol), then was heated to 60° C. and stirred for 1 hour. The reaction was poured into saturated aqueous NH$_4$Cl solution (10 mL) to quench the reaction, extracted with EtOAc (3×10 mL), the combined organic phase was washed by brine, dried and concentrated in vacuo, the resulting crude product was purified via preparative TLC (EtOAc/petroleum ether=1/3) to afford compound 51 (4.10 mg, yield 14%). $^1$H NMR (500 MHz, CDCl$_3$) δ 8.71 (d, J=5.2 Hz, 1H), 8.17 (d, J=8.3 Hz, 1H), 8.01 (d, J=8.3 Hz, 1H), 7.68 (t, J=7.1 Hz, 1H), 7.49 (d, J=5.7 Hz, 4H), 7.28 (s, 1H), 6.71 (d, J=5.2 Hz, 1H), 5.11-5.09 (m, 1H), 2.81-2.73 (m, 2H), 2.38-2.34 (m, 1H), 2.26-2.23 (m, 2H), 2.22-2.18 (m, 2H), 2.12-2.00 (m, 2H), 1.89-1.82 (m, 2H), 1.02-0.96 (m, 2H), 0.91-0.84 (m, 1H). LCMS m/z 421.11 [M+H]$^+$.

Example 53. Preparation of Compound 52

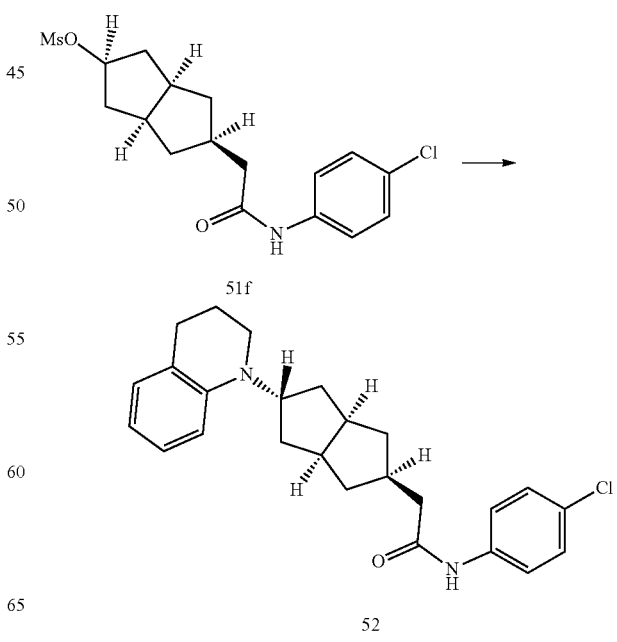

51f

52

51f (5 mg, 0.013 mmol) was weight and added 1,2,3,4-tetrahydro-quinoline, and stirred for 3.0 hours without solvent. The crude product was purified via column chromatography (EtOAc/petroleum ether=0-1/5) to afford compound 52 (2.67 mg, yield 49%). $^1$H NMR (500 MHz, CDCl$_3$) δ 7.47 (d, J=8.7 Hz, 2H), 7.28 (d, J=8.7 Hz, 2H), 7.09-7.05 (m, 2H), 6.94 (d, J=7.3 Hz, 1H), 6.68 (d, J=8.0 Hz, 1H), 6.55 (t, J=7.3 Hz, 1H), 4.17-4.13 (m, 1H), 3.18 (t, J=5.8 Hz, 2H), 2.72 (t, J=6.3 Hz, 2H), 2.54 (d, J=6.2 Hz, 2H), 2.42 (d, J=6.5 Hz, 2H), 2.31-2.20 (m, 3H), 1.90-1.88 (m, 2H), 1.74-1.68 (m, 2H), 1.62-1.59 (m, 2H), 0.89-0.84 (m, 2H). LCMS m/z 409.33 [M+H]$^+$.

Example 54. Preparation of Compound 53

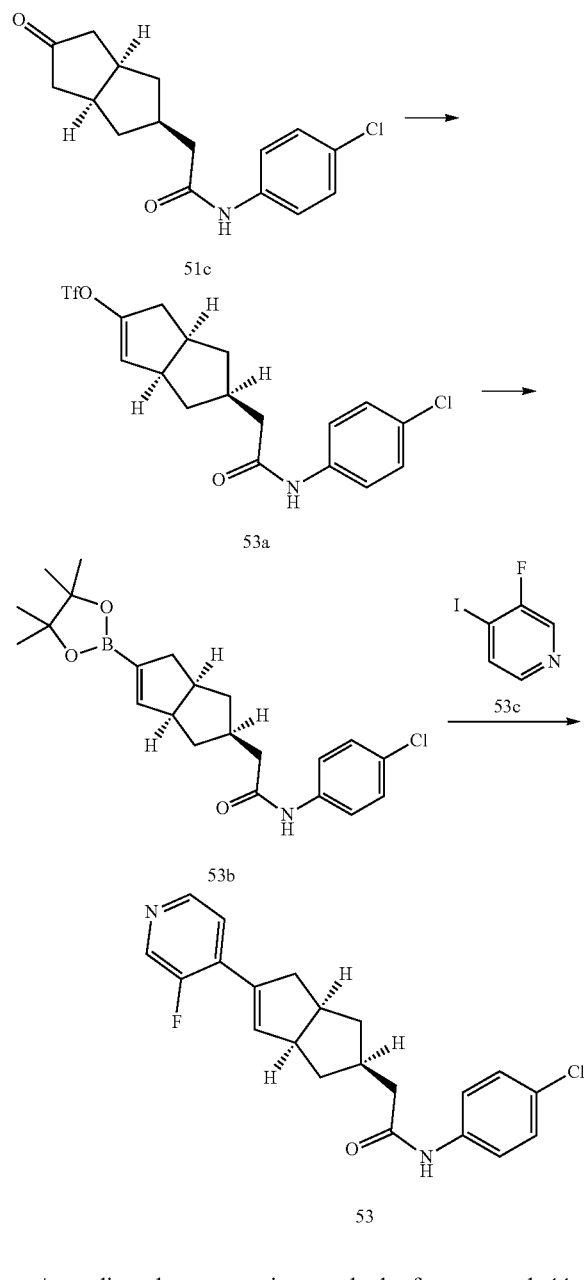

According the preparation method of compound 44c, starting material compound 51c, went through two steps to afford compound 53b, then reacted with compound 53c to afford compound 53. $^1$H NMR (500 MHz, CDCl$_3$) δ 8.41 (d, J=3.3 Hz, 1H), 8.34 (d, J=4.9 Hz, 1H), 7.46 (d, J=8.5 Hz, 2H), 7.28 (d, J=8.8 Hz, 2H), 7.18-7.16 (m, 1H), 7.08 (s, 1H), 6.52 (s, 1H), 3.40 (d, J=7.4 Hz, 1H), 2.98-2.94 (m, 1H), 2.81-2.78 (m, 1H), 2.52 (d, J=17.5 Hz, 1H), 2.35-2.33 (m, 2H), 2.26-2.22 (m, 1H), 1.14-1.12 (m, 2H), 1.04-1.02 (m, 1H), 0.88-0.85 (m, 1H). LCMS m/z 371.25 [M+H]$^+$.

Example 55. Preparation of Compound 54

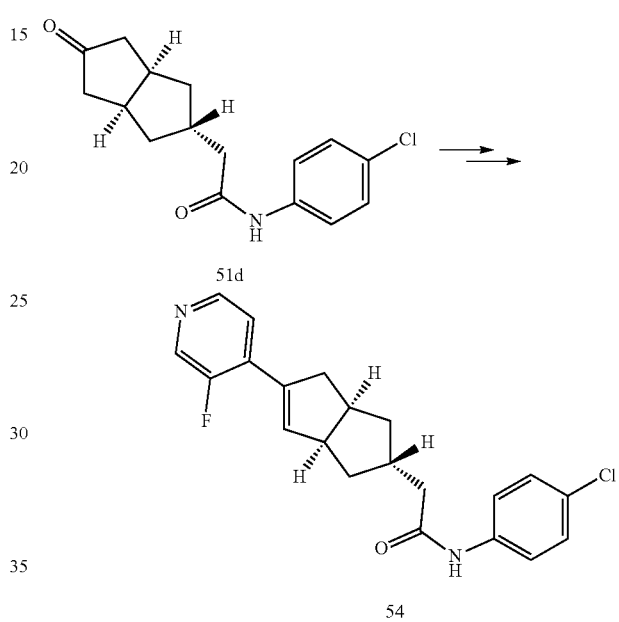

Same as the preparation method of compound 53, compound 51d went through multistep reaction to afford compound 54. $^1$H NMR (500 MHz, CDCl$_3$) δ 8.40 (s, 1H), 8.33 (d, J=5.0 Hz, 1H), 7.45 (d, J=8.1 Hz, 2H), 7.28 (d, J=6.2 Hz, 2H), 7.15-7.13 (m, 2H), 6.40 (s, 1H), 3.52-3.48 (m, 1H), 3.13-3.08 (m, 1H), 2.67 (d, J=14.3 Hz, 1H), 2.50 (d, J=16.5 Hz, 1H), 2.34-2.31 (m, 2H), 1.95-1.89 (m, 2H), 1.80-1.77 (m, 1H), 1.51-1.47 (m, 2H), 1.14-1.13 (m, 1H), 0.89-0.87 (m, 1H). LCMS m/z 371.24 [M+H]$^+$.

Example 56. Preparation of Compound 55

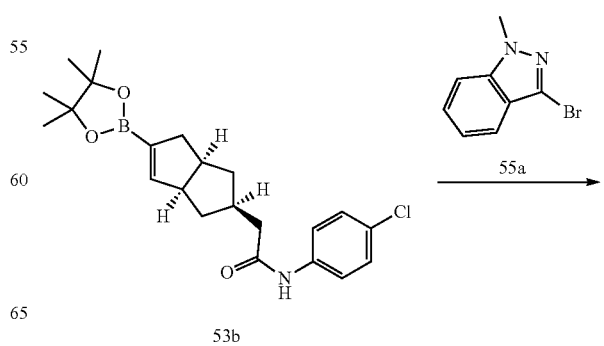

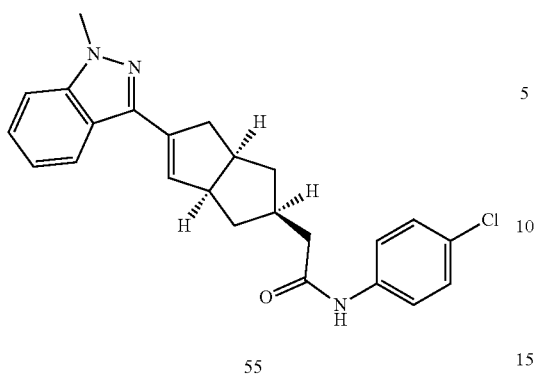

55

Compound 55 was prepared from compound 53b and compound 55a, detailed synthetic procedures refer to the preparation of compound 53. $^1$H NMR (500 MHz, CDCl$_3$) δ 7.85 (d, J=8.2 Hz, 1H), 7.40 (t, J=4.3 Hz, 2H), 7.35-7.29 (m, 2H), 7.22 (d, J=2.0 Hz, 2H), 7.13-7.10 (m, 1H), 7.02 (s, 1H), 6.31 (s, 1H), 3.98 (s, 3H), 3.41-3.36 (m, 1H), 3.09 (dd, J=16.2, 8.8 Hz, 1H), 2.78-2.71 (m, 1H), 2.36-2.24 (m, 5H), 2.20-2.16 (m, 1H), 2.00-1.96 (m, 1H). LCMS m/z 406.3 [M+H]$^+$.

Example 57. Preparation of Compound 56

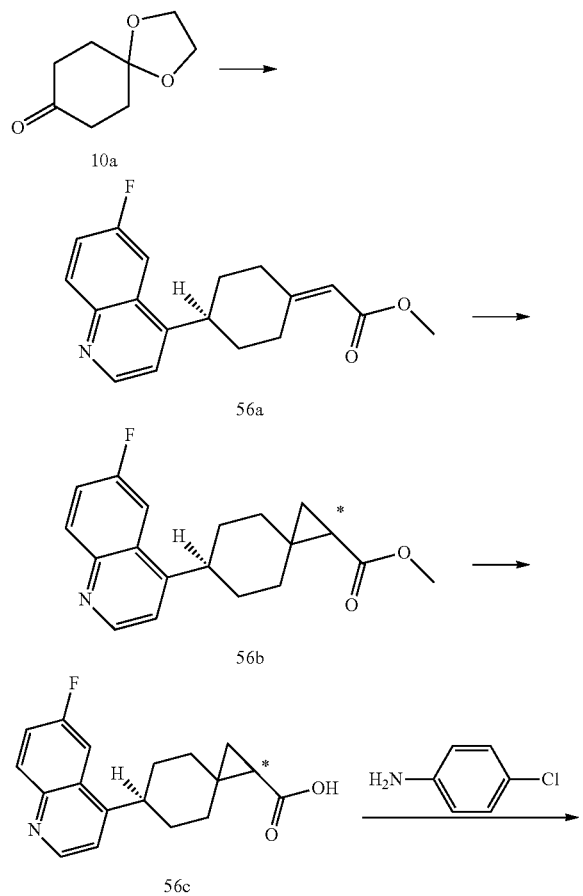

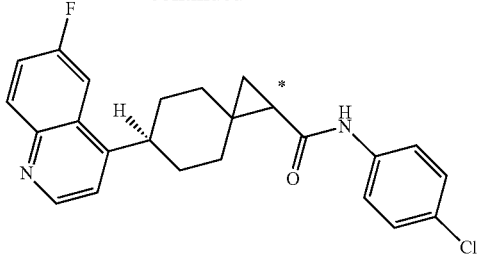

56

According the preparation of compound 1 and compound 10, compound 56a was prepared from compound 10a. $^1$H NMR (500 MHz, CDCl$_3$) δ 8.73 (d, J=4.6 Hz, 1H), 8.06 (dd, J=9.2, 5.8 Hz, 1H), 7.63 (dd, J=10.4, 2.6 Hz, 1H), 7.45-7.38 (m, 1H), 7.18 (d, J=4.5 Hz, 1H), 5.68 (s, 1H), 4.03 (dd, J=15.2, 4.7 Hz, 1H), 3.65 (s, 3H), 3.39 (t, J=12.0 Hz, 1H), 2.47-2.38 (m, 2H), 2.13 (dd, J=9.3, 6.0 Hz, 3H), 1.74-1.59 (m, 2H).

The DMSO solution of trimethyl sulfoxonium iodide (18 mg, 0.08 mmol) was added NaH (4 mg, 0.9 mmol) at 0° C., stirred for 1 hour at room temperature, then was cooled to 0° C. and was dropped DMSO solution of compound 56a (20 mg, 0.06 mmol). After the dropping, the reaction was warmed to room temperature, stirred overnight. TLC analysis tracking the reaction was finished. The reaction solution was added water, extracted with EtOAc (3×10 mL), the combined organic phase was washed by brine, dried over Na$_2$SO$_4$, and filtered and concentrated in vacuo, the resulting crude product was purified via preparative TLC (50%, EtOAc/petroleum ether) to afford colorless oil compound 56b (8 mg, yield 38%).

Compound 56b (8 mg, 0.03 mmol) was dissolved in MeOH (3 mL), then was added LiOH aqueous solution (10M, 5 mL), stirred 1 hour at room temperature, TLC analysis showed the starting material 56b was consumed. The reaction solution was concentrated, adjusted the pH value to 5-6 by using diluted HCl (3 N), extracted with EtOAc (3×10 mL), dried over Na$_2$SO$_4$, filtered and concentrated in vacuo to afford white crude solid 56c (7 mg, yield 92%).

Compound 56c (7 mg, 0.02 mmol), 4-chloroaniline (5 mg, 0.04 mmol), HOBT (5 mg, 0.04 mmol), EDCI (7 mg, 0.04 mmol), DIPEA (10 mg, 0.08 mmol) were dissolved in DMF (1 mL), stirred overnight at room temperature, TLC analysis tracking the reaction was finished. The reaction solution was concentrated to remove the solvent, added water, extracted with EtOAc three times, the combined organic phase was washed by brine, dried over Na$_2$SO$_4$, filtered and concentrated in vacuo, the resulting crude product was purified via preparative TLC (50%, EtOAc/petroleum ether) to afford white solid compound 56 (3.56 mg, yield 37%). $^1$H NMR (500 MHz, CDCl$_3$) δ 8.71 (d, J=4.1 Hz, 1H), 8.06 (dd, J=8.7, 5.8 Hz, 1H), 7.60 (dd, J=10.4, 2.0 Hz, 1H), 7.44 (d, J=8.8 Hz, 2H), 7.43-7.36 (m, 2H), 7.23 (d, J=8.7 Hz, 2H), 3.23-3.15 (m, 1H), 2.15-2.07 (m, 2H), 1.98 (d, J=12.7 Hz, 1H), 1.93-1.82 (m, 2H), 1.42 (d, J=3.4 Hz, 1H), 1.43-1.31 (m, 3H), 1.05 (d, J=13.5 Hz, 1H), 0.95 (dd, J=7.5, 4.4 Hz, 1H). LCMS m/z 409.2 [M+H]$^+$.

Example 58. Preparation of Compound 57

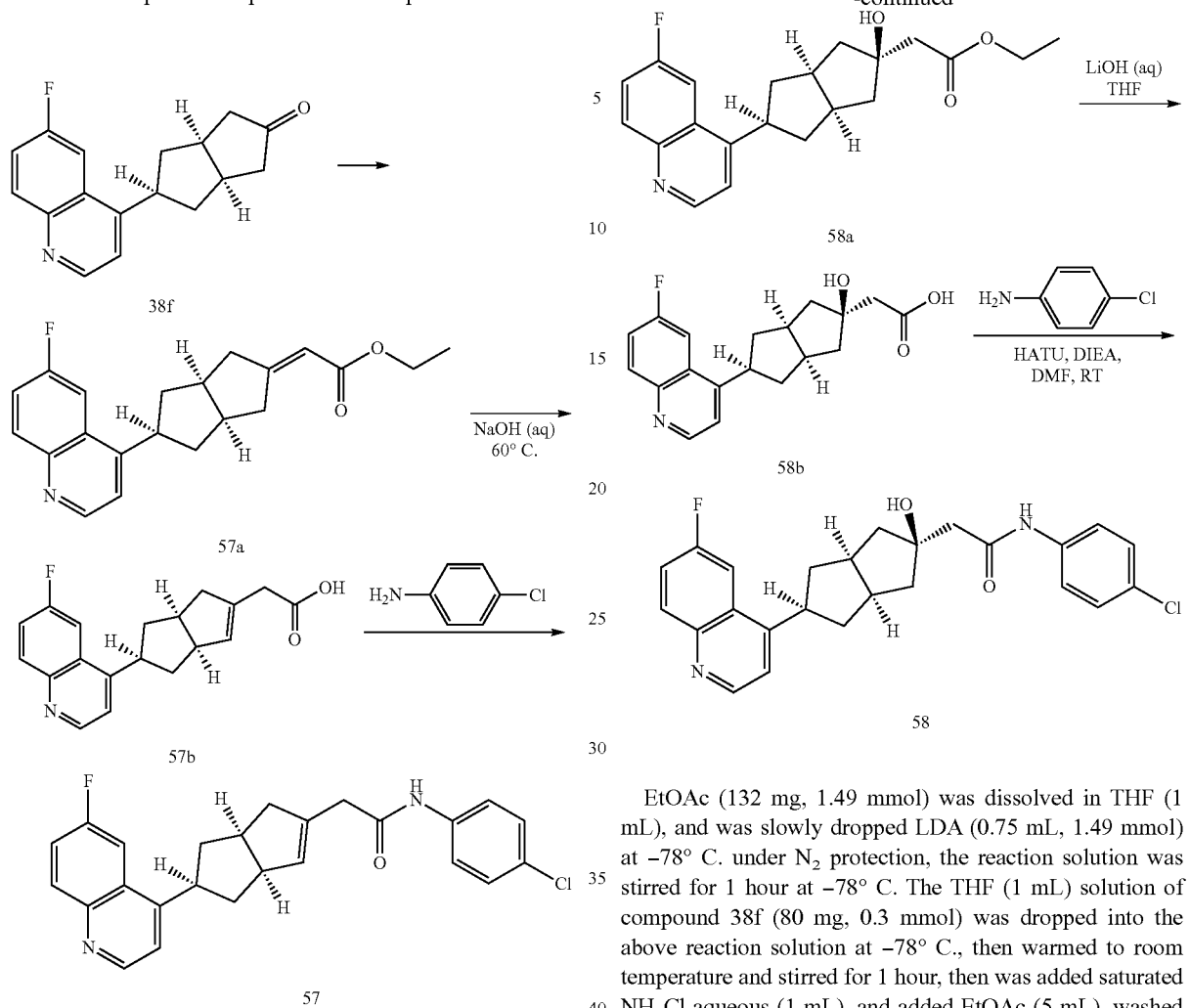

According the preparation method of compound 1 and compound 10, starting material compound 38f was used for synthesis of compound 57b, then synthesized to racemic compound 57. ¹H NMR (500 MHz, CDCl₃) δ 8.78 (d, J=4.3 Hz, 1H), 8.13 (dd, J=9.1, 5.7 Hz, 1H), 7.71 (dd, J=10.4, 2.6 Hz, 1H), 7.49 (dd, J=8.6, 2.1 Hz, 1H), 7.47-7.44 (m, 2H), 7.36-7.34 (m, 2H), 7.28 (d, J=8.7 Hz, 2H), 5.72-5.65 (m, 1H), 3.63-3.56 (m, 1H), 3.45 (dd, J=15.9, 7.9 Hz, 1H), 3.21 (q, J=15.6 Hz, 2H), 3.00-2.94 (m, 1H), 2.73 (dd, J=16.8, 8.8 Hz, 1H), 2.59-2.54 (m, 1H), 2.42 (dt, J=11.7, 5.7 Hz, 1H), 2.23 (d, J=16.7 Hz, 1H), 1.60-1.55 (m, 1H), 1.53-1.46 (m, 1H). LCMS m/z 421.3 [M+H]⁺.

Example 59. Preparation of Compound 58

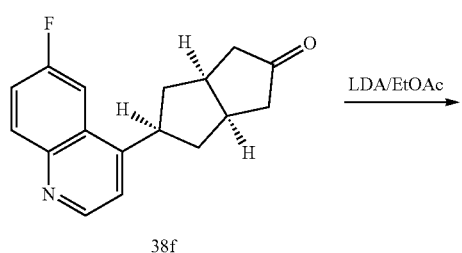

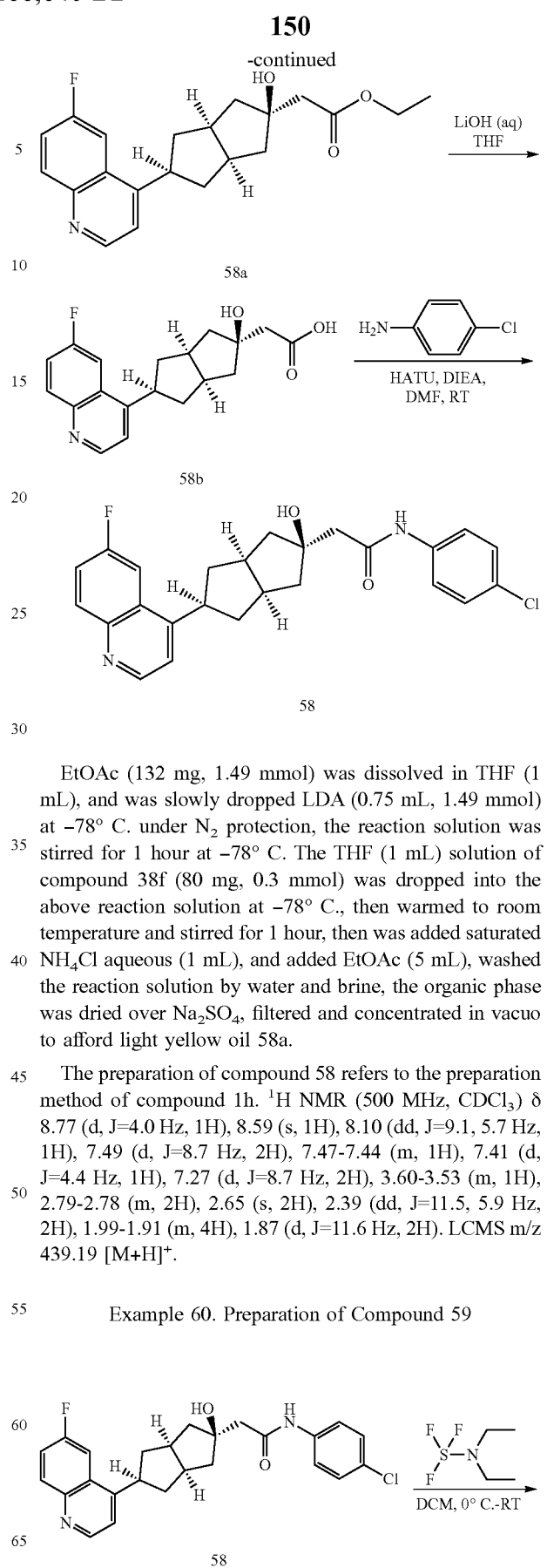

EtOAc (132 mg, 1.49 mmol) was dissolved in THF (1 mL), and was slowly dropped LDA (0.75 mL, 1.49 mmol) at −78° C. under N₂ protection, the reaction solution was stirred for 1 hour at −78° C. The THF (1 mL) solution of compound 38f (80 mg, 0.3 mmol) was dropped into the above reaction solution at −78° C., then warmed to room temperature and stirred for 1 hour, then was added saturated NH₄Cl aqueous (1 mL), and added EtOAc (5 mL), washed the reaction solution by water and brine, the organic phase was dried over Na₂SO₄, filtered and concentrated in vacuo to afford light yellow oil 58a.

The preparation of compound 58 refers to the preparation method of compound 1h. ¹H NMR (500 MHz, CDCl₃) δ 8.77 (d, J=4.0 Hz, 1H), 8.59 (s, 1H), 8.10 (dd, J=9.1, 5.7 Hz, 1H), 7.49 (d, J=8.7 Hz, 2H), 7.47-7.44 (m, 1H), 7.41 (d, J=4.4 Hz, 1H), 7.27 (d, J=8.7 Hz, 2H), 3.60-3.53 (m, 1H), 2.79-2.78 (m, 2H), 2.65 (s, 2H), 2.39 (dd, J=11.5, 5.9 Hz, 2H), 1.99-1.91 (m, 4H), 1.87 (d, J=11.6 Hz, 2H). LCMS m/z 439.19 [M+H]⁺.

Example 60. Preparation of Compound 59

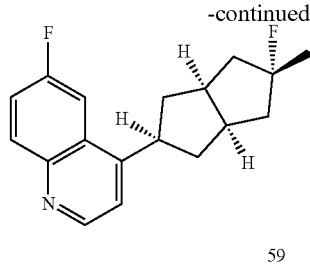

59

Compound 58 (13 mg, 0.03 mmol) was dissolved in CH₂Cl₂ (1.5 mL), was added (diethylamino)sulfur trifluoride (14 mg, 0.088 mmol) at 0° C. and N₂ protection, then warmed to room temperature, TLC analysis tracking the reaction until it was finished, then was concentrated in vacuo to remove CH₂Cl₂. The crude product was purified by preparative TLC (50%, EtOAc/petroleum ether) to afford white solid compound 59. $^1$H NMR (500 MHz, CD₃OD) δ 8.74 (d, J=4.7 Hz, 1H), 8.06 (dd, J=9.2, 5.6 Hz, 1H), 7.92 (dd, J=10.6, 2.7 Hz, 1H), 7.62-7.51 (m, 4H), 7.33-7.26 (m, 2H), 3.96-3.88 (m, 1H), 3.06-2.94 (m, 2H), 2.85 (d, J=19.9 Hz, 2H), 2.53-2.44 (m, 2H), 2.41-2.31 (m, 2H), 1.85 (dd, J=14.1, 7.8 Hz, 1H), 1.77 (dd, J=14.1, 7.8 Hz, 1H), 1.63-1.57 (m, 2H). LCMS m/z 441.22 [M+H]⁺.

Example 61. Preparation of Compound 60

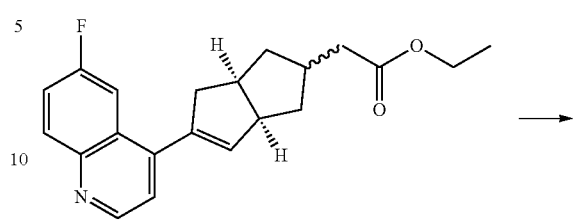

Compound 3a was reacted with MeI under the action of LDA at low temperature to afford intermediate 60a, then preparation of 60 was referred the preparation of compound 3. LCMS m/z 451.16 [M+H]⁺.

Example 62. Preparation of Compound 61

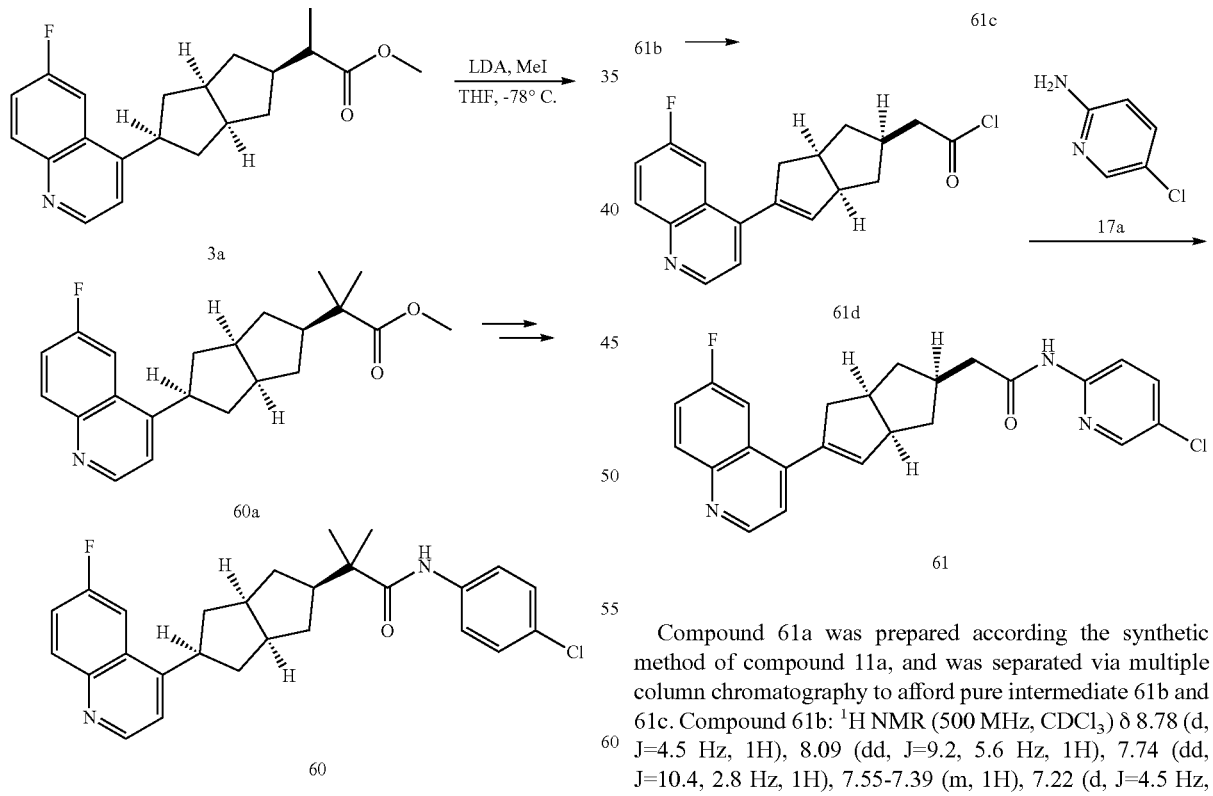

Compound 61a was prepared according the synthetic method of compound 11a, and was separated via multiple column chromatography to afford pure intermediate 61b and 61c. Compound 61b: $^1$H NMR (500 MHz, CDCl₃) δ 8.78 (d, J=4.5 Hz, 1H), 8.09 (dd, J=9.2, 5.6 Hz, 1H), 7.74 (dd, J=10.4, 2.8 Hz, 1H), 7.55-7.39 (m, 1H), 7.22 (d, J=4.5 Hz, 1H), 5.98 (d, J=1.8 Hz, 1H), 4.14 (q, J=7.1 Hz, 2H), 3.52-3.34 (m, 1H), 3.09-3.03 (m, 1H), 2.89-2.81 (m, 1H), 2.52 (dd, J=16.5, 1.7 Hz, 1H), 2.43-2.36 (m, 2H), 2.34-2.25 (m, 2H), 2.25-2.17 (m, 2H), 1.26 (t, J=7.1 Hz, 3H), 1.19-1.06 (m, 2H). Compound 61c: $^1$H NMR (500 MHz, CDCl₃)

δ 8.79 (d, J=4.5 Hz, 1H), 8.11 (dd, J=9.2, 5.6 Hz, 1H), 7.77-7.65 (m, 1H), 7.53-7.38 (m, 1H), 7.24 (d, J=4.5 Hz, 1H), 5.87 (d, J=2.0 Hz, 1H), 4.15 (q, J=7.1 Hz, 2H), 3.56 (t, J=8.4 Hz, 1H), 3.25-3.10 (m, 1H), 3.10-2.94 (m, 1H), 2.59-2.49 (m, 1H), 2.48-2.40 (m, 1H), 2.40-2.33 (m, 2H), 1.90 (dd, J=12.6, 5.8 Hz, 1H), 1.79 (dd, J=12.6, 5.8 Hz, 1H), 1.63-1.53 (m, 1H), 1.52-1.43 (m, 1H), 1.27 (t, J=7.1 Hz, 3H).

Compound 61b was ester hydrolysized to afford acid then was transferred to acyl chloride 61d. Compound 61d reacted with 17a to afford compound 61. Detailed procedures refer to the preparation method of compound 26. $^1$H NMR (500 MHz, CDCl$_3$) δ 8.80 (d, J=4.5 Hz, 1H), 8.23 (d, J=7.2 Hz, 1H), 8.21 (s, 1H), 8.12 (dd, J=9.1, 5.6 Hz, 1H), 7.87 (s, 1H), 7.76 (dd, J=10.3, 2.8 Hz, 1H), 7.67 (dd, J=8.8, 2.6 Hz, 1H), 7.52-7.44 (m, 1H), 6.01 (d, J=1.6 Hz, 1H), 3.49 (d, J=6.8 Hz, 1H), 3.18-2.97 (m, 1H), 2.89 (t, J=9.2 Hz, 1H), 2.55 (d, J=16.6 Hz, 1H), 2.51 (d, J=6.5 Hz, 2H), 2.42-2.36 (m, 2H), 2.32-2.28 (m, 1H), 1.28-1.13 (m, 2H). LCMS m/z 424.14 [M+H]$^+$.

Example 63. Preparation of Compound 62

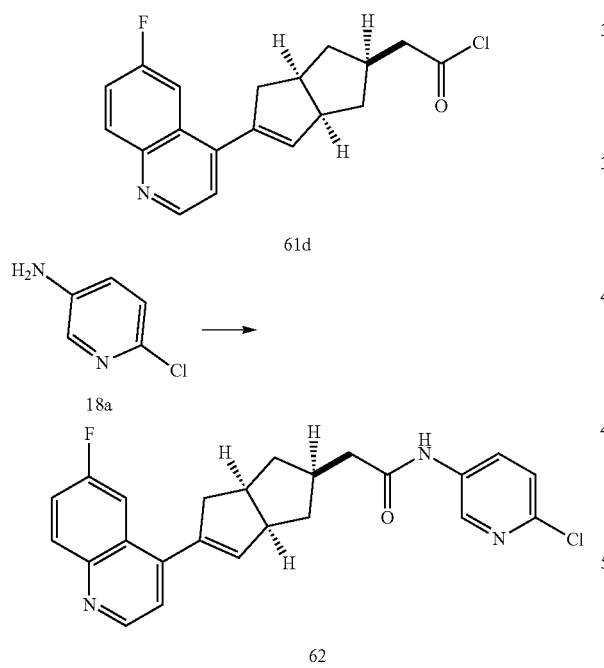

Compound 61d reacted with 2-chloro-5-aminopyridine 18a to afford the racemic compound 62. Detailed procedure refer to the preparation method of compound 11. $^1$H NMR (500 MHz, CDCl$_3$) δ 8.80 (d, J=4.5 Hz, 1H), 8.36 (d, J=2.8 Hz, 1H), 8.20 (dd, J=8.6, 2.7 Hz, 1H), 8.11 (dd, J=9.2, 5.6 Hz, 1H), 7.76 (dd, J=10.4, 2.8 Hz, 1H), 7.54-7.40 (m, 1H), 7.31 (d, J=8.7 Hz, 1H), 7.24 (d, J=4.5 Hz, 2H), 6.01 (d, J=1.6 Hz, 1H), 3.54-3.42 (m, 1H), 3.16-3.03 (m, 1H), 2.93-2.87 (m, 1H), 2.55 (d, J=16.8 Hz, 1H), 2.50 (d, J=5.5 Hz, 2H), 2.44-2.34 (m, 2H), 2.33-2.27 (m, 1H), 1.27-1.12 (m, 2H). LCMS m/z 424.12 [M+H]$^+$.

Example 64. Preparation of Compound 63

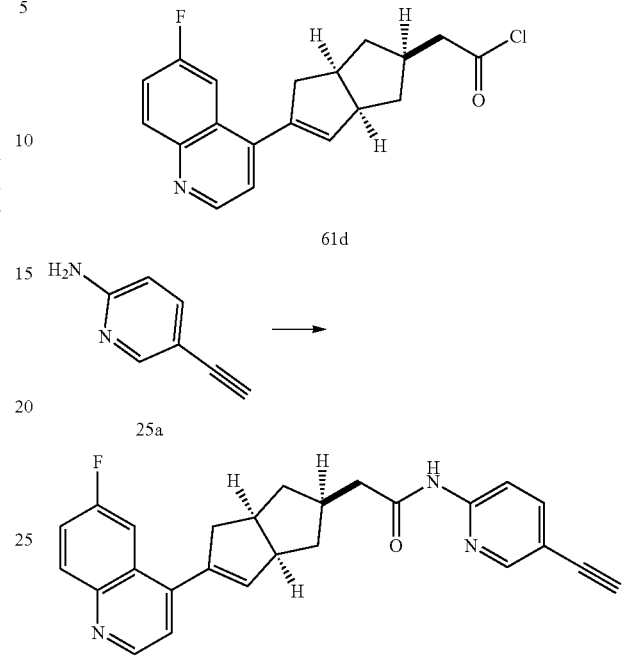

Same as the preparation method of compound 61, compound 61d and compound 25a reacted to prepare the compound 63. $^1$H NMR (500 MHz, CDCl$_3$) δ 8.80 (d, J=4.5 Hz, 1H), 8.38 (d, J=2.0 Hz, 1H), 8.22 (d, J=8.8 Hz, 1H), 8.15-8.07 (m, 1H), 7.89 (s, 1H), 7.83-7.72 (m, 2H), 7.51-7.48 (m, 1H), 6.08-5.97 (m, 1H), 3.53-3.47 (m, 1H), 3.17 (s, 1H), 3.13-3.05 (m, 1H), 2.93-2.85 (m, 1H), 2.56 (d, J=17.7 Hz, 1H), 2.51 (d, J=6.6 Hz, 2H), 2.44-2.36 (m, 2H), 2.33-2.28 (m, 1H), 1.25-1.17 (m, 2H). LCMS m/z 412.20 [M+H]$^+$.

Example 65. Preparation of Compound 64

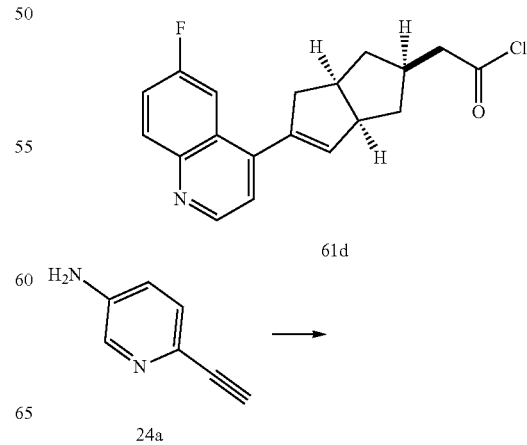

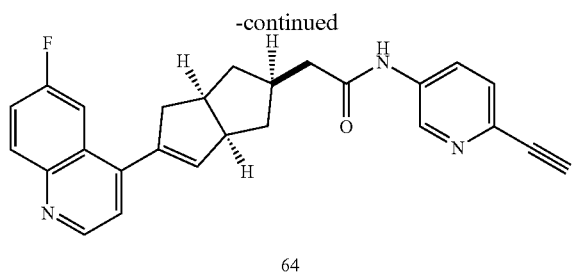

64

Compound 61d and compound 24a reacted to prepare the compound 64. $^1$H NMR (500 MHz, CDCl$_3$) δ 8.80 (d, J=4.5 Hz, 1H), 8.50 (d, J=2.5 Hz, 1H), 8.25 (d, J=8.5 Hz, 1H), 8.11 (dd, J=9.2, 5.6 Hz, 1H), 7.76 (dd, J=10.4, 2.8 Hz, 1H), 7.51-7.44 (m, 2H), 7.24 (d, J=4.5 Hz, 1H), 6.01 (d, J=1.7 Hz, 1H), 3.53-3.47 (m, 1H), 3.12 (s, 1H), 3.11-3.05 (m, 1H), 2.94-2.83 (m, 1H), 2.55 (d, J=16.5 Hz, 1H), 2.51 (d, J=6.0 Hz, 2H), 2.47-2.36 (m, 2H), 2.35-2.26 (m, 1H), 1.23-1.14 (m, 2H). LCMS m/z 206.74 [½M+H]$^+$.

Example 66. Preparation of Compound 65

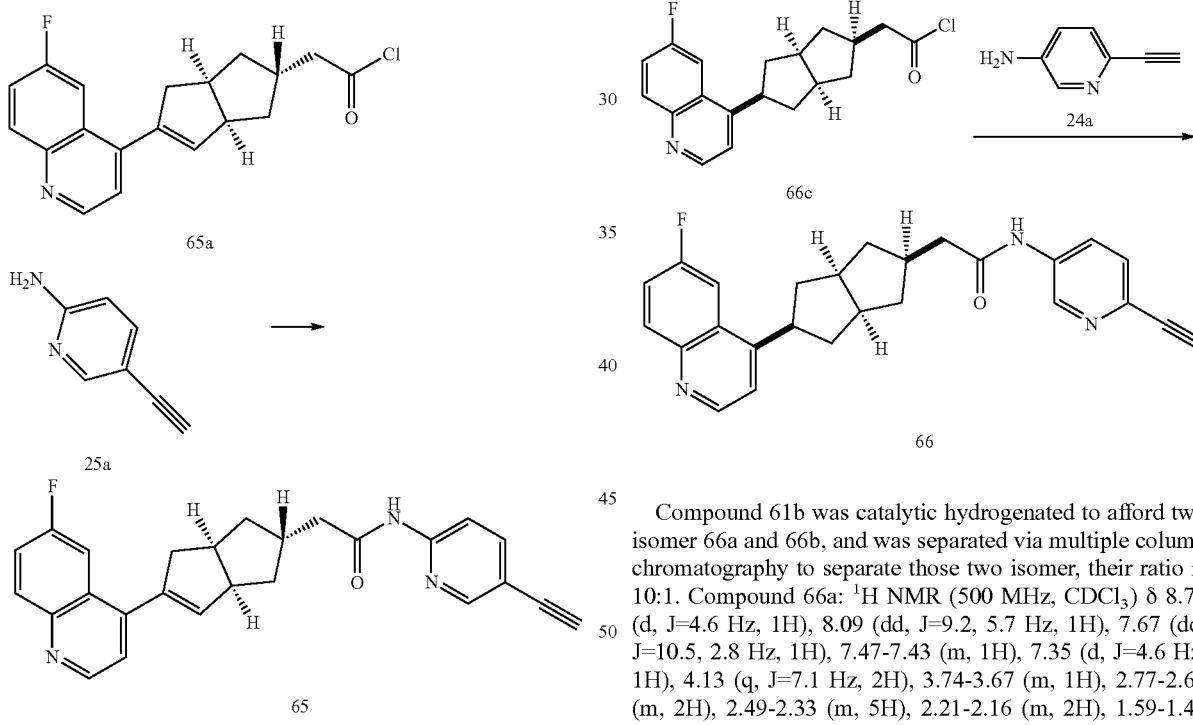

Compound 61c was ester hydrolysis to afford acid, then was transformed to acyl chloride 65a. Compound 65a reacted with compound 25a to prepare compound 65. Refer to the synthesis of compound 26. $^1$H NMR (500 MHz, CDCl$_3$) δ 8.80 (d, J=4.5 Hz, 1H), 8.39 (d, J=1.9 Hz, 1H), 8.22 (d, J=8.7 Hz, 1H), 8.11 (dd, J=9.2, 5.6 Hz, 1H), 7.90 (s, 1H), 7.80 (dd, J=8.6, 2.1 Hz, 1H), 7.76 (dd, J=10.4, 2.8 Hz, 1H), 7.51-7.45 (m, 1H), 7.24-7.23 (m, 1H), 5.90 (d, J=2.0 Hz, 1H), 3.65-3.60 (m, 1H), 3.24-3.19 (m, 1H), 3.17 (s, 1H), 3.11-3.06 (m, 1H), 2.61-2.55 (m, 2H), 2.50-2.46 (m, 2H), 1.98 (dd, J=12.5, 5.7 Hz, 1H), 1.88 (dd, J=12.5, 5.3 Hz, 1H), 1.63 (dd, J=22.0, 9.3 Hz, 2H). LCMS m/z 412.22 [M+H]$^+$.

Example 67. Preparation of Compound 66

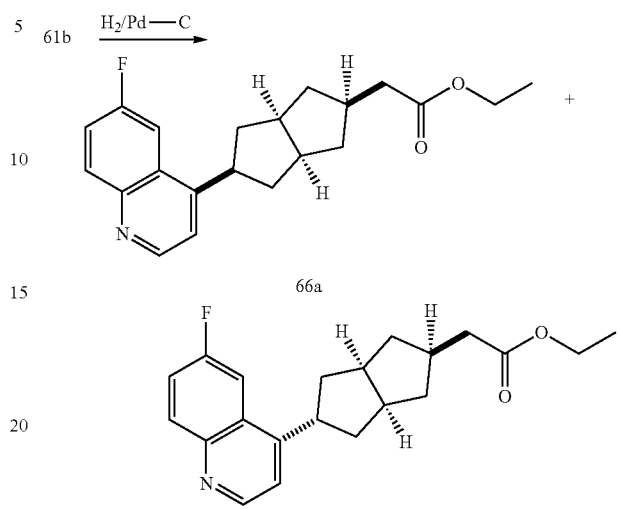

Compound 61b was catalytic hydrogenated to afford two isomer 66a and 66b, and was separated via multiple column chromatography to separate those two isomer, their ratio is 10:1. Compound 66a: $^1$H NMR (500 MHz, CDCl$_3$) δ 8.78 (d, J=4.6 Hz, 1H), 8.09 (dd, J=9.2, 5.7 Hz, 1H), 7.67 (dd, J=10.5, 2.8 Hz, 1H), 7.47-7.43 (m, 1H), 7.35 (d, J=4.6 Hz, 1H), 4.13 (q, J=7.1 Hz, 2H), 3.74-3.67 (m, 1H), 2.77-2.60 (m, 2H), 2.49-2.33 (m, 5H), 2.21-2.16 (m, 2H), 1.59-1.43 (m, 2H), 1.26 (t, J=7.1 Hz, 3H), 1.09-1.03 (m, 2H). The stereo configuration of compound 66a was confirmed by NOESY.

Compound 66a was ester hydrolysis to afford acid, then was transformed to acyl chloride 66c. Compound 66c reacted with compound 24a to prepare compound 66. $^1$H NMR (500 MHz, CD$_3$OD) δ 8.74 (d, J=4.7 Hz, 1H), 8.69 (d, J=2.2 Hz, 1H), 8.15 (dd, J=8.6, 2.5 Hz, 1H), 8.06 (dd, J=9.2, 5.6 Hz, 1H), 7.90 (dd, J=10.6, 2.7 Hz, 1H), 7.61-7.58 (m, 1H), 7.57 (d, J=4.5 Hz, 1H), 7.54 (d, J=8.6 Hz, 1H), 3.92-3.85 (m, 1H), 3.69 (s, 1H), 2.85-2.73 (m, 2H), 2.58-2.46 (m, 3H), 2.47-2.39 (m, 2H), 2.26-2.18 (m, 2H), 1.61-1.54 (m, 2H), 1.19 (dd, J=19.3, 11.5 Hz, 2H). LCMS m/z 414.29 [M+H]$^+$.

Example 68. Preparation of Compound 67

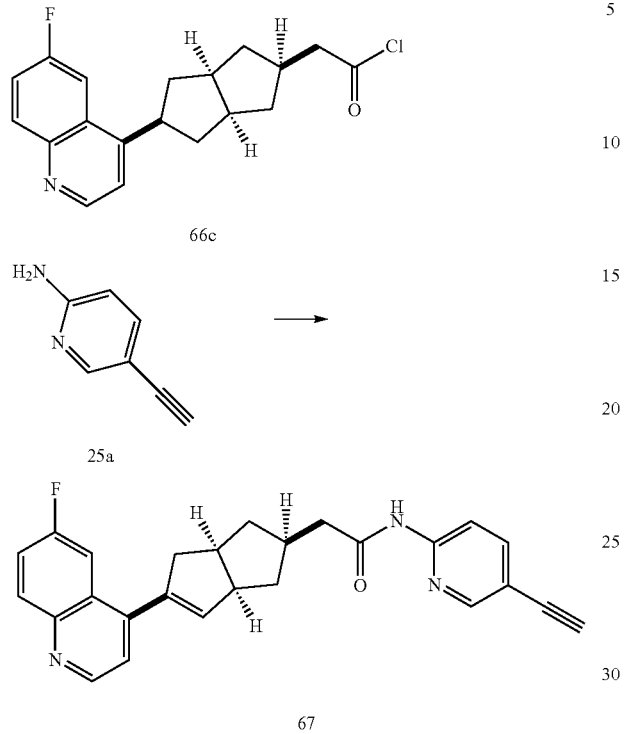

Compound 66c reacted with compound 25a to prepare compound 67. $^1$H NMR (500 MHz, CD$_3$OD) δ 8.76 (d, J=4.7 Hz, 1H), 8.38 (s, 1H), 8.13 (d, J=8.6 Hz, 1H), 8.07 (dd, J=9.2, 5.5 Hz, 1H), 7.93 (dd, J=10.5, 2.7 Hz, 1H), 7.82 (dd, J=8.6, 2.2 Hz, 1H), 7.63-7.57 (m, 2H), 3.93-3.86 (m, 1H), 3.64 (s, 1H), 2.87-2.71 (m, 2H), 2.57-2.48 (m, 3H), 2.47-2.38 (m, 2H), 2.22 (dd, J=12.2, 6.4 Hz, 2H), 1.61-1.55 (m, 2H), 1.19 (dd, J=19.5, 11.7 Hz, 1H). LCMS m/z 414.19 [M+H]$^+$.

Example 69. Preparation of Compound 68

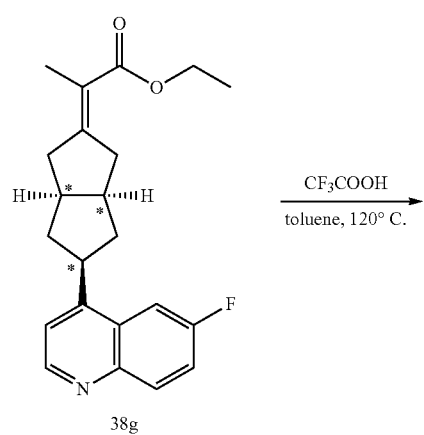

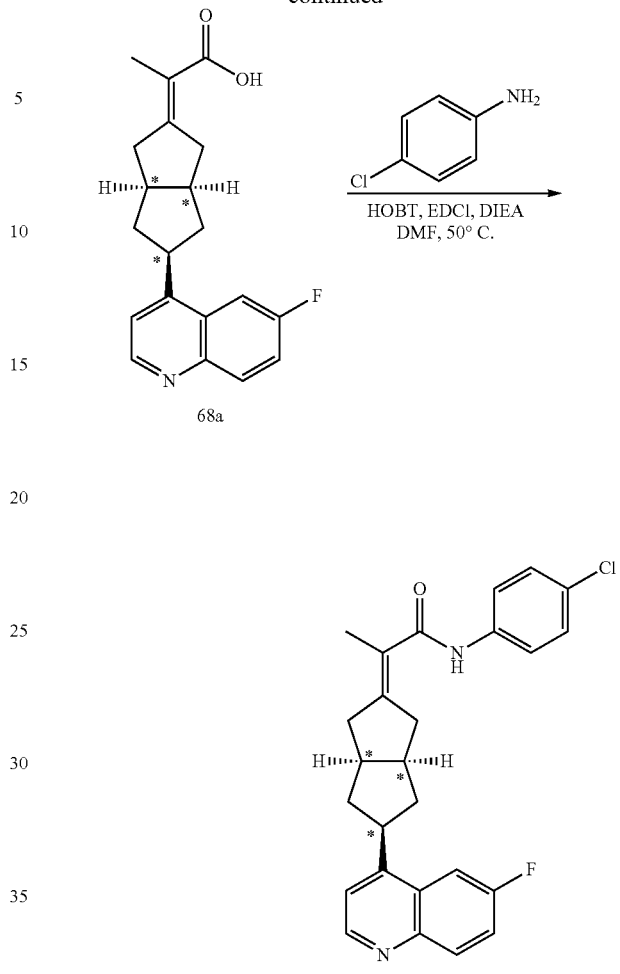

Compound 38g (30 mg, 0.085 mmol) was dissolved in toluene (1 mL), was added trifluoroacetic acid (194 mg, 1.70 mmol), and was heated to 120° C. in seal tube and stirred to react 5 hour, adjusted its pH value to 7 by using saturated NaHCO$_3$ aqueous, extracted with EtOAc (3×5 mL), the combined organic phase was dried over Na$_2$SO$_4$ and filtered. The filtrate was concentrated in vacuo to afford crude product 68a (25 mg, 91%), which was used for next step without further purification.

Compound 68a reacted with 4-chlorobenzenamine to afford compound 68. Refer the preparation method of compound 38. $^1$H NMR (500 MHz, CD$_3$OD) δ 8.73 (d, J=4.7 Hz, 1H), 8.06 (dd, J=9.3, 5.5 Hz, 1H), 7.89 (dd, J=10.6, 2.7 Hz, 1H), 7.64-7.55 (m, 3H), 7.54 (d, J=4.6 Hz, 1H), 7.33-7.28 (m, 2H), 3.87-3.74 (m, 1H), 2.89-2.77 (m, 3H), 2.66 (dd, J=17.3, 8.3 Hz, 1H), 2.53-2.36 (m, 4H), 1.95 (s, 3H), 1.57-1.46 (m, 2H). LCMS m/z 435.26 [M+H]$^+$.

Example 70. Preparation of Compound 69

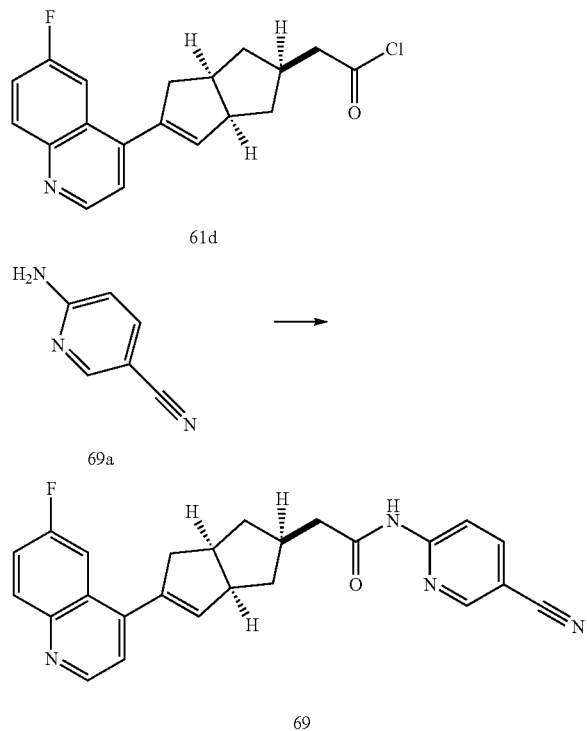

Same as the preparation method of compound 61, Compound 61d reacted with compound 69a to prepare racemic compound 69. LCMS m/z 413.4 [M+H]⁺.

Example 71. Preparation of Compound 70

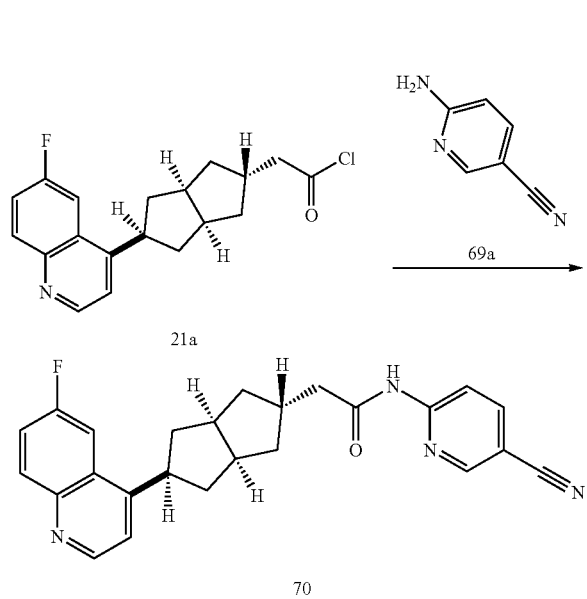

Same as the preparation method of compound 21, Compound 21a reacted with compound 69a to prepare compound 70. LCMS m/z 415.4 [M+H]⁺.

Example 72. Preparation of Compound 71

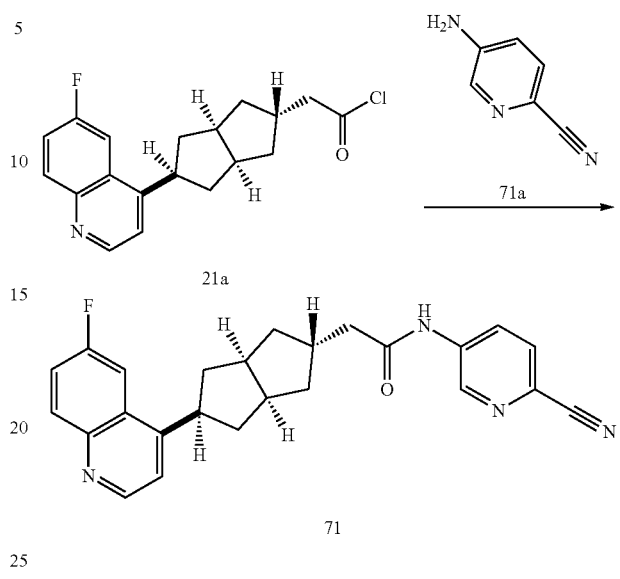

Same as the preparation method of compound 26, compound 21a reacted with compound 71a to prepare compound 71. $^1$H NMR (500 MHz, CDCl$_3$) δ 8.72 (d, J=4.5 Hz, 1H), 8.53 (d, J=2.4 Hz, 1H), 8.37 (dd, J=8.6, 2.5 Hz, 1H), 8.03 (dd, J=9.2, 5.7 Hz, 1H), 7.64-7.59 (m, 2H), 7.46 (s, 1H), 7.42-7.37 (m, 1H), 7.28 (d, J=4.5 Hz, 1H), 3.43-3.35 (m, 1H), 2.72 (dd, J=12.9, 7.2 Hz, 2H), 2.56-2.47 (m, 1H), 2.44 (d, J=7.0 Hz, 2H), 2.36-2.28 (m, 2H), 1.72 (dd, J=12.7, 5.6 Hz, 2H), 1.41-1.30 (m, 4H). LCMS m/z 415.2 [M+H]⁺.

Example 73. Preparation of Compound 72

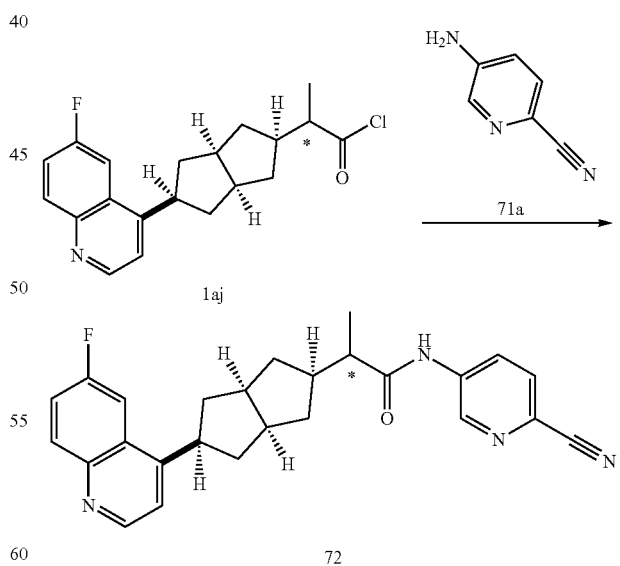

Same as the preparation method of compound 26, compound 1aj reacted with compound 71a to prepare compound 72. $^1$H NMR (500 MHz, CDCl$_3$) δ 8.80 (d, J=4.6 Hz, 1H), 8.61 (d, J=2.5 Hz, 1H), 8.47 (dd, J=8.6, 2.6 Hz, 1H), 8.10 (dd, J=9.2, 5.7 Hz, 1H), 7.68 (d, J=8.8 Hz, 1H), 7.66 (s, 1H), 7.62 (s, 1H), 7.49-7.46 (m, 1H), 7.34 (d, J=4.6 Hz, 1H), 3.77-3.70 (m, 1H), 2.72 (d, J=3.5 Hz, 2H), 2.46-2.39 (m, 2H), 2.34-2.19 (m, 3H), 2.17-2.13 (m, 1H), 1.52-1.46 (m, 2H), 1.30 (d, J=6.4 Hz, 3H), 1.17-1.01 (m, 2H). LCMS m/z 429.2 [M+H]⁺.

Example 74. Preparation of Compound 73

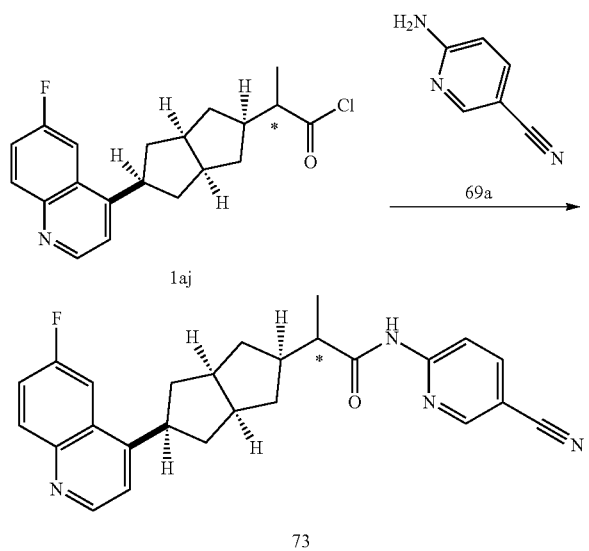

1aj

73

Same as the preparation method of compound 26, compound 1aj reacted with compound 69a to afford compound 73. ¹H NMR (500 MHz, CDCl₃) δ 8.80 (d, J=4.5 Hz, 1H), 8.55 (d, J=2.1 Hz, 1H), 8.39 (d, J=8.8 Hz, 1H), 8.17-8.09 (m, 1H), 8.00 (s, 1H), 7.95 (dd, J=8.8, 2.2 Hz, 1H), 7.68 (dd, J=10.4, 2.5 Hz, 1H), 7.51-7.41 (m, 1H), 7.37 (d, J=4.3 Hz, 1H), 3.77-3.70 (m, 1H), 2.83-2.55 (m, 2H), 2.45-2.39 (m, 2H), 2.35-2.22 (m, 3H), 2.20-2.10 (m, 1H), 1.51-1.48 (m, 2H), 1.30 (d, J=6.1 Hz, 3H), 1.21-1.00 (m, 2H). LCMS m/z 429.23 [M+H]⁺.

Example 75. Preparation of Compound 74

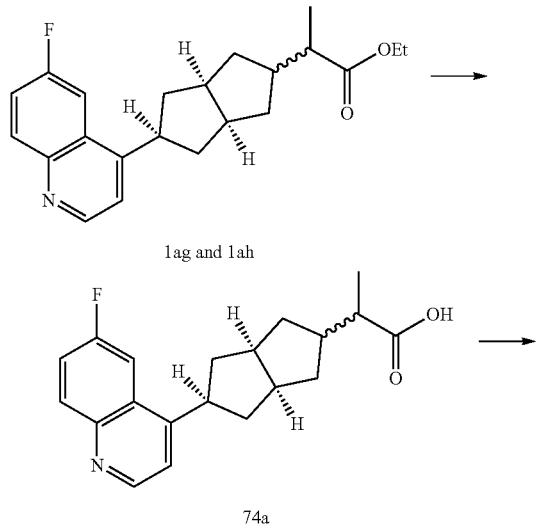

1ag and 1ah

74a

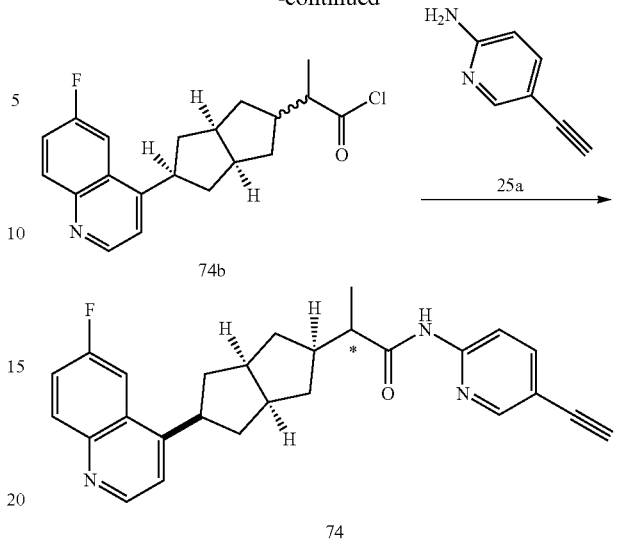

74b

74

In the example 1 of the synthetic procedure of compound 1, intermediate 1af was catalytic hydrogenated by Pd/C to afford mixture of compound 1ag and 1ab. Those mixture are hard to separate, so in the practical experiment, the mixture was hydrolyzed to afford acid 74a, then transformed to acyl chloride 74b, then reacted with compound 25a to prepare the compound 74. (The preparation method is same as the synthesis of compound 26). Main product 74: ¹H NMR (500 MHz, CDCl₃) δ 8.73 (d, J=4.5 Hz, 1H), 8.32 (d, J=1.7 Hz, 1H), 8.16 (d, J=8.6 Hz, 1H), 8.03 (dd, J=9.2, 5.7 Hz, 1H), 7.80 (s, 1H), 7.72 (dd, J=8.7, 2.2 Hz, 1H), 7.60 (dd, J=10.4, 2.7 Hz, 1H), 7.42-7.36 (m, 1H), 7.29 (d, J=4.5 Hz, 1H), 3.69-3.62 (m, 1H), 3.09 (s, 1H), 2.68-2.60 (m, 2H), 2.37-2.31 (m, 2H), 2.21-2.17 (m, 3H), 2.13-2.06 (m, 1H), 1.47-1.41 (m, 2H), 1.22 (d, J=6.5 Hz, 3H), 1.11-0.98 (m, 2H). LCMS m/z 428.2 [M+H]⁺.

Example 76. Preparation of Compound 75

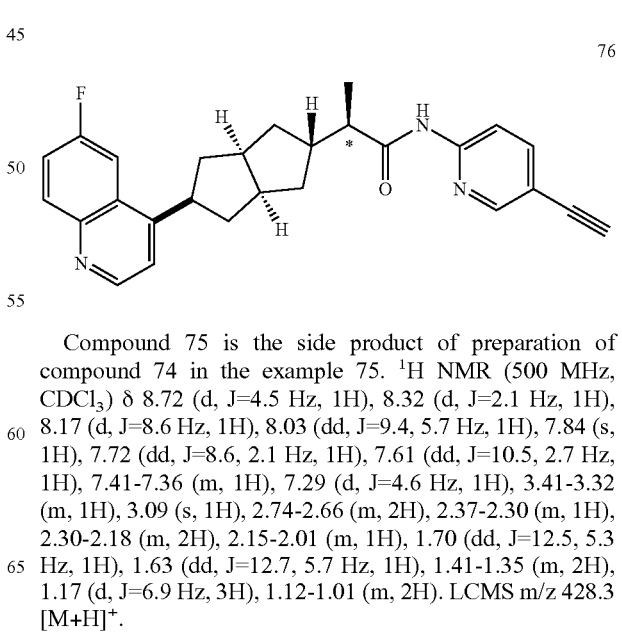

76

Compound 75 is the side product of preparation of compound 74 in the example 75. ¹H NMR (500 MHz, CDCl₃) δ 8.72 (d, J=4.5 Hz, 1H), 8.32 (d, J=2.1 Hz, 1H), 8.17 (d, J=8.6 Hz, 1H), 8.03 (dd, J=9.4, 5.7 Hz, 1H), 7.84 (s, 1H), 7.72 (dd, J=8.6, 2.1 Hz, 1H), 7.61 (dd, J=10.5, 2.7 Hz, 1H), 7.41-7.36 (m, 1H), 7.29 (d, J=4.6 Hz, 1H), 3.41-3.32 (m, 1H), 3.09 (s, 1H), 2.74-2.66 (m, 2H), 2.37-2.30 (m, 1H), 2.30-2.18 (m, 2H), 2.15-2.01 (m, 1H), 1.70 (dd, J=12.5, 5.3 Hz, 1H), 1.63 (dd, J=12.7, 5.7 Hz, 1H), 1.41-1.35 (m, 2H), 1.17 (d, J=6.9 Hz, 3H), 1.12-1.01 (m, 2H). LCMS m/z 428.3 [M+H]⁺.

Example 77. Preparation of Compound 76

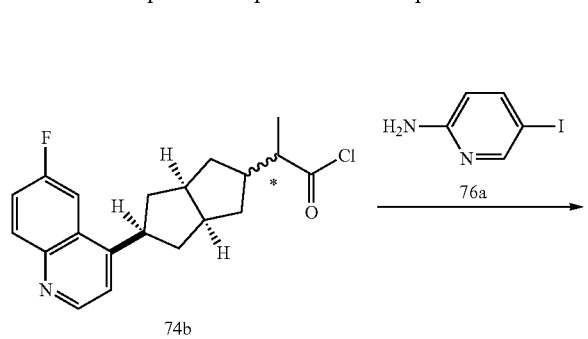

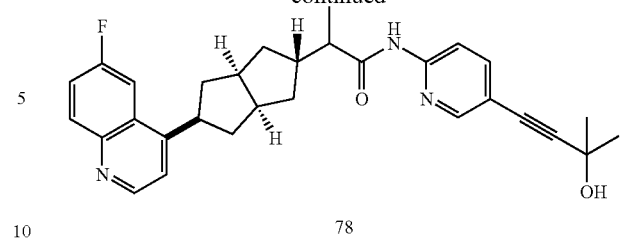

Compound 76 was prepared according the preparation method of compound 74 in the example of 75, intermediate 74b reacted with 76a to afford mixture of two isomers. $^1$H NMR (500 MHz, CDCl$_3$) δ 8.73 (d, J=4.6 Hz, 1H), 8.39 (d, J=2.1 Hz, 1H), 8.03 (d, J=8.7 Hz, 2H), 7.89 (dd, J=8.8, 2.2 Hz, 1H), 7.72 (s, 1H), 7.60 (dd, J=10.5, 2.7 Hz, 1H), 7.42-7.37 (m, 1H), 7.29 (d, J=4.5 Hz, 1H), 3.69-3.63 (m, 1H), 2.63 (t, J=6.9 Hz, 2H), 2.40-2.14 (m, 5H), 2.13-2.04 (m, 1H), 1.37-1.32 (m, 2H), 1.21 (d, J=6.5 Hz, 3H), 1.11-0.99 (m, 2H). LCMS m/z 530.1 [M+H]$^+$.

Example 78. Preparation of Compound 77

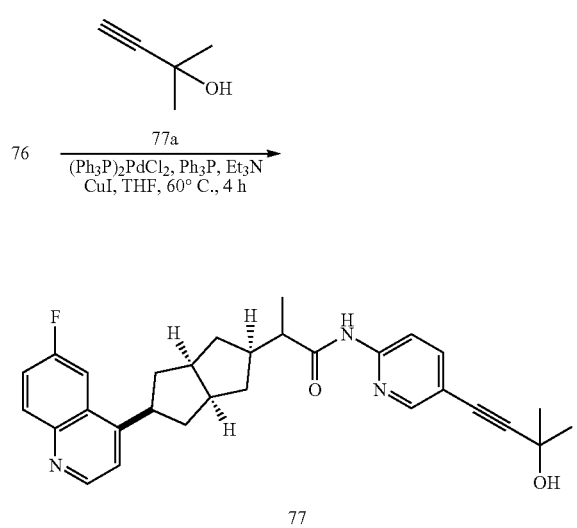

Compound 76 (20 mg, 0.04 mmol), 77a (10 mg, 0.12 mmol), (Ph$_3$P)$_2$PdCl$_2$ (5 mg), Ph$_3$P (2 mg), Et$_3$N (38 mg, 0.40 mmol) and CuI (1 mg) were dissolved in THF (2 mL), heated to 60° C. and stirred for 4 hours. The reaction solution was slowly poured into water, extracted with EtOAc (3×5 mL), the combined organic phase was dried over Na$_2$SO$_4$ and filtered. The filtrate was concentrated in vacuo. The crude product was purified via preparative TLC (MeOH/CH$_2$Cl$_2$=5%) to afford white solid compound 77. Compound 77 is the main product. $^1$H NMR (500 MHz, CDCl$_3$) δ 8.73 (d, J=4.6 Hz, 1H), 8.24 (d, J=1.5 Hz, 1H), 8.14 (d, J=8.7 Hz, 1H), 8.03 (dd, J=9.2, 5.7 Hz, 1H), 7.85 (s, 1H), 7.65 (dd, J=8.6, 2.1 Hz, 1H), 7.43-7.35 (m, 2H), 7.29 (d, J=4.6 Hz, 1H), 3.69-3.62 (m, 1H), 2.66-2.60 (m, 2H), 2.40-2.27 (m, 2H), 2.21-2.16 (m, 3H), 2.13-2.04 (m, 1H), 1.56 (s, 6H), 1.48-1.39 (m, 2H), 1.20 (d, J=7.3 Hz, 3H), 1.12-1.05 (m, 1H), 1.01 (dd, J=19.6, 11.4 Hz, 1H). LCMS m/z 243.8 [M/2+H]$^+$.

Example 79. Preparation of Compound 78

Compound 78 is the byproduct of the preparation of compound 77 in example 78. LCMS m/z 486.2 [M+H]$^+$.

Example 80. Preparation of Compound 79

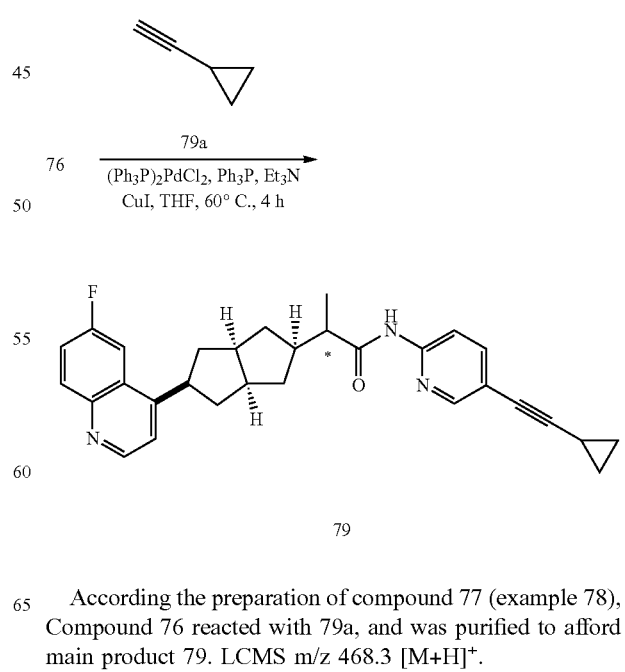

According the preparation of compound 77 (example 78), Compound 76 reacted with 79a, and was purified to afford main product 79. LCMS m/z 468.3 [M+H]$^+$.

Example 81. Preparation of Compound 80

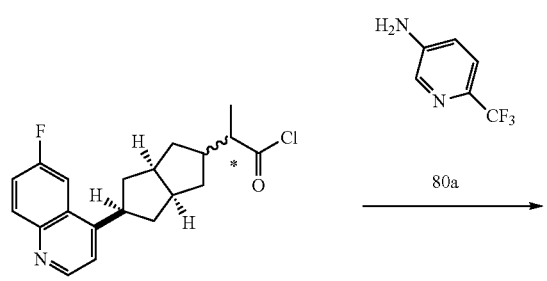

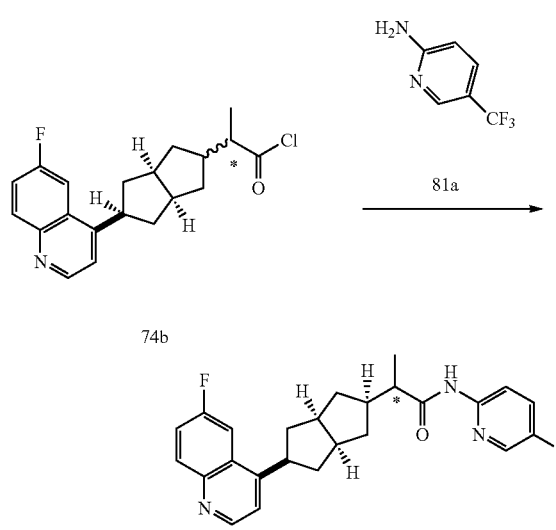

According the preparation of compound 76 (example 77), Compound 74b reacted with 80a, and was purified to afford main product 80. ¹H NMR (500 MHz, CDCl₃) δ 8.80 (d, J=4.6 Hz, 1H), 8.62 (d, J=2.3 Hz, 1H), 8.49 (d, J=8.6 Hz, 1H), 8.10 (dd, J=9.2, 5.7 Hz, 1H), 7.78-7.60 (m, 2H), 7.50-7.45 (m, 1H), 7.44 (s, 1H), 7.35 (d, J=4.5 Hz, 1H), 3.77-3.70 (m, 1H), 2.75-2.69 (m, 2H), 2.45-2.40 (m, 2H), 2.36-2.24 (m, 3H), 2.20-2.12 (m, 1H), 1.51-1.47 (m, 2H), 1.31 (d, J=6.5 Hz, 3H), 1.19-1.03 (m, 2H). LCMS m/z 472.2 [M+H]⁺.

Example 82. Preparation of Compound 81

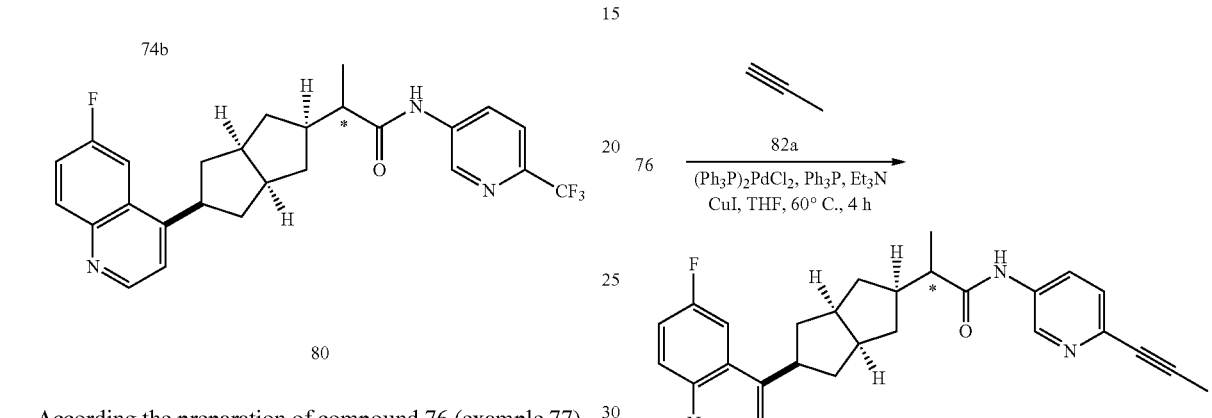

According the preparation of compound 76 (example 77), Compound 74b reacted with 81a, and was purified to afford main product 81. ¹H NMR (500 MHz, CDCl₃) δ 8.80 (d, J=4.6 Hz, 1H), 8.53 (s, 1H), 8.39 (d, J=8.8 Hz, 1H), 8.10 (dd, J=9.1, 5.7 Hz, 1H), 8.01 (s, 1H), 7.92 (d, J=2.3 Hz, 1H), 7.67 (dd, J=10.4, 2.7 Hz, 1H), 7.49-7.42 (m, 1H), 7.36 (d, J=4.6 Hz, 1H), 3.76-3.69 (m, 1H), 2.74-2.68 (m, 2H), 2.45-2.38 (m, 2H), 2.32-2.20 (m, 3H), 2.20-2.11 (m, 1H), 1.52-1.48 (m, 2H), 1.30 (d, J=6.3 Hz, 3H), 1.20-1.02 (m, 2H). LCMS m/z 472.2 [M+H]⁺.

Example 83. Preparation of Compound 82

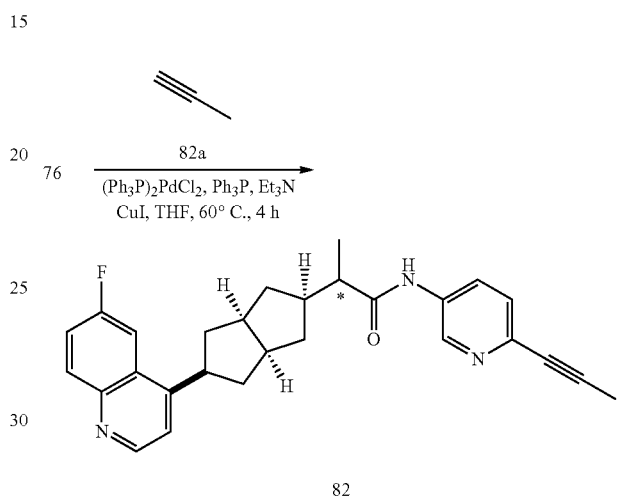

According the preparation of compound 77 (example 78), Compound 76 reacted with 82a, and was purified to afford main product 82. ¹H NMR (500 MHz, CDCl₃) δ 8.73 (d, J=4.5 Hz, 1H), 8.21 (d, J=1.8 Hz, 1H), 8.11 (d, J=8.6 Hz, 1H), 8.03 (dd, J=9.2, 5.7 Hz, 1H), 7.83 (s, 1H), 7.65-7.57 (m, 2H), 7.39 (ddd, J=9.2, 8.0, 2.8 Hz, 1H), 7.29 (d, J=4.6 Hz, 1H), 3.65 (dq, J=18.0, 5.9 Hz, 1H), 2.68-2.55 (m, 2H), 2.33 (ddd, J=18.7, 12.2, 5.8 Hz, 2H), 2.24-2.13 (m, 3H), 2.12-2.05 (m, 1H), 1.99 (s, 3H), 1.43 (dt, J=12.2, 10.0 Hz, 2H), 1.21 (d, J=6.6 Hz, 3H), 1.10-1.04 (m, 1H), 1.02-0.95 (m, 1H). LCMS m/z 442.2 [M+H]⁺.

Example 84. Preparation of Compound 83

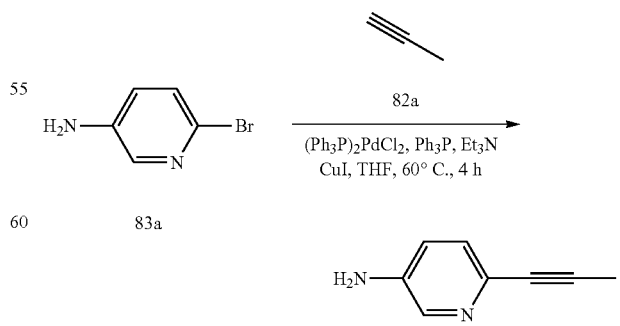

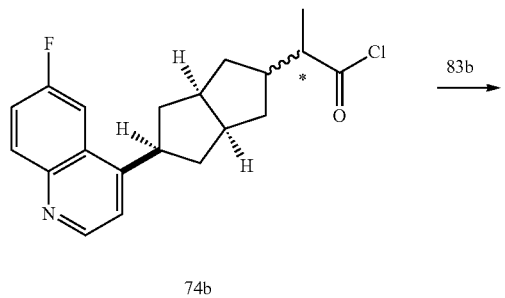

74b

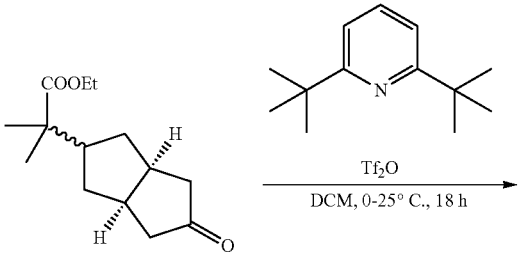

84b (5:1)

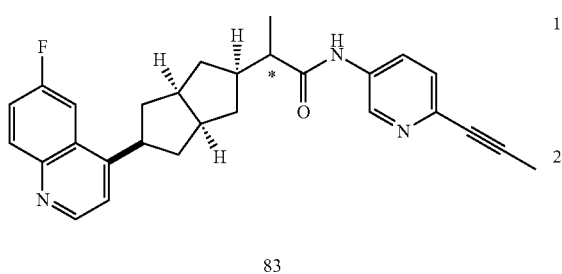

83

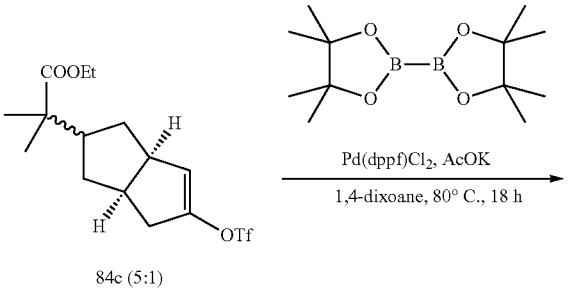

84c (5:1)

Intermediate 83b was prepared by the reaction of 83a and 82a (Refer to the preparation method of compound 77 in the example 78). Compound 74b reacted with 83b, and was purified to afford main product 83 (refer to the preparation of compound 76. $^1$H NMR (500 MHz, CDCl$_3$) δ 8.73 (d, J=4.5 Hz, 1H), 8.40 (d, J=2.4 Hz, 1H), 8.13 (dd, J=8.6, 2.6 Hz, 1H), 8.03 (dd, J=9.2, 5.7 Hz, 1H), 7.61 (dd, J=10.4, 2.7 Hz, 1H), 7.43-7.35 (m, 2H), 7.30-7.25 (m, 2H), 3.66 (ddd, J=17.9, 11.9, 5.9 Hz, 1H), 2.63 (d, J=7.3 Hz, 2H), 2.38-2.31 (m, 2H), 2.26-2.15 (m, 3H), 2.12-2.07 (m, 1H), 1.98 (s, 3H), 1.42 (dd, J=19.2, 12.0 Hz, 2H), 1.20 (d, J=7.1 Hz, 3H), 1.07 (dd, J=11.6, 8.1 Hz, 1H), 1.01-0.94 (m, 1H). LCMS m/z 442.2 [M+H]$^+$.

Example 85. Preparation of Compound 84

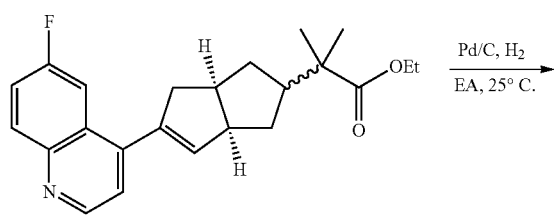

84d (5:1)

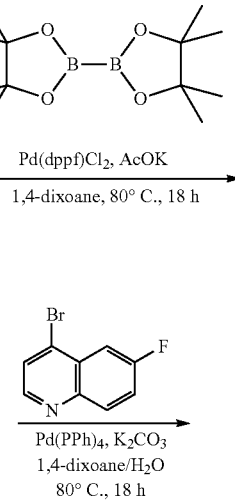

84e (5:1)

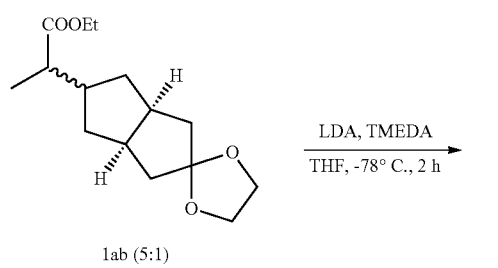

1ab (5:1)

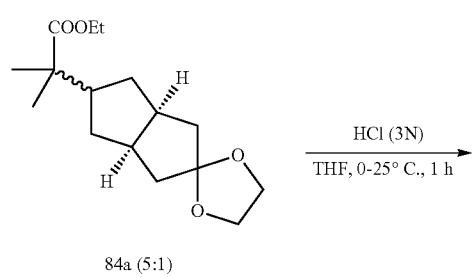

84a (5:1)

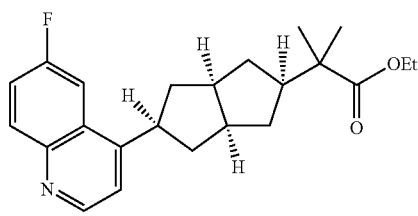

84f (major)

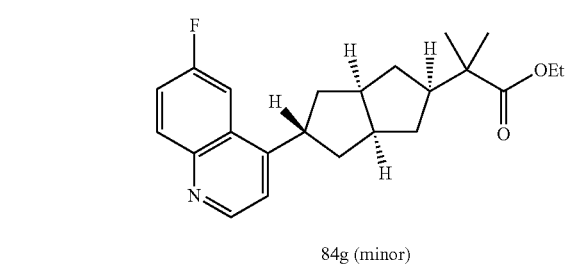

84g (minor)

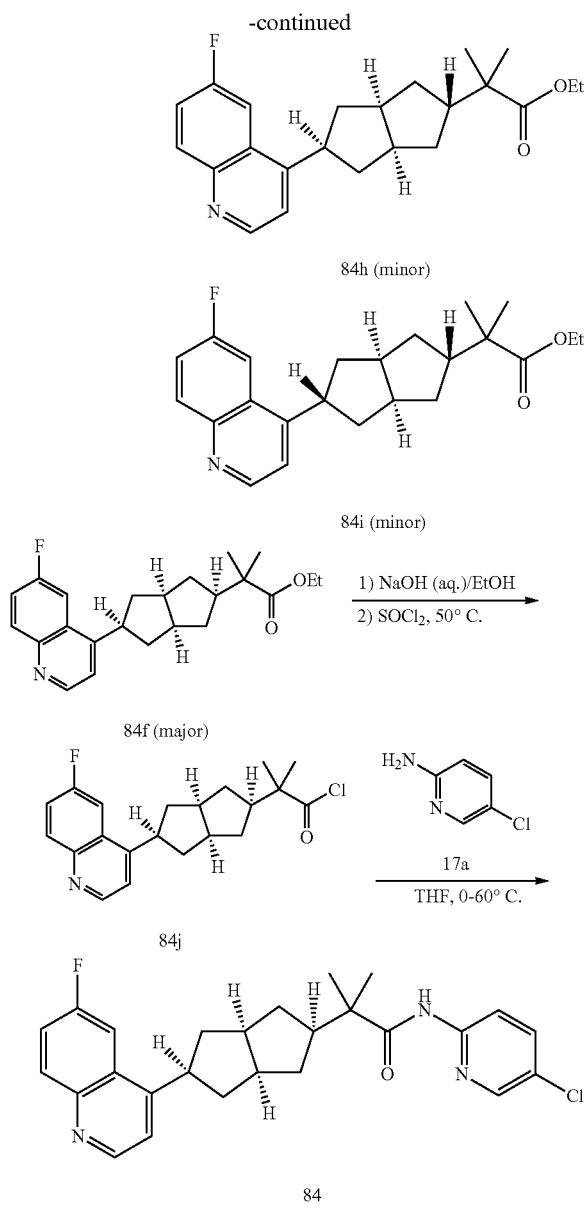

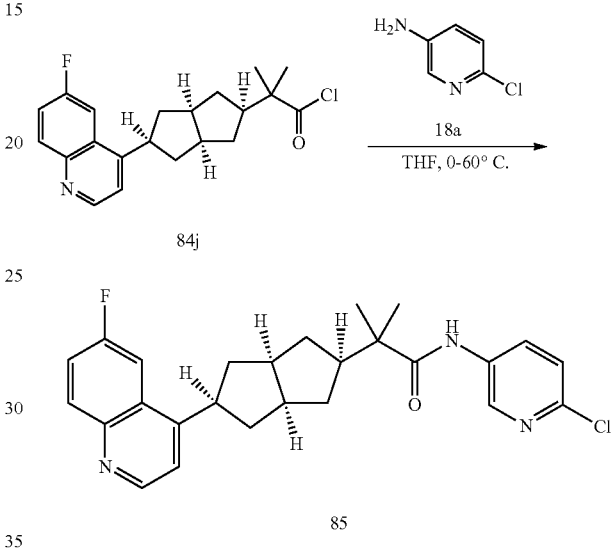

phy. Therefore, the mixture continued to be used for the next step (ester hydrolysis and preparation of acyl chloride). Finally, in amides preparation, the three small amounts of isomers could be separated via preparative TLC. $^1$H NMR (500 MHz, CD$_3$OD) δ 8.72 (d, J=4.7 Hz, 1H), 8.29 (d, J=2.6 Hz, 1H), 8.10 (d, J=8.9 Hz, 1H), 8.04 (dd, J=9.2, 5.6 Hz, 1H), 7.88 (dd, J=10.6, 2.8 Hz, 1H), 7.79 (dd, J=8.9, 2.6 Hz, 1H), 7.59-7.54 (m, 2H), 3.90-3.83 (m, 1H), 2.76-2.73 (m, 2H), 2.51-2.45 (m, 1H), 2.44-2.38 (m, 2H), 2.00-1.95 (m, 2H), 1.58-1.50 (m, 2H), 1.28 (s, 6H), 1.35-1.26 (m, 2H). LCMS m/z 452.2 [M+H]$^+$.

Example 86. Preparation of Compound 85

Same as the preparation method of compound 26, compound 84j reacted with compound 18a to prepare compound 85. $^1$H NMR (500 MHz, CD$_3$OD) δ 8.72 (d, J=4.7 Hz, 1H), 8.58 (d, J=2.7 Hz, 1H), 8.09-8.03 (m, 2H), 7.88 (dd, J=10.6, 2.7 Hz, 1H), 7.59-7.54 (m, 2H), 7.41 (d, J=8.7 Hz, 1H), 3.31-3.29 (m, 1H), 2.79-2.69 (m, 2H), 2.50-2.45 (m, 1H), 2.44-2.38 (m, 2H), 2.03-1.95 (m, 2H), 1.58-1.51 (m, 2H), 1.28 (s, 6H), 1.32-1.23 (m, 2H). LCMS m/z 452.2 [M+H]$^+$.

Example 87. Preparation of Compound 86

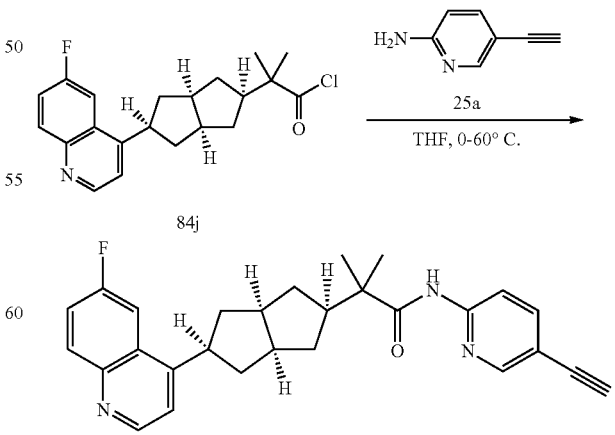

Compound 1ab (3.0 g, 11.18 mmol) and TMEDA (2.6 g, 22.36 mmol) were dissolved in THF (20 mL) and were cooled to −78° C. under N$_2$ protection, and were slowly added LDA (11.18 mL, 22.36 mmol), stirred for 1 hour at −78° C., then MeI (3.17 g, 22.36 mmol) was added to the above solution, and stirred for 30 minutes (a lot of white solid was precipitated). Saturated NH$_4$Cl aqueous solution (20 mL) was added to the reaction, extracted with EtOAc (3×30 mL), the combined organic phase was dried over Na$_2$SO$_4$ and filtered. The filtrate was concentrated in vacuo. The crude product was purified via column chromatography (EtOAc/petroleum ether=0-10%) to afford colorless oil compound 84a (1.9 g, yield 60%).

Starting from compound 84a and referring to the synthetic route of compound 1, compound 84e was synthesized by multi-step synthesis. The main product 84f and three other isomers (small amount) were obtained by catalytic hydrogenation of compound 84e. In this step, these isomers and main products were close to each other in TLC, and it was difficult to be separated via silica gel column chromatogra- Same as the preparation method of compound 26, compound 84j reacted with compound 25a to prepare compound 86. ¹H NMR (500 MHz, CD₃OD) δ 8.72 (d, J=4.7 Hz, 1H), 8.39 (d, J=1.6 Hz, 1H), 8.10 (d, J=8.7 Hz, 1H), 8.05 (dd, J=9.2, 5.6 Hz, 1H), 7.88 (dd, J=10.6, 2.8 Hz, 1H), 7.84 (dd, J=8.7, 2.3 Hz, 1H), 7.61-7.52 (m, 2H), 3.90-3.83 (m, 1H), 3.65 (s, 1H), 2.75-2.73 (m, 2H), 2.51-2.45 (m, 1H), 2.44-2.38 (m, 2H), 2.00-1.95 (m, 2H), 1.58-1.51 (m, 2H), 1.28 (s, 6H), 1.32-1.25 (m, 2H). LCMS m/z 442.3 [M+H]⁺.

Example 88. Preparation of Compound 87

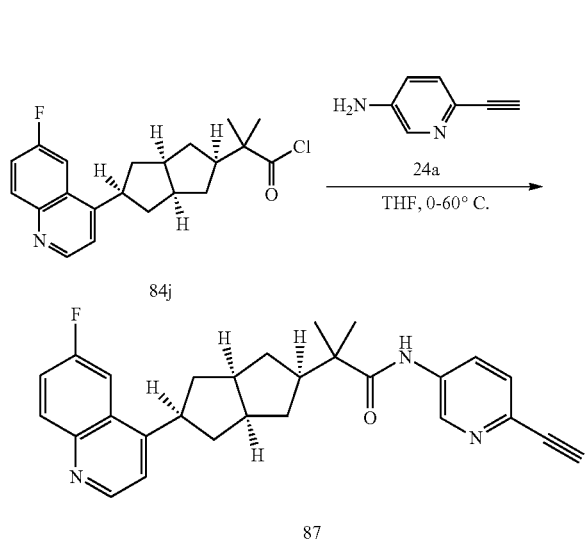

Same as the preparation method of compound 26, compound 84j reacted with compound 24a to prepare compound 87. ¹H NMR (500 MHz, CD₃OD) δ 8.73-8.72 (m, 2H), 8.12 (dd, J=8.6, 2.5 Hz, 1H), 8.05 (dd, J=9.2, 5.6 Hz, 1H), 7.88 (dd, J=10.6, 2.8 Hz, 1H), 7.59-7.53 (m, 3H), 3.90-3.83 (m, 1H), 3.69 (s, 1H), 2.74-2.73 (m, 2H), 2.51-2.46 (m, 1H), 2.44-2.38 (m, 2H), 2.00-1.95 (m, 2H), 1.58-1.51 (m, 2H), 1.28 (s, 6H), 1.32-1.25 (m, 2H). LCMS m/z 442.2 [M+H]⁺.

Example 89. Preparation of Compound 88

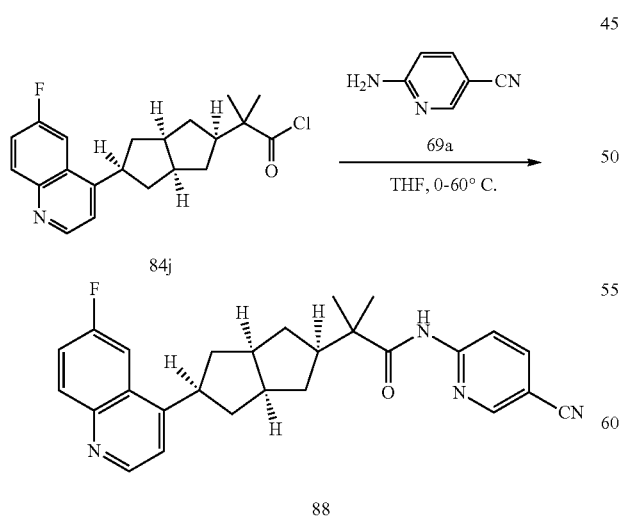

Same as the preparation method of compound 26, compound 84j reacted with compound 69a to prepare compound 88. ¹H NMR (500 MHz, CDCl₃) δ 8.81 (d, J=4.6 Hz, 1H), 8.62 (d, J=2.5 Hz, 1H), 8.45 (dd, J=8.6, 2.6 Hz, 1H), 8.12 (dd, J=9.2, 5.7 Hz, 1H), 7.70-7.67 (m, 2H), 7.52 (s, 1H), 7.50-7.46 (m, 1H), 7.37 (d, J=4.6 Hz, 1H), 3.77-3.70 (m, 1H), 2.73-2.66 (m, 2H), 2.45-2.36 (m, 3H), 2.04-2.01 (m, 2H), 1.53-1.48 (m, 2H), 1.35 (s, 6H), 1.29-1.20 (m, 2H). LCMS m/z 443.2 [M+H]⁺.

Example 90. Preparation of Compound 89

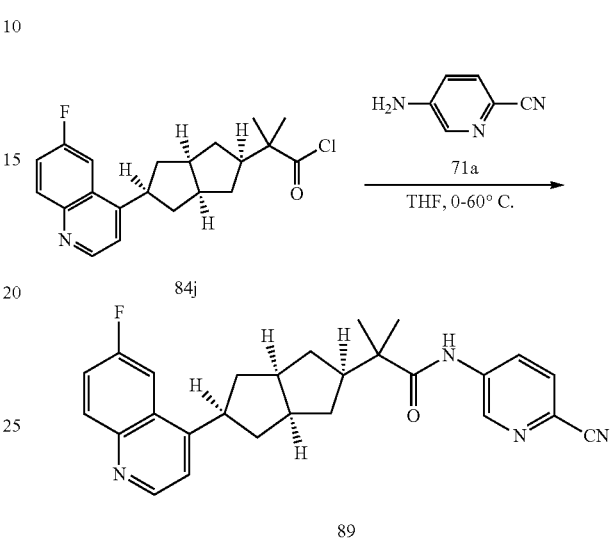

Same as the preparation method of compound 26, compound 84j reacted with compound 71a to prepare compound 89. ¹H NMR (500 MHz, CDCl₃) δ 8.73 (d, J=4.6 Hz, 1H), 8.49 (d, J=1.5 Hz, 1H), 8.33 (d, J=8.8 Hz, 1H), 8.10 (s, 1H), 8.06 (s, 1H), 7.88 (dd, J=8.8, 2.2 Hz, 1H), 7.61 (dd, J=10.4, 2.5 Hz, 1H), 7.43-7.40 (m, 1H), 7.31 (s, 1H), 3.69-3.64 (m, 1H), 2.65-2.58 (m, 2H), 2.37-2.28 (m, 3H), 1.97-1.91 (m, 2H), 1.48-1.40 (m, 2H), 1.26 (s, 6H), 1.18-1.13 (m, 2H). LCMS m/z 443.3 [M+H]⁺.

Example 91. Preparation of Compound 90

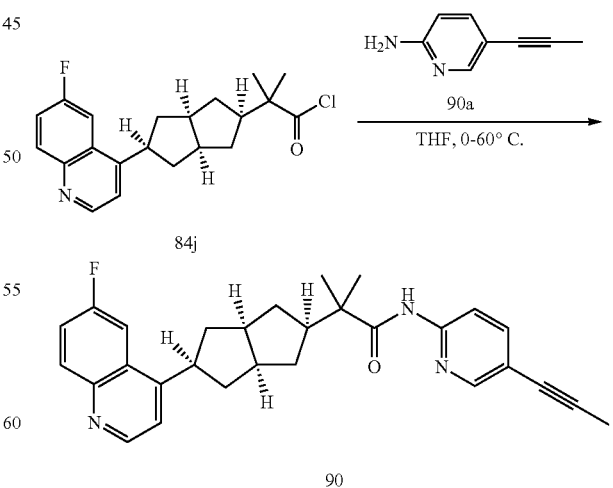

Same as the preparation method of compound 26, compound 84 reacted with compound 90a to prepare compound 90. ¹H NMR (500 MHz, CDCl₃) δ 8.80 (d, J=4.5 Hz, 1H), 8.30 (d, J=1.8 Hz, 1H), 8.20 (d, J=8.7 Hz, 1H), 8.12 (dd, J=9.1, 5.7 Hz, 1H), 8.00 (s, 1H), 7.71-7.67 (m, 2H), 7.49-7.45 (m, 1H), 7.37 (d, J=4.5 Hz, 1H), 3.76-3.69 (m, 1H), 2.75-2.65 (m, 2H), 2.43-2.35 (m, 3H), 2.07 (s, 3H), 2.04-1.99 (m, 2H), 1.54-1.47 (m, 2H), 1.32 (s, 6H), 1.26-1.20 (m, 2H). LCMS m/z 456.2 [M+H]⁺.

Example 92. Preparation of Compound 91

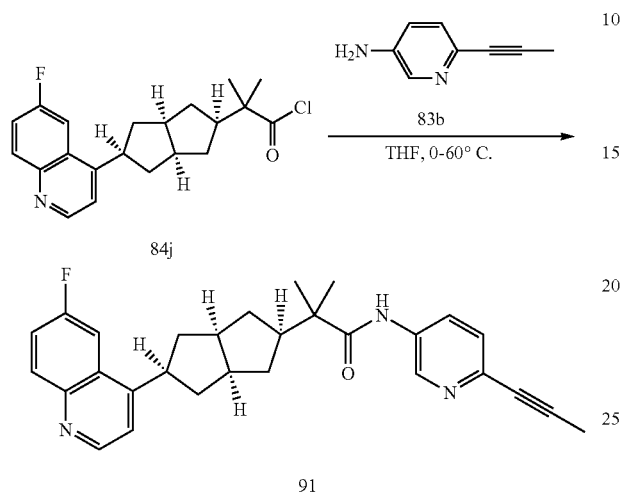

Same as the preparation method of compound 26, compound 84j reacted with compound 83b to prepare compound 91. ¹H NMR (500 MHz, CDCl₃) δ 8.81 (d, J=4.6 Hz, 1H), 8.46 (d, J=2.5 Hz, 1H), 8.19 (dd, J=8.6, 2.6 Hz, 1H), 8.14 (s, 1H), 7.69 (dd, J=10.4, 2.7 Hz, 1H), 7.50-7.47 (m, 1H), 7.39-7.35 (m, 3H), 3.77-3.70 (m, 1H), 2.75-2.65 (m, 2H), 2.44-2.36 (m, 3H), 2.08 (s, 3H), 2.05-2.00 (m, 2H), 1.55-1.48 (m, 2H), 1.33 (s, 6H), 1.26-1.20 (m, 2H). LCMS m/z 456.2 [M+H]⁺.

Example 93. Preparation of Compound 92

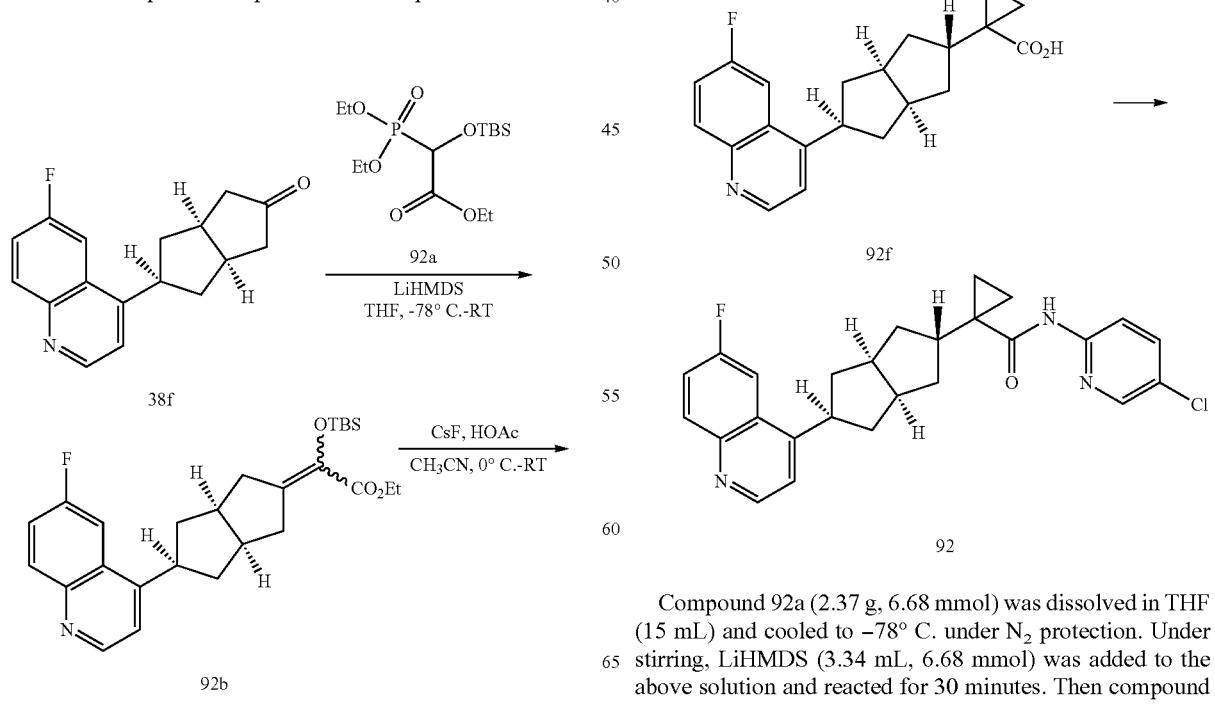

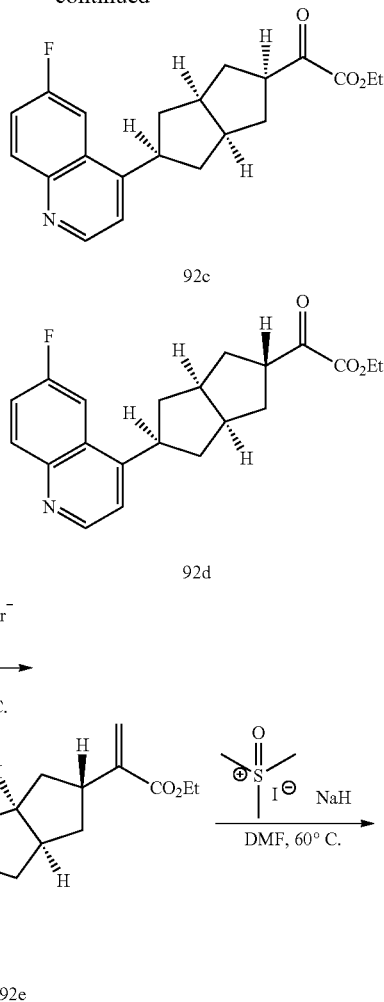

Compound 92a (2.37 g, 6.68 mmol) was dissolved in THF (15 mL) and cooled to −78° C. under N₂ protection. Under stirring, LiHMDS (3.34 mL, 6.68 mmol) was added to the above solution and reacted for 30 minutes. Then compound 38f (1.5 g, 5.57 mmol) THF (5 mL) solution was added to the mixture. After reacting for 2 hours, saturated NH₄Cl aqueous solution (30 mL) was added. The aqueous phase was extracted with ethyl acetate (3×10 mL), the combined organic phase was washed with brine, then dried (anhydrous sodium sulfate) and filtered, and filtrate was concentrated, purified by column chromatography (ethyl acetate/petroleum ether=0-10%) to afford colorless oil 92b (1.9 g, yield 73%).

At 0° C., the MeCN (10 mL) solution of compound 92b (1.9 g, 4.05 mmol) was added CsF (3.07 g, 20.23 mmol) and acetic acid (2.43 g, 40.45 mmol). After adding, the mixture was stirred for 30 minutes at 0° C. Then it was slowly warmed to room temperature and reacted until the raw material disappears. The reaction mixture was adjusted to pH 7 with saturated NaHCO₃ aqueous solution, and the organic phase was separated and the water phase was extracted by ethyl acetate (3×10 mL). The combined organic phase was washed with brine, dried over Na₂SO₄ and filtered. The filtrate was concentrated in vacuo. The crude product was purified via column chromatography (EtOAc/petroleum ether=0-20%) to afford white solid 92c (280 mg) and colorless oily liquid 92d (450 mg).

At −78° C. and N2 protection, the THF (3 mL) solution of methyltriphenylphosphonium bromide (503 mg, 1.41 mmol) was added KHMDS (1N THF solution, 1.41 mL). After stirring for 1 hour at −78 C, the tetrahydrofuran (2 mL) solution of compound 92d (250 mg, 0.7 mmol) was added to the above reaction, then warmed to room temperature and stirred for 1 hour at room temperature. The reaction was quenched by adding saturated NH₄Cl solution (1 mL) and diluted with ethyl acetate (10 mL). The organic phase was separated and the water phase was extracted with ethyl acetate (3×10 mL). The combined organic phase was washed with water and brine one time in turn. The organic phase is dried over Na₂SO₄ and filtered. The filtrate was concentrated in vacuo to afford the crude product, which was purified via column chromatography (EtOAc/petroleum ether=0-100%) to afford colorless oil compound 92e (120 mg, yield 48%).

TMSI (48 mg, 0.51 mmol) and NaH (24 mg, 0.41 mmol) were placed in a reaction bottle, was added DMF (1 mL) at 0° C. and stirred for 10 minutes. Then the reaction was heated to 60° C., and the DMF (1.5 mL) solution of compound 92e (0.34 mg, mmol) was added to the above reaction, and stirred overnight at this temperature. Saturated ammonium chloride (1 mL) was added to quench the reaction and dilute with ethyl acetate (10 mL), the mixture was washed by brine one time, and the organic phase was dried over Na₂SO₄ and filtered. The filtrate was concentrated in vacuo to afford the crude product, which was purified via column chromatography (EtOAc) to afford white solid compound 92f (mg, yield 37%).

According the synthesis steps and methods of compound 26, compound 92 was prepared by acyl chloride starting from compound 92f. ¹H NMR (500 MHz, CD₃OD) δ 8.73 (d, J=4.7 Hz, 1H), 8.27 (d, J=2.5 Hz, 1H), 8.09 (d, J=8.9 Hz, 1H), 8.05 (dd, J=9.2, 5.6 Hz, 1H), 7.89 (dd, J=10.6, 2.8 Hz, 1H), 7.77 (dd, J=8.9, 2.6 Hz, 1H), 7.61 (d, J=4.7 Hz, 1H), 7.59-7.55 (m, 1H), 3.61-3.54 (m, 1H), 2.87-2.77 (m, 3H), 2.41-2.36 (m, 2H), 1.63 (dd, J=12.8, 5.8 Hz, 2H), 1.53 (dd, J=21.3, 12.2 Hz, 2H), 1.42-1.36 (m, 2H), 1.05 (q, J=4.6 Hz, 2H), 0.86 (dd, J=6.7, 4.8 Hz, 2H). LCMS m/z 450.1 [M+H]⁺.

Example 94. Preparation of Compound 93

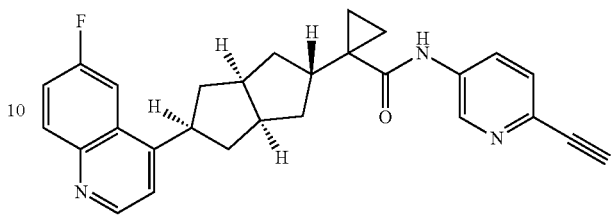

93

The preparation method of compound 93 is as same as the preparation method of compound 92. ¹H NMR (500 MHz, CDCl₃) δ 8.80 (d, J=4.5 Hz, 1H), 8.50 (d, J=2.3 Hz, 1H), 8.21 (dd, J=8.6, 2.6 Hz, 1H), 8.15 (dd, J=9.2, 5.7 Hz, 1H), 7.70 (dd, J=10.4, 2.7 Hz, 1H), 7.59 (s, 1H), 7.51-7.47 (m, 1H), 7.46 (d, J=8.6 Hz, 1H), 7.40 (d, J=4.4 Hz, 1H), 3.48-3.43 (m, 1H), 3.12 (s, 1H), 2.80-2.74 (m, 2H), 2.73-2.67 (m, 1H), 2.46-2.41 (m, 2H), 1.66 (dd, J=12.9, 5.8 Hz, 2H), 1.47-1.38 (m, 4H), 1.12 (q, J=4.8 Hz, 2H), 0.87 (q, J=4.9 Hz, 2H). LCMS m/z 440.2 [M+H]⁺.

Example 95. Preparation of Compound 94

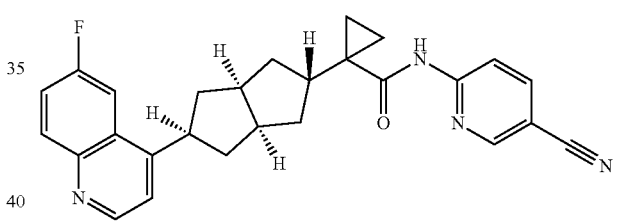

94

The preparation method of compound 94 is as same as the preparation method of compound 92. ¹H NMR (500 MHz, CDCl₃) δ 8.82 (d, J=4.5 Hz, 1H), 8.54 (d, J=1.6 Hz, 1H), 8.36 (dd, J=8.8, 0.5 Hz, 1H), 8.21 (s, 1H), 8.14 (dd, J=9.2, 5.7 Hz, 1H), 7.93 (dd, J=8.8, 2.2 Hz, 1H), 7.70 (dd, J=10.4, 2.7 Hz, 1H), 7.52-7.46 (m, 1H), 7.40 (d, J=4.5 Hz, 1H), 3.51-3.44 (m, 1H), 2.83-2.70 (m, 3H), 2.48-2.43 (m, 2H), 1.68 (dd, J=12.9, 5.9 Hz, 2H), 1.49-1.36 (m, 4H), 1.17 (q, J=4.7 Hz, 2H), 0.92 (q, J=4.9 Hz, 2H). LCMS m/z 441.2 [M+H]⁺.

Example 96. Preparation of Compound 95

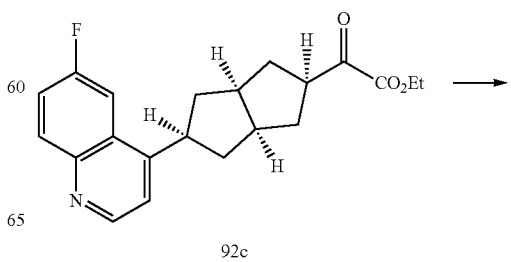

92c

-continued

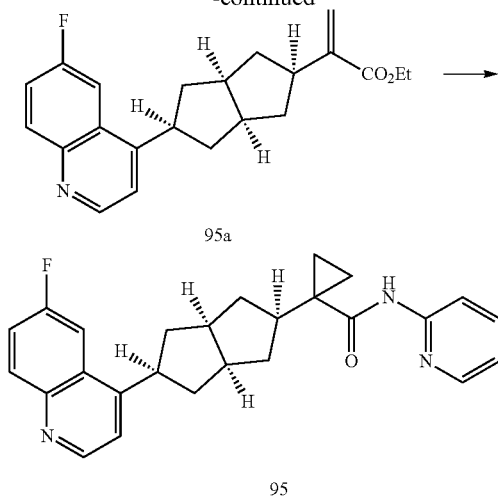

95a

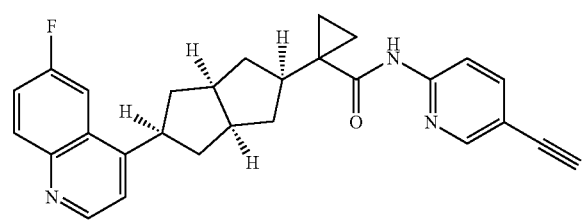

95

Compound 95a was prepared from compound 92c according the preparation method of compound 92e. The stereo configuration of compound 95a was confirmed by NOESY. $^1$H NMR (500 MHz, CDCl$_3$) δ 8.65 (d, J=4.4 Hz, 1H), 7.96 (dd, J=9.2, 5.7 Hz, 1H), 7.55 (dd, J=10.5, 2.7 Hz, 1H), 7.36-7.28 (m, 1H), 7.23 (d, J=4.6 Hz, 1H), 6.00 (s, 1H), 5.44 (d, J=1.1 Hz, 1H), 4.08 (q, J=7.1 Hz, 2H), 3.65-3.51 (m, 1H), 2.97-2.89 (m, 1H), 2.70-2.53 (m, 2H), 2.33-2.23 (m, 2H), 2.19-2.07 (m, 2H), 1.45-1.36 (m, 2H), 1.17 (t, J=5.7 Hz, 3H), 1.16-1.12 (m, 2H).

Compound 95 was prepared from compound 95a according the preparation method of compound 92. $^1$H NMR (500 MHz, CDCl$_3$) δ 8.73 (d, J=4.5 Hz, 1H), 8.15 (dd, J=6.8, 6.1 Hz, 2H), 8.04 (dd, J=9.1, 5.6 Hz, 2H), 7.64-7.57 (m, 2H), 7.44-7.37 (m, 1H), 7.29 (d, J=4.6 Hz, 1H), 3.74-3.61 (m, 1H), 2.76-2.59 (m, 3H), 2.41-2.30 (m, 2H), 2.14-2.02 (m, 2H), 1.49-1.37 (m, 2H), 1.10 (q, J=4.5 Hz, 2H), 1.03-0.96 (m, 2H), 0.80 (dd, J=6.7, 4.6 Hz, 2H). LCMS m/z 450.1 [M+H]$^+$.

Example 97. Preparation of Compound 96

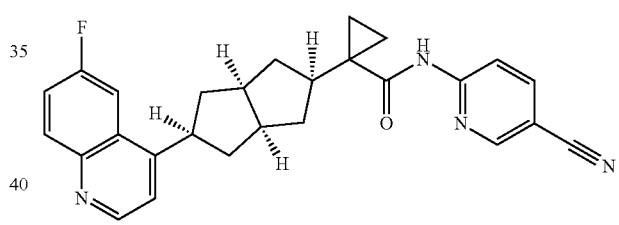

96

The preparation method of compound 96 is as same as the preparation method of compound 92. $^1$H NMR (500 MHz, CDCl$_3$) δ 8.73 (d, J=4.6 Hz, 1H), 8.33 (d, J=1.7 Hz, 1H), 8.14 (d, J=8.6 Hz, 1H), 8.08 (s, 1H), 8.05 (dd, J=8.5, 6.1 Hz, 1H), 7.72 (dd, J=8.7, 2.2 Hz, 1H), 7.61 (dd, J=10.4, 2.7 Hz, 1H), 7.45-7.37 (m, 1H), 7.30 (d, J=4.4 Hz, 1H), 3.71-3.64 (m, 1H), 3.10 (s, 1H), 2.76-2.59 (m, 3H), 2.40-2.30 (m, 2H), 2.16-2.03 (m, 2H), 1.43 (dd, J=12.2, 4.2 Hz, 2H), 1.11 (q, J=4.5 Hz, 2H), 1.01-0.96 (m, 2H), 0.80 (dd, J=6.8, 4.6 Hz, 2H). LCMS m/z 440.1 [M+H]$^+$.

Example 98. Preparation of Compound 97

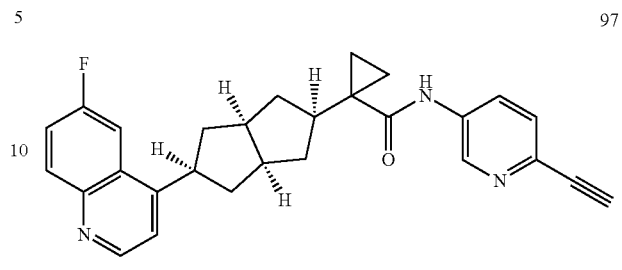

97

The preparation method of compound 97 is as same as the preparation method of compound 92. $^1$H NMR (500 MHz, CDCl$_3$) δ 8.74 (d, J=4.7 Hz, 1H), 8.42 (d, J=2.5 Hz, 1H), 8.16 (dd, J=8.5, 2.7 Hz, 1H), 8.05 (d, J=6.2 Hz, 1H), 7.62-7.60 (m, 2H), 7.43-7.39 (m, 1H), 7.30 (d, J=5.7 Hz, 1H), 3.71-3.66 (m, 1H), 3.06 (s, 1H), 2.72-2.61 (m, 3H), 2.38 (dd, J=12.8, 6.6 Hz, 2H), 2.31-2.22 (m, 2H), 2.11-2.03 (m, 2H), 1.09 (dd, J=6.6, 4.4 Hz, 2H), 1.03-1.01 (m, 2H), 0.83-0.80 (m, 2H). LCMS m/z 220.1 [M/2+H]$^+$.

Example 99. Preparation of Compound 98

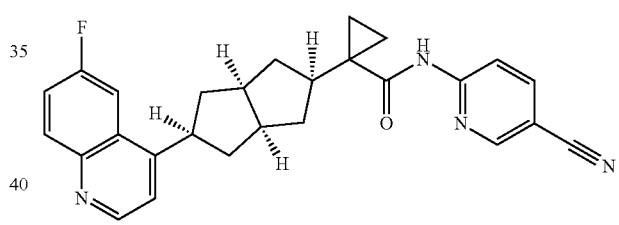

98

The preparation method of compound 98 is as same as the preparation method of compound 92. $^1$H NMR (500 MHz, CDCl$_3$) δ 8.73 (d, J=4.5 Hz, 1H), 8.51-8.46 (m, 1H), 8.30 (d, J=8.8 Hz, 1H), 8.23 (s, 1H), 8.04 (dd, J=9.2, 5.7 Hz, 1H), 7.87 (dd, J=8.8, 2.2 Hz, 1H), 7.61 (dd, J=10.4, 2.7 Hz, 1H), 7.43-7.38 (m, 1H), 7.29 (d, J=4.6 Hz, 1H), 3.71-3.64 (m, 1H), 2.75-2.61 (m, 3H), 2.41-2.32 (m, 2H), 2.13-2.03 (m, 2H), 1.46-1.39 (m, 2H), 1.13 (dd, J=6.8, 4.5 Hz, 2H), 1.04-0.96 (m, 2H), 0.85 (dd, J=6.9, 4.6 Hz, 2H). LCMS m/z 441.3 [M+H]$^+$.

Example 100. Preparation of Compound 99

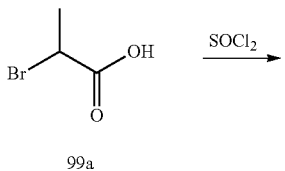

99a

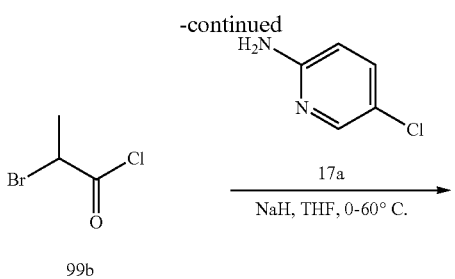

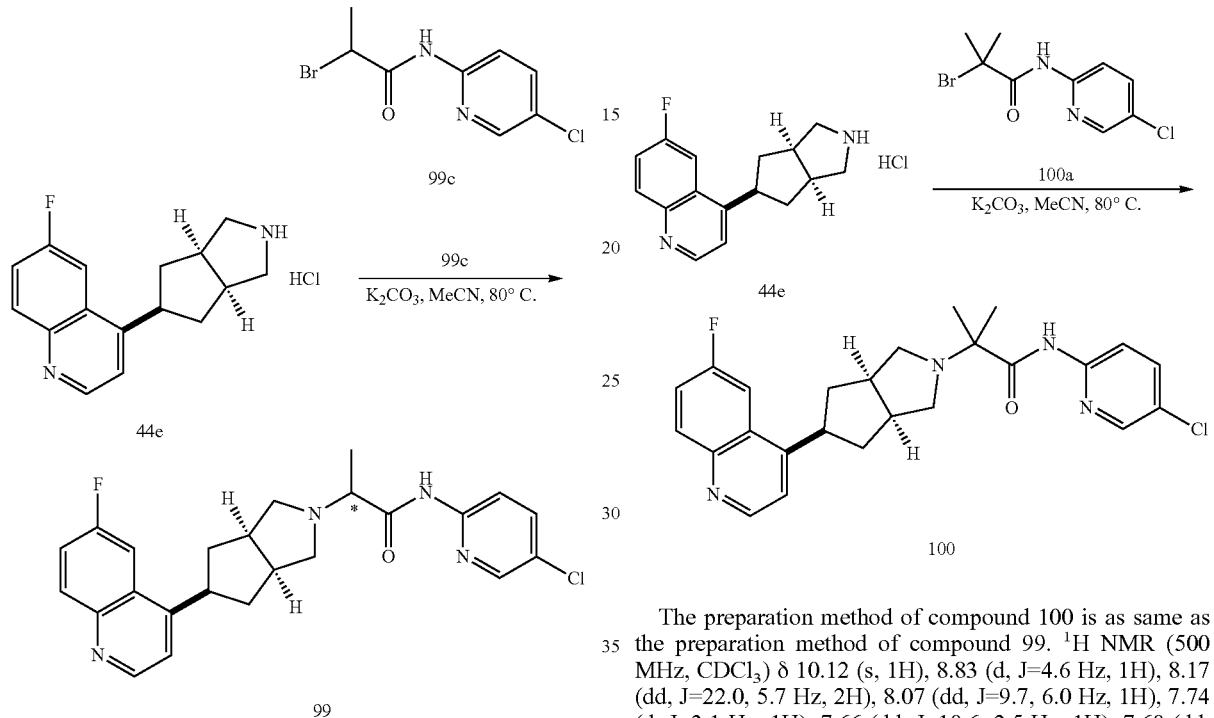

Compound 99a (100 mg, 0.65 mmol) was dissolved in SOCl$_2$ (5 mL), the reaction was heated to 50° C. and stirred for 30 minutes. The reaction was concentrated to afford colorless oil 99b (112 mg, yield 100%). The crude products was used directly for the next reaction without further purification.

2-Amino-5-chloropyridine (101 mg, 0.78 mmol) was dissolved in THF (2 mL), and was slowly added 60% NaH (52 mg, 1.31 mmol) in ice-water bath, warmed to room temperature and stirred for 1 hour. This mixture was slowly added into the THF (1 mL) solution of compound 99b (112 mg, 0.65 mmol). The reaction was heated to 60° C. and stirred for 3 hours. The reaction solution was slowly added to the saturated NaHCO$_3$ solution and extracted with ethyl acetate (3×10 mL). The combined organic phase is dried (anhydrous sodium sulfate), filtered and concentrated in vacuo. The crude product was purified via column chromatography (ethyl acetate/petroleum ether=0-20%) to afford yellow solid compound 99c (82 mg, yield 47.63%).

44e (20 mg, 0.07 mmol), 99c (22 mg, 0.08 mmol), potassium carbonate (29 mg, 0.21 mmol) were dissolved in acetonitrile (3 mL) and then heated to 80 C for overnight reaction. The reaction liquid was added with water, extracted with ethyl acetate (3×10 mL), combined with organic phase, dried with Na$_2$SO$_4$, filtered, concentrated in vacuo, and purified by preparative TLC (ethyl acetate/petroleum ether=100%) to afford white solid compound 99 (2 mg). $^1$H NMR (500 MHz, CDCl$_3$) δ 9.77 (s, 1H), 8.82 (d, J=4.6 Hz, 1H), 8.19 (d, J=2.3 Hz, 1H), 8.15 (d, J=8.8 Hz, 1H), 8.07 (dd, J=9.1, 5.7 Hz, 1H), 7.65 (dd, J=10.4, 2.5 Hz, 1H), 7.63-7.58 (m, 2H), 7.44-7.38 (m, 1H), 3.50 (ddd, J=17.9, 12.1, 5.7 Hz, 1H), 3.14 (q, J=7.0 Hz, 1H), 2.72 (dd, J=19.8, 10.4 Hz, 4H), 2.49-2.39 (m, 4H), 1.69 (dd, J=20.6, 12.2 Hz, 2H), 1.33 (d, J=7.0 Hz, 3H). LCMS m/z 439.2 [M+H]$^+$.

Example 101. Preparation of Compound 100

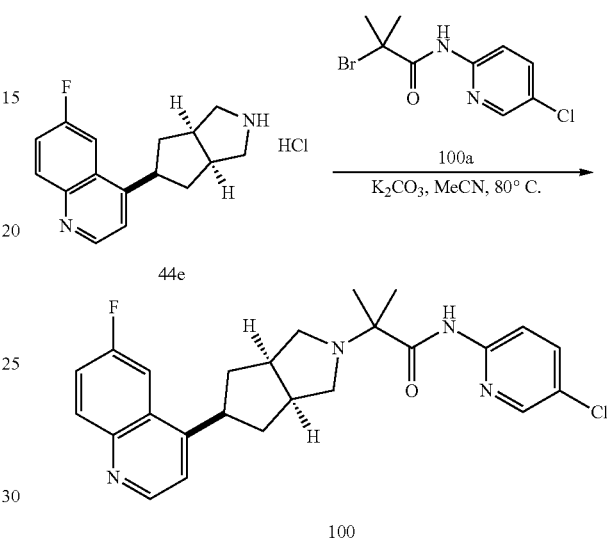

The preparation method of compound 100 is as same as the preparation method of compound 99. $^1$H NMR (500 MHz, CDCl$_3$) δ 10.12 (s, 1H), 8.83 (d, J=4.6 Hz, 1H), 8.17 (dd, J=22.0, 5.7 Hz, 2H), 8.07 (dd, J=9.7, 6.0 Hz, 1H), 7.74 (d, J=3.1 Hz, 1H), 7.66 (dd, J=10.6, 2.5 Hz, 1H), 7.60 (dd, J=8.8, 2.4 Hz, 1H), 7.43 (dd, J=7.9, 1.2 Hz, 1H), 3.57-3.44 (m, 1H), 2.72 (dd, J=12.0, 6.9 Hz, 2H), 2.60 (d, J=9.1 Hz, 2H), 2.50 (dd, J=9.1, 6.2 Hz, 2H), 2.45-2.39 (m, 2H), 1.75-1.67 (m, 2H), 1.28 (s, 6H). LCMS m/z 453.2 [M+H]$^+$.

Example 102. Preparation of Compound 101

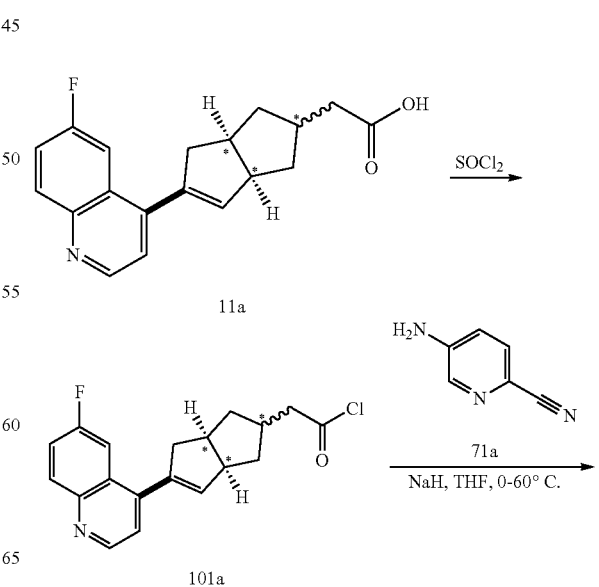

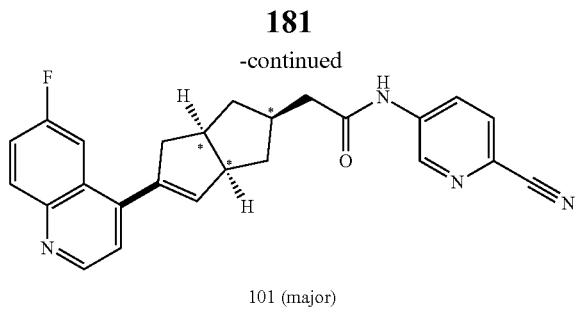

101 (major)

The preparation method of compound 101 is as same as the preparation method of compound 26. $^1$H NMR (500 MHz, CDCl$_3$) δ 8.73 (d, J=4.5 Hz, 1H), 8.53 (d, J=2.4 Hz, 1H), 8.37 (dd, J=8.6, 2.5 Hz, 1H), 8.05 (dd, J=9.2, 5.7 Hz, 1H), 7.68 (dd, J=10.3, 2.7 Hz, 1H), 7.61 (d, J=8.6 Hz, 1H), 7.42 (dd, J=8.6, 2.3 Hz, 1H), 7.40-7.37 (m, 1H), 7.17 (d, J=4.4 Hz, 1H), 5.94 (d, J=1.5 Hz, 1H), 3.44 (d, J=7.0 Hz, 1H), 3.03 (dd, J=16.5, 8.7 Hz, 1H), 2.85 (dd, J=17.0, 8.2 Hz, 1H), 2.49 (d, J=7.3 Hz, 3H), 2.40-2.30 (m, 2H), 2.24 (dd, J=12.6, 6.2 Hz, 1H), 1.15-1.07 (m, 2H). LCMS m/z 413.2 [M+H]$^+$.

Example 103. Preparation of Compound 102

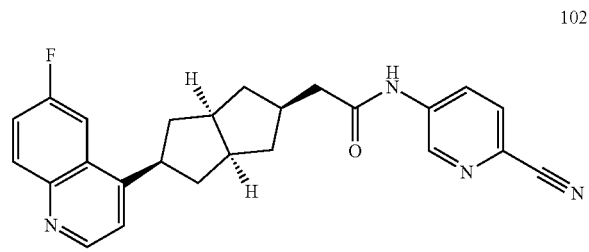 [SMILES: N#Cc1ccc(NC(=O)C[C@@H]2C[C@@H]3C[C@H](c4ccnc5ccc(F)cc45)C[C@@H]3C2)cn1]

102

The preparation method of compound 102 is as same as the preparation method of compound 26. $^1$H NMR (500 MHz, CDCl$_3$) δ 8.81 (d, J=4.6 Hz, 1H), 8.60 (d, J=2.5 Hz, 1H), 8.45 (dd, J=8.6, 2.6 Hz, 1H), 8.11 (dd, J=9.2, 5.7 Hz, 1H), 7.70-7.68 (m, 2H), 7.50-7.48 (m, 1H), 7.47-7.46 (m, 1H), 7.37 (d, J=4.6 Hz, 1H), 3.76 (ddd, J=18.0, 11.9, 5.8 Hz, 1H), 2.79-2.73 (m, 2H), 2.54 (d, J=1.6 Hz, 2H), 2.48-2.42 (m, 2H), 2.31-2.26 (m, 2H), 1.54-1.49 (m, 3H), 1.13 (dd, J=18.7, 11.2 Hz, 2H). Ms m/z 415.20 [M+H]$^+$.

Example 104. Preparation of Compound 103

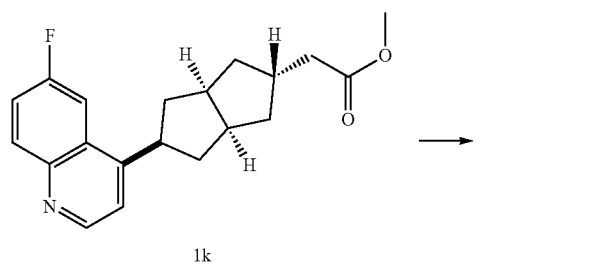

1k

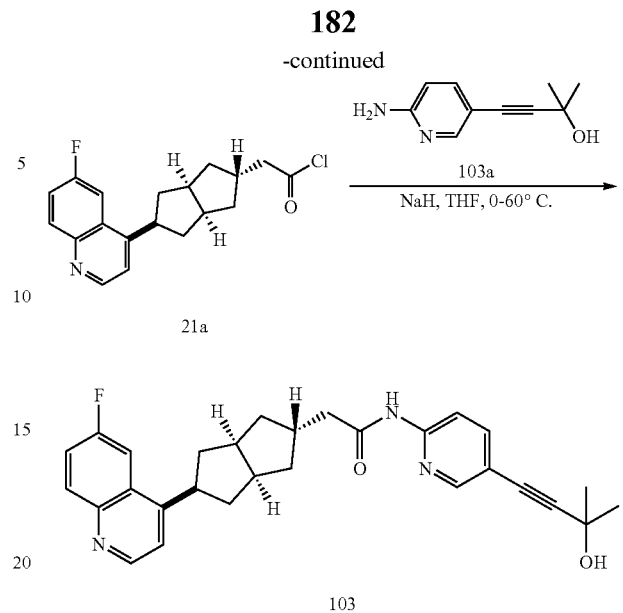

21a

103

Compound 103 was prepared by ester hydrolysis of compound 1k, formation of acyl chloride and reaction with compound 103a. Detailed procedures refer to the preparation method of compound 26. LCMS m/z 472.2 [M+H]$^+$.

Example 105. Preparation of Compound 104 and Compound 105

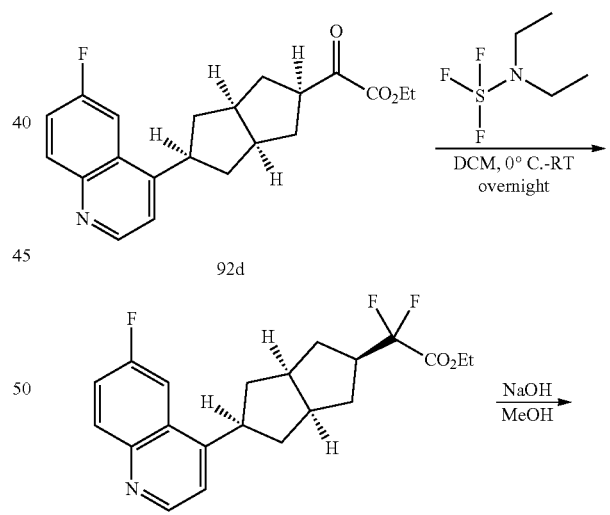

92d

104a

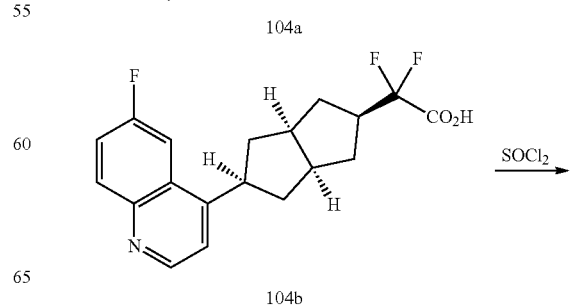

104b

183
-continued

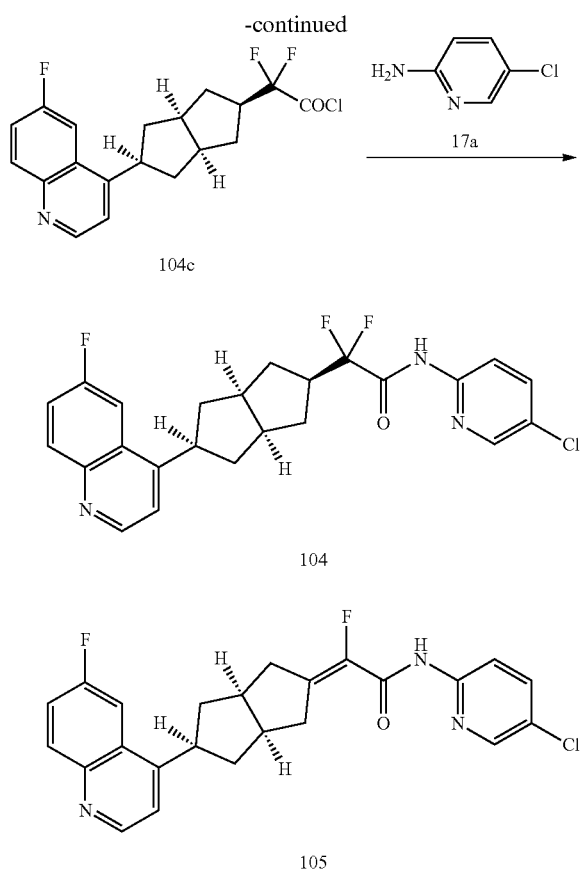

184
Example 106. Preparation of Compound 106

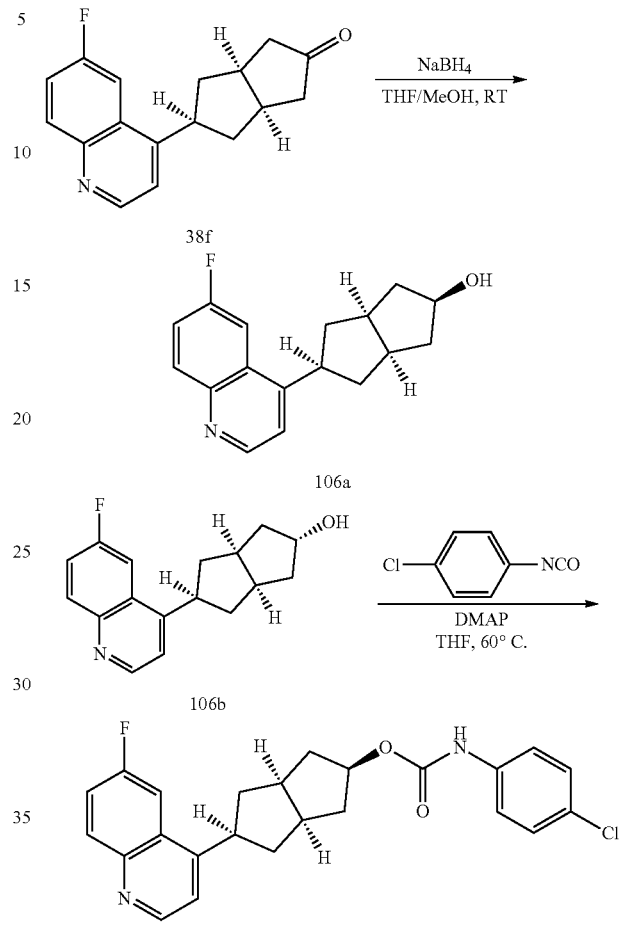

At 0° C. and stirring condition, DAST (0.56 mg, mmol) was added to a solution of compound 92d (mg, 0.11 mmol) in CH$_2$Cl$_2$ (2 mL). The reaction was warmed to room temperature and stirred overnight. Then the reaction was added saturated NaHCO$_3$ solution, added CH$_2$Cl$_2$ (5 mL), the reaction solution was washed by water, collected organic phase, dried over Na$_2$SO$_4$, filtered and concentrated in vacuo, and purified via column chromatography (ethyl acetate/petroleum ether=0-30%) to afford colorless oil 104a (mg, yield 66%). Compound 104a was ester hydrolyzed, transformated to acyl chloride, and then reacted with the compound 17a to prepare the compound 104. Compound 105 is a by-product of preparation of compound 104, and because it is very close to the product, it is separated by multiple preparative TLC separation in the final step of the reaction. One of the separation conditions is (acetone/petroleum ether=0-100%). It was not carefully studied for which step, and how the compound 105 was produced. Compound 104: $^1$H NMR (500 MHz, CDCl$_3$) δ 8.81 (d, J=4.4 Hz, 1H), 8.62 (s, 1H), 8.31 (d, J=2.4 Hz, 1H), 8.23 (d, J=8.9 Hz, 1H), 8.15 (dd, J=8.9, 5.7 Hz, 1H), 7.75 (dd, J=8.8, 2.5 Hz, 1H), 7.69 (dd, J=10.3, 2.4 Hz, 1H), 7.51-7.47 (m, 1H), 7.37 (d, J=4.4 Hz, 1H), 3.49 (ddd, J=17.7, 12.0, 5.4 Hz, 1H), 3.02-2.92 (m, 1H), 2.89-2.83 (m, 2H), 2.50-2.37 (m, 2H), 1.86 (td, J=12.5, 8.0 Hz, 2H), 1.76 (dd, J=12.9, 6.3 Hz, 2H), 1.46-1.39 (m, 2H). LCMS m/z 460.07 [M+H]$^+$. Compound 105: LCMS m/z 440.07 [M+H]$^+$.

Compound 38f (50 mg, 0.185 mmol) was dissolved in THF/MeOH (1:1, 2 mL), then sodium borohydride (11 mg, 0.278 mmol) was added at room temperature and stirred for 1 hour. The saturated ammonium chloride solution (0.5 mL) was added to quench the reaction and diluted with ethyl acetate (5 mL). The reaction solution was washed with water once, and the organic phase was separated, and dried (anhydrous sodium sulfate), filterated and concentrated in vacuo, the crude compounds 106a and 106b were obtained (the ratio of 106a and 106b is about 3:1 according to NMR data). The crude product is used directly for the next reaction.

The mixture of 106a and 106b (13 mg, 0.048 mmol) were dissolved in THF (2 mL), then was added DMAP (12 mg, 0.096 mmol) at room temperature. After stirring for several minutes, p-chlorophenyl isocyanate (11 mg, 0.072 mmol) was added. The reaction mixture stirred for 3 hours at 60° C., diluted with ethyl acetate (5 mL), washed the reaction with water, collected organic phase, dried over Na$_2$SO$_4$, filtered and concentrated at reduced pressure. The crude product was purified via preparative TLC (ethyl acetate: petroleum ether=0-100%) to afford white solid compound 106 (4 mg, yield 20%). $^1$H NMR (500 MHz, CD$_3$OD) δ 8.69 (s, 1H), 8.05 (dd, J=9.2, 5.6 Hz, 1H), 7.90 (dd, J=10.6, 2.7 Hz, 1H), 7.57 (ddd, J=9.2, 8.2, 2.8 Hz, 2H), 7.41 (d, J=8.5 Hz, 2H), 7.26-7.23 (m, 2H), 5.21-5.18 (m, 1H), 3.77-3.70 (m, 1H), 2.90-2.81 (m, 2H), 2.44-2.41 (m, 2H), 2.22-2.17 (m, 2H), 1.86 (d, J=14.1 Hz, 2H), 1.78 (d, J=8.4 Hz, 2H). LCMS m/z 425.1 [M+H]+. [Note: Under this condition, a small amount of isomer 106b did not react with 4-chlorophenyl isocyanate. In addition, the stereo configurations of compounds 106a, 106b and 106c are temporarily assigned and not final confirmed.]

Example 107. Preparation of Compound 107 and Compound 108

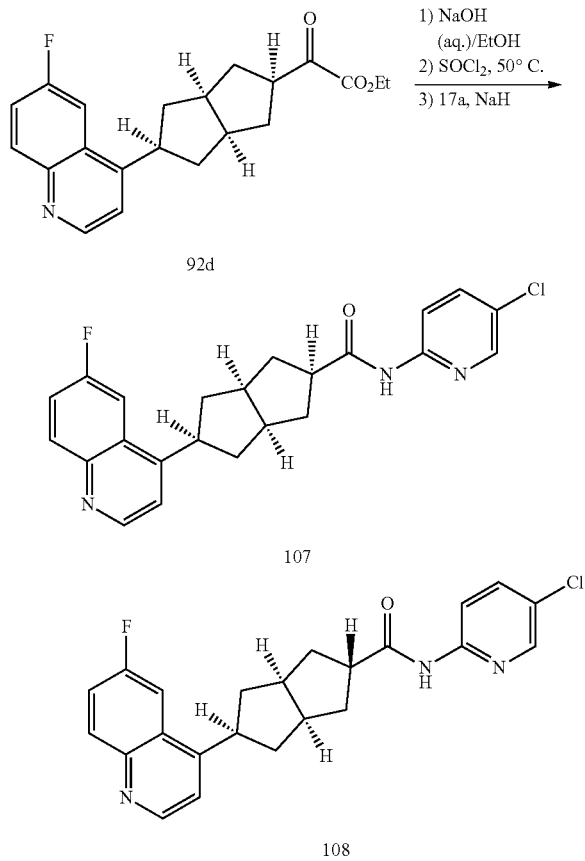

Compound 107 (main product) and compound 108 (byproduct) were synthesized by ester hydrolysis of compound 92d, acyl chloride formation and reaction with compound 17a. Detail procedure refers to the preparation method of compound 26. [Note: In these reactions, decarbonization was occurred. In addition, the stereo configurations of compounds 107 and 108 are temporarily assigned and not ultimately confirmed.]

Compound 107: $^1$H NMR (500 MHz, CDCl$_3$) δ 8.82 (d, J=4.5 Hz, 1H), 8.30 (s, 1H), 8.24 (d, J=8.9 Hz, 1H), 8.22 (d, J=2.4 Hz, 1H), 8.14 (dd, J=9.2, 5.7 Hz, 1H), 7.68 (ddd, J=8.7, 5.8, 2.7 Hz, 2H), 7.48 (ddd, J=9.2, 8.0, 2.8 Hz, 1H), 7.32 (d, J=4.6 Hz, 1H), 3.53-3.45 (m, 1H), 2.99-2.85 (m, 3H), 2.51-2.42 (m, 2H), 2.07 (td, J=12.8, 8.0 Hz, 2H), 1.88 (dd, J=13.0, 6.2 Hz, 2H), 1.37 (td, J=12.4, 9.1 Hz, 2H). LCMS m/z 410.2 [M+H]+.

Compound 108: $^1$H NMR (500 MHz, CD$_3$OD) δ 8.75 (d, J=4.7 Hz, 1H), 8.25 (d, J=2.6 Hz, 1H), 8.15 (d, J=8.9 Hz, 1H), 8.06 (dd, J=9.2, 5.6 Hz, 1H), 7.90 (dd, J=10.6, 2.8 Hz, 1H), 7.76 (dd, J=8.9, 2.6 Hz, 1H), 7.59 (t, J=3.8 Hz, 1H), 7.58-7.55 (m, 1H), 3.92 (dq, J=18.1, 6.0 Hz, 1H), 3.11 (ddd, J=10.9, 6.9, 3.9 Hz, 1H), 2.87-2.82 (m, 2H), 2.45-2.40 (m, 2H), 2.27 (dt, J=13.0, 7.7 Hz, 2H), 1.78 (td, J=12.8, 7.8 Hz, 2H), 1.70 (td, J=12.3, 8.2 Hz, 2H). LCMS m/z 410.2 [M+H]+.

Example 108

1. Test Method for IDO Inhibition Activity Based on HEK293T Cells:

The first step: cell transfection and plating. 5×106 293T cells were separately seeded in two T75 flasks and incubated overnight at 37° C. in a 5% CO$_2$ incubator. 0.6 μL of a mixture containing 1.5 μg of hIDO1 plasmid and 300 μL of opti-MEM was made into a mixture A; 18 μL of liposome fugene 6 was mixed with 300 μL of opti-MEM to prepare a mixture B, and allowed to stand at room temperature for 5 minutes. Mixture A and Mix B were mixed, placed at room temperature for 20 minutes, added to a 293T culture flask, and the other flask was used as a control and incubated overnight at 37° C. in a 5% CO$_2$ incubator. The medium was discarded, digested with trypsin, and after digestion, the cells were neutralized with serum-containing medium, and the cells were blown to cause the cells to fall off. Pipette the cell suspension into a centrifuge tube and centrifuge at a speed of 800-1000 for 1-3 minutes. Aspirate the cell supernatant from the centrifuge tube. Add an appropriate volume of medium to the tube and gently blister to resuspend the cells. Count using a Vi-Cell XR cytometer. Adjust the cell suspension to the appropriate concentration. The cell suspension was added to a white-well 96-well plate at 80 μL/well. The second step: preparation and addition of the compound. Compounds were formulated in DMSO at 600 μM and the compounds were diluted in DMSO according to a multiple of the following table to give 6 concentration gradients of the compound. The 200× compound prepared in DMSO was formulated into a 10× dilution solution in proportion to the corresponding cell culture medium. Add 10 μL of 10× corresponding compound dilution and 10 μL of 10×TRP to each well, except for Min. Incubate for 16 hours in a 37° C. incubator. The third step: detection and analysis. Cell morphology was observed under an inverted microscope. 80 μL of the supernatant was added to a 3894 plate, and 10 μL of 6.1 N trichloroacetic acid was added to each well, shaken for 2 minutes, and placed in a 50-degree incubator for 30 minutes. Centrifuged at 2500 rpm for 10 minutes. Take 70 μL of the supernatant and transfer to a 3635 UV plate, add 70 μL of the reaction solution, and shake for 2 minutes to make the reaction uniform. Use EnSpire (PE) to detect data with an OD of 480 nm. The cell culture plate 3903 was allowed to stand at room temperature for 30 minutes. 100 μL/well of the cell activity detecting reagent was added to the culture plate. Mix on a shaker for 2 minutes to induce cell lysis. The 96-well plate was allowed to stand at room temperature for 10 minutes to stabilize the luminescence signal. Paste the white base film on the bottom of the plate and the plate was tested in Flexstation 3 (the relevant setting is: Illumination, integration time 500 ms). Record the experimental results obtained from the analysis.

The activities of representative compounds are shown in Table 1. The IC$_{50}$ value is expressed by: A: IC$_{50}$ value≤10 nM; B: 10 nM<IC$_{50}$ value≤50 nM; C: 50 nM<IC$_{50}$ value≤100 nM; D: IC$_{50}$ value>100 nM.

TABLE 1

IDO inhibitory activity of HEK293T cells (IC$_{50}$)

| Compound | Activity |
| --- | --- |
| Compound 1 | A |
| Compound 1A | A |
| Compound 1B | A |
| Compound 2 | B |
| Compound 4 | B |
| Compound 5 | A |
| Compound 6 | B |
| Compound 7 | B |
| Compound 9 | D |
| Compound 10 | D |
| Compound 11 | B |
| Compound 12 | D |
| Compound 22 | B |
| Compound 26 | B |
| Compound 27 | B |
| Compound 34 | A |
| Compound 38 | A |
| Compound 40 | B |
| Compound 42 | B |
| Compound 45 | B |
| Compound 50 | B |
| Compound 51 | D |
| Compound 57 | B |
| Compound 67 | A |
| Compound 68 | A |
| Compound 72 | A |
| Compound 73 | A |
| Compound 74 | B |
| Compound 79 | B |
| Compound 84 | A |
| Compound 85 | A |
| Compound 86 | A |
| Compound 87 | A |
| Compound 88 | A |
| Compound 90 | A |
| Compound 92 | A |
| Compound 93 | A |
| Compound 94 | B |
| Compound 95 | A |
| Compound 96 | A |

2. Hela Cell-Based IDO Inhibitory Activity Test Method

The first step: cell plating. Prepare complete medium and mix well. Cell lines that are in good growth state are selected. Remove the cell culture flask from the incubator and check the cell name, media type and cell generation number on the bottle. The medium was discarded, digested with trypsin, and after digestion, the cells were neutralized with serum-containing medium, and the cells were blown to cause the cells to fall off. Pipette the cell suspension into a centrifuge tube and centrifuge at a speed of 800-1000 for 3-5 minutes. Aspirate the cell supernatant from the centrifuge tube. Add an appropriate volume of medium to the tube and gently blister to resuspend the cells. Count using a Vi-Cell XR cytometer. Adjust the cell suspension to the appropriate concentration. The cell suspension was added to a white-well 96-well plate at 80 μl/well according to the schematic below. The second step: preparation and addition of the compound. Compounds were formulated in DMSO at 600 μM and the compounds were diluted in DMSO according to a multiple of the following table to give 6 concentration gradients of the compound. The 200× compound prepared in DMSO was formulated into a 10× dilution solution in proportion to the corresponding cell culture medium. After 24 hours of cell seeding, 10 μL of 10× corresponding compound dilution and 10 μL of 10×IFNγ were added to each well. Incubate for 48 hours in a 37° C. incubator. The third step: detection and analysis. Cell morphology was observed under an inverted microscope. 80 μL of the supernatant was added to a 3894 plate, 10 μL of 6.1 N trichloroacetic acid was added to each well, shaken for 2 minutes, and placed in a 50-degree incubator for 30 minutes. Centrifuge, 2500 rpm for 10 minutes.

Take 70 μL of the supernatant and transfer to a 3635 UV plate, add 70 μL of the reaction solution, and shake for 2 minutes to make the reaction uniform. Use EnSpire (PE) to detect data with an OD of 480 nm. The cell culture plate 3903 was allowed to stand at room temperature for 30 minutes. 100 μL/well of the cell activity detecting reagent was added to the culture plate. Mix on a shaker for 2 minutes to induce cell lysis. The 96-well plate was allowed to stand at room temperature for 10 minutes to stabilize the luminescence signal. Paste the white base film on the bottom of the plate and tested with Flexstation3 plate (the relevant setting is: Illumination, integration time 500 ms). Record the experimental results obtained from the analysis.

The activity of representative compounds is shown in Table 2. The IC$_{50}$ value is expressed in the following manner:

A: IC$_{50}$ value≤5 nM; B: 5 nM<IC$_{50}$ value≤25 nM; C: 25 nM<IC$_{50}$ value≤100 nM; D: IC$_{50}$ value>100 nM.

TABLE 2

Hela cell IDO inhibitory activity (IC$_{50}$)

| Compound code | IDO inhibitory activity |
| --- | --- |
| Compound 1 | A |
| Compound 1A | A |
| Compound 1B | A |
| Compound 2 | B |
| Compound 3 | D |
| Compound 4 | A |
| Compound 5 | A |
| Compound 6 | B |
| Compound 7 | B |
| Compound 8 | B |
| Compound 9 | D |
| Compound 10 | D |
| Compound 11 | A |
| Compound 12 | C |
| Compound 13 | D |
| Compound 14 | D |
| Compound 15 | D |
| Compound 16 | D |
| Compound 17 | B |
| Compound 18 | A |
| Compound 19 | A |
| Compound 20 | A |
| Compound 21 | B |
| Compound 22 | B |
| Compound 23 | A |
| Compound 24 | A |
| Compound 25 | A |
| Compound 26 | A |
| Compound 26A | A |
| Compound 26B | A |
| Compound 27 | A |
| Compound 28 | D |
| Compound 29 | C |
| Compound 30 | D |
| Compound 31 | D |
| Compound 32 | D |
| Compound 33 | C |
| Compound 34 | A |
| Compound 35 | B |
| Compound 36 | A |
| Compound 37 | A |
| Compound 38 | A |
| Compound 39 | A |

TABLE 2-continued

Hela cell IDO inhibitory activity (IC$_{50}$)

| Compound code | IDO inhibitory activity |
|---|---|
| Compound 40 | A |
| Compound 41 | B |
| Compound 42 | A |
| Compound 43 | C |
| Compound 44 | A |
| Compound 45 | B |
| Compound 46 | C |
| Compound 47 | C |
| Compound 48 | D |
| Compound 49 | B |
| Compound 50 | B |
| Compound 51 | D |
| Compound 52 | D |
| Compound 53 | D |
| Compound 54 | D |
| Compound 55 | D |
| Compound 56 | B |
| Compound 57 | A |
| Compound 58 | B |
| Compound 59 | B |
| Compound 60 | A |
| Compound 61 | B |
| Compound 62 | A |
| Compound 63 | A |
| Compound 64 | A |
| Compound 65 | B |
| Compound 66 | A |
| Compound 67 | A |
| Compound 68 | A |
| Compound 69 | A |
| Compound 70 | A |
| Compound 71 | B |
| Compound 72 | A |
| Compound 73 | A |
| Compound 74 | A |
| Compound 75 | B |
| Compound 76 | A |
| Compound 77 | A |
| Compound 78 | C |
| Compound 79 | D |
| Compound 80 | A |
| Compound 81 | B |
| Compound 82 | D |
| Compound 83 | D |
| Compound 84 | D |
| Compound 85 | B |
| Compound 86 | A |
| Compound 87 | A |
| Compound 88 | A |
| Compound 89 | A |
| Compound 90 | A |
| Compound 91 | A |
| Compound 92 | A |
| Compound 93 | A |
| Compound 94 | A |
| Compound 95 | A |
| Compound 96 | A |
| Compound 97 | B |
| Compound 98 | A |
| Compound 99 | B |
| Compound 100 | D |
| Compound 101 | B |
| Compound 102 | A |
| Compound 103 | D |
| Compound 104 | C |
| Compound 105 | D |
| Compound 106 | D |
| Compound 107 | D |
| Compound 108 | B |

All literatures mentioned in the present application are incorporated herein by reference, as though each one is individually incorporated by reference. Additionally, it should be understood that after reading the above contents, those skilled in the art can make various changes and modifications to the present invention. These equivalents also fall within the scope defined by the appended claims.

The invention claimed is:

1. A compound of the following formula (I), or its optical isomers, pharmaceutically acceptable salts, prodrugs, deuterated derivatives, hydrates, or solvates thereof:

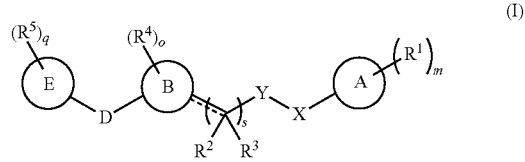

wherein:

═ represents single bond or double bond;

X is bond, NH, N(C$_{1-4}$ alkyl), O, C(O), C(S), C(O)NH, C(O)O, or C(O)NCH$_3$;

Y is bond, NH, N(C$_{1-4}$ alkyl), O, C(O), C(S), or C(O)NH;

with the proviso that the structure formed by the combination of X, Y, B and s is an achievable structure;

A is C$_{6-10}$ aryl, 5-to 15-membered heteroaryl, C$_{1-8}$ alkyl, C$_{2-8}$ alkenyl, C$_{2-8}$ alkynyl, C$_{3-10}$ cycloalkyl, or 4-to 20-membered heterocyclic group;

B is selected from the group consisting of:

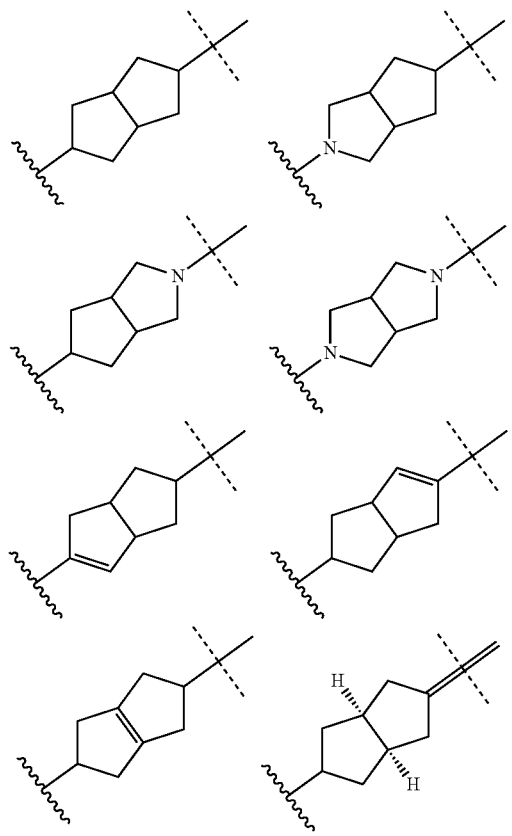

-continued

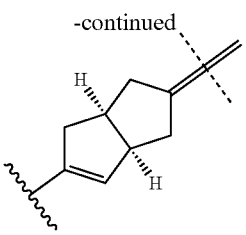

and when B is

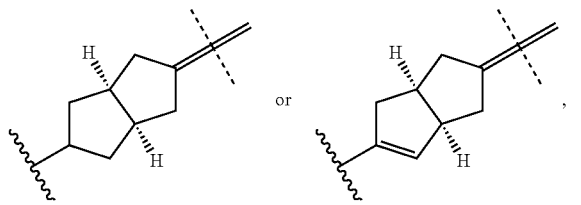

then s is 1, meanwhile R³ in CR²R³ is absent;
D is bond;
E is selected from the group consisting of:

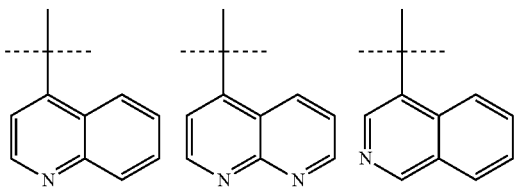

each R¹ is independently selected from the group consisting of hydrogen, deuterium, halogen, $C_{1-4}$ alkyl, hydroxyl, $C_{1-4}$ alkoxy, hydroxyl $C_{1-4}$ alkyl, hydroxyl $C_{1-4}$ alkoxy, $C_{2-4}$ alkenyl, $C_{2-4}$ alkynyl, $C_{3-10}$ cycloalkyl, 4- to 10-membered heterocyclic group, $NR^{10}R^{11}$, cyano, $C(O)R^{12}$, $C(O)NR^{10}R^{11}$, $OC(O)NR^{10}R^{11}$, $NR^{10}C(O)NR^{10}R^{11}$, $NR^{10}SO_2R^{12}$, $NR^{10}SO_2NR^{10}R^{11}$, $CO_2R^{13}$, halo ($C_{1-4}$ alkyl), $C_{1-4}$ alkoxy ($C_{1-4}$ alkyl), halo ($C_{1-4}$ alkoxy), $C_{1-4}$ alkoxy ($C_{1-4}$ alkoxy), $C_{1-4}$ alkoxy (halo$C_{1-4}$ alkoxy), $C_{1-4}$ alkoxy ($C_{2-4}$ alkenyl), $C_{1-4}$ alkoxy ($C_{2-4}$ alkynyl), S—$C_{1-4}$ alkyl, bis ($C_{1-4}$ alkyl) amino ($C_{1-4}$ alkoxy), $(CR^8R^9)_n$—C(O)—NHOH, $O(CR^8R^9)_n$—C(O)—NHOH, $NR^{10}(CR^8R^9)_n$—C(O)—NHOH,

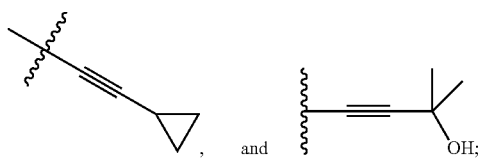

or two R¹ together with the carbon atom to which it is attached forms C=O, $C_{3-8}$ cycloalkyl, or 4-to 8-membered heterocyclic group containing 1-2 atom(s) selected from N, O or S, wherein said cycloalkyl or heterocyclic group is optionally substituted by 1-2 $R^{14}$;
or when two R¹ are attached to two adjacent carbon atoms, the two R¹ together with the carbon atoms to which they attached form a $C_{3-8}$ cycloalkyl or 4- to 8-membered heterocyclyl group containing 1-2 atom(s) selected from N, O or S, wherein the cycloalkyl or heterocyclic group is optionally substituted by 1-2 $R^{14}$; herein, each $R^{14}$ is independently selected from the group consisting of hydrogen, deuterium, halogen, $C_{1-4}$ alkyl, hydroxyl, $C_{1-4}$ alkoxy, CN, $NR^{10}R^{11}$, $C_{3-6}$ cycloalkyl, 4- to 8-membered heterocyclic group containing 1-2 atom(s) selected from N, O or S, $C_{6-10}$ aryl, 5- to 10-membered heteroaryl, and =O; with the proviso that the definition of above-described R¹ and A ensures that the structure forms an achievable structure;

R² and R³ are each independently selected from the group consisting of hydrogen, deuterium, $C_{1-8}$ alkyl, $C_{2-8}$ alkenyl, $C_{2-8}$ alkynyl, halo $C_{1-8}$ alkyl, $C_{3-8}$ cycloalkyl, 4-to 8-membered heterocyclyl comprising 1-2 atom(s) selected from N, O or S, $C_{6-10}$ aryl, 5- to 10-membered heteroaryl, $C_{3-6}$ cycloalkyl ($C_{1-4}$ alkyl), (4- to 8-membered heterocyclyl containing 1-2 atom(s) selected from N, O or S) $C_{1-4}$ alkyl, ($C_{6-10}$ aryl) $C_{1-4}$ alkyl, (5- to 10-membered heteroaryl) $C_{1-4}$ alkyl, fluoro, OH, CN, $CO_2H$, $C(O)NH_2$, $NR^{10}R^{11}$, $C_{1-4}$ alkoxy, $(CR^8R^9)_p$—OH, $(CR^8R^9)_p$—Z—$(CR^8R^9)_r$—$CO_2H$, $(CR^8R^9)_p$—Z—$(CR^8R^9)_r$—$C(O)NH_2$, $(CR^8R^9)_p$—Z—$(CR^8R^9)_r$—$C(O)NHR^{10}$, $(CR^8R^9)_p$—Z—$(CR^8R^9)_r$—$C(O)NR^{10}R^{11}$, $(CR^8R^9)_p$—Z—$(CR^8R^9)_r$—C(O)NHOH; wherein, Z is bond, CH=CH, C≡C, O, S, $NR^7$, C(O), $C_{3-8}$ cycloalkyl, 4- to 8 membered heterocyclyl, $C_{6-10}$ aryl, and 5- to 10-membered heteroaryl; or R³ is absent;

or R² and R³ together with the carbon atom to which it is attached forms C=O, $C_{3-8}$ cycloalkyl or 4- to 8-membered heterocyclic group containing 1-2 atom(s) selected from N, O or S;

or R² and the carbon atom attached with R² and one or two carbon atoms on B together form $C_{3-6}$ cycloalkyl or 3- to 6-membered heterocyclic group containing 1-2 atom(s) selected from N, O or S, wherein the cyclic structure is spiro or fused ring;

and the definition of above R² and R³ ensures that they together with other groups form an achievable structure;

each $R^4$ independently is hydrogen, deuterium, halo, $C_{1-4}$ alkyl, hydroxyl, CN, or $C_{1-4}$ alkoxy, or when two $R^4$ attached to the same carbon atom, these two $R^4$ connect together with the carbon to form carbonyl group (C=O), or when two $R^4$ attach to two adjacent carbon atoms, the two $R^4$ and two carbon atoms form an oxygen-containing three membered heterocyclic structure;

each $R^5$ is independently hydrogen, deuterium, halogen, $C_{1-4}$ alkyl, $C_{2-4}$ alkenyl, $C_{2-4}$ alkynyl, $C_{3-6}$ cycloalkyl, 4- to 6-membered heterocyclic group containing 1-2 atom(s) selected from N, O or S, $C_6$ aryl, 5- to 6-membered heteroaryl, halo $C_{1-4}$ alkyl, hydroxyl, CN, halo $C_{1-4}$ alkoxy, $C(O)R^{12}$, $CO_2R^{13}$, $CONR^{10}R^{11}SO_2NR^{10}R^{11}$; $NR^{10}SO_2NR^{10}R^{11}$, $NR^{10}C(O)R^{12}$, or =O;

each $R^6$ is independently hydrogen, deuterium, halogen, $C_{1-4}$ alkyl, hydroxyl, CN, or $C_{1-4}$ alkoxy;

$R^7$ is hydrogen, $C_{1-4}$ alkyl, $C_{3-6}$ cycloalkyl, 4- to 8-membered heterocyclic group, $C(O)C_{1-4}$ alkyl, or $C(O)C_{3-6}$ cycloalkyl;

$R^8$ and $R^9$ are each independently selected from the group consisting of hydrogen, deuterium, halogen, $C_{1-4}$ alkyl, hydroxyl, CN, and $C_{1-4}$ alkoxy;

$R^{10}$ and $R^{11}$ are each independently selected from the group consisting of hydrogen, $C_{1-4}$ alkyl, $C_{3-8}$ cycloalkyl, 4- to 8-membered heterocyclic group, 6-membered aryl, 5- to 6-membered heteroaryl, C$_{1-4}$ alkoxy (C$_{1-4}$ alkyl), and bis (C$_{1-4}$ alkyl) amino (C$_{1-4}$ alkyl), wherein the cycloalkyl, heterocyclyl, aryl, or heteroaryl is optionally substituted by 1-3 R$^{14}$, wherein R$^{14}$ is as defined above; or R$^{10}$ and R$^{11}$ connect together with the nitrogen atom to form a 4- to 8-membered ring structure, which additionally contains 0-2 heteroatom(s) selected from N, O, S, provided that the ring formed is an achievable structure; and this ring structure is optionally substituted by 1-3 R$^{14}$;

R$^{12}$ is C$_{1-4}$ alkyl, C$_{2-4}$ alkenyl, C$_{2-4}$ alkynyl, C$_{3-8}$ cycloalkyl, 4- to 8-membered heterocyclic group, 6-membered aryl, or 5- to 6-membered heteroaryl;

R$^{13}$ is hydrogen, C$_{1-4}$ alkyl, C$_{3-6}$ cycloalkyl, 4- to 8-membered heterocyclic group containing 1-2 atom(s) selected from N, O or S, 6-membered aryl, 5- to 6-membered heteroaryl; wherein the alkyl, cycloalkyl, heterocyclyl, aryl and heteroaryl groups is optionally substituted by halogen, CN, or hydroxyl, provided that the structure formed is an achievable structure;

R$^{14}$ is hydrogen, C$_{1-4}$ alkyl, C$_{3-6}$ cycloalkyl, 4- to 8-membered heterocyclic group containing 1-2 atom(s) selected from N, O or S, 6-membered aryl, or 5- to 6-membered heteroaryl;

m is 0, 1, 2 or 3;
n is 0, 1, 2 or 3;
o is 0, 1, 2, or 3;
p is 0, 1, 2, 3 or 4;
q is 0, 1, 2, or 3;
r is 0, 1, 2, 3 or 4;
s is 0 or 1;

wherein the statement "none of R$^1$, R$^2$ and R$^3$ contain C(O)—NH—OH group" refers to none of R$^1$, R$^2$ and R$^3$ is C(O)—NH—OH group, and none of R$^1$, R$^2$ and R$^3$ comprise C(O)—NH—OH structure fragment, wherein each of the above alkyl, alkenyl, alkynyl, cycloalkyl, heterocyclyl, aryl, and heteroaryl groups is optionally and independently substituted by 1-3 substituents each independently selected from the group consisting of hydrogen, deuterium, halogen, C$_{1-4}$ alkyl, C$_{2-4}$ alkenyl, C$_{2-4}$ alkynyl, halo (C$_{1-4}$ alkyl), C$_{3-8}$ cycloalkyl, 4- to 8-membered heterocyclic group containing 1-2 atom(s) selected from N, O or S, C$_{6-10}$ aryl, 5- to 10-membered heteroaryl, OH, CN, NO$_2$, OR$^{13}$, SR$^{13}$, N(R$^7$)$_2$, C(O)R$^{12}$, CO$_2$R$^{13}$, CONR$^{10}$R$^{11}$, and SO$_2$NR$^{10}$R$^{11}$; in the substituents, the definitions of each group are as described above.

2. The compound of claim 1, wherein,
X is NH, N(C$_{1-4}$ alkyl), O, C(O), C(O)O, C(O)NH, or C(O)NCH$_3$;
Y is NH, N(C$_{1-4}$ alkyl), O, C(O), or C(O)NH.

3. The compound of claim 2, wherein the Y—X is a combination selected from the following:

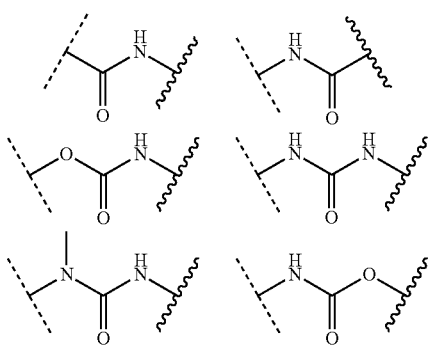

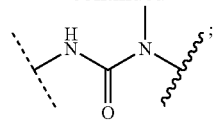

／ refers to the point connecting to A, ╱ refers to the point connecting to CR$^2$R$^3$.

4. The compound of claim 1, wherein R$^2$ is hydrogen, deuterium or fluorine fluoro, R$^3$ is C$_{1-4}$ alkyl, C$_{2-4}$ alkenyl, C$_{2-4}$ alkynyl, halo (C$_{1-4}$ alkyl), hydroxy, C$_{1-4}$ alkoxy, C$_{3-6}$ cycloalkyl, (CR$^8$R$^9$)$_p$—Z—(CR$^8$R$^9$)$_r$—CO$_2$H, or (CR$^8$R$^9$)$_p$—Z—(CR$^8$R$^9$)$_r$—C(O)NHOH.

5. The compound of claim 1, wherein R$^2$ and R$^3$ are each independently selected from the group consisting of hydrogen, deuterium, fluoro, and C$_{1-4}$ alkyl, or R$^2$ and R$^3$ together with the carbon atom to which they connected form C$_{3-6}$ cycloalkyl or C=O.

6. The compound of claim 5, wherein R$^2$ and R$^3$ are each independently methyl, or R$^2$ and R$^3$ together with the carbon atom to which they attached to form a cyclopropyl group.

7. The compound of claim 1, wherein the B is a structure selected from the following:

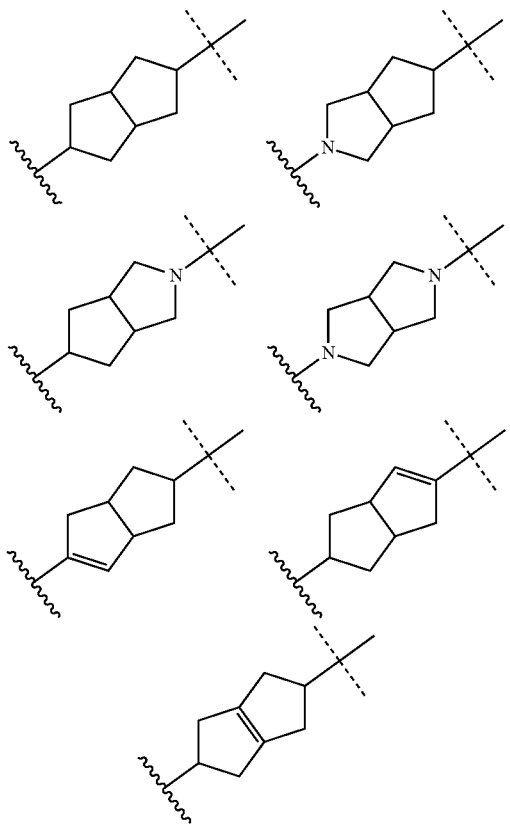

／ refers to the point connecting to D, ╱ refers to the point connecting to CR$_2$R$_3$; the definitions of the other groups are as described above.

8. The compound of claim 1, wherein A is C$_{6-10}$ aryl, 5- to 15-membered heteroaryl, C$_{3-10}$ cycloalkyl, or 4- to 15-membered heterocyclic group, or A is selected from the following:

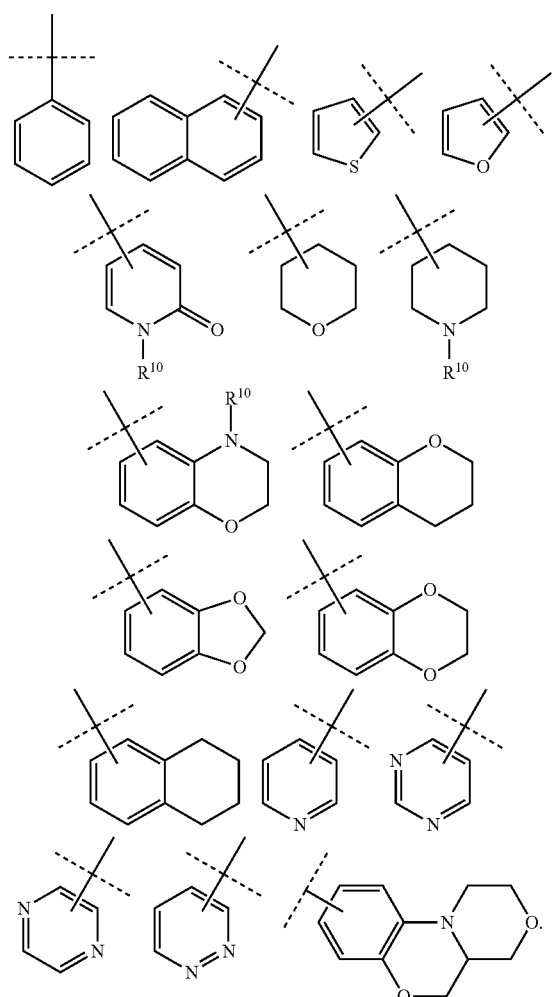

9. The compound of claim 1, wherein each $R^1$ is independently halogen, $C_{1-4}$ alkyl, $C_{1-4}$ alkoxy, $C_{2-4}$ alkenyl, $C_{2-4}$ alkynyl, cyano, $C(O)R^{12}$, $NR^{10}SO_2NR^{10}R^{11}$, $CO_2R^{13}$, $CONR^{10}R^{11}$, halo ($C_{1-4}$ alkyl), halo ($C_{1-4}$ alkoxy), $(CR^8R^9)_n$—C(O)—NHOH,

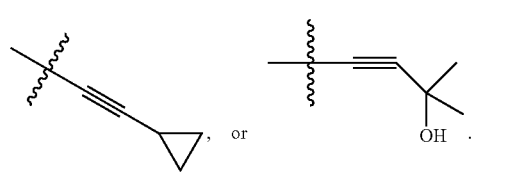

, or ...

10. The compound of claim 1, wherein B is selected from the group consisting of

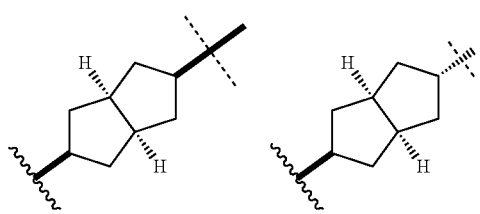

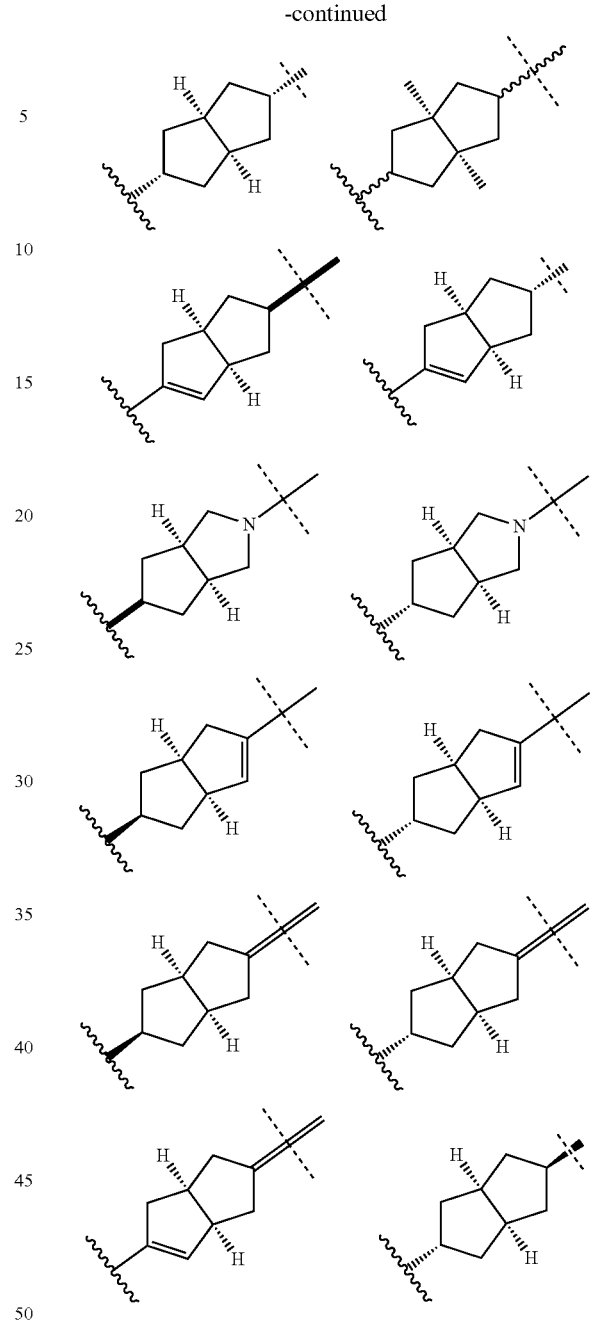

wherein ∕ refers to the point connecting to D, ∕ refers to the point connecting to $CR_2R_3$; provided that when B is

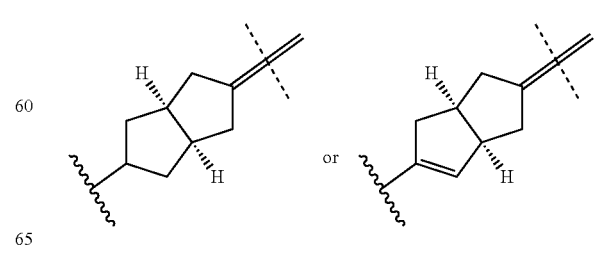

then the $R^3$ in $CR^2R^3$ is absent.

11. The compound of claim 1, wherein the compound is of the following structure:

(I-a)

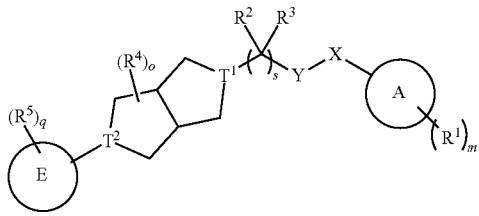

wherein $T^1$ and $T^2$ are each independently selected from $CR^{15}$ or N, where $R^{15}$ is H, F, or OH;

Y—X is

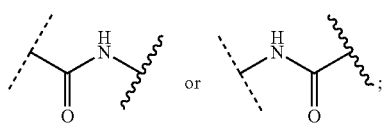

╱ refers to the point connecting to A, ╱ refers to the point connecting to $CR^2R^3$.

12. The compound of claim 11, wherein the compound is of the following structure:

(I-aa)

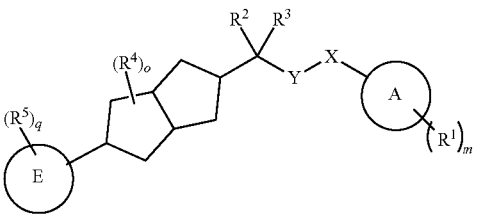

Y—X is

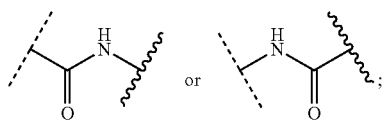

╱ refers to the point connecting to A, ╱ refers to the point connecting to $CR^2R^3$.

13. The compound of claim 1, wherein the compound is of the following structure:

(I-b)

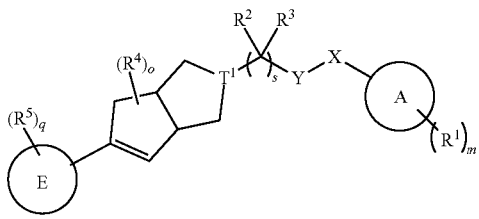

(I-c)

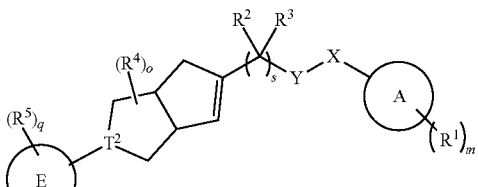

(I-d)

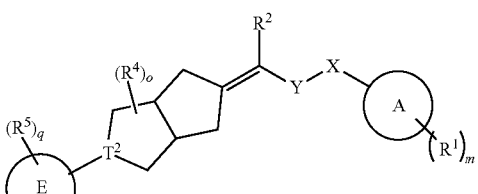

wherein $T^1$ and $T^2$ are each independently selected from $CR^{15}$ or N, wherein $R^{15}$ is H, F, or OH, Y—X is

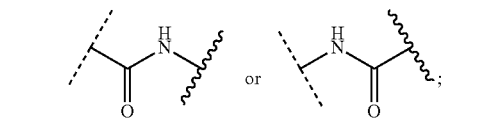

╱ refers to the point connecting to A, ╱ refers to the point connecting to $CR^2R^3$.

14. The compound of claim 13, wherein the compound is of the following structure:

(I-ba)

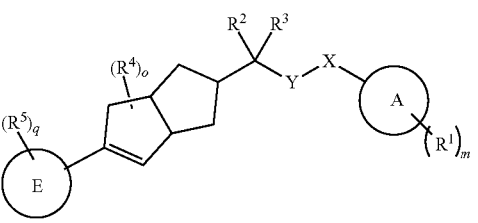

(I-ca)

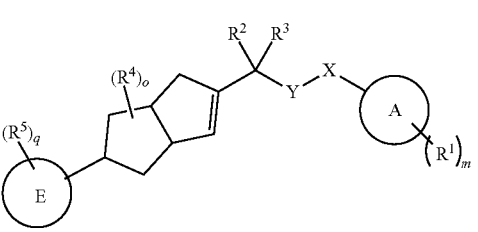

(I-da)

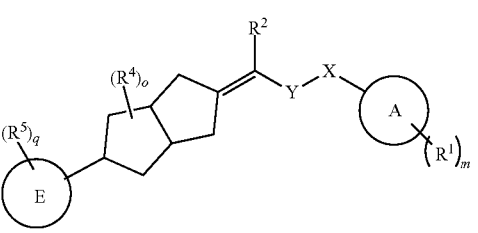

Y—X is

╱ refers to the point connecting to A, ╱ refers to the point connecting to $CR^2R^3$.

15. The compound of claim 1, wherein the compound is of the following structure:
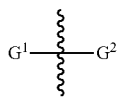
wherein the G¹ is selected from the following group:
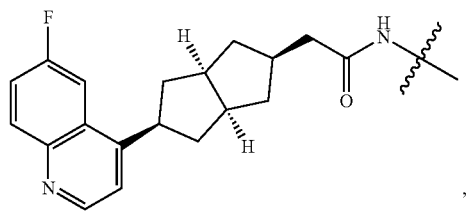,
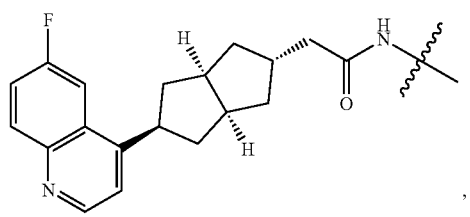,
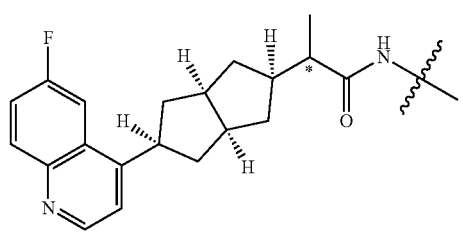,
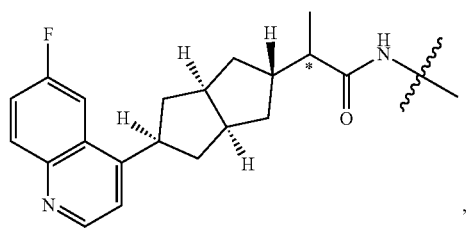,
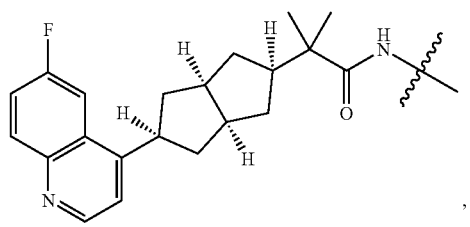,
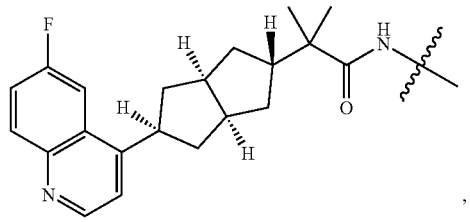,
-continued
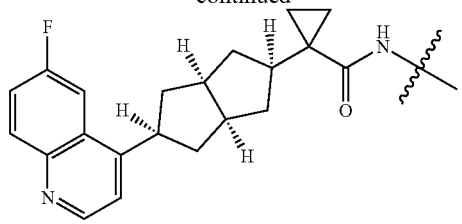,
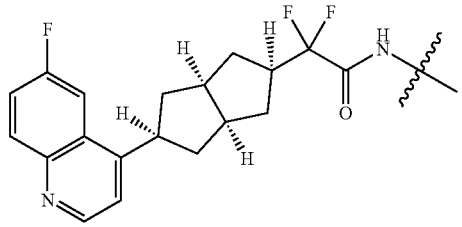,
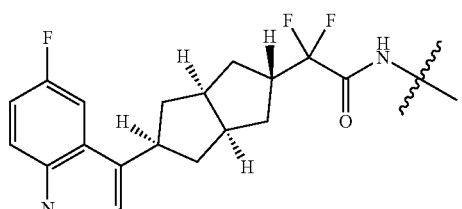,
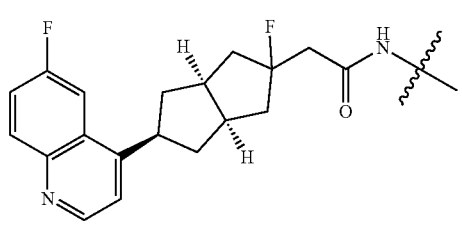,
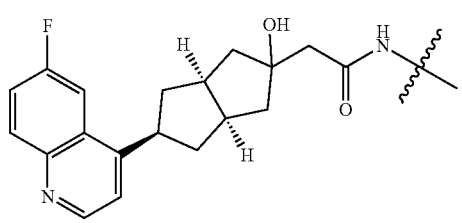,
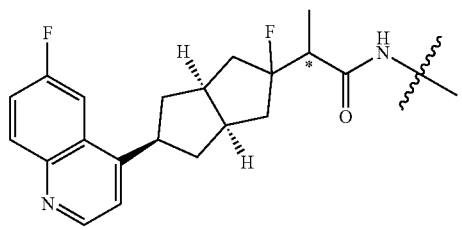,
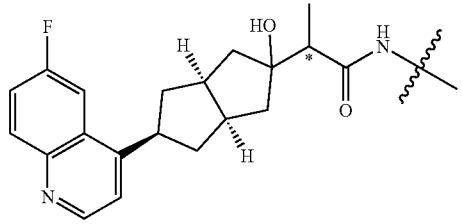, 201
-continued
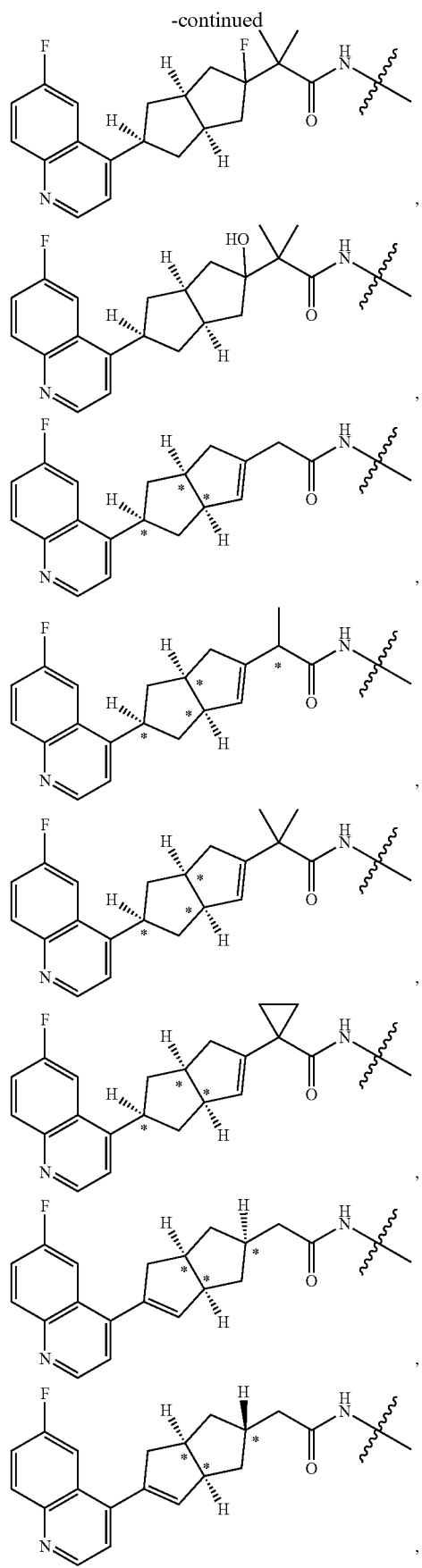
202
-continued
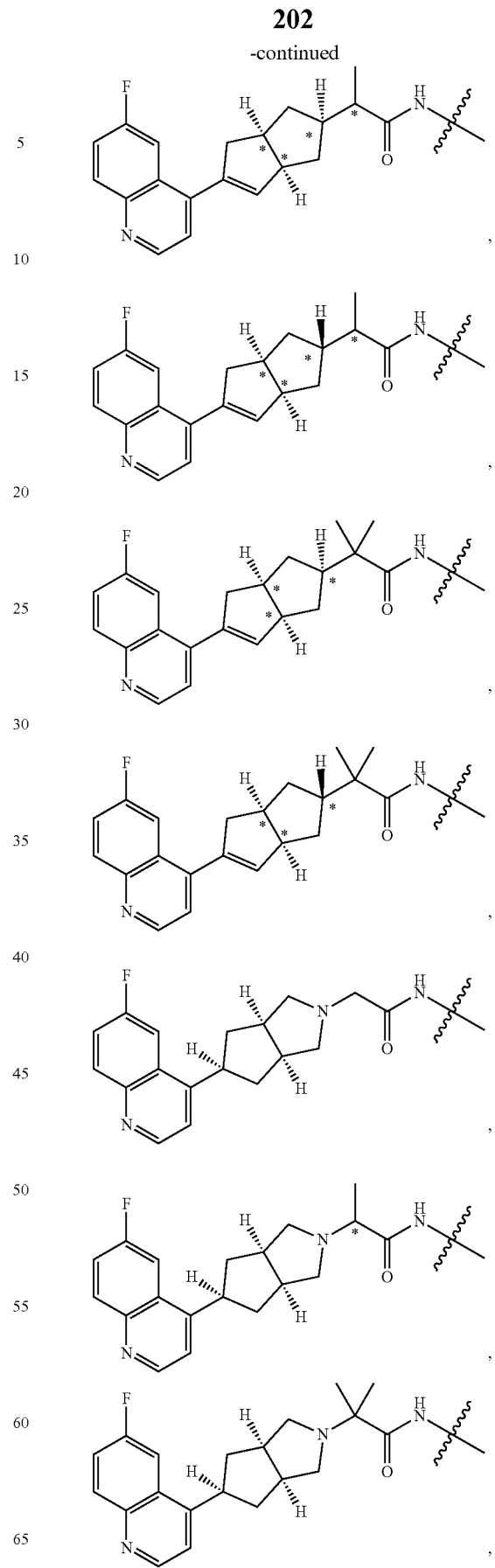

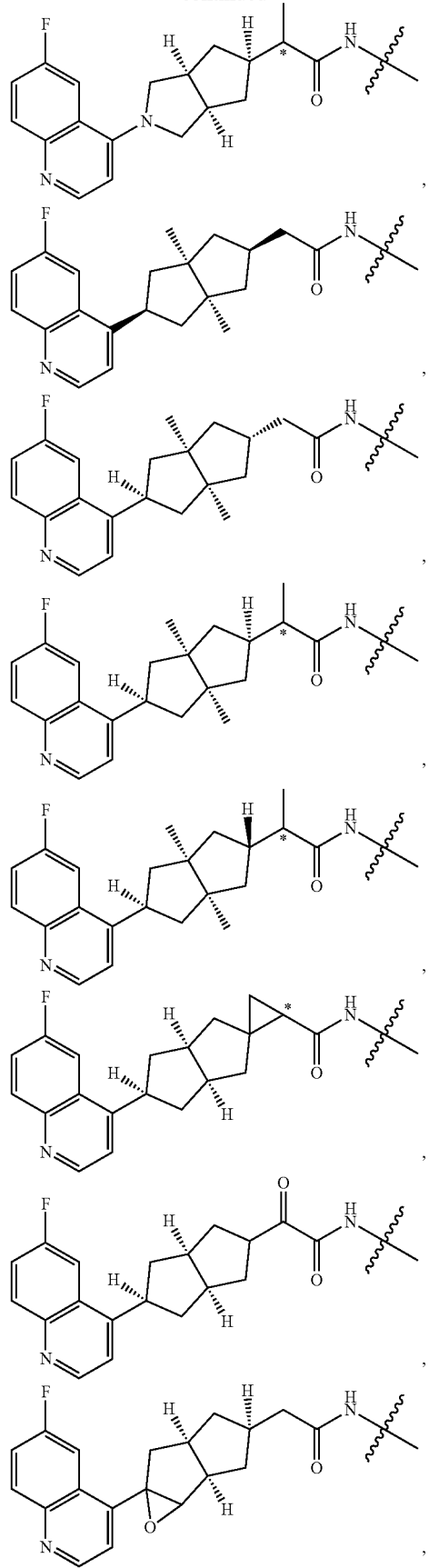
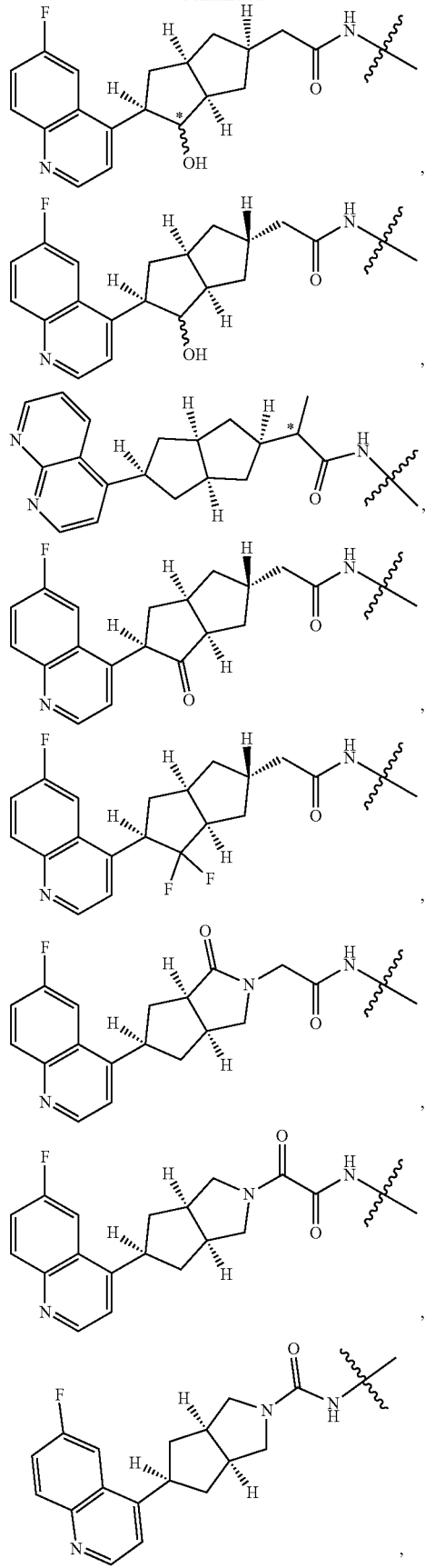

-continued
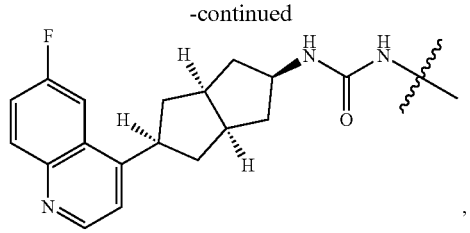,
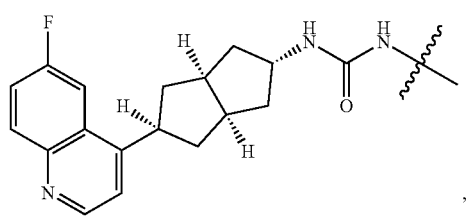,
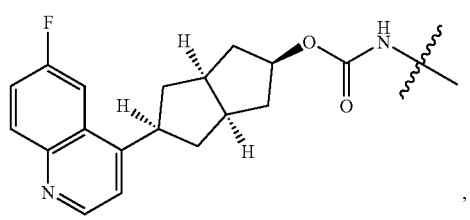,
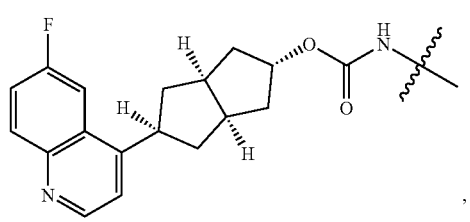,
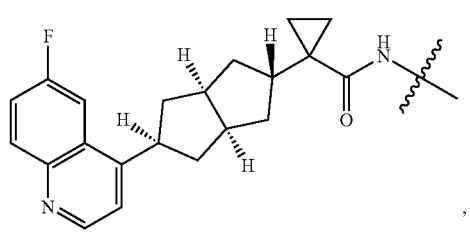,
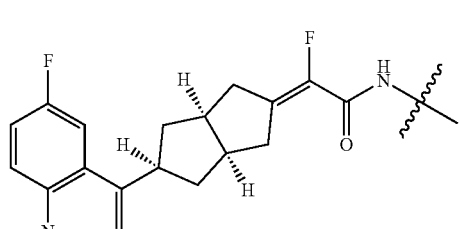,
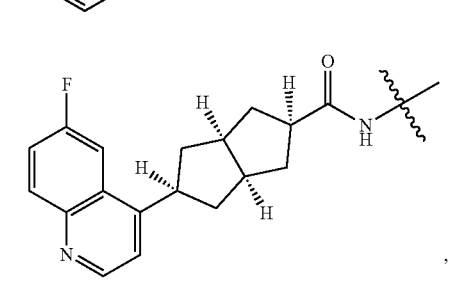,
-continued
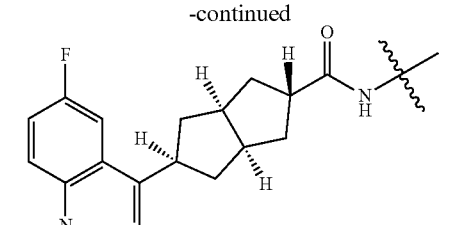,
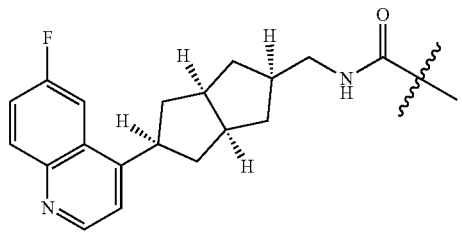,
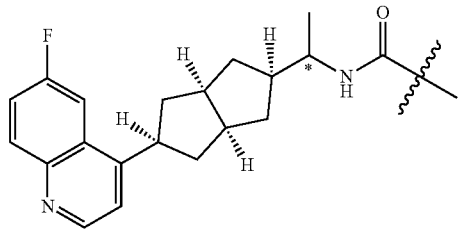,
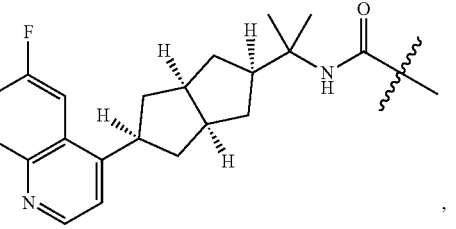, or
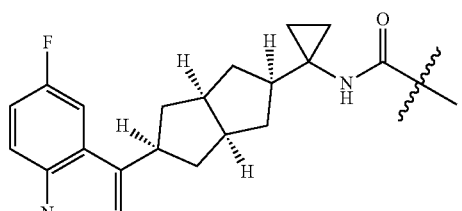;
the G2 is selected from the group consisting of:
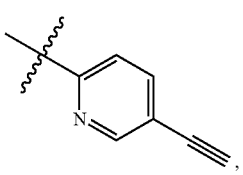 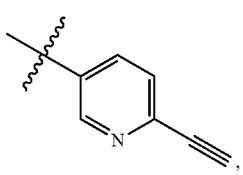,
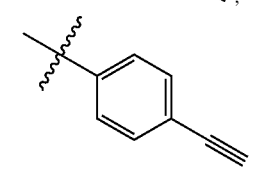 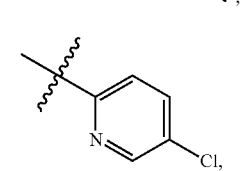

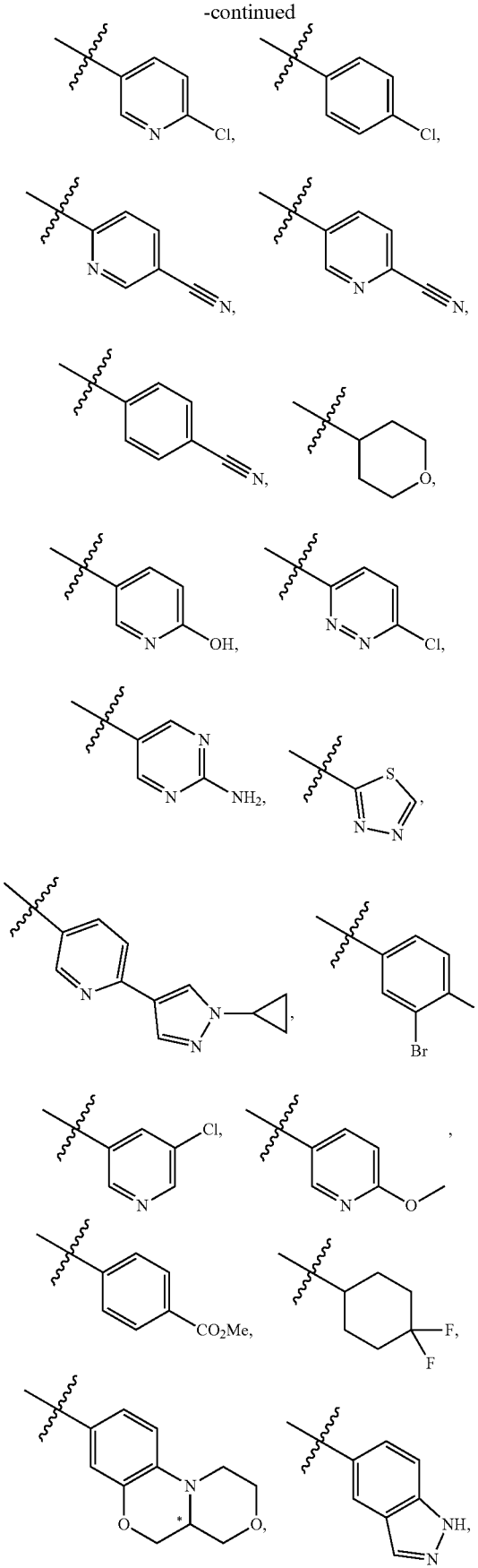
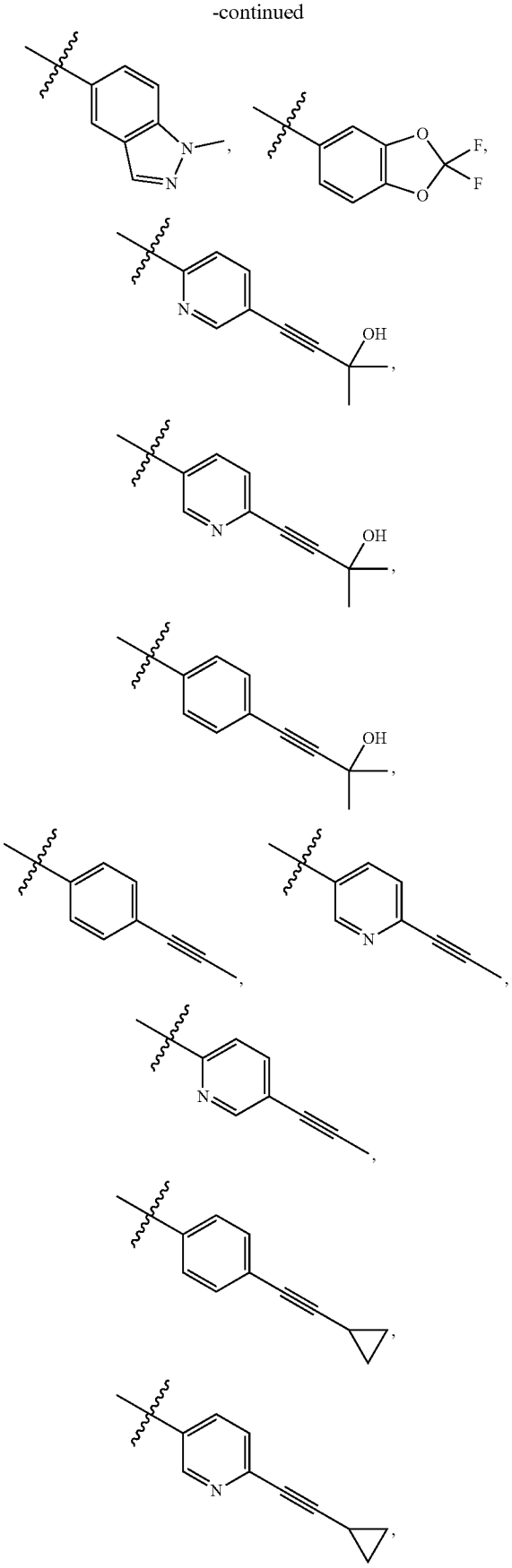

-continued
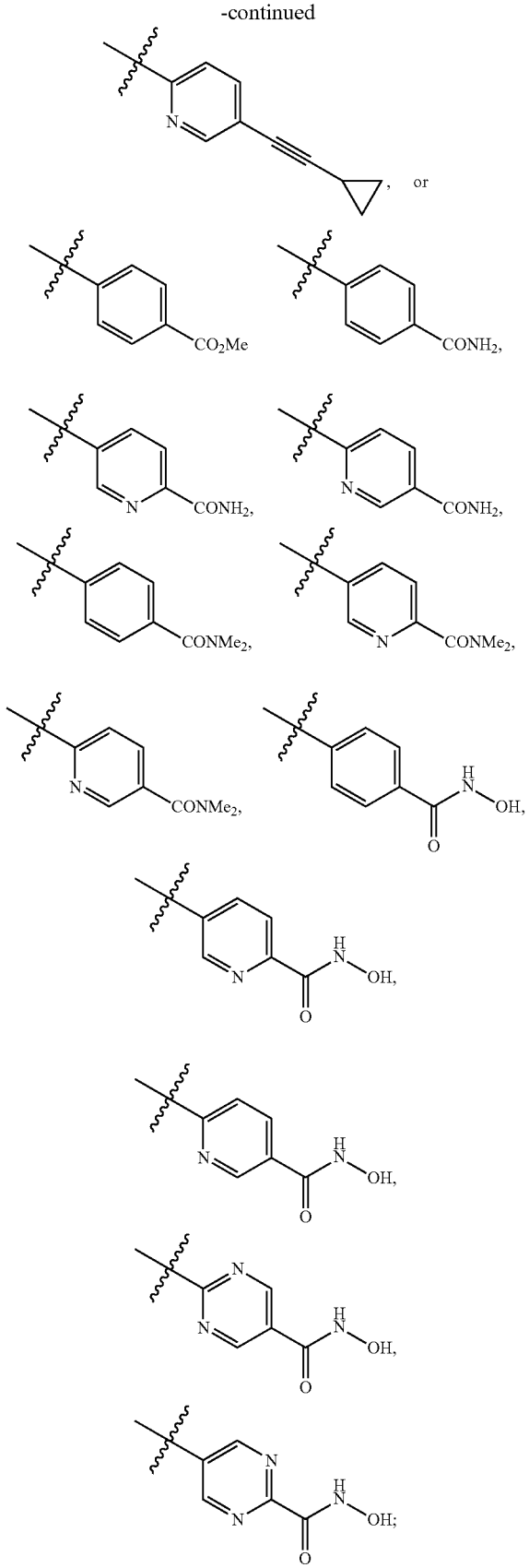
and wherein * indicates a chiral center.
16. The compound of claim 15, wherein, the G1 is selected from the group consisting of:
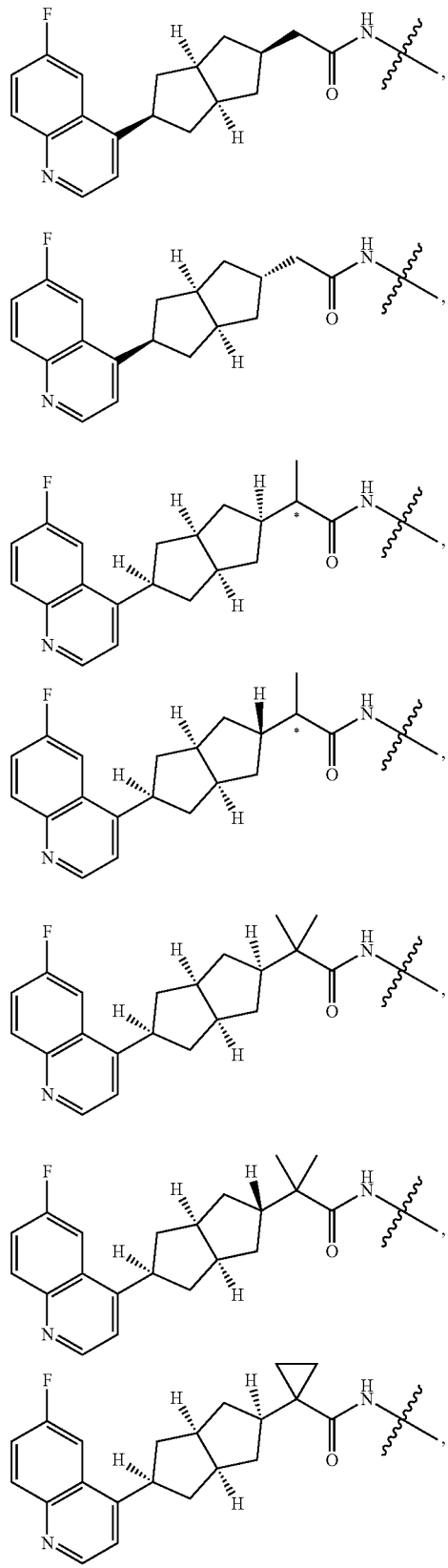

211
-continued
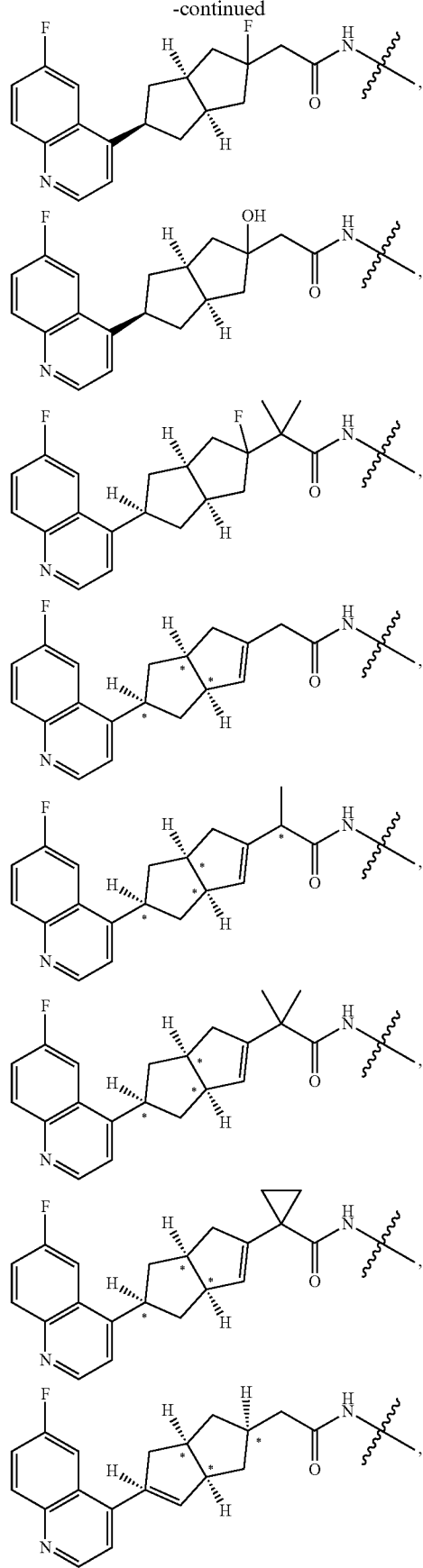
212
-continued
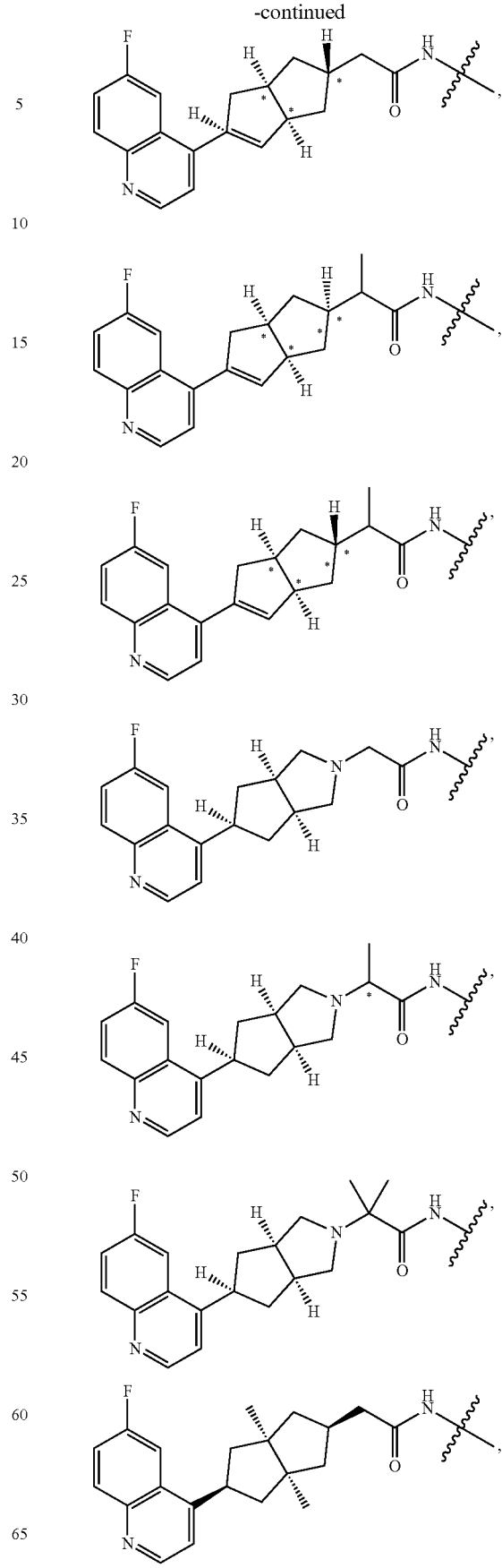

-continued
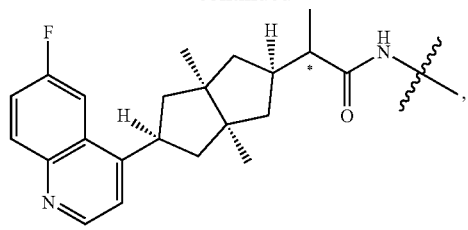
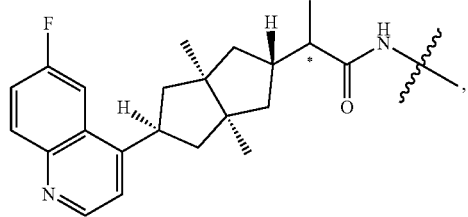
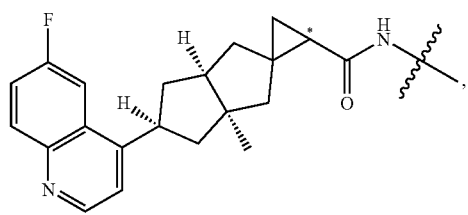
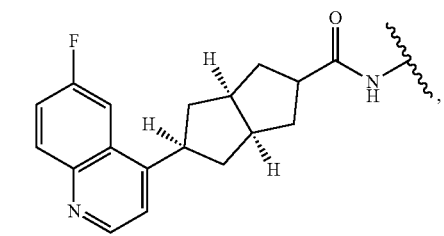
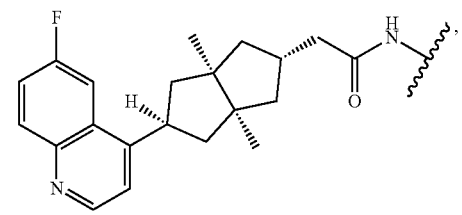
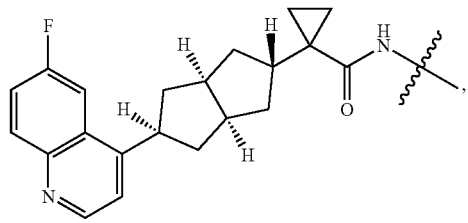
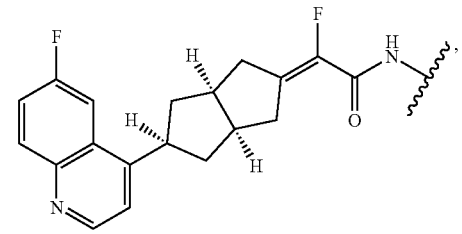
-continued
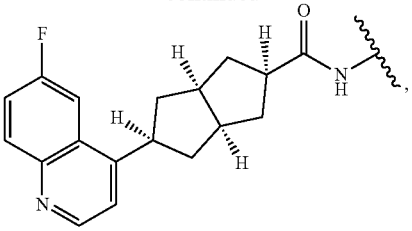
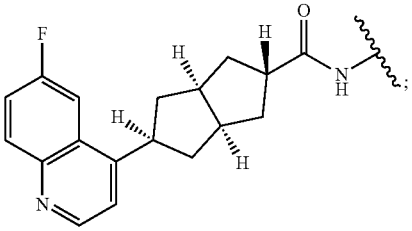
the G2 is selected from the group consisting of:
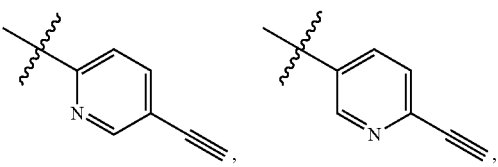
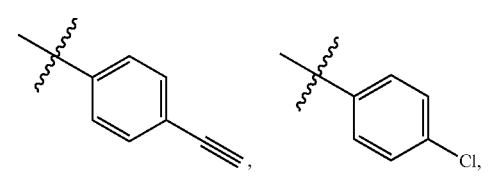
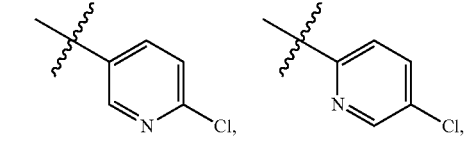
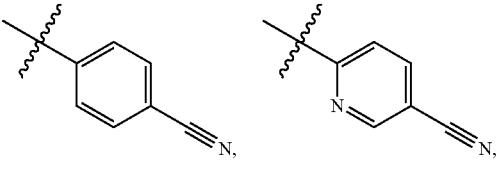
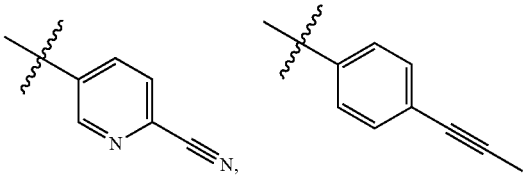
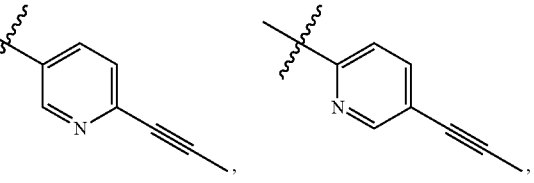

215
-continued
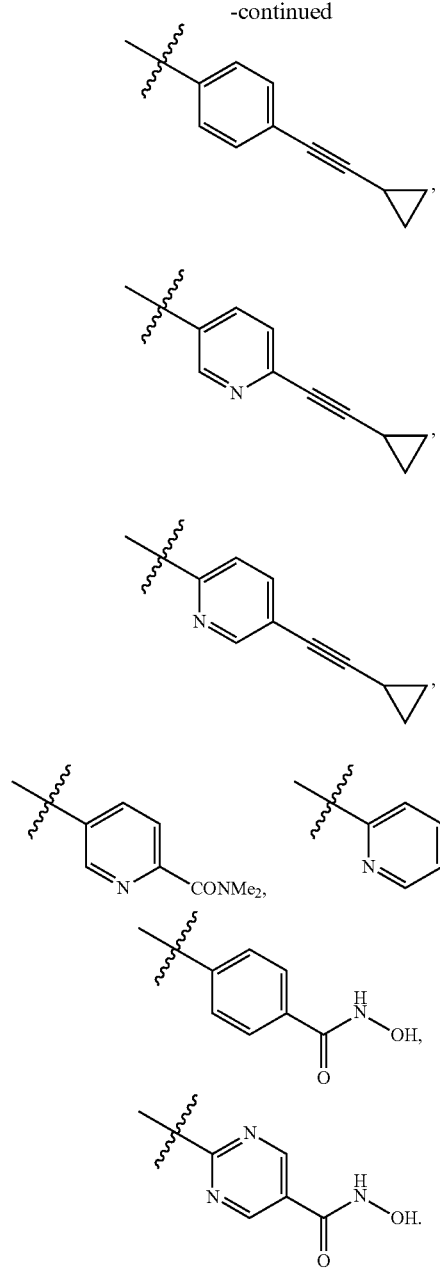
17. The compound of formula (I) according to claim 1, wherein the compound is selected from the group consisting of
216
-continued
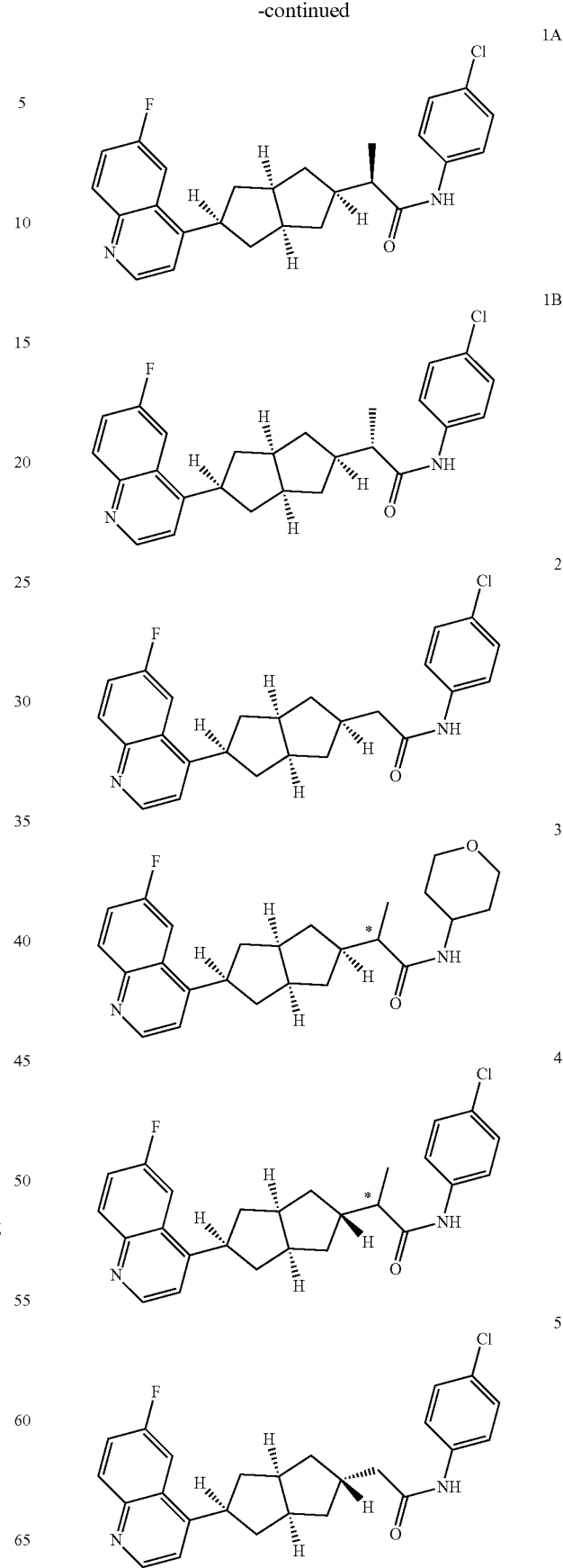

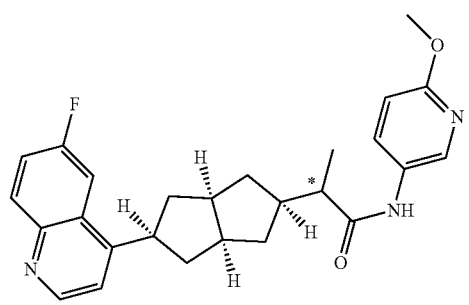
6
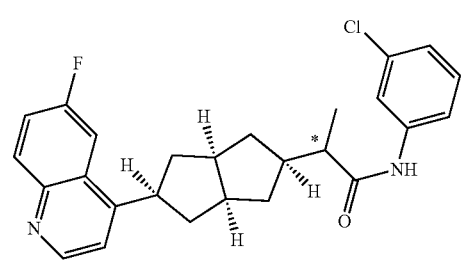
7
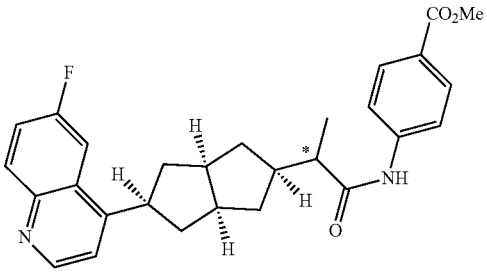
8
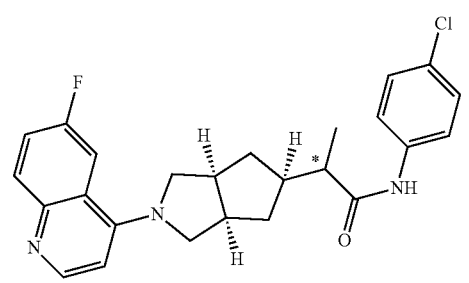
9
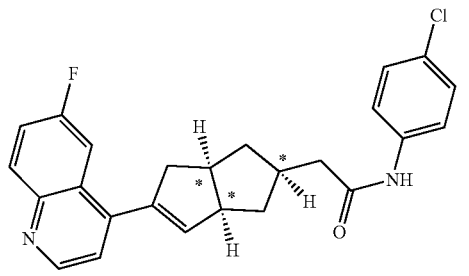
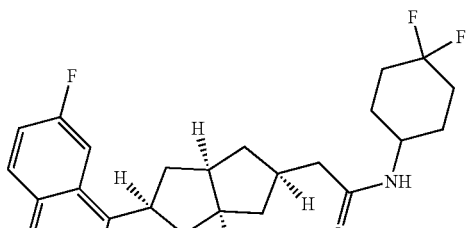
12
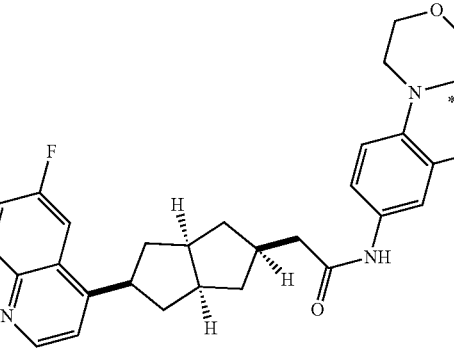
13
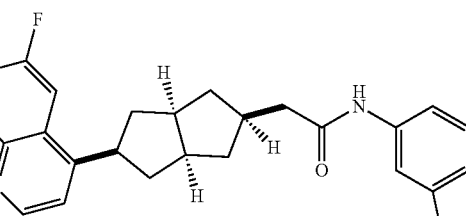
14
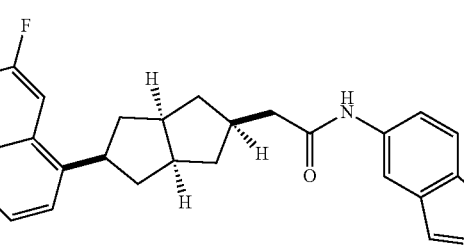
15
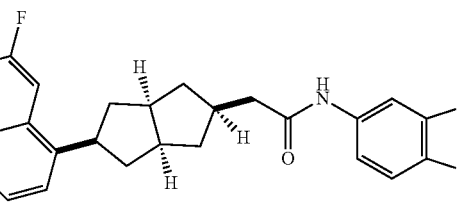
16
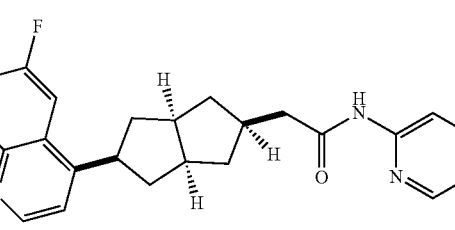
17

18
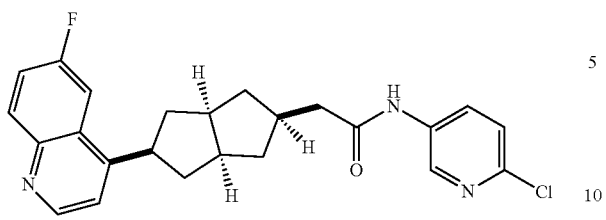
19
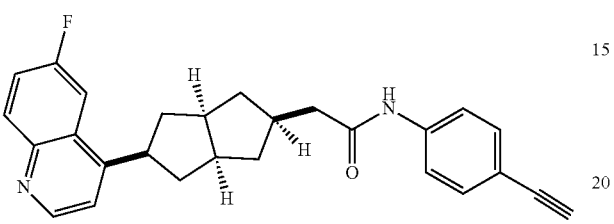
20
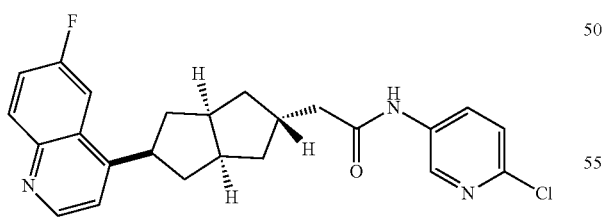
21
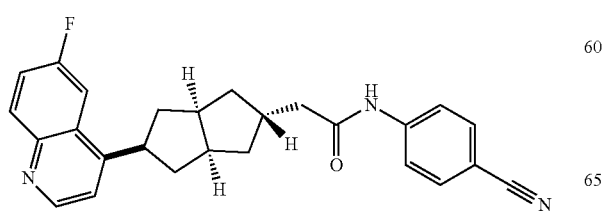
22
23
24
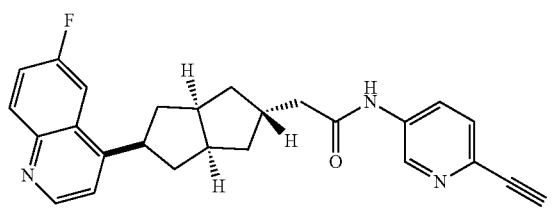
25
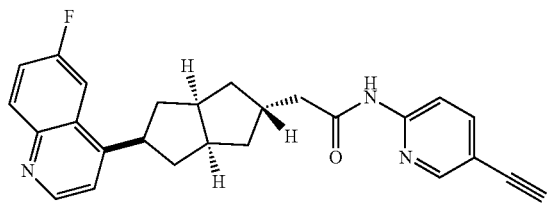
26
26A
26B
27

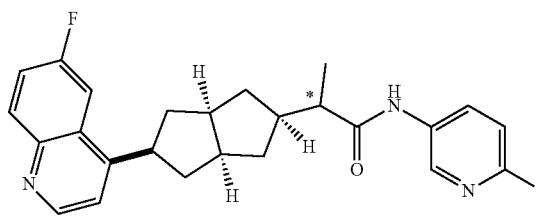
28
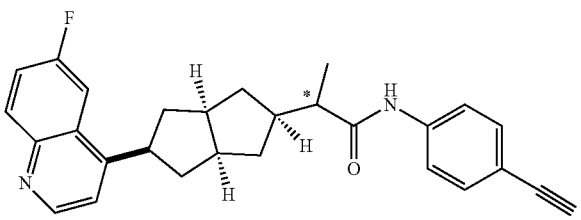
34
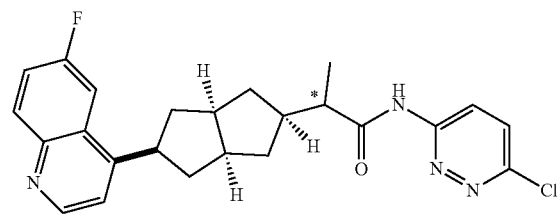
29
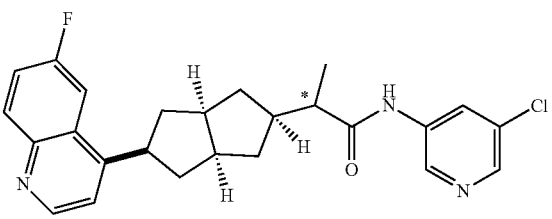
35
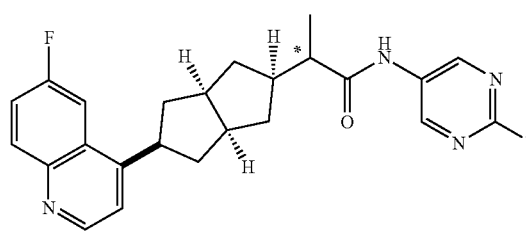
30
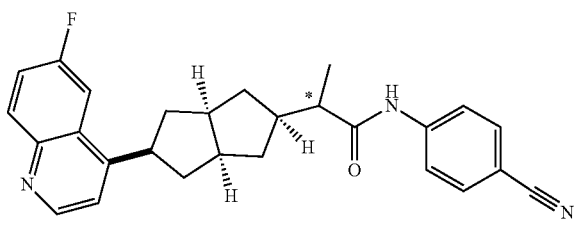
36
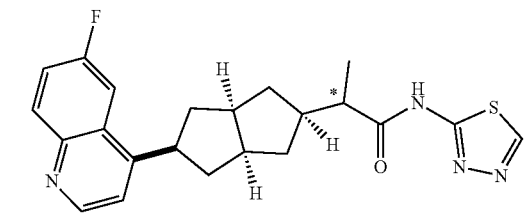
31
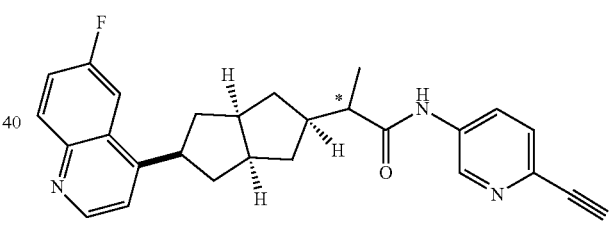
37
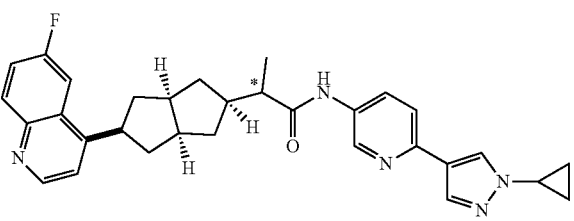
32
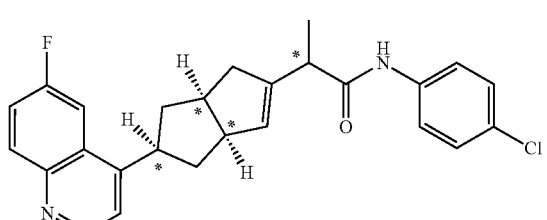
38
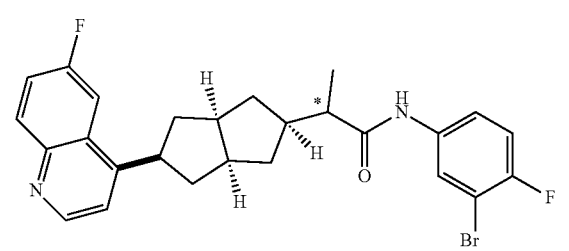
33
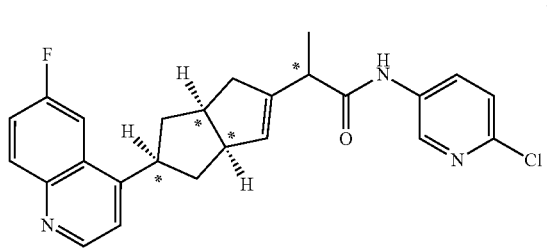
39

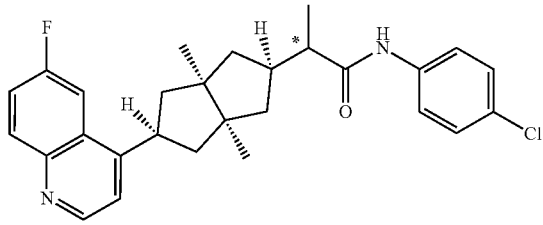
40
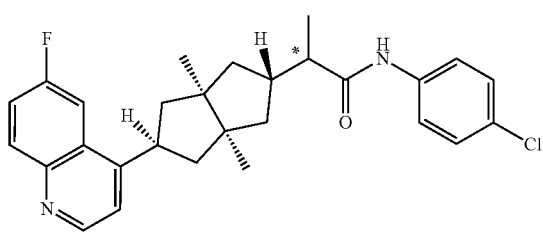
41
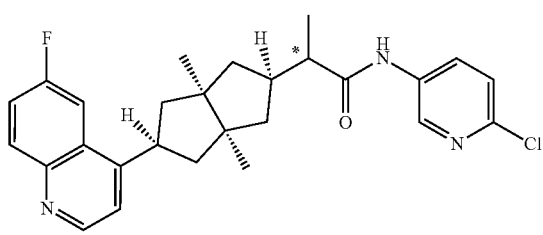
42
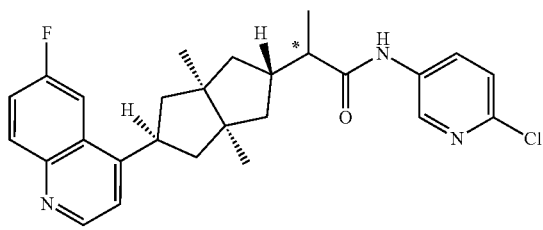
43
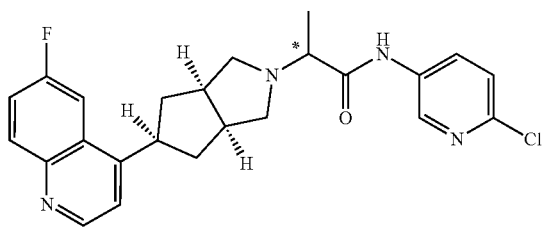
44
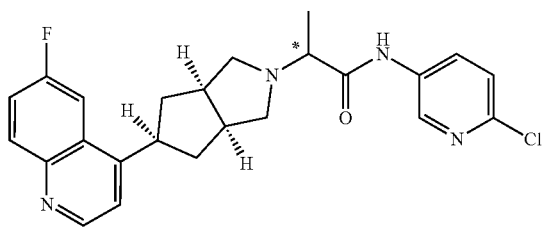
45
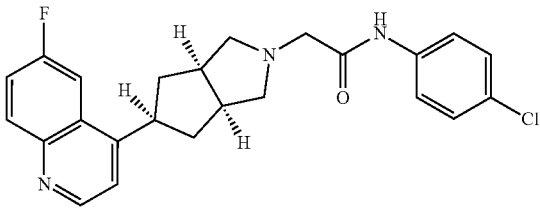
46
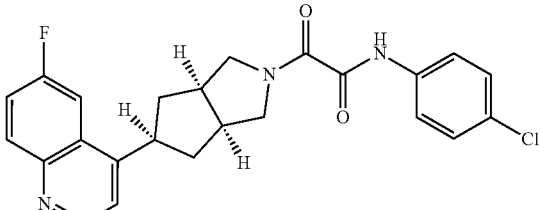
47
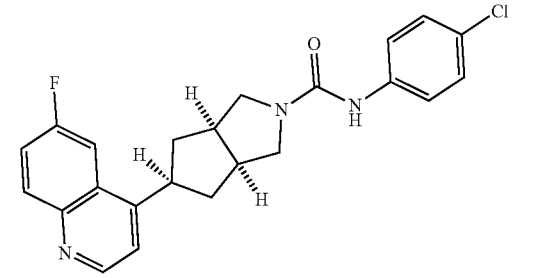
48
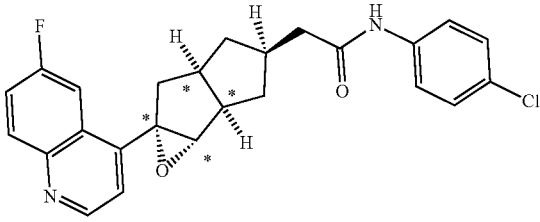
49
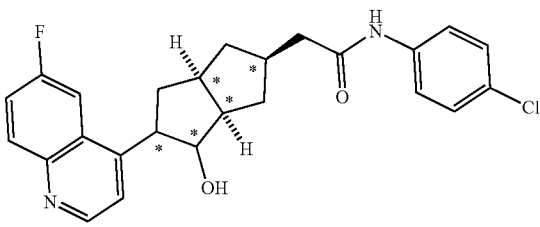
50
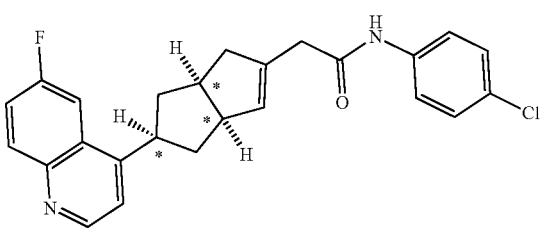
57

58
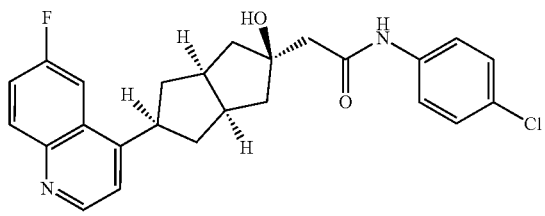
59
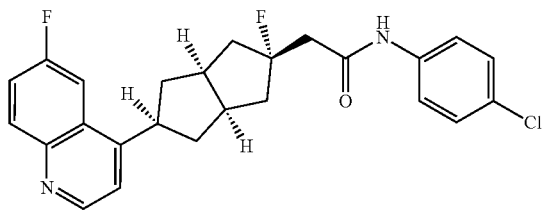
60
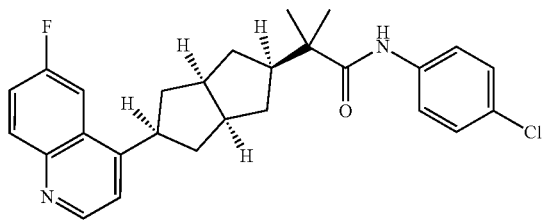
61
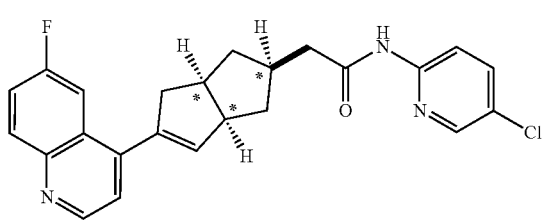
62
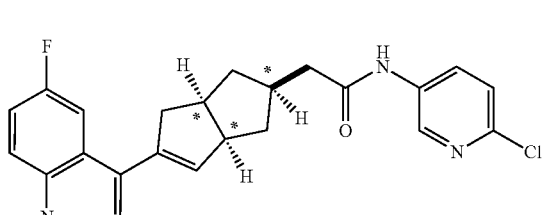
63
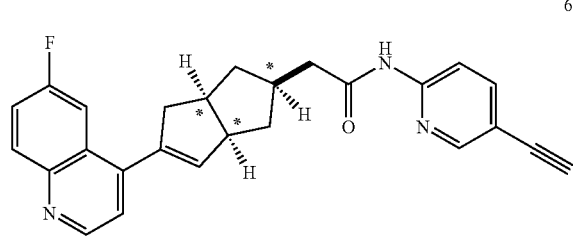
64
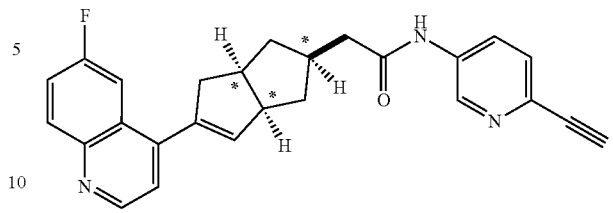
65
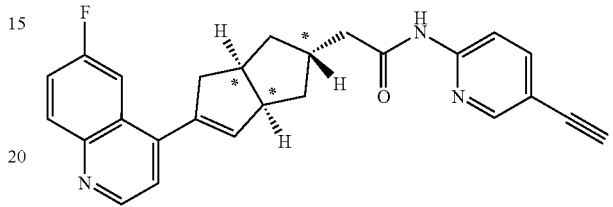
66
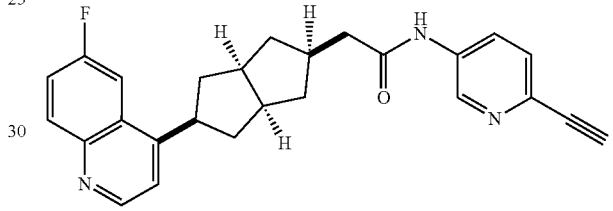
67
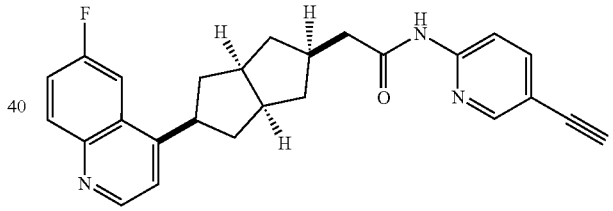
68
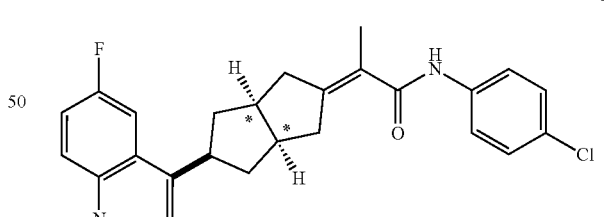
69
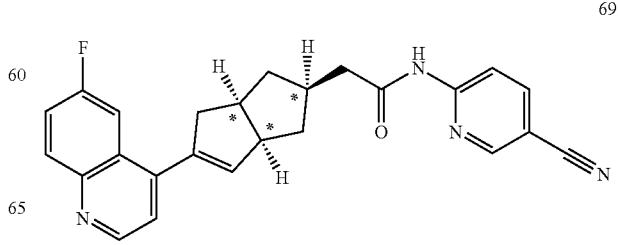

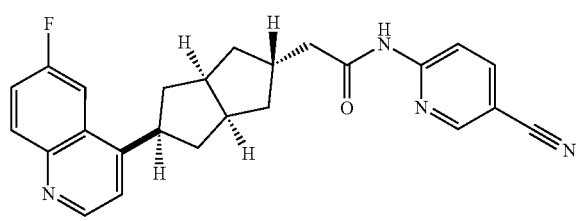
70
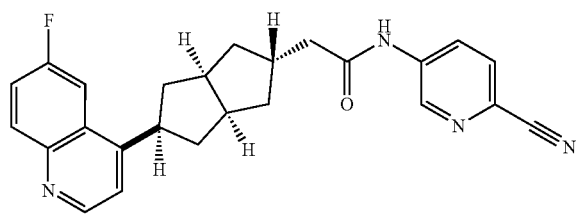
71
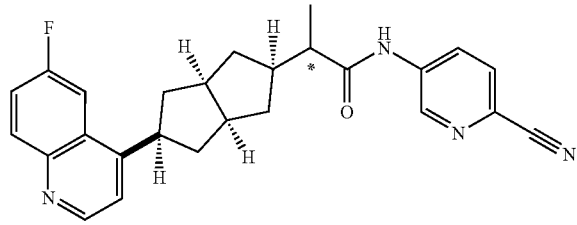
72
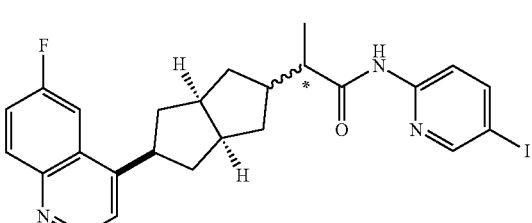
76
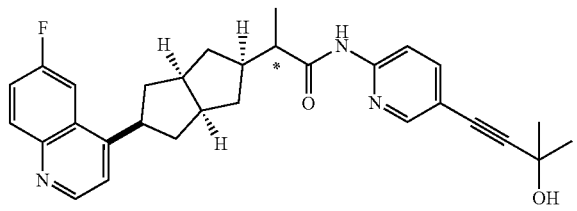
77
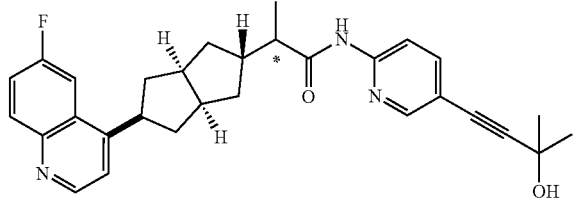
78
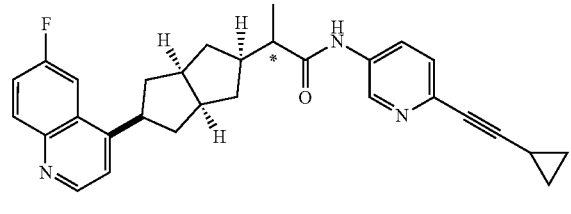
79
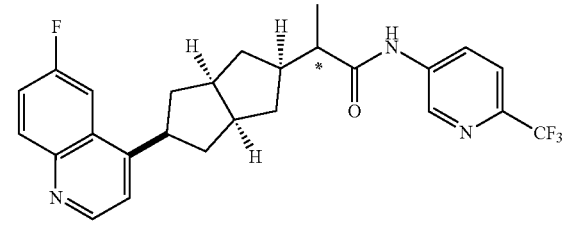
80
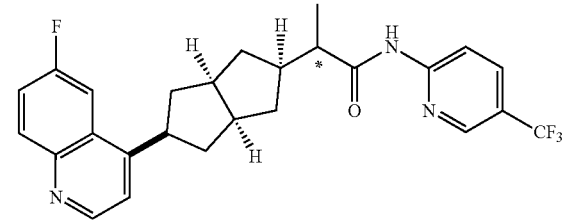
81

82
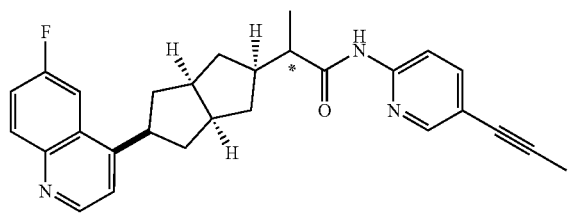
83
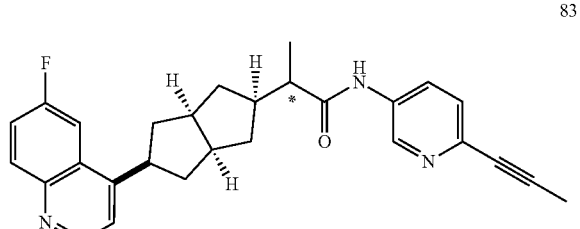
84
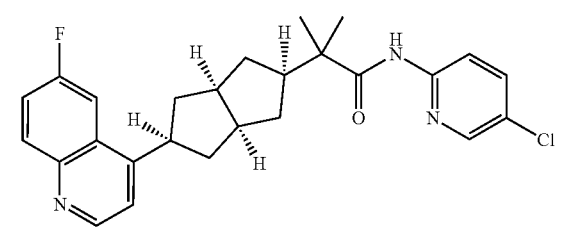
85
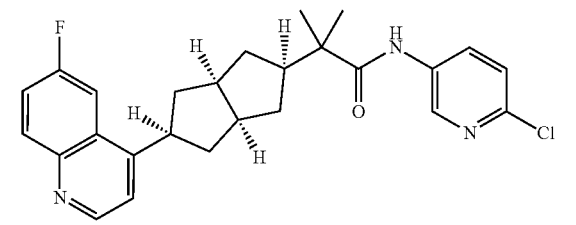
86
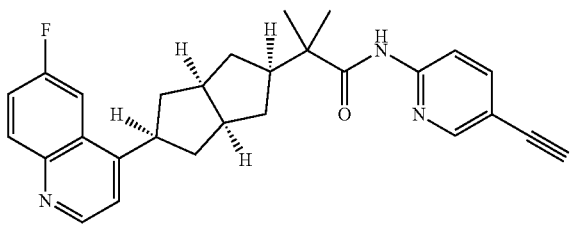
87
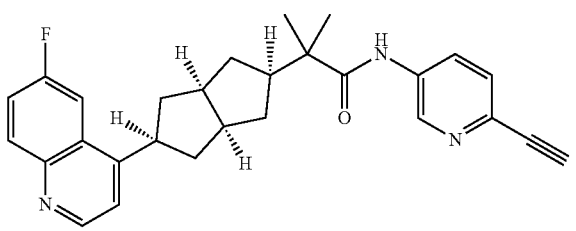
88
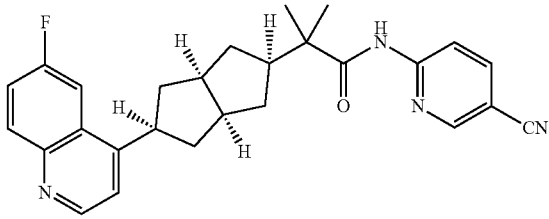
89
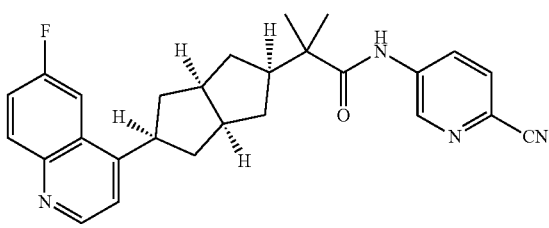
90
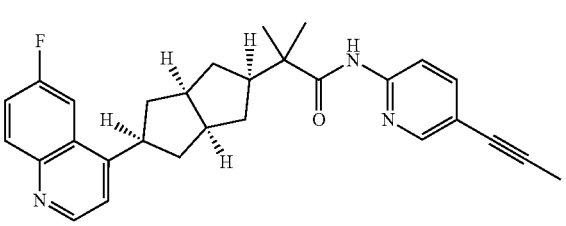
91
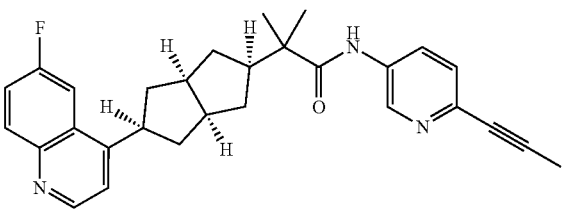
92
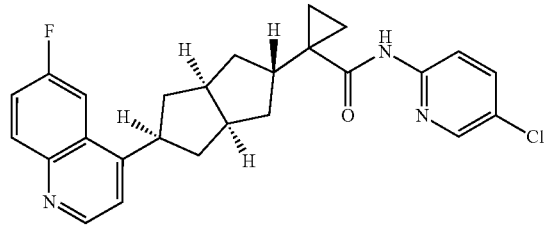
93
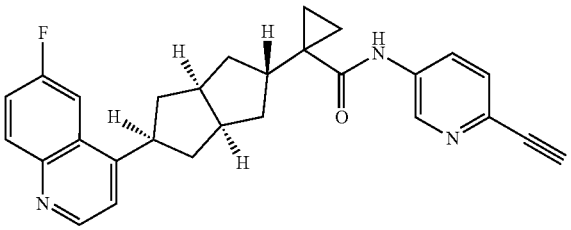

94
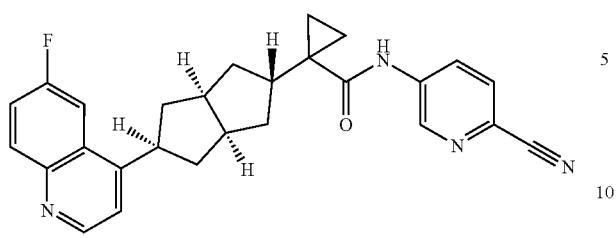
95
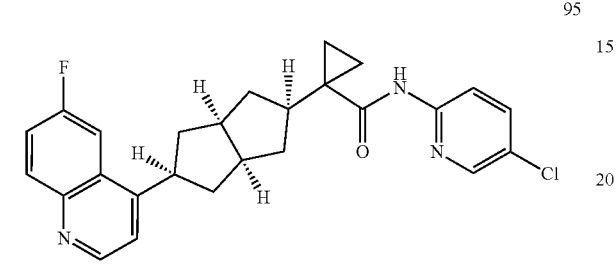
96
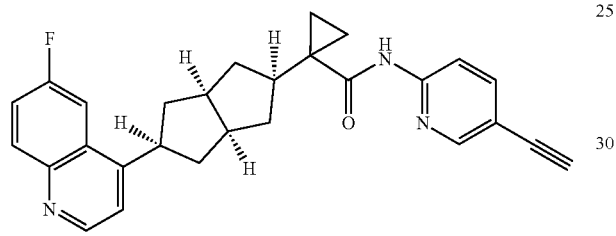
97
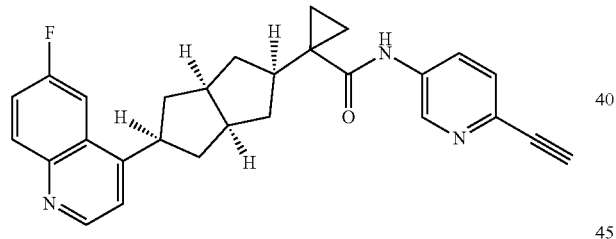
98
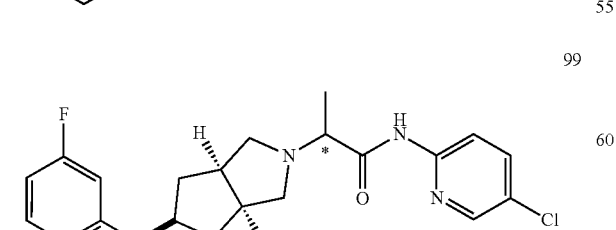
99
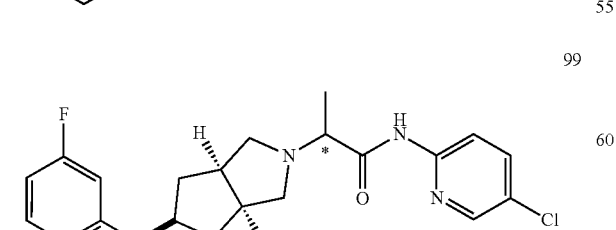
100
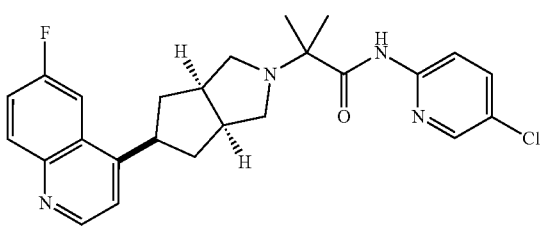
101
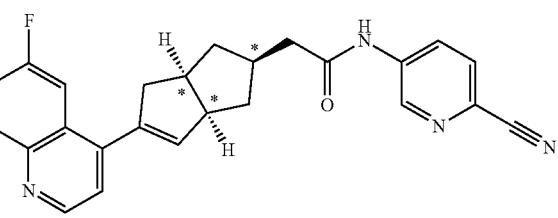
102
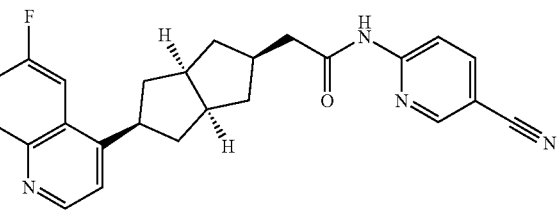
104
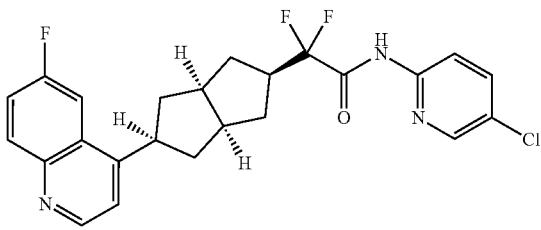
105
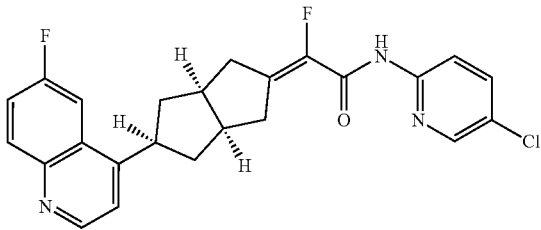
106
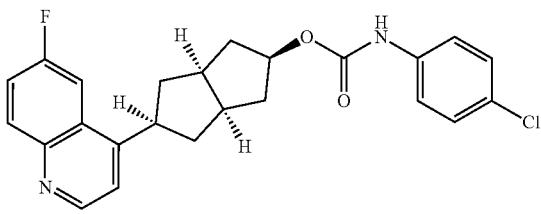

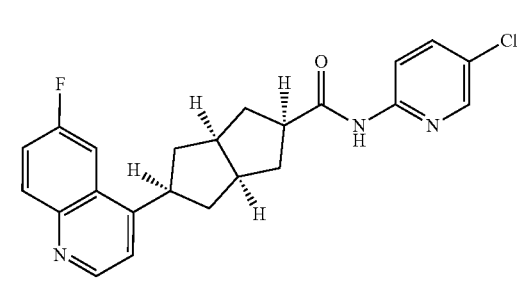
107
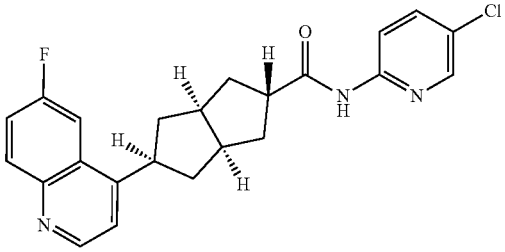
108
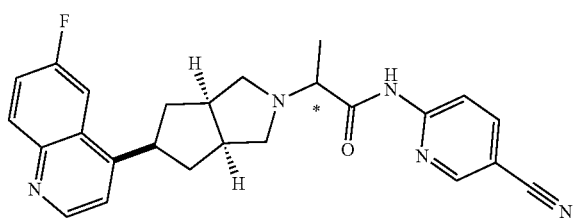
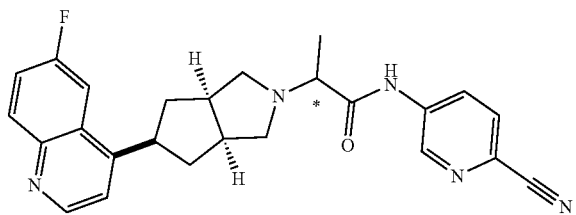
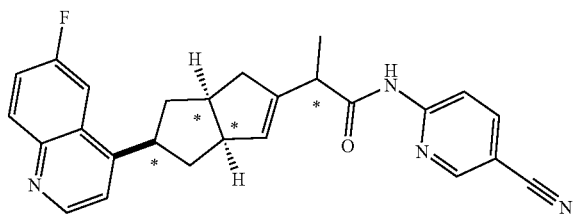
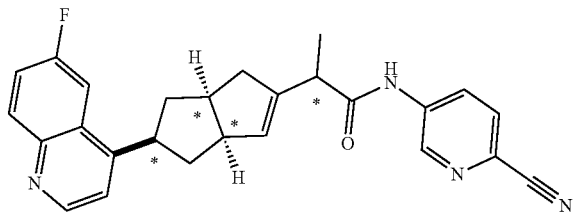
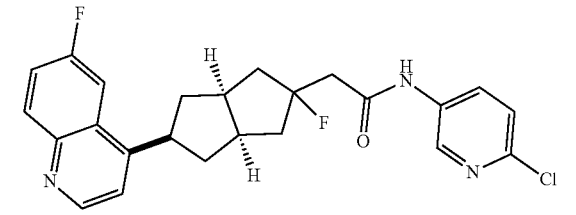
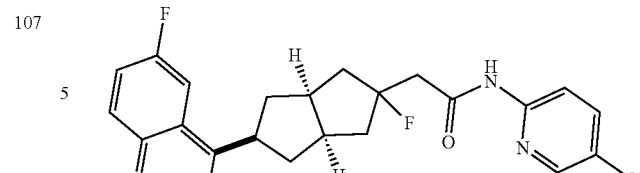
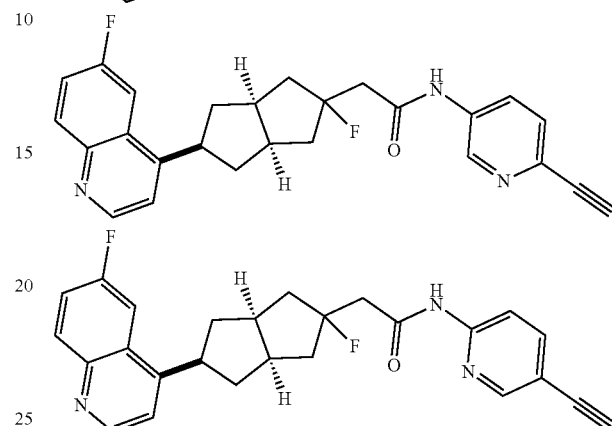
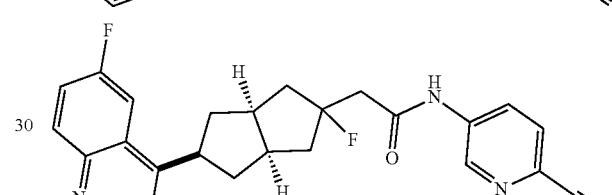
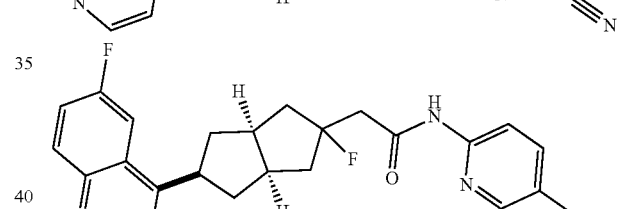
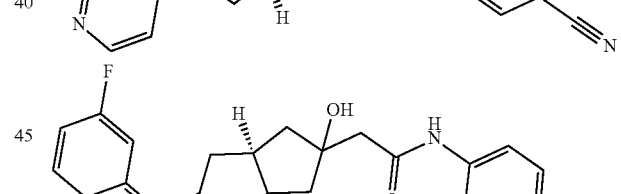
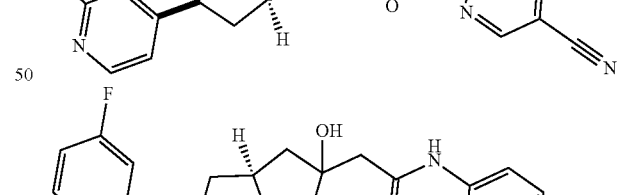
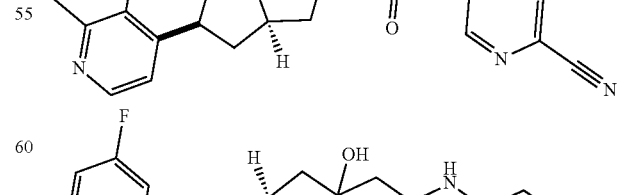
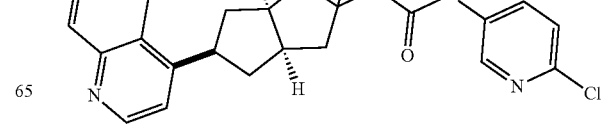

235
-continued
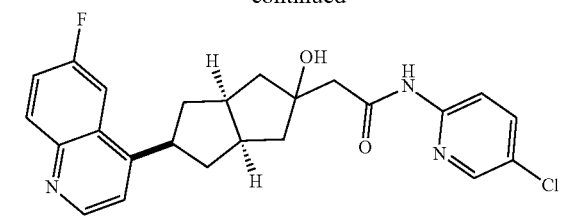
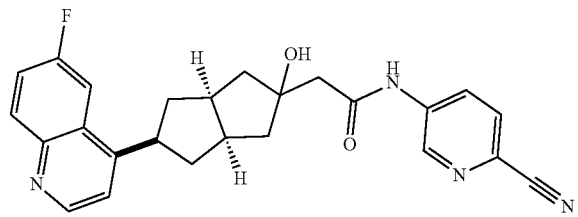
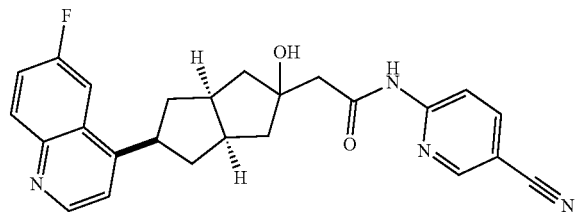
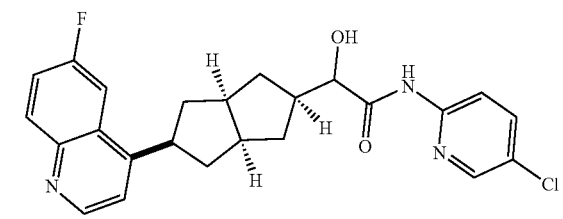
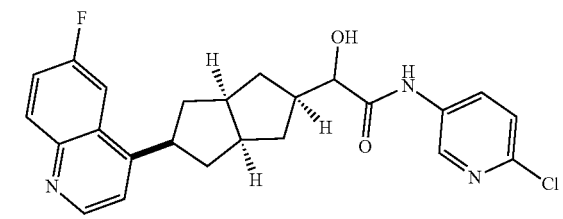
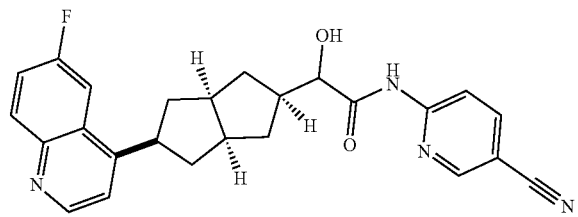
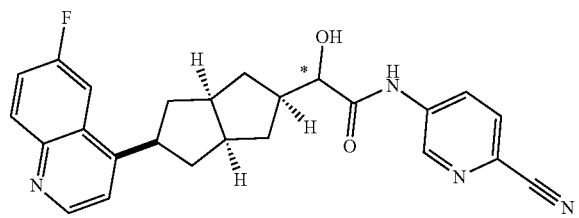
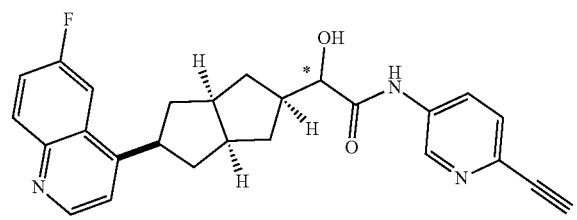
236
-continued
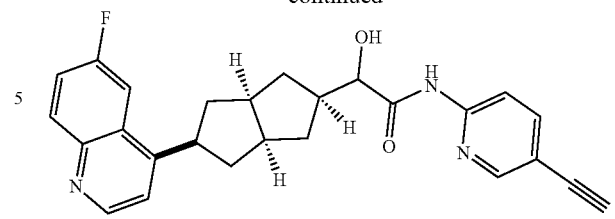
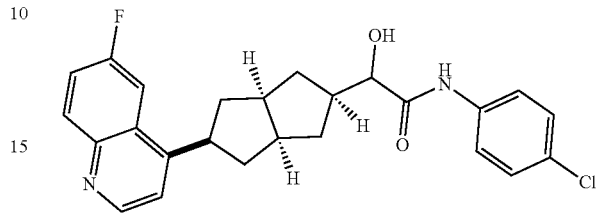
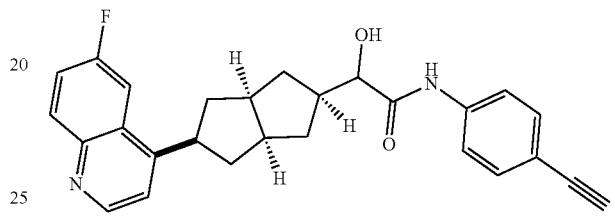
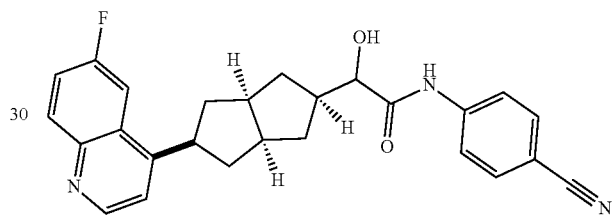
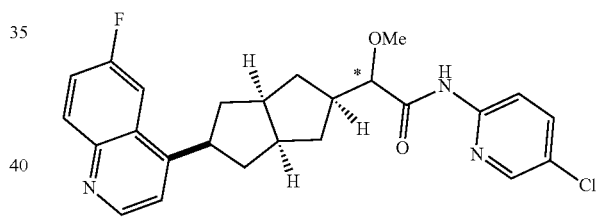
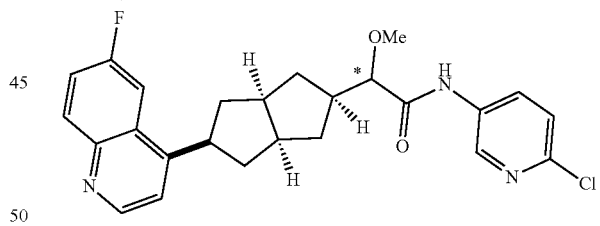
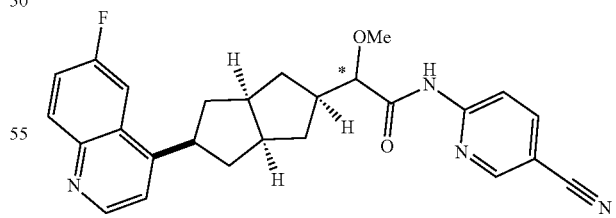
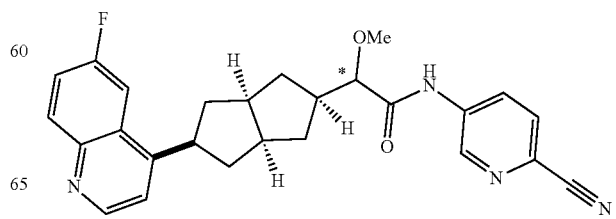

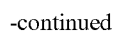
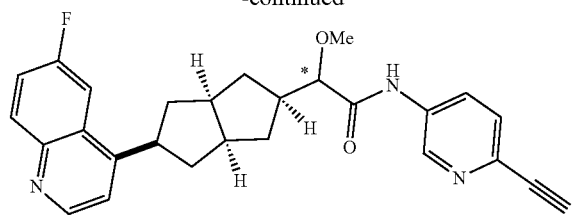
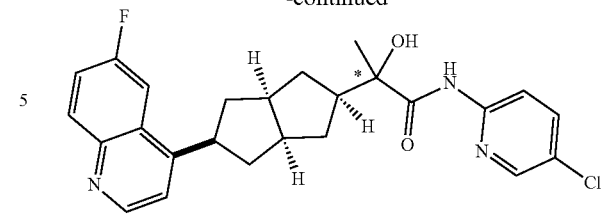
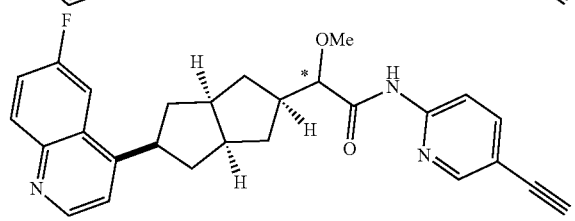
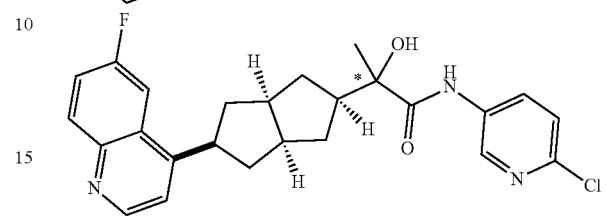
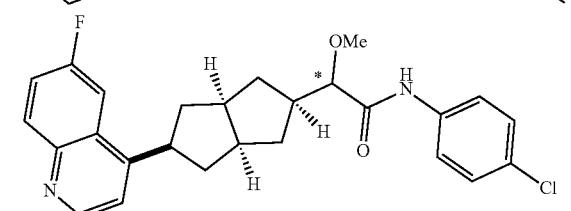
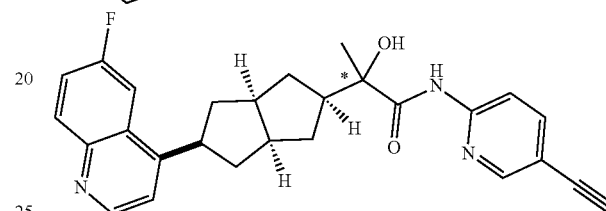
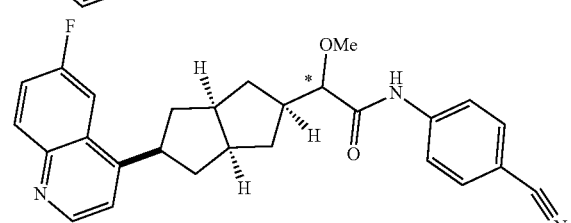
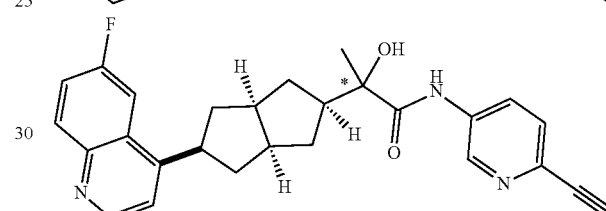
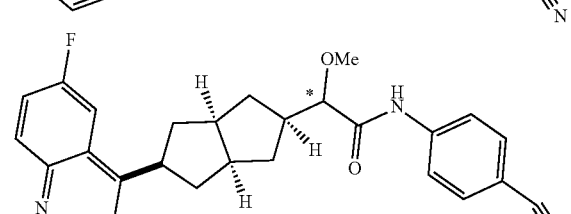
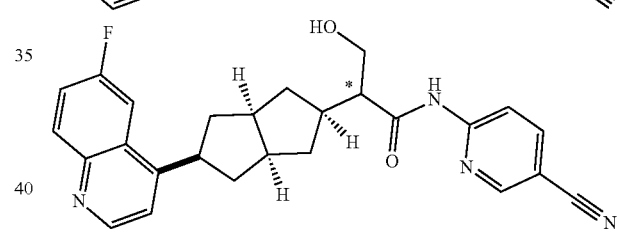
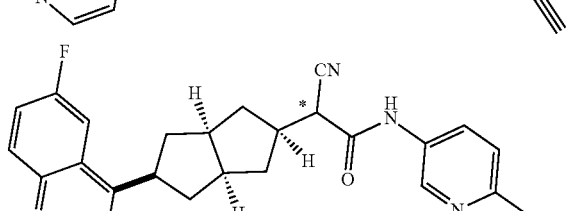
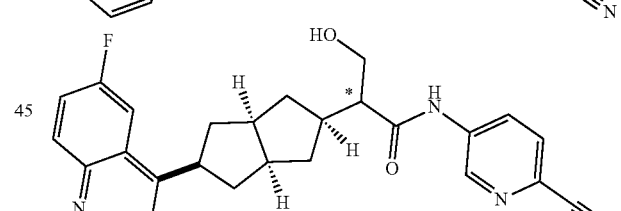
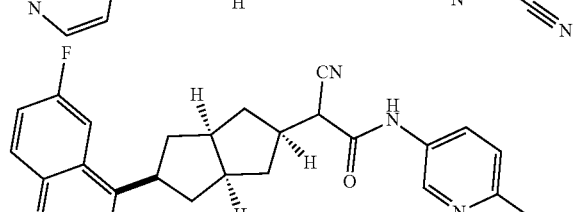
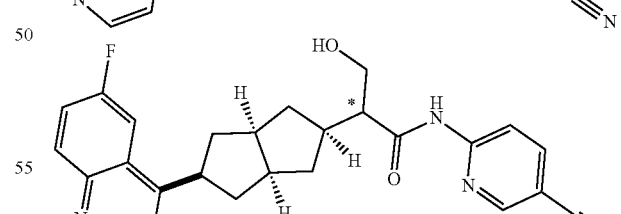
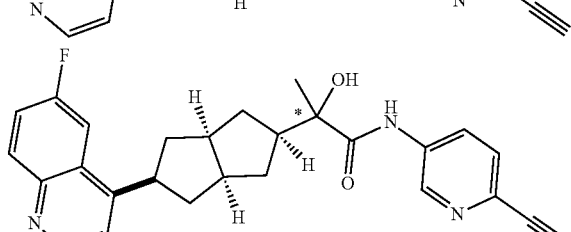
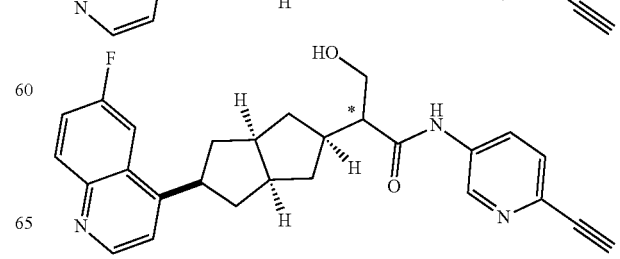

239
-continued
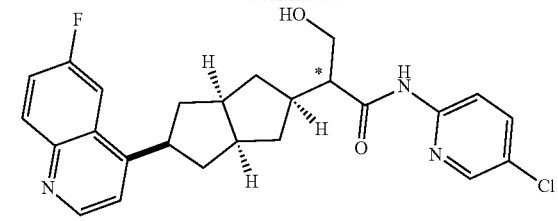
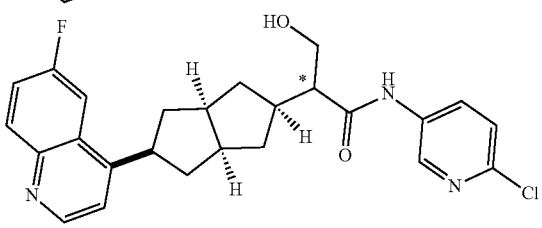
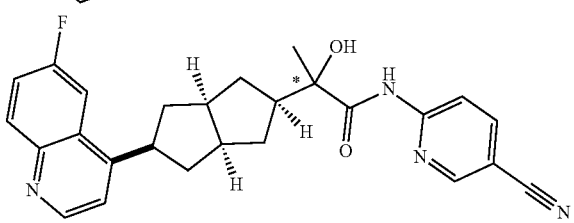
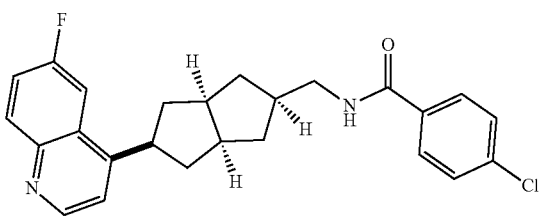
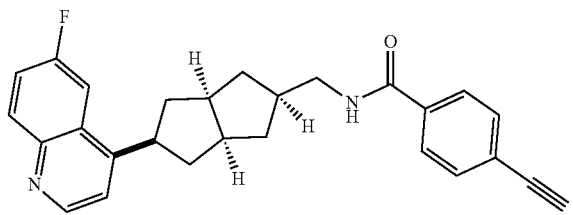
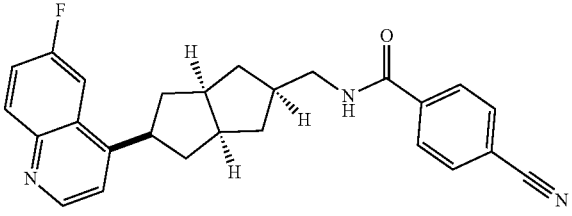
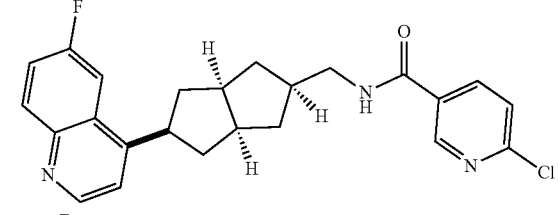
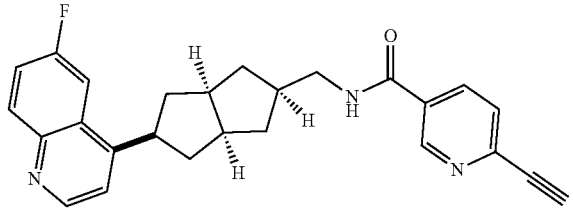
240
-continued
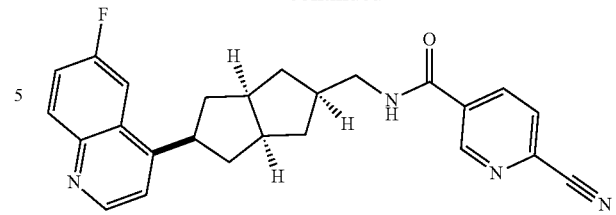
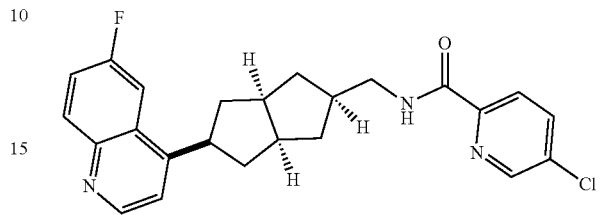
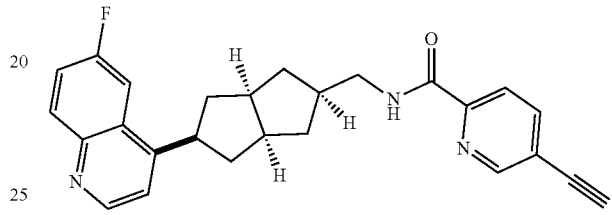
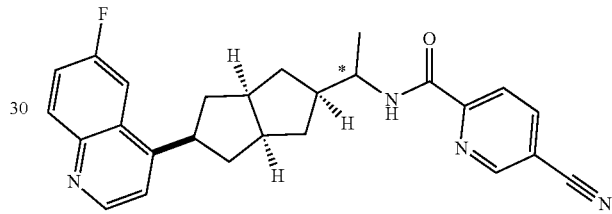
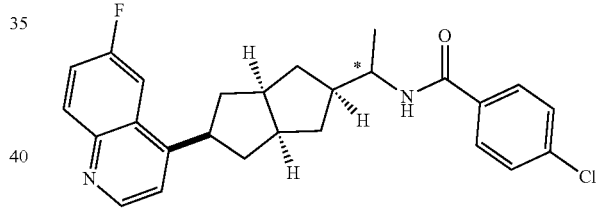
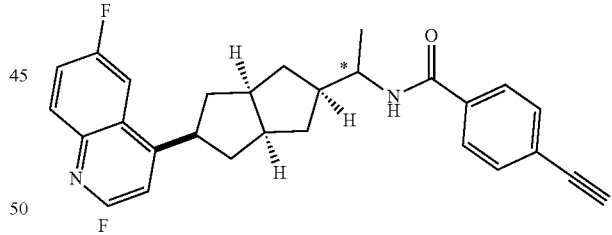
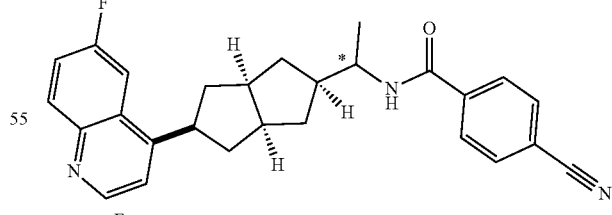
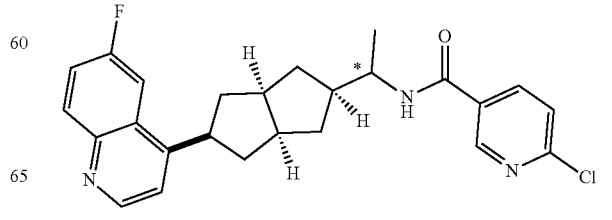

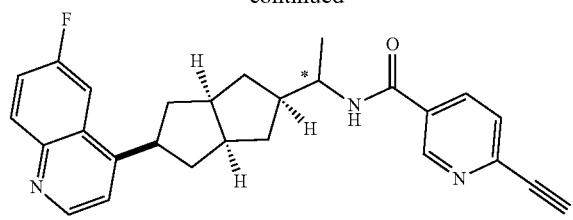
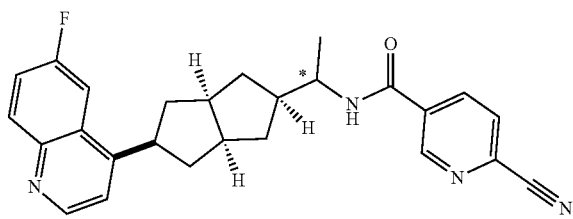
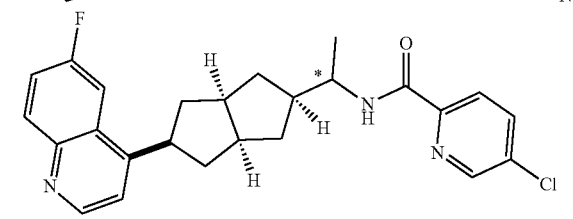
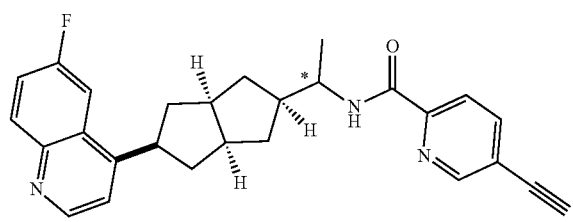
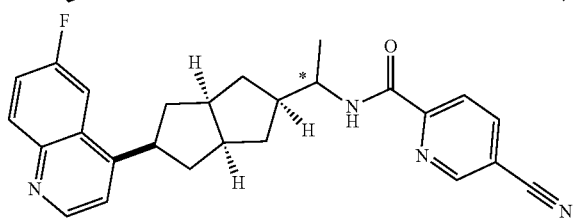
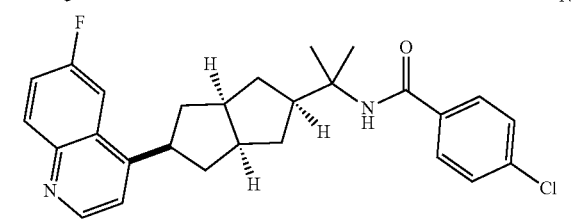
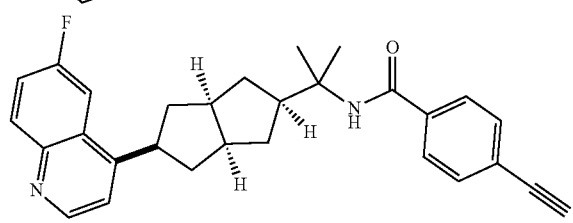
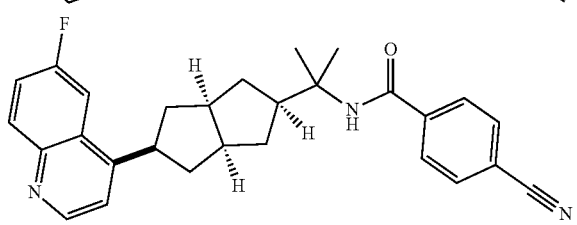
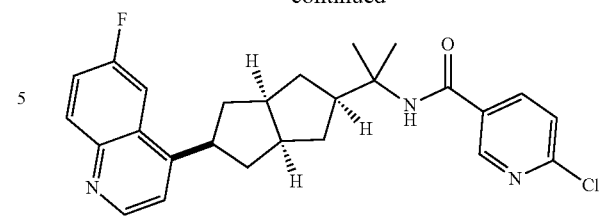
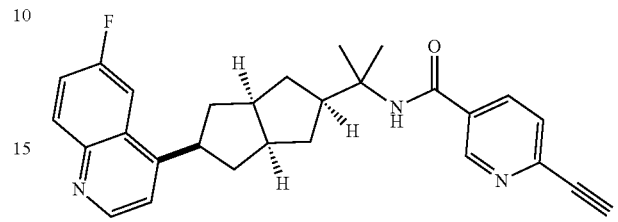
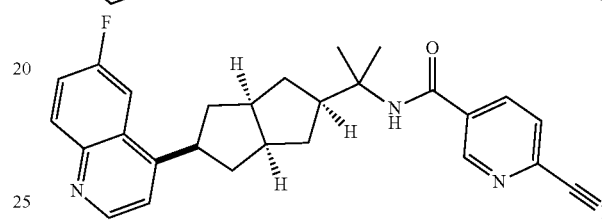
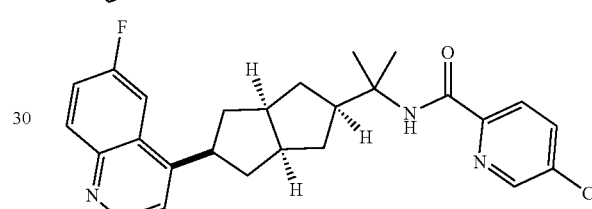
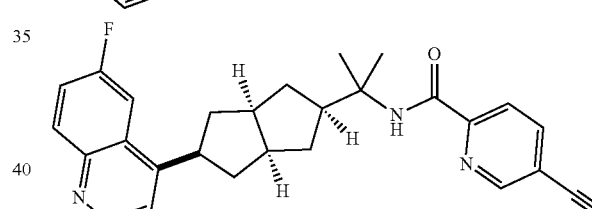
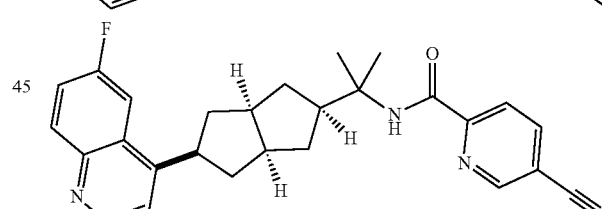
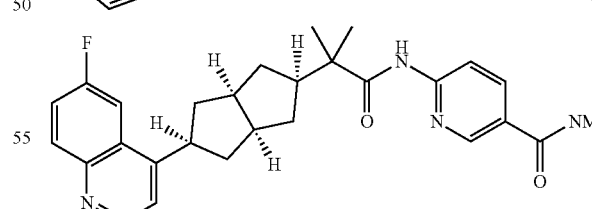
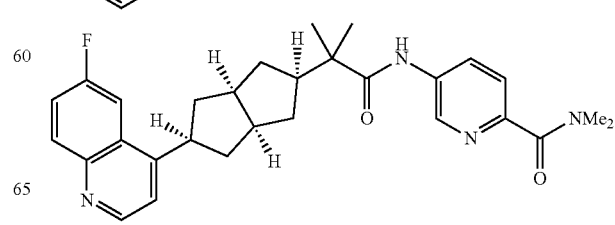

-continued
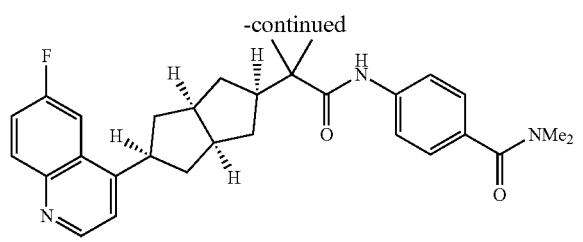
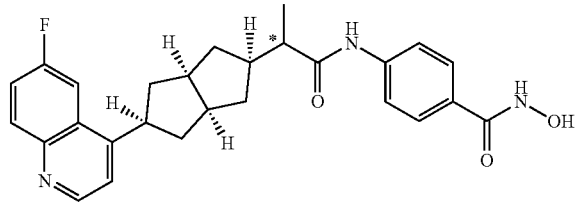
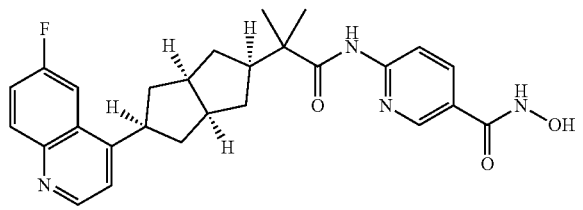
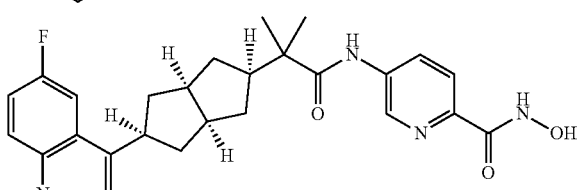
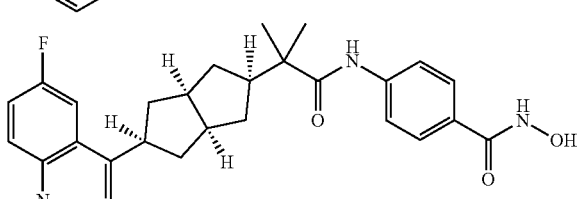
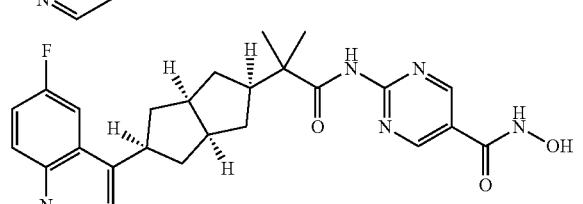
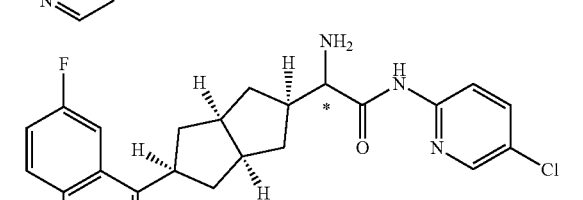
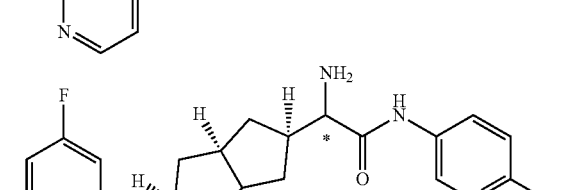
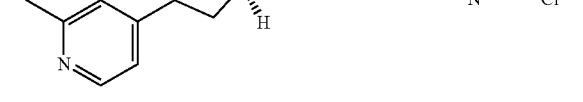
-continued
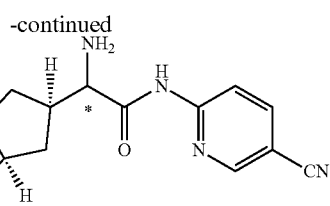
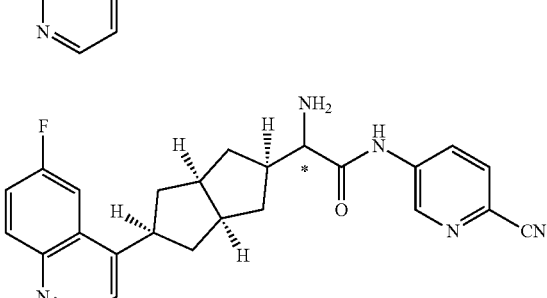
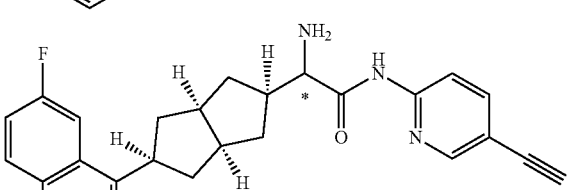
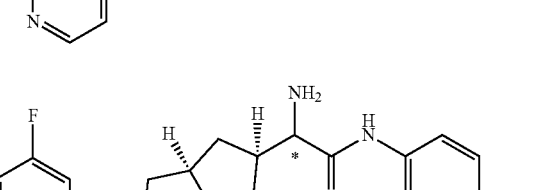
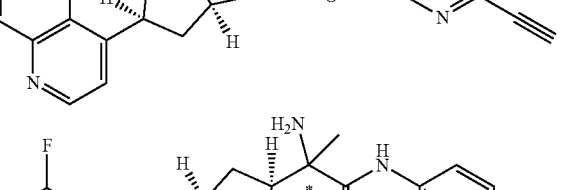
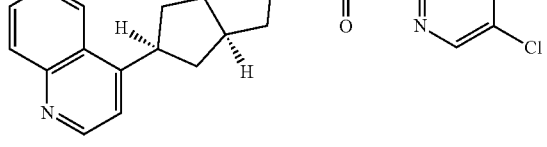
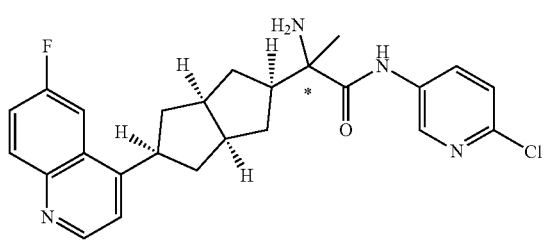
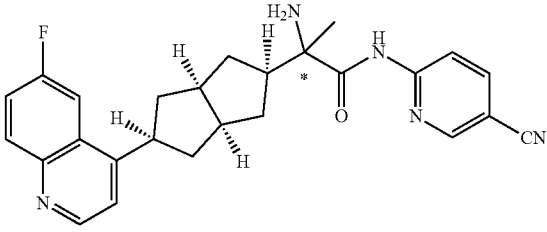

-continued
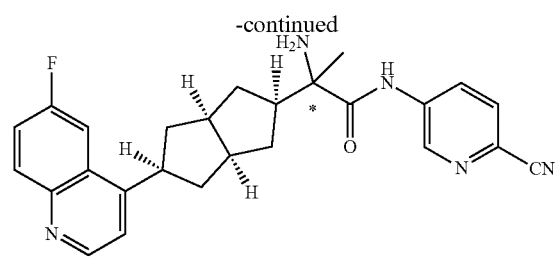
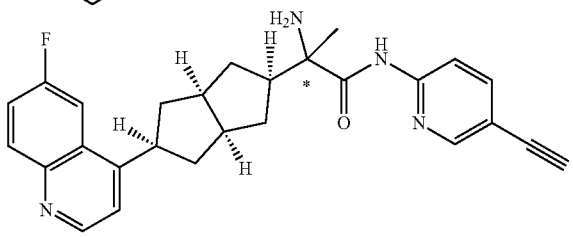
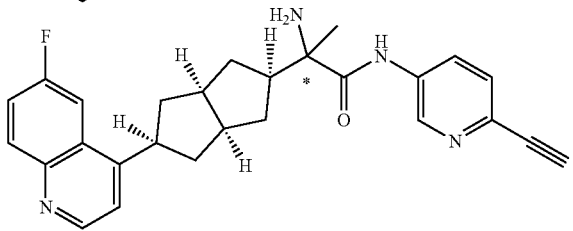
wherein * indicates a chiral center.
18. The compound of claim 1, wherein the compound is of the following structure:
wherein the G$^1$ is selected from the following group:
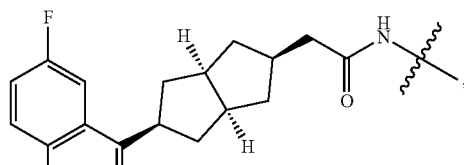
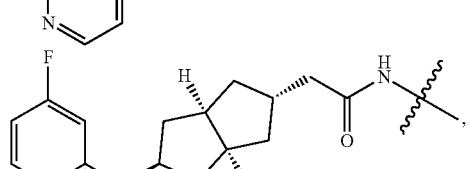
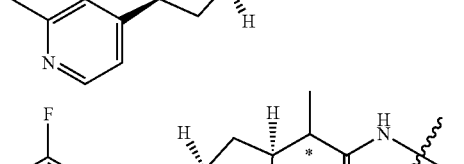
-continued
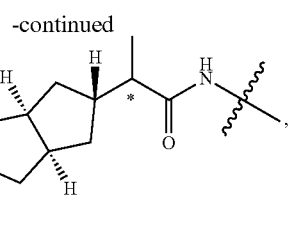
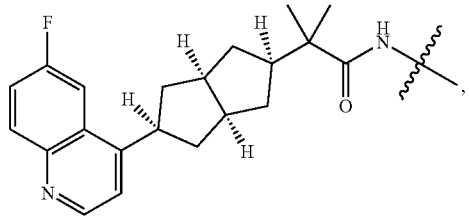
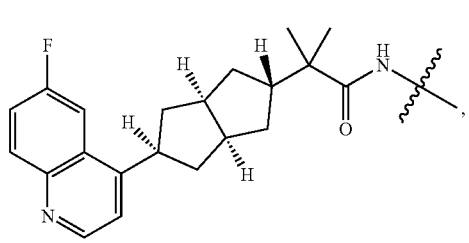
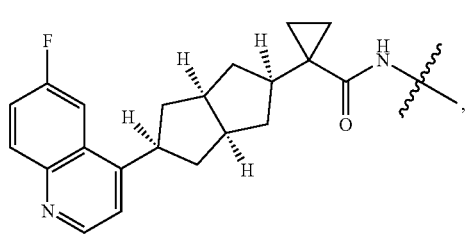
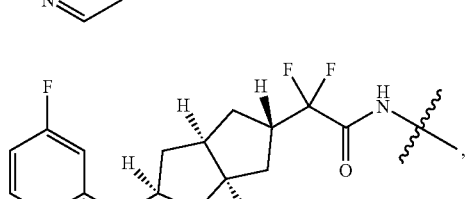
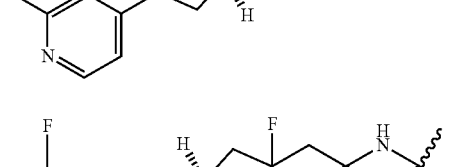
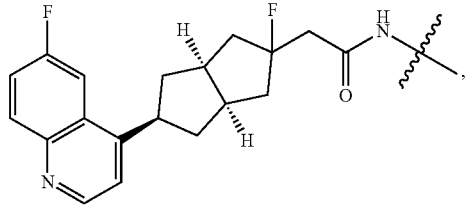

247
-continued
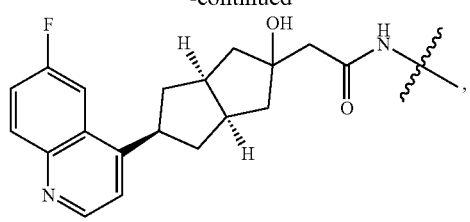
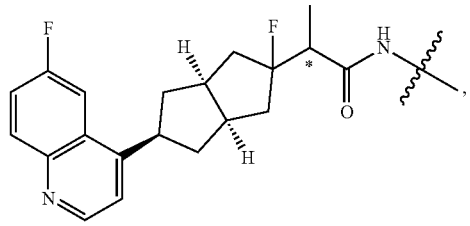
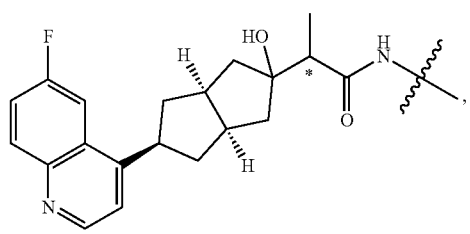
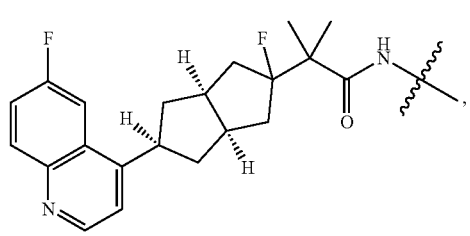
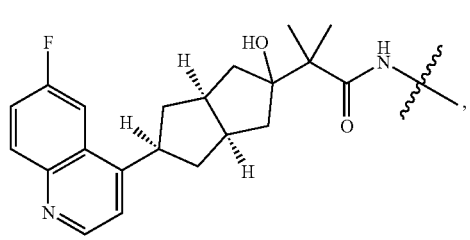
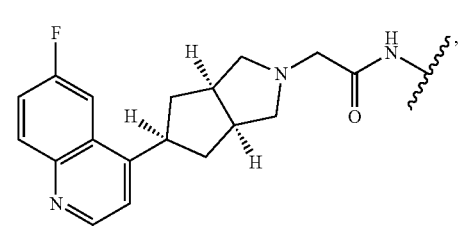
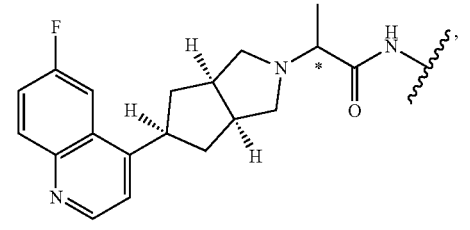
248
-continued
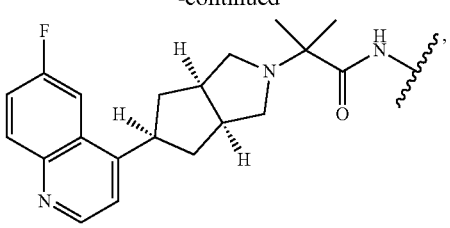
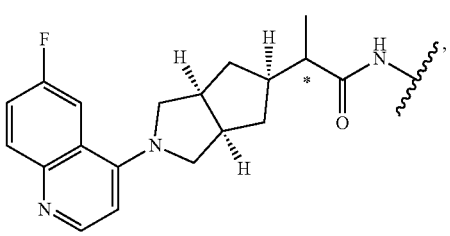
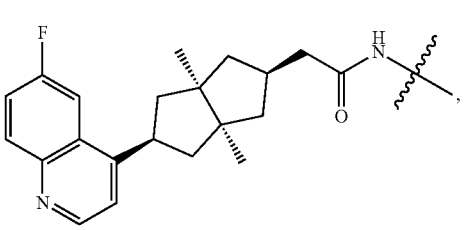
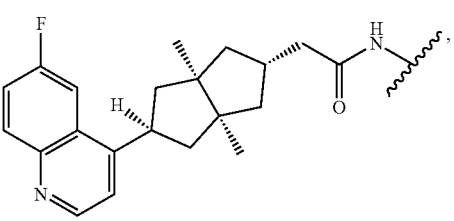
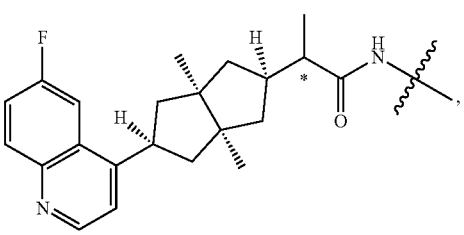
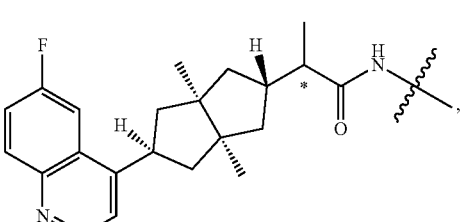
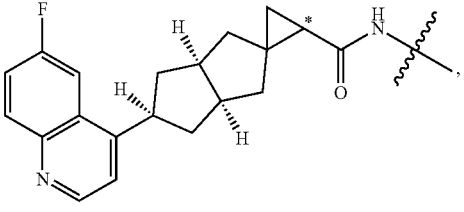

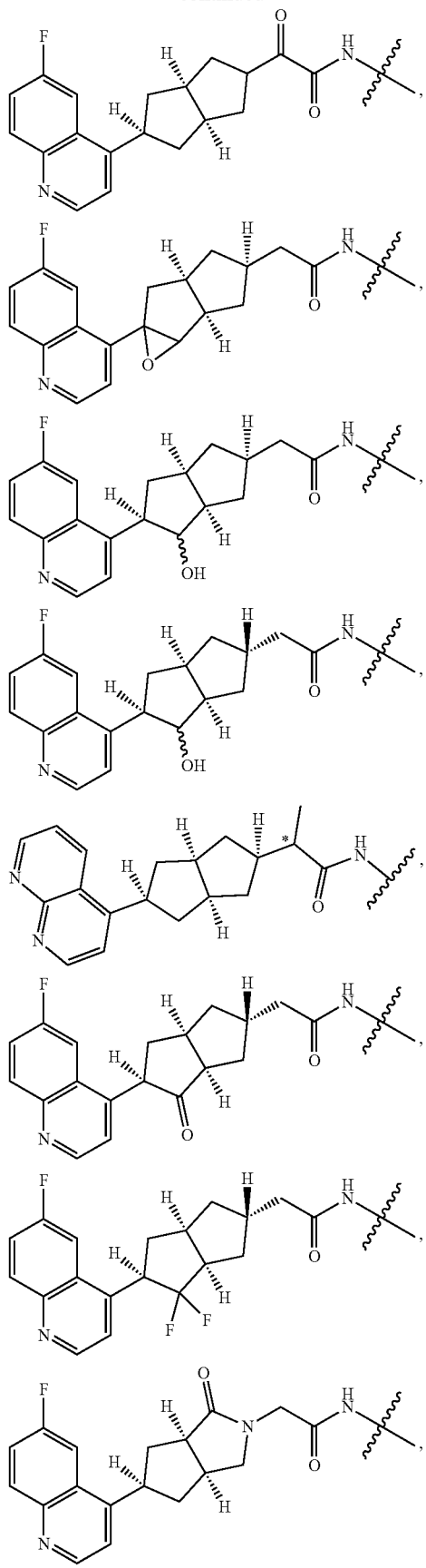
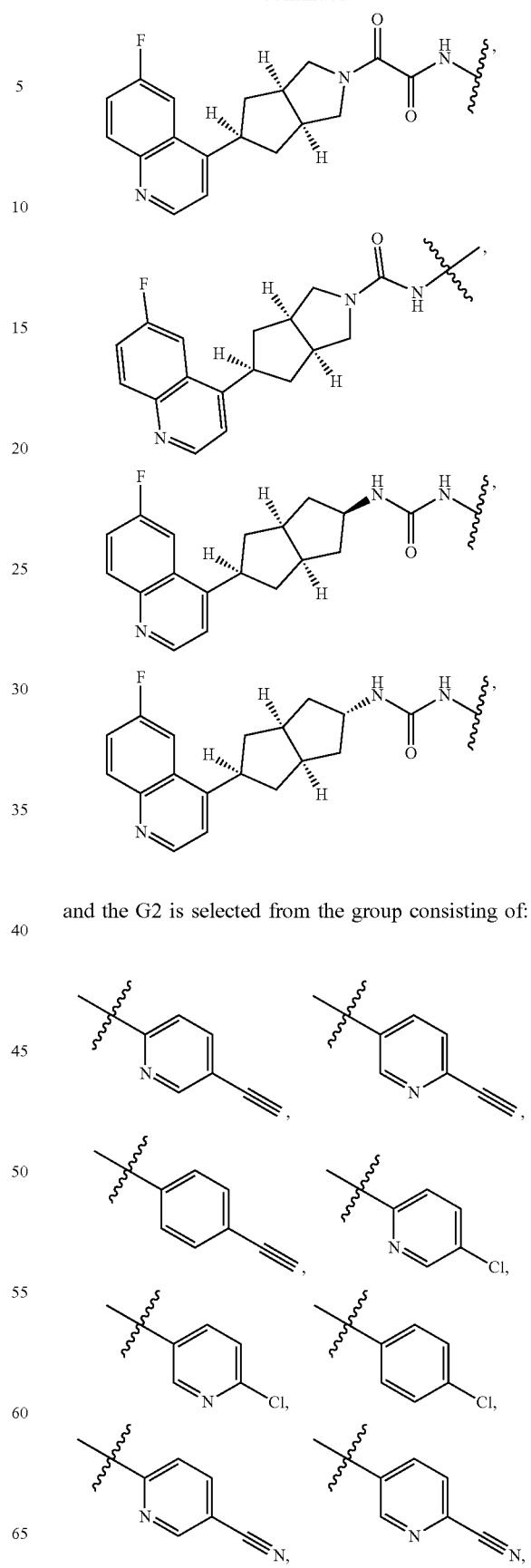
and the G2 is selected from the group consisting of:
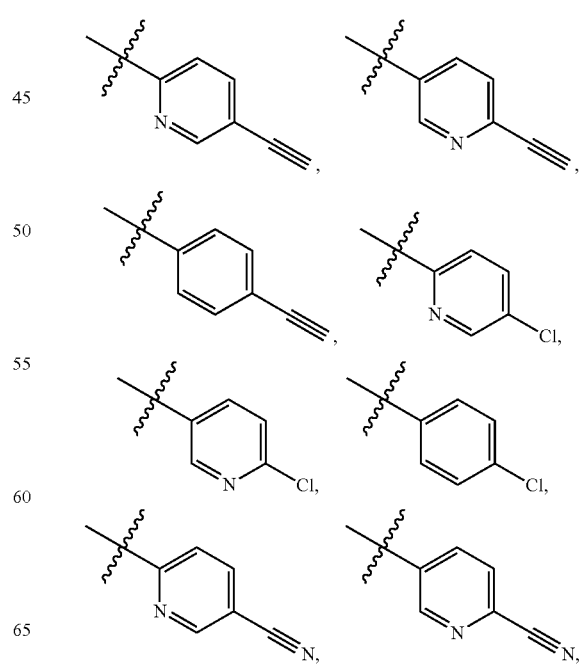

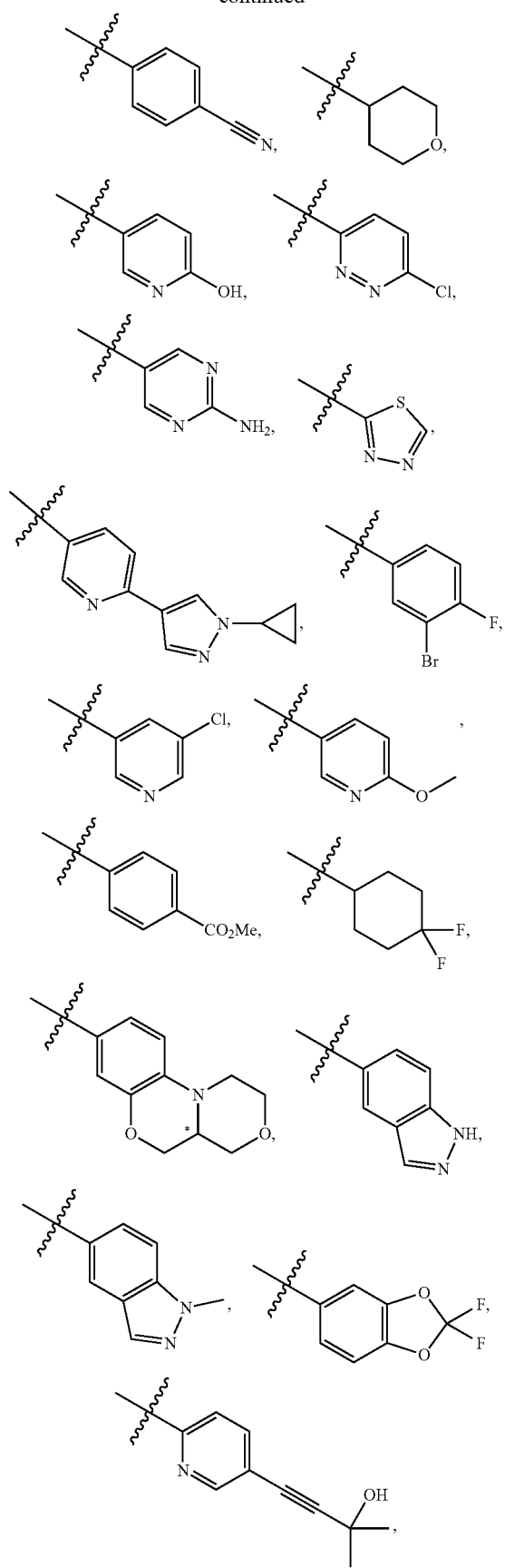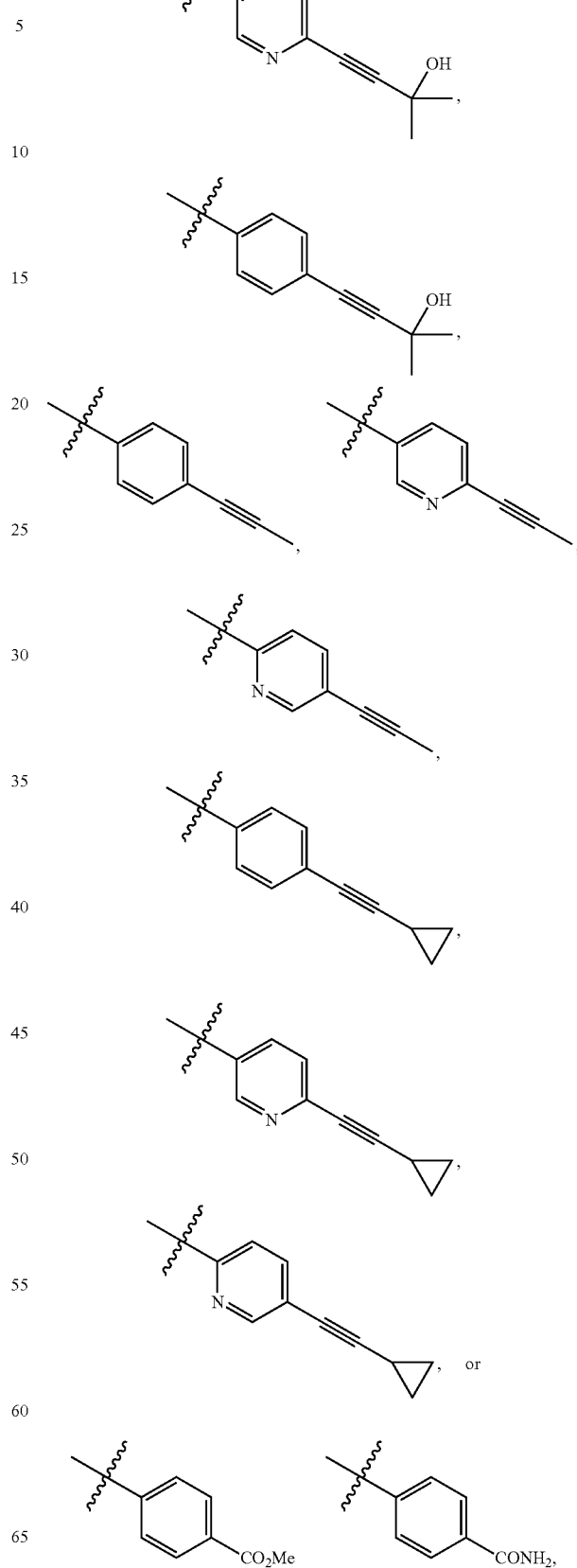

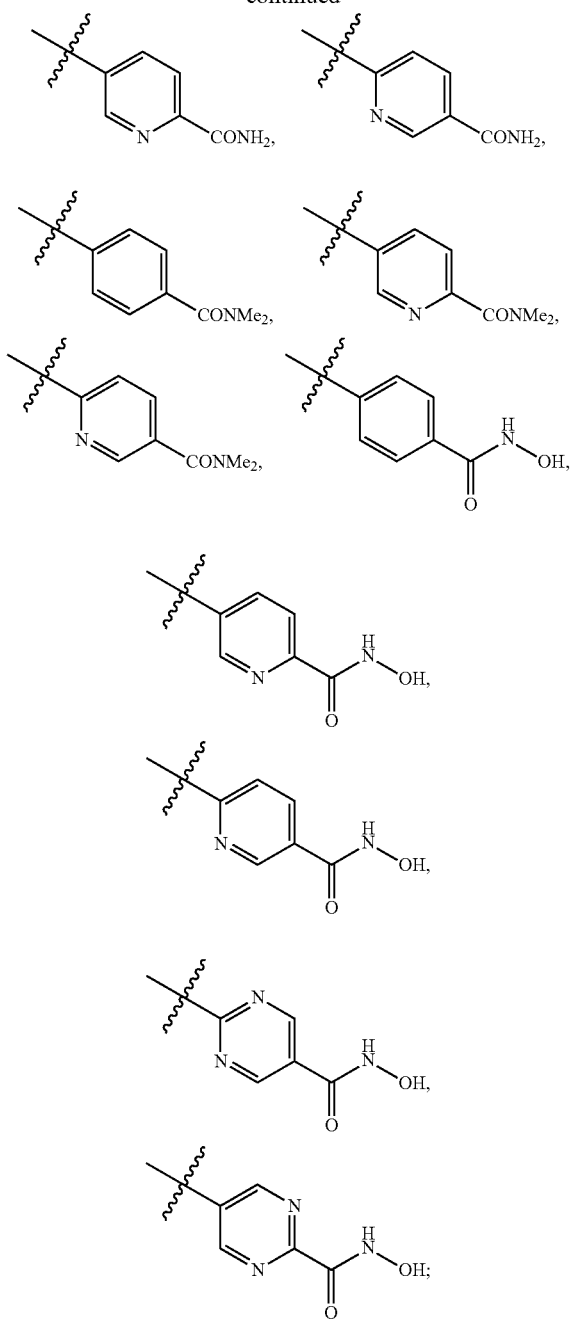
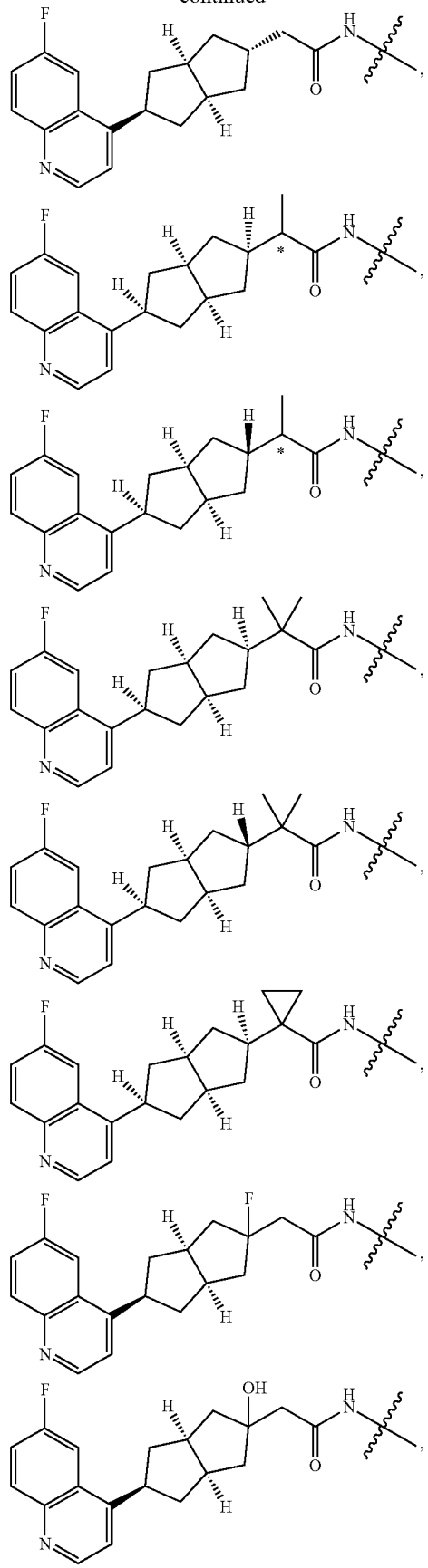
wherein * indicates a chiral center.
19. The compound of claim 18, wherein, the G1 is selected from the group consisting of:
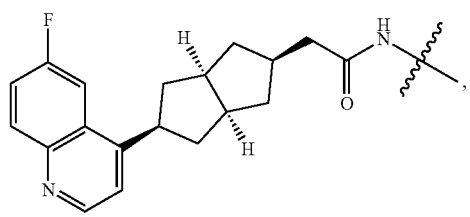

-continued
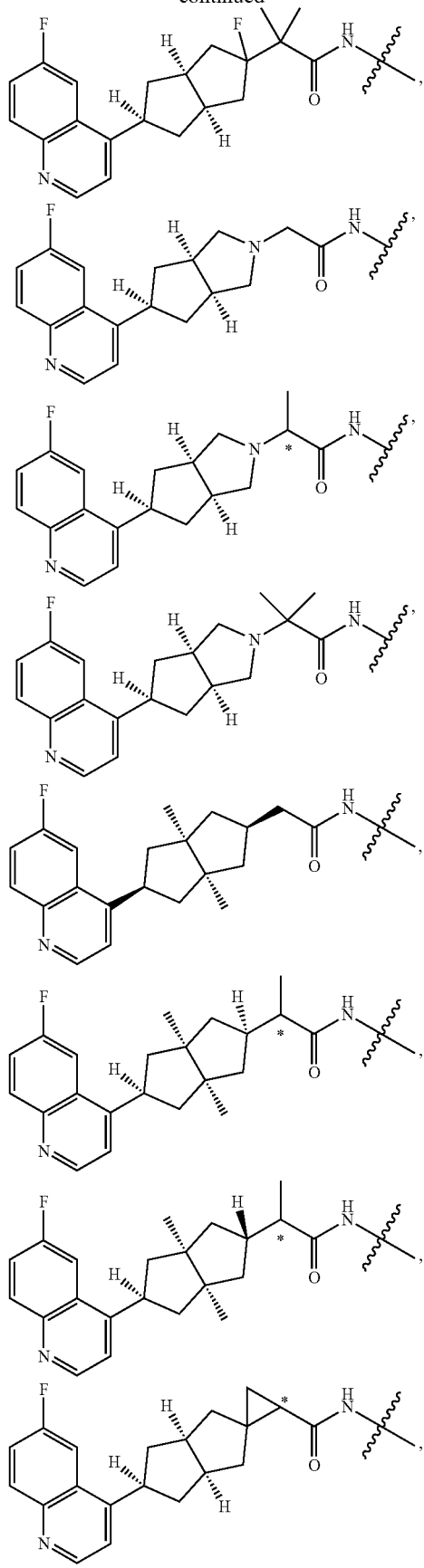
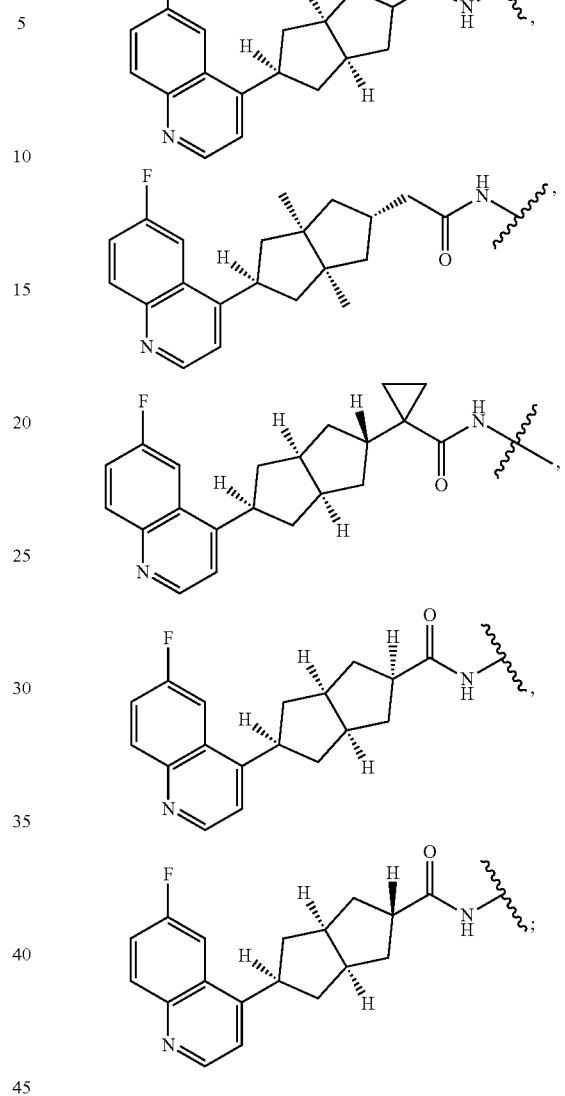
and the G2 is selected from the group consisting of:
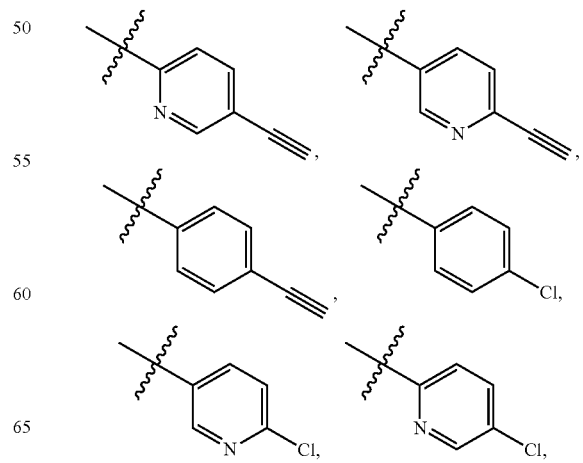

-continued
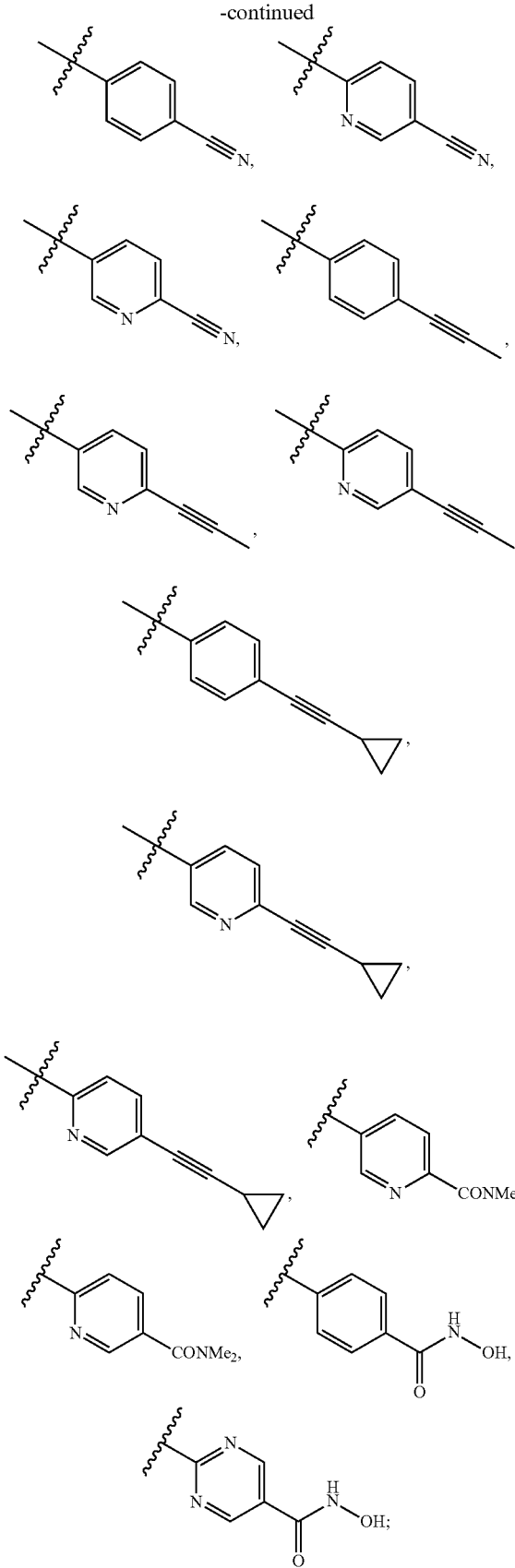
wherein * indicates a chiral center.
20. The compound of formula (I) according to claim 1, wherein the compound is selected from the group consisting of:
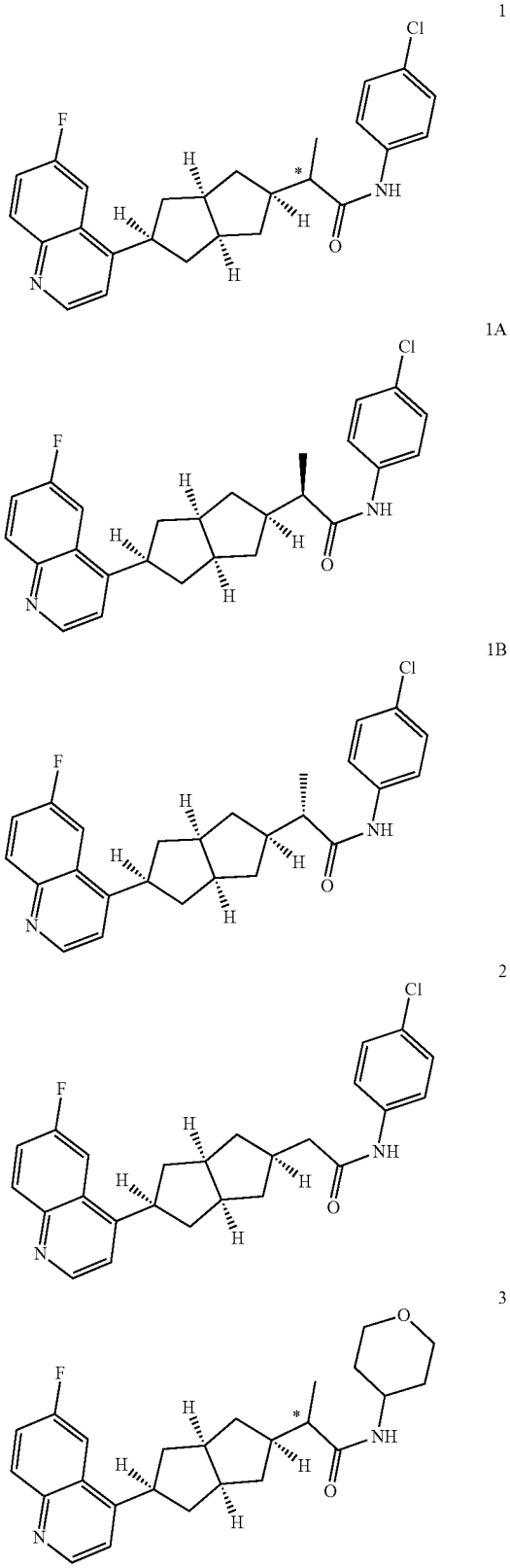

259
-continued
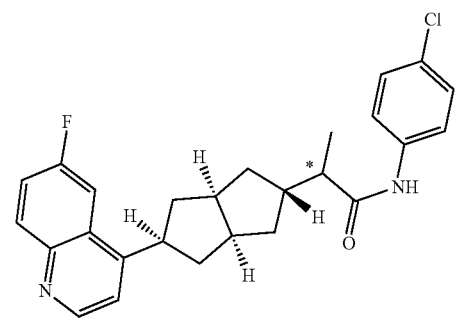
4
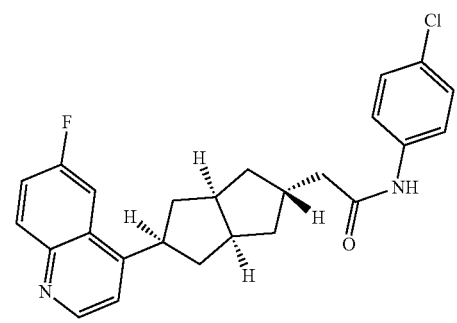
5
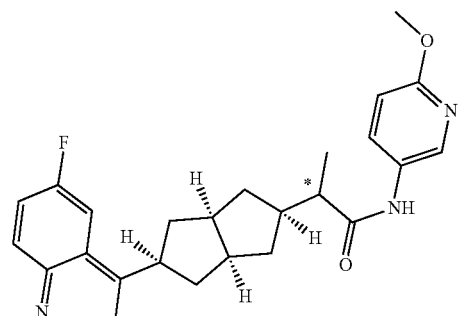
6
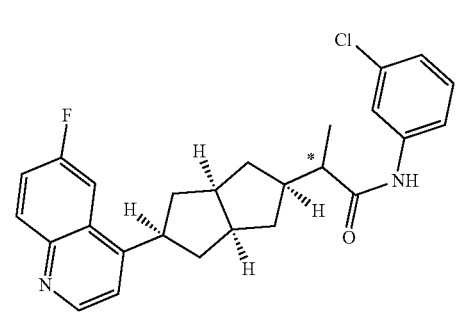
7
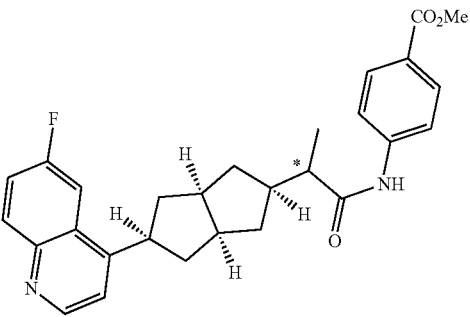
8
260
-continued
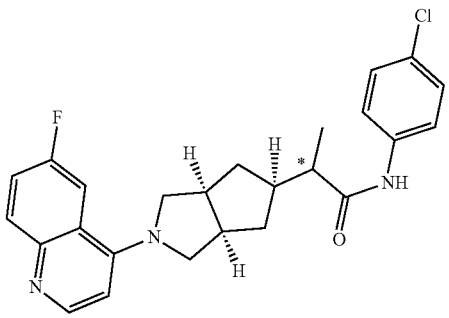
9
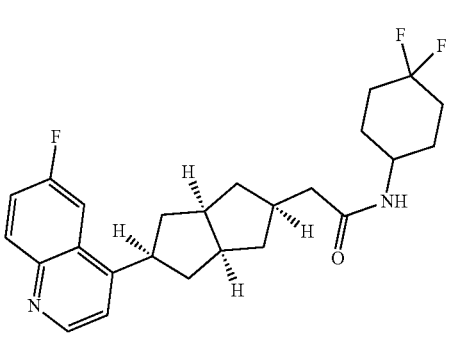
12
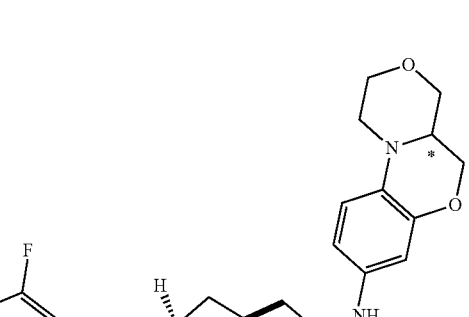
13
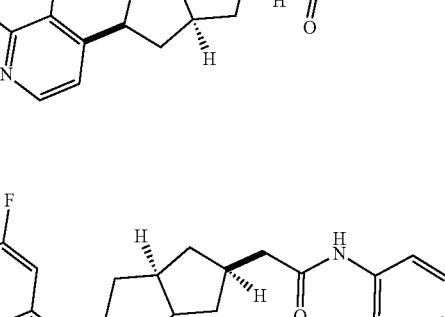
14
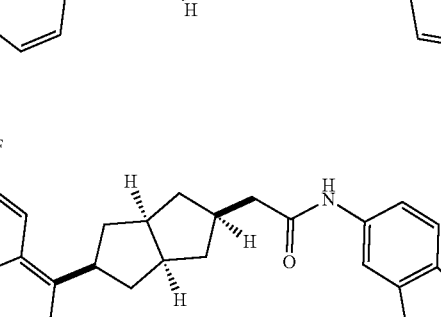
15

16
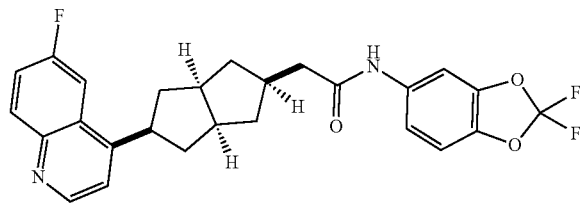
17
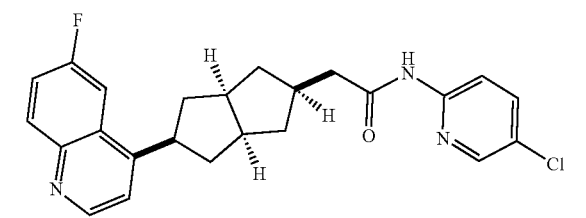
18
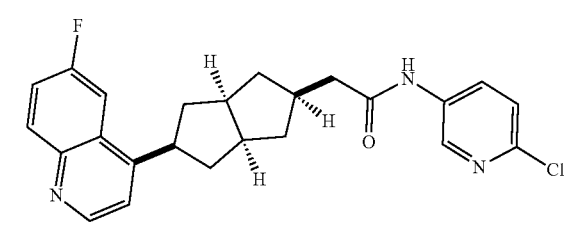
19
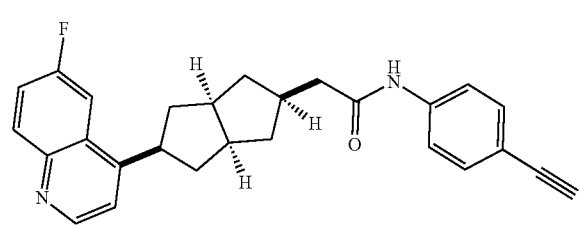
20
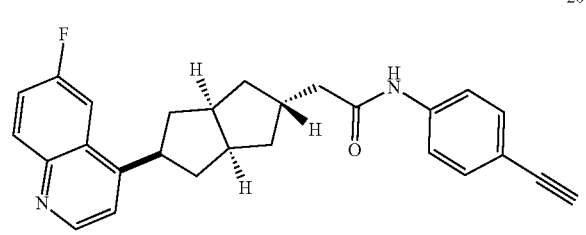
21
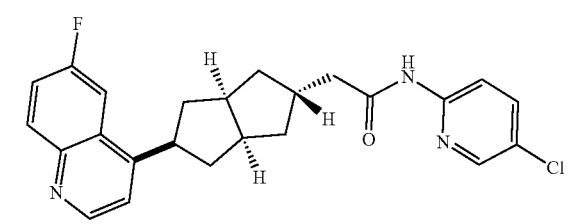
22
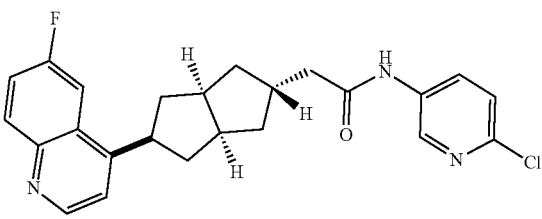
23
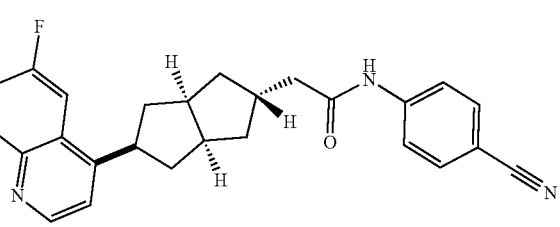
24
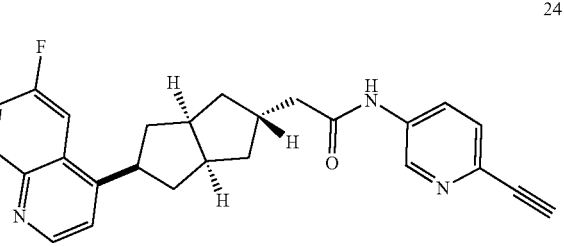
25
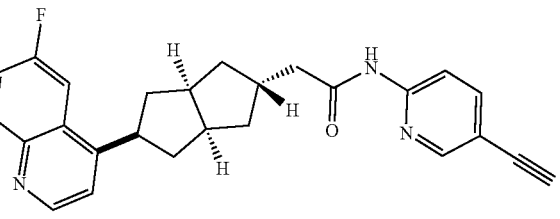
26
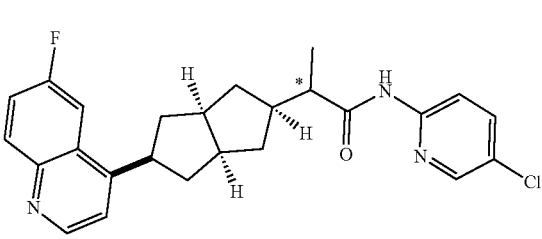
26A
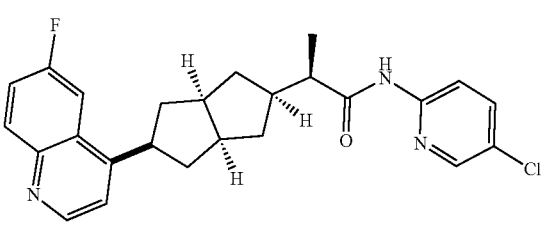

263
-continued
26B
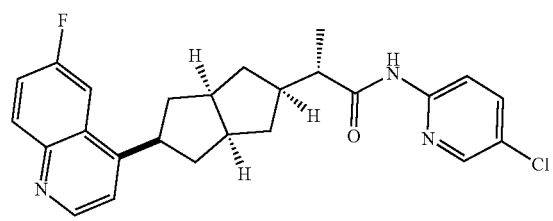
27
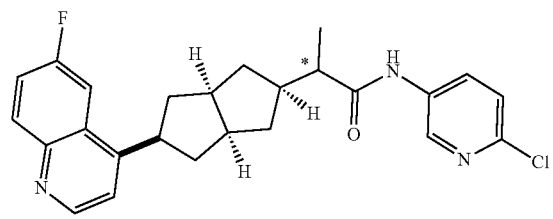
28
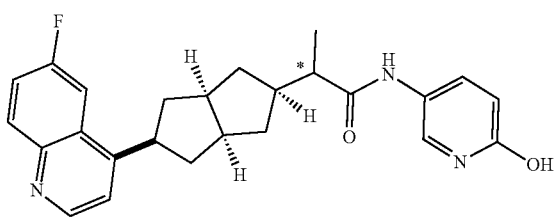
29
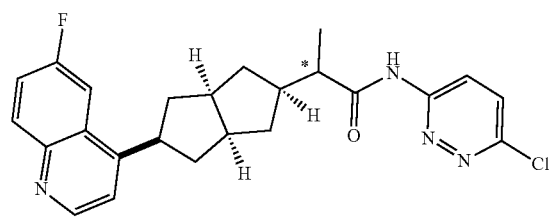
30
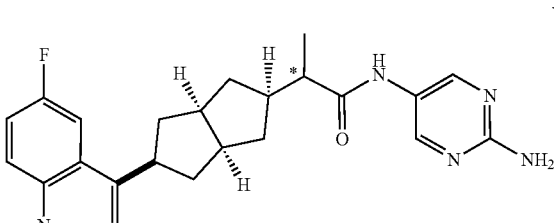
31
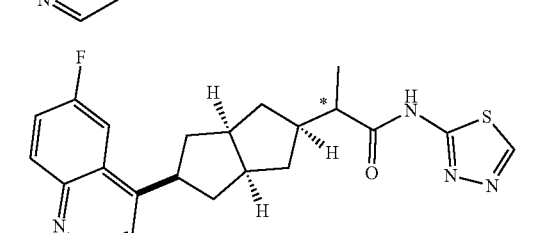
32
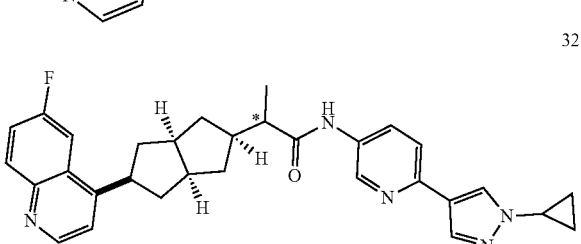
264
-continued
33
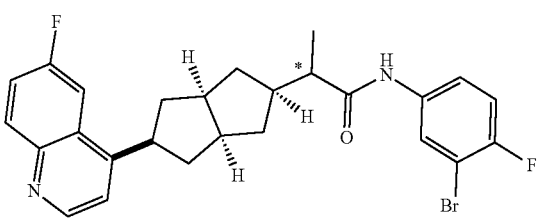
34
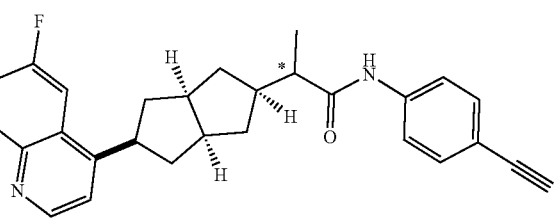
35
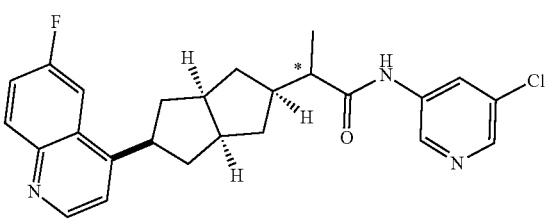
36
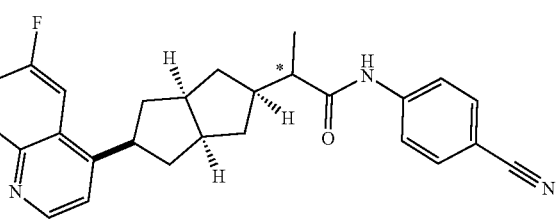
37
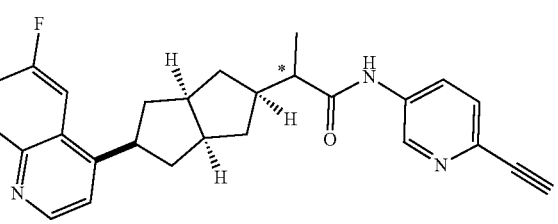
40
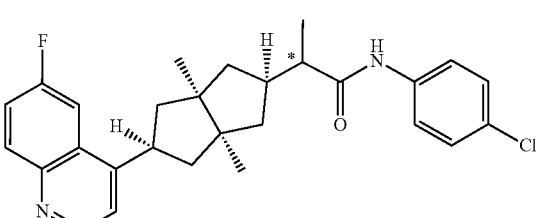

41
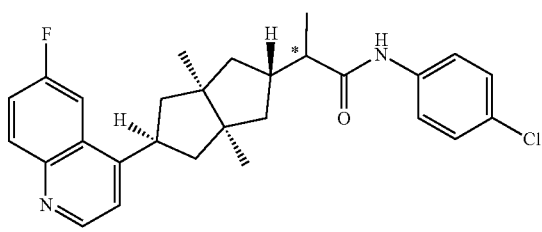
42
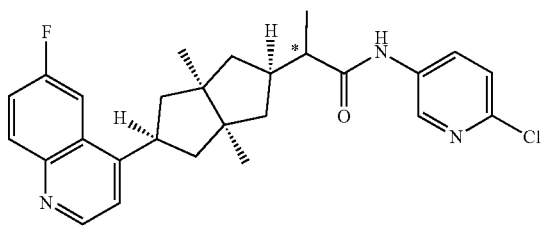
43
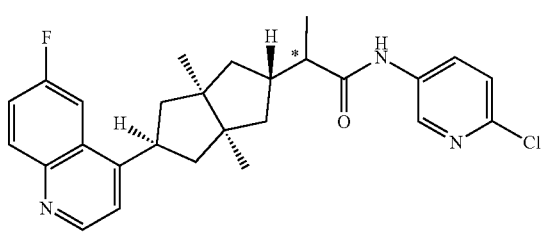
44
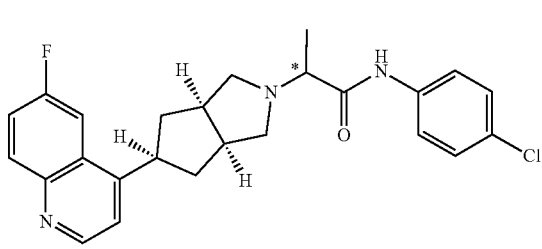
45
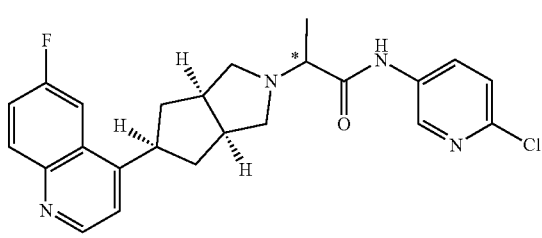
46
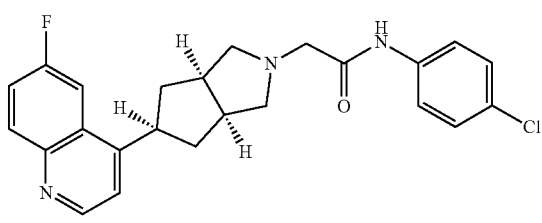
47
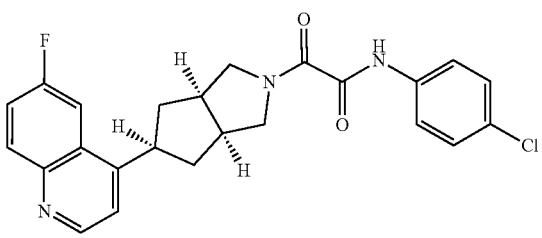
48
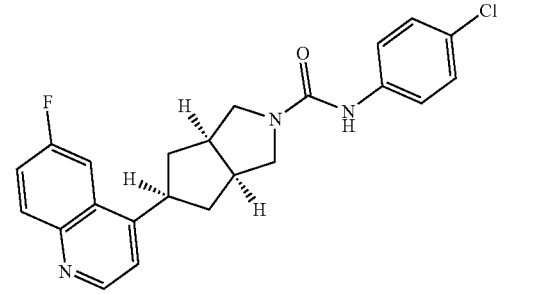
49
50
58
59

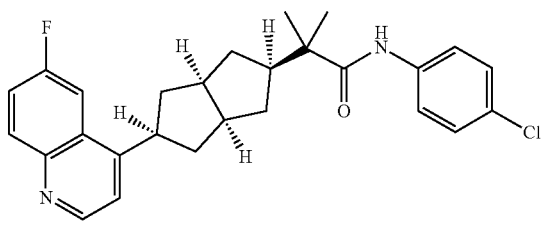
60
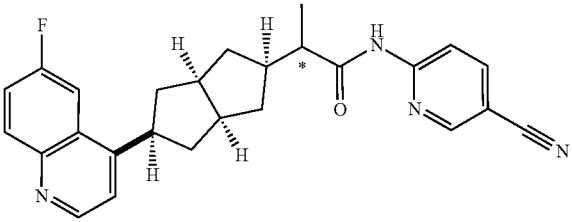
73
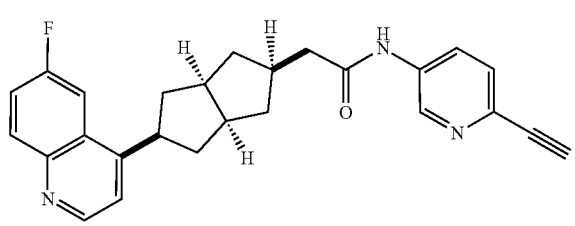
66
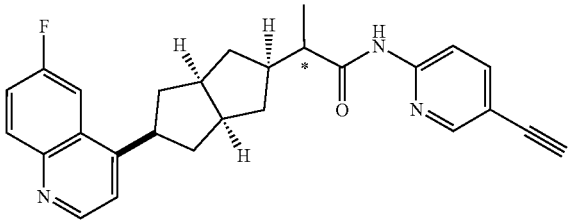
74
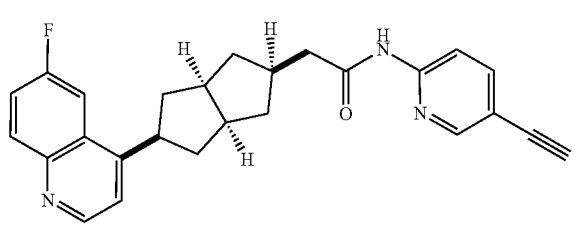
67
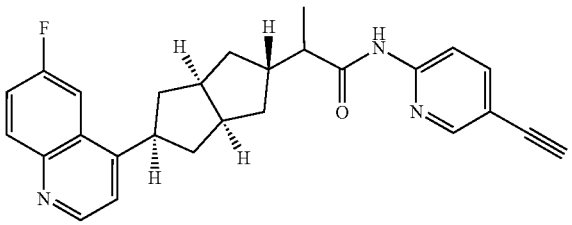
75
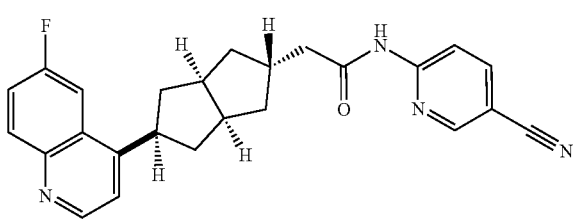
70
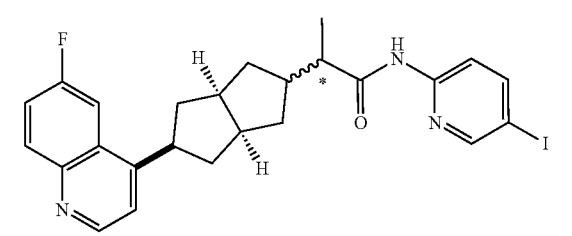
76
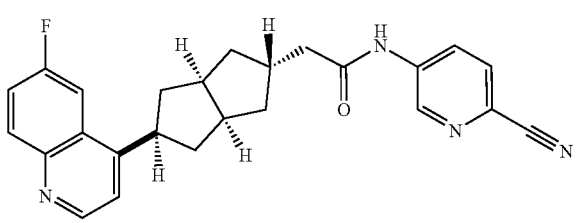
71
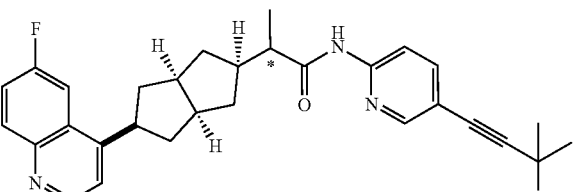
77
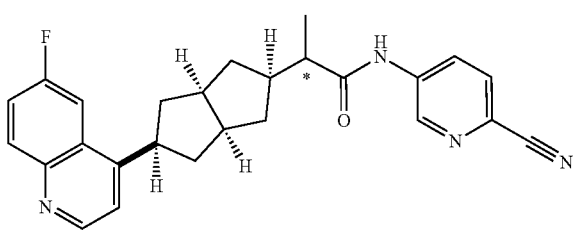
72
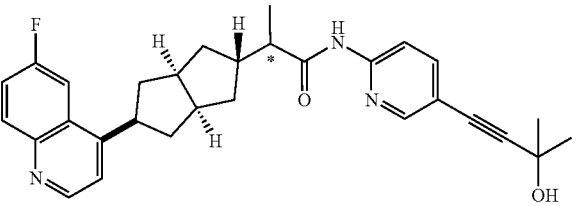
78

79
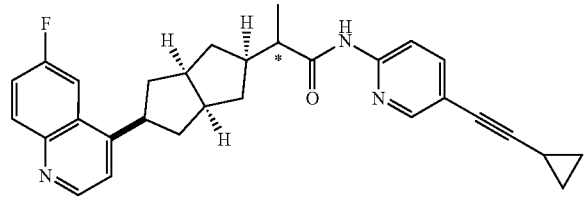
85
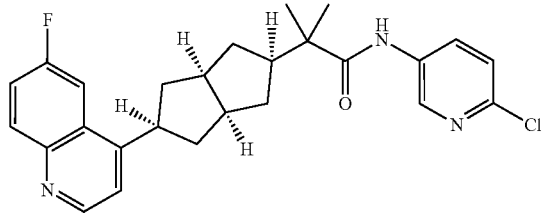
80
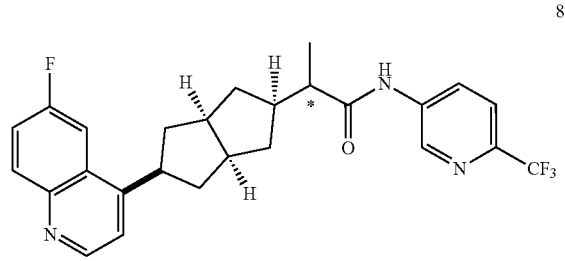
86
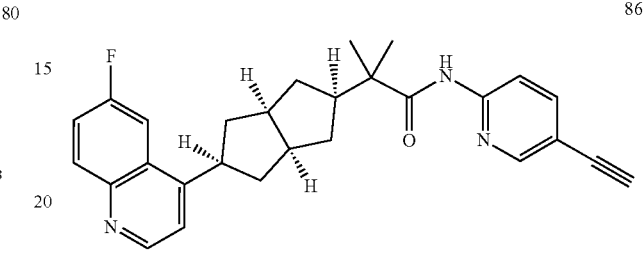
81
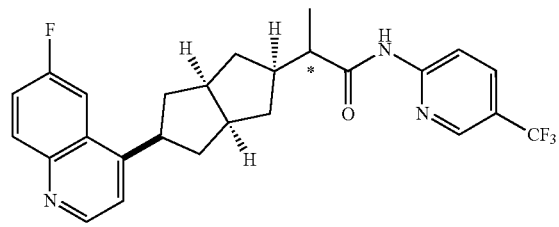
87
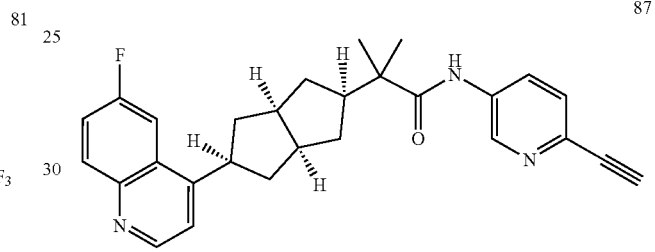
82
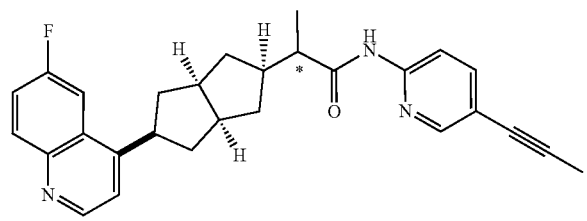
88
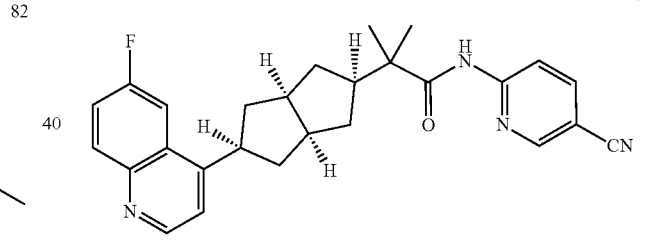
83
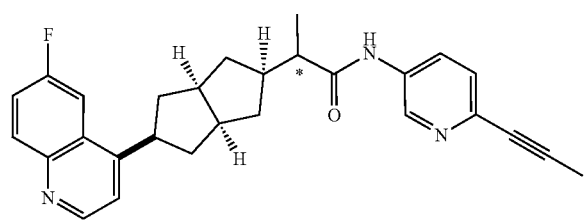
89
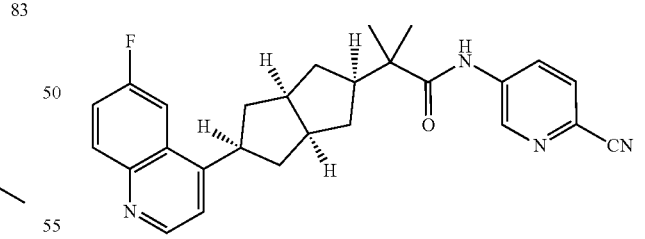
84
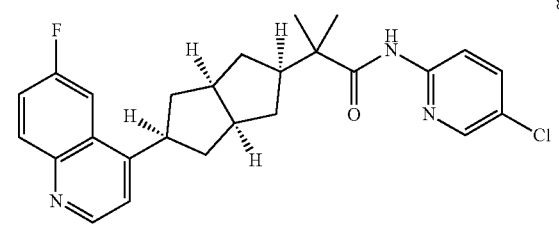
90
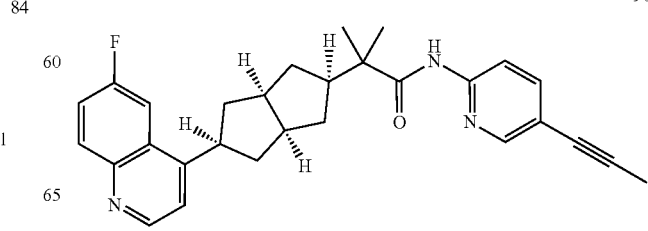

91
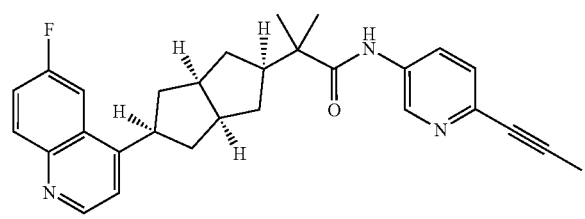
92
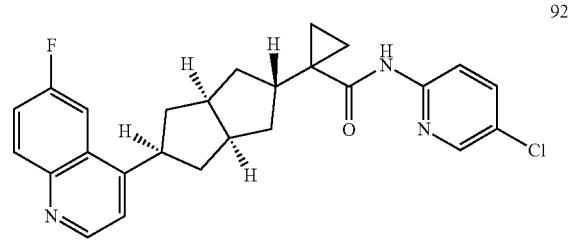
93
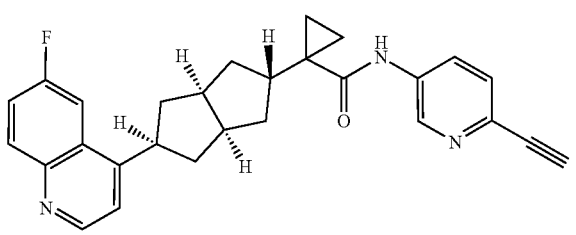
94
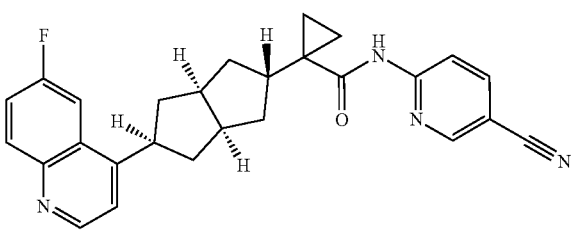
95
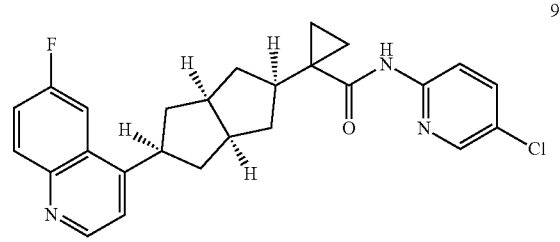
96
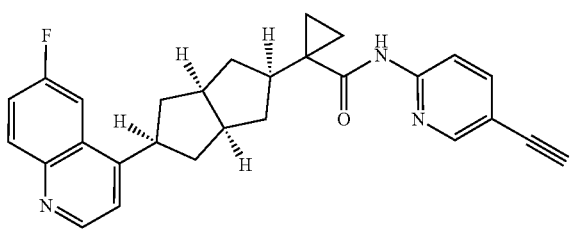
97
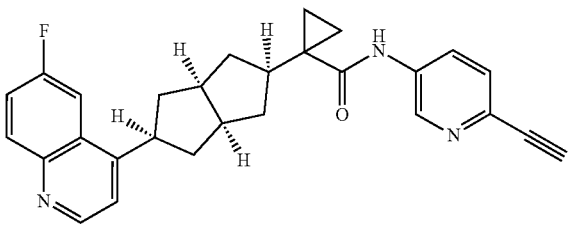
98
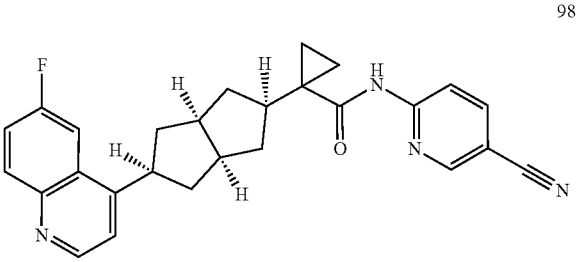
99
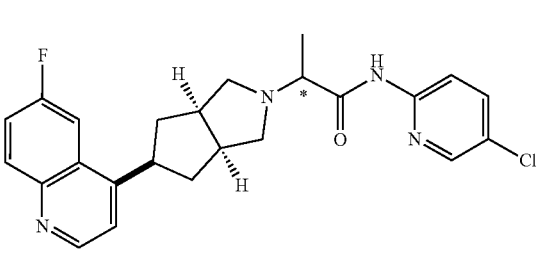
100
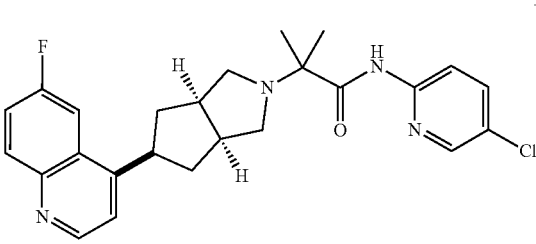
102
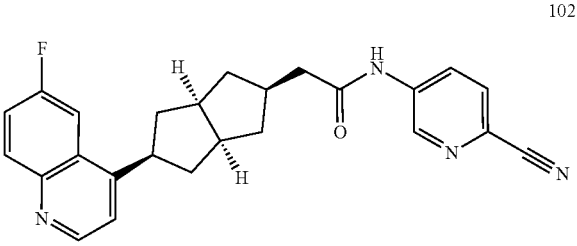
104
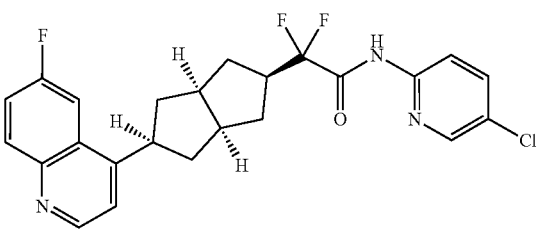

273
-continued
106
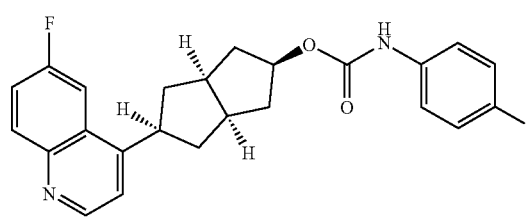
107
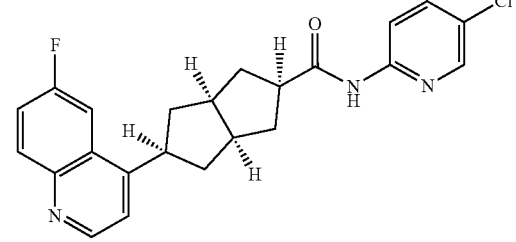
108
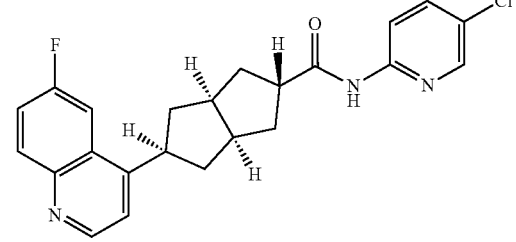
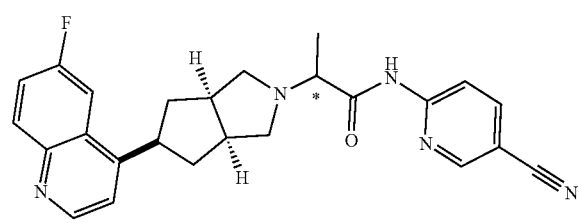
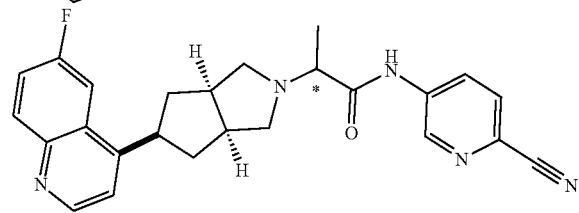
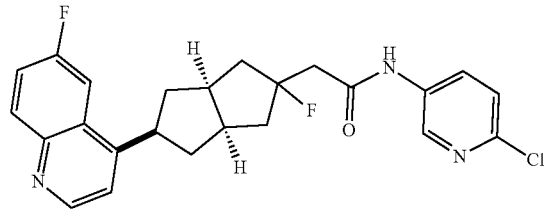
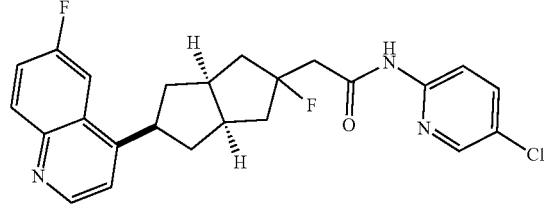
274
-continued
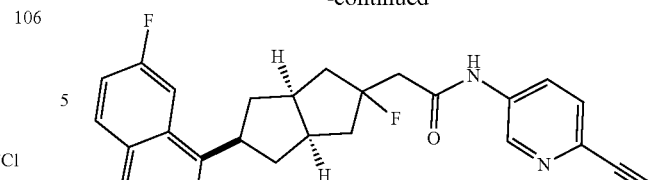
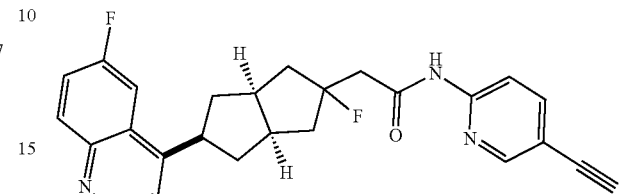
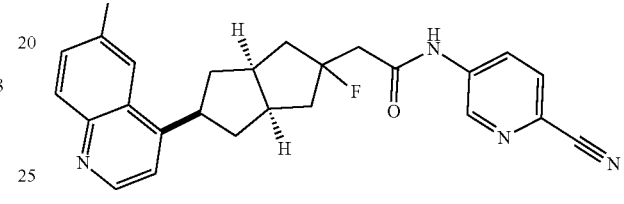
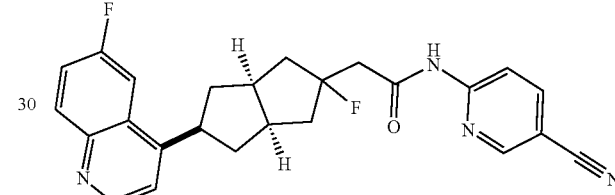
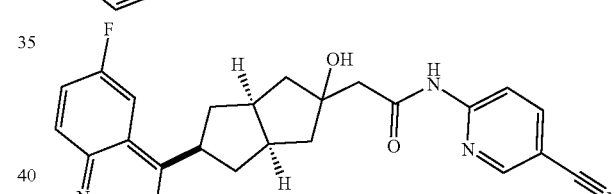
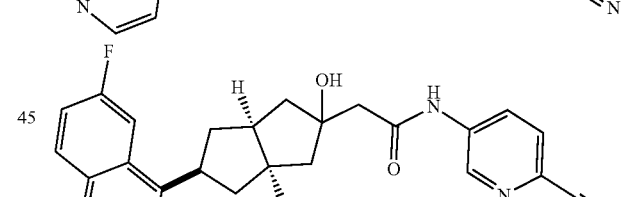
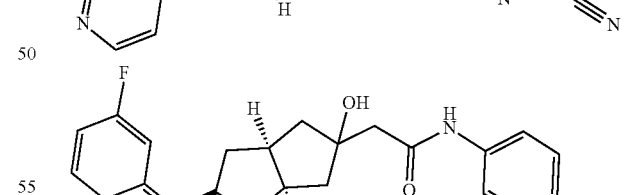
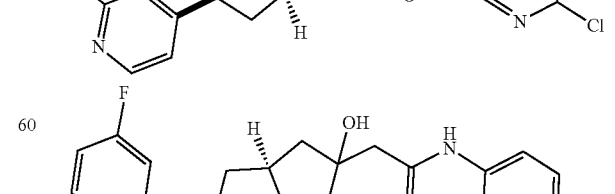
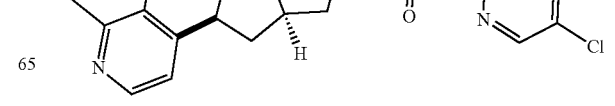

275
-continued
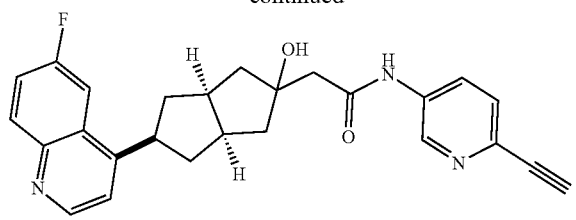
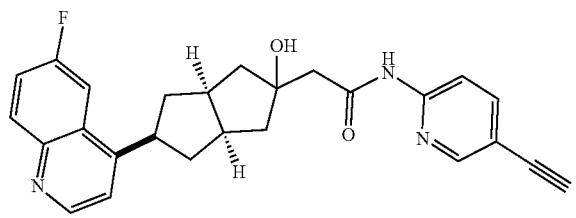
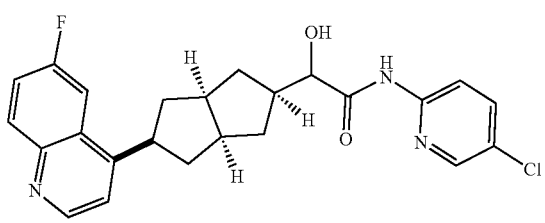
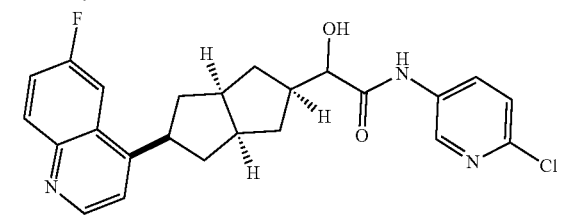
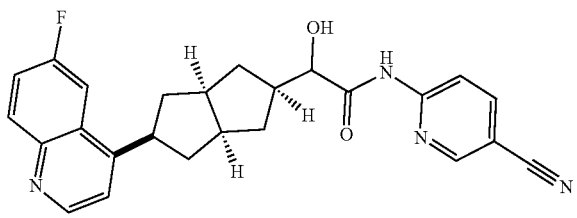
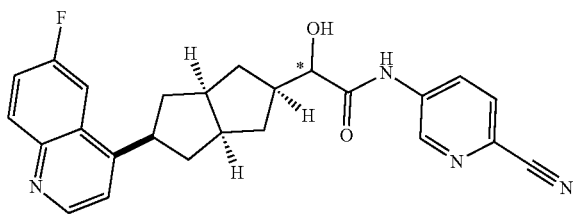
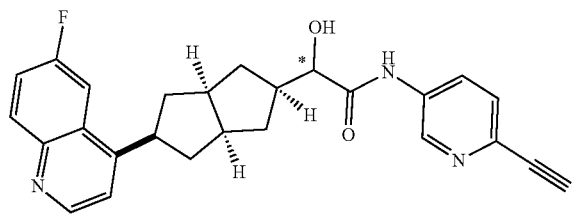
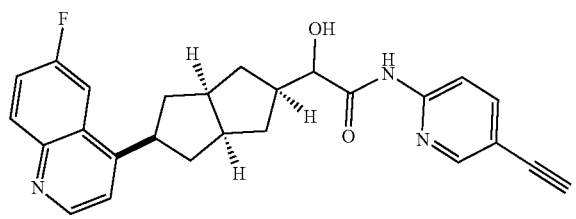
276
-continued
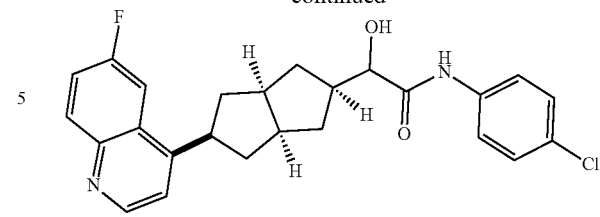
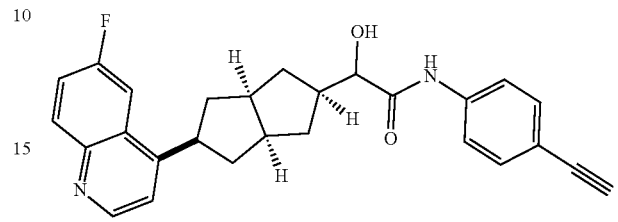
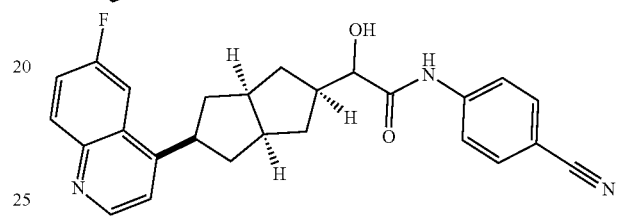
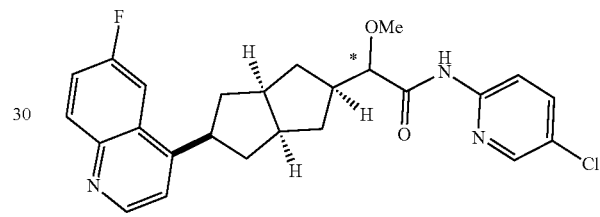
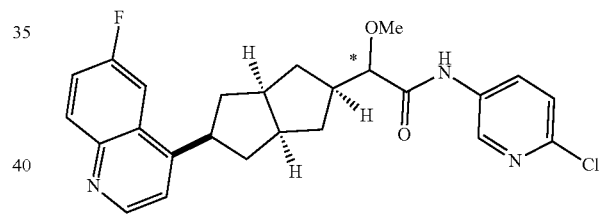
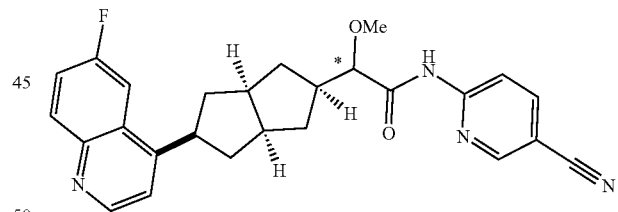
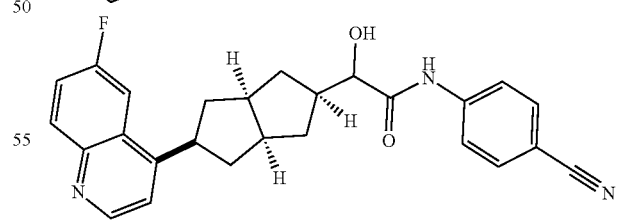
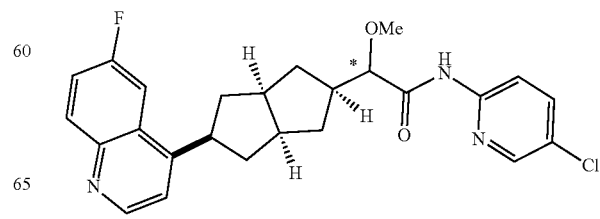

277
-continued
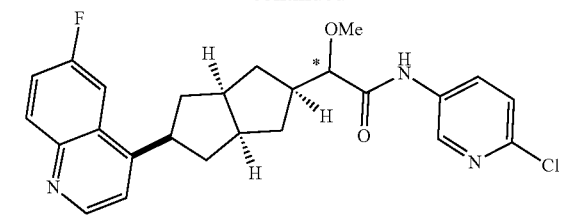
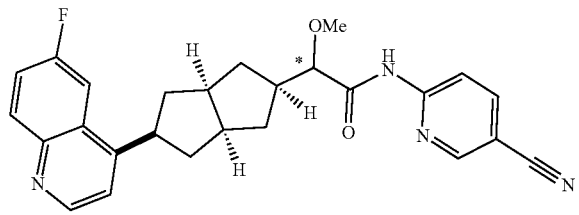
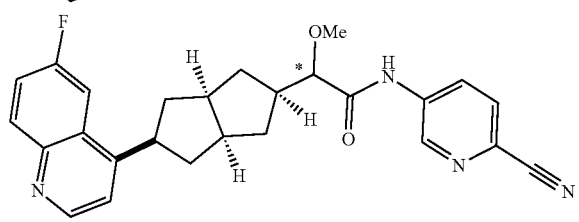
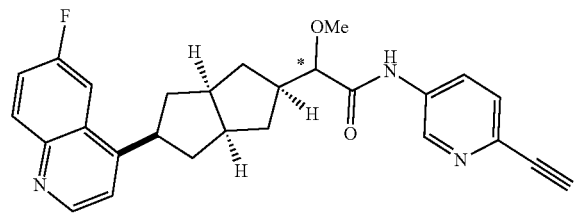
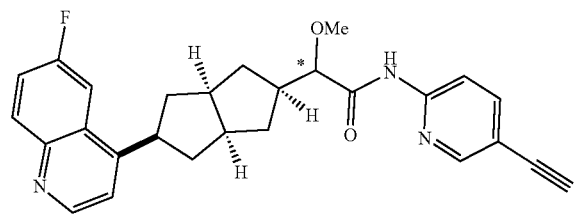
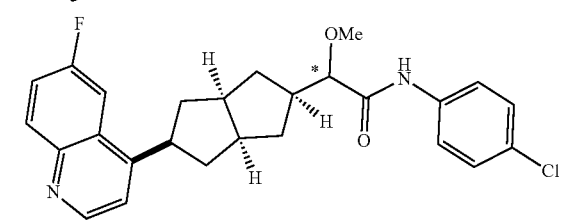
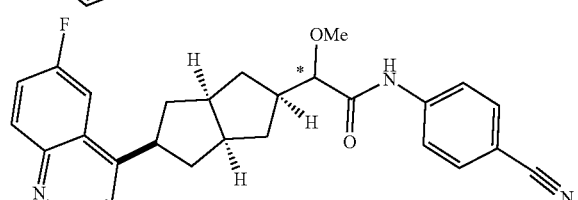
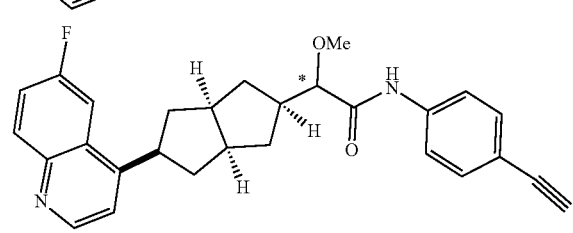
278
-continued
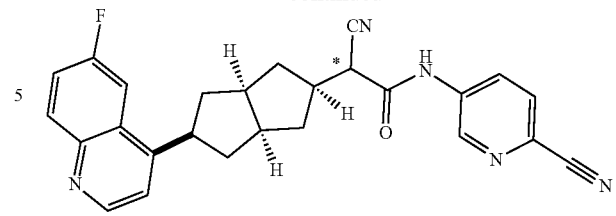
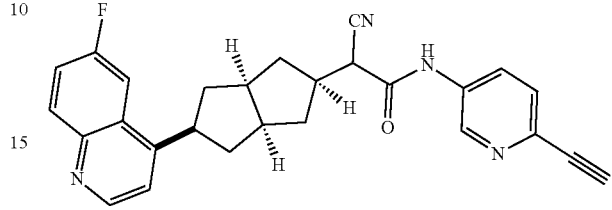
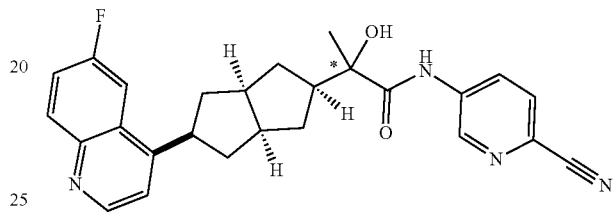
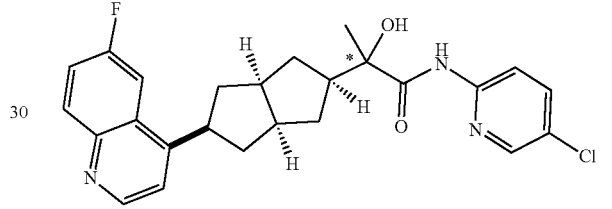
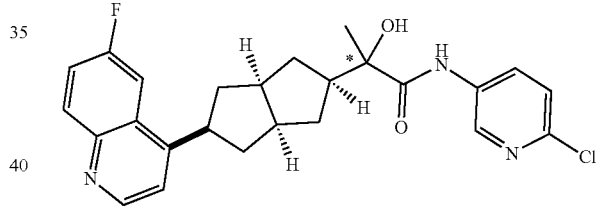
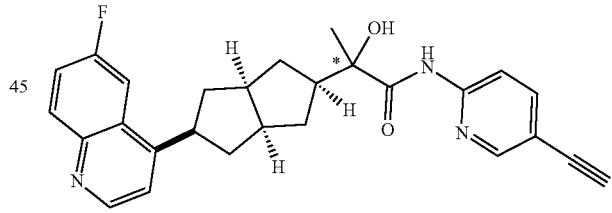
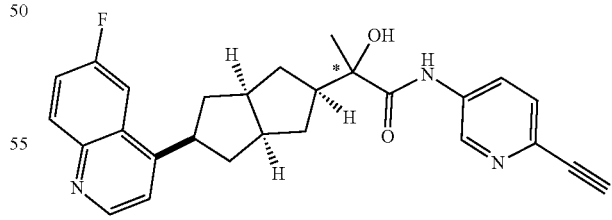
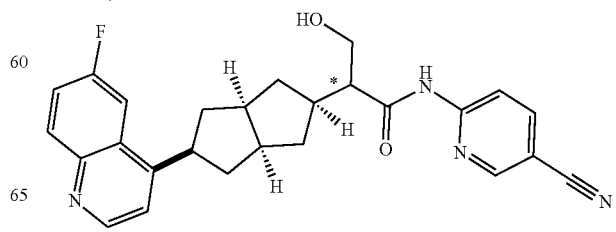

279
-continued
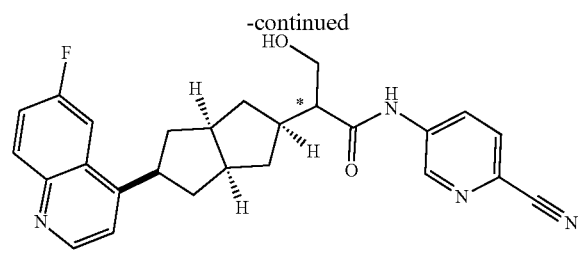
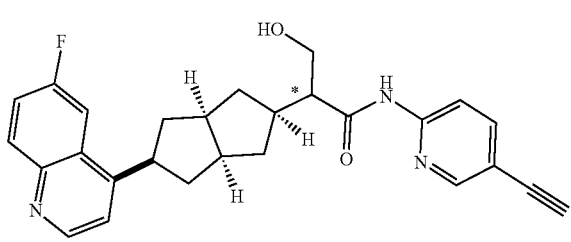
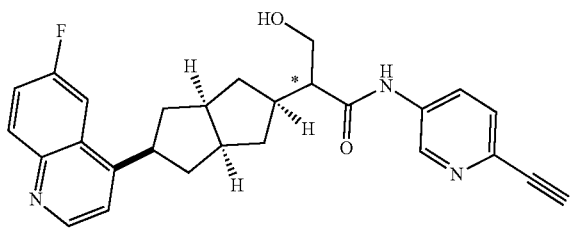
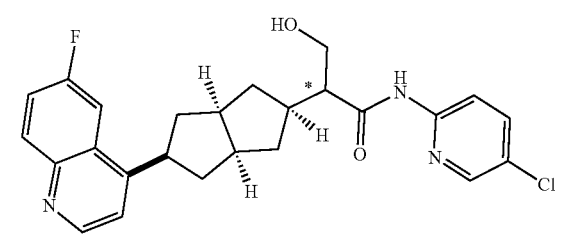
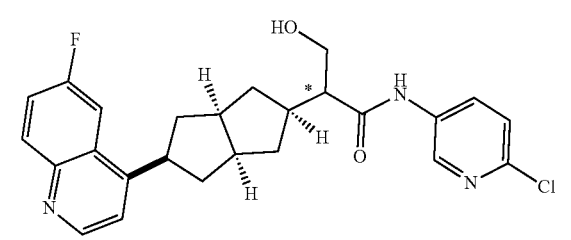
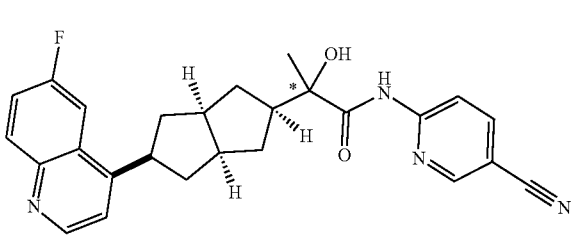
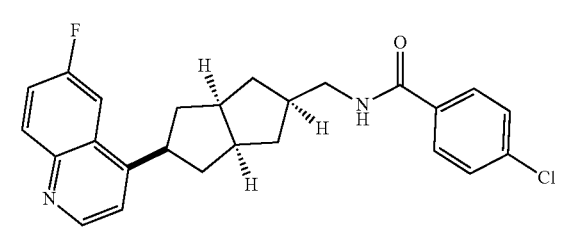
280
-continued
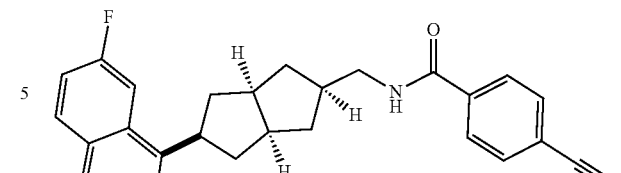
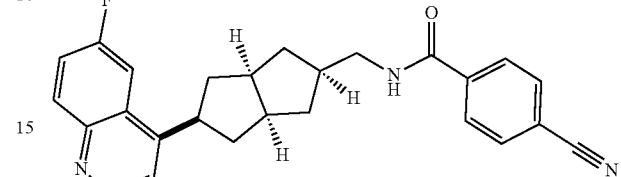
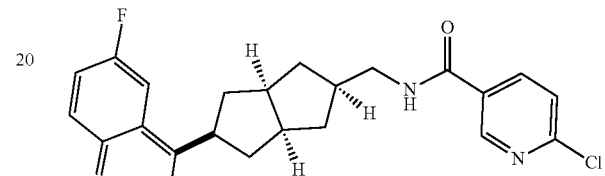
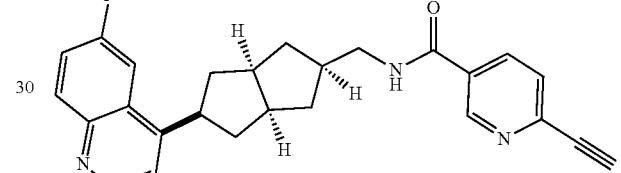
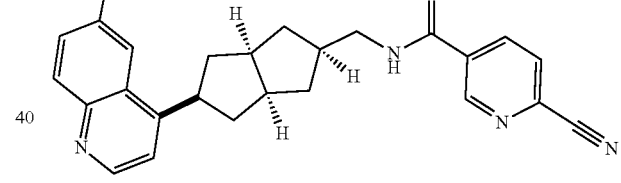
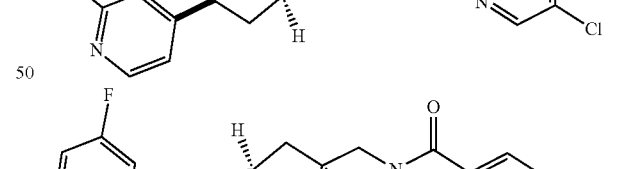
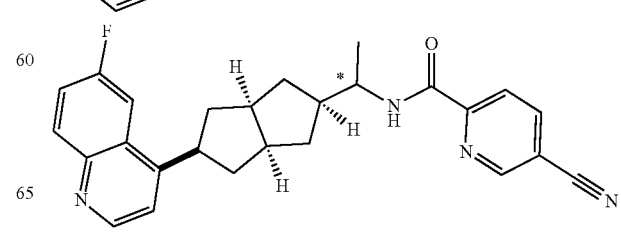

281
-continued
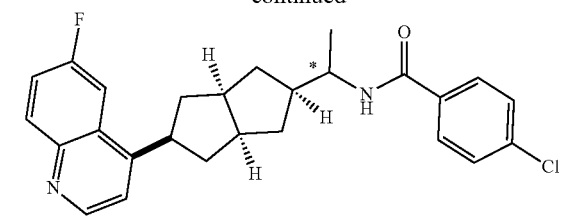
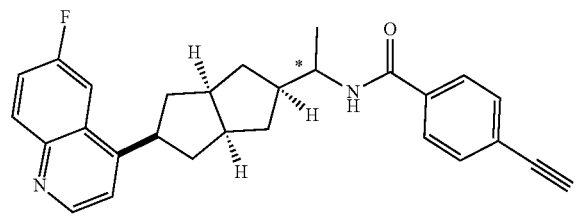
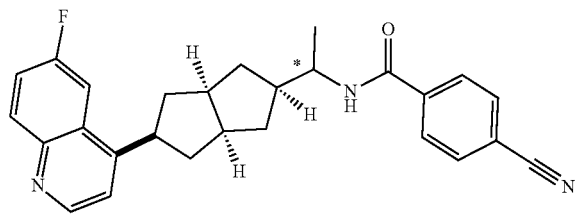
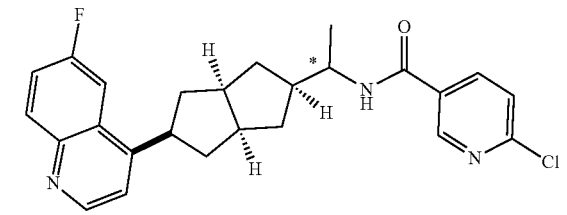
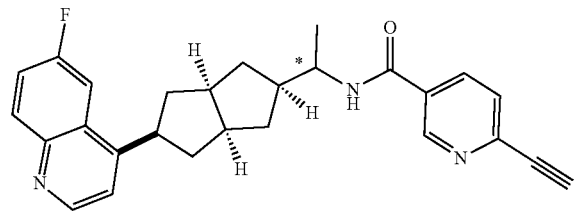
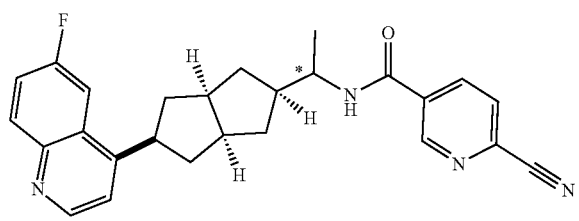
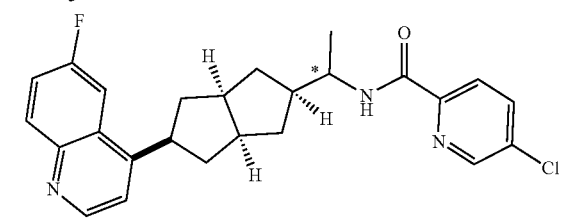
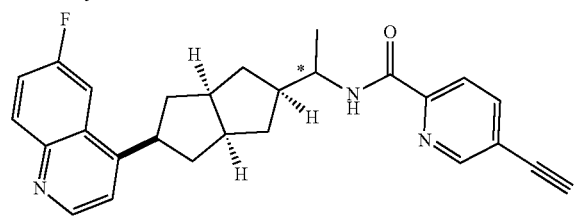
282
-continued
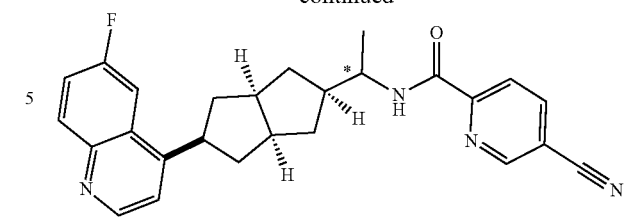
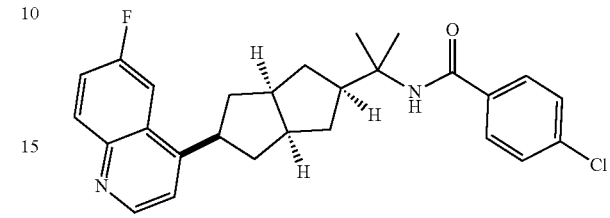
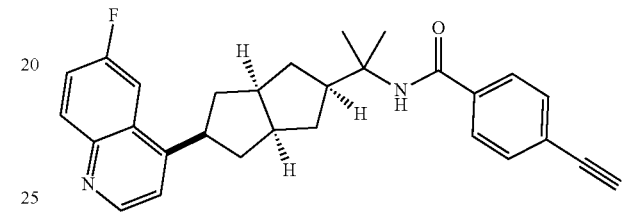
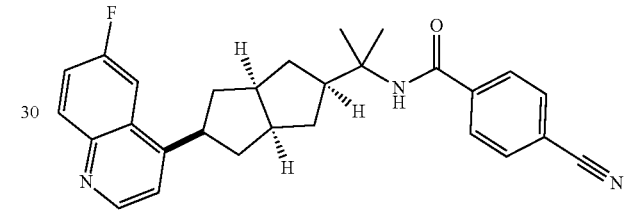
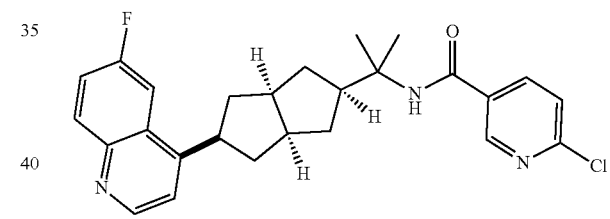
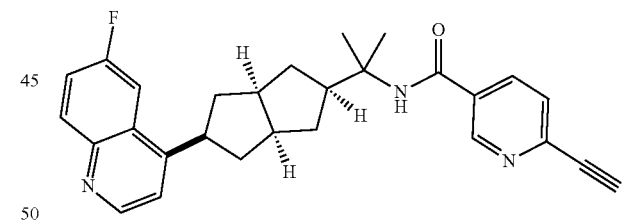
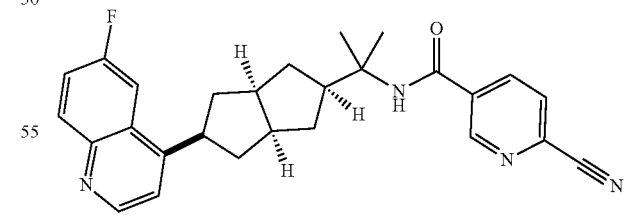
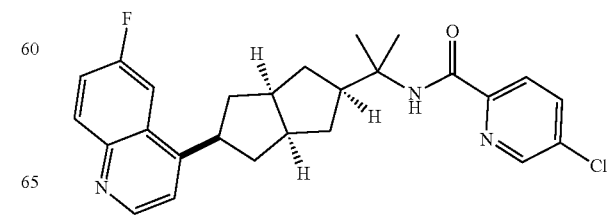

283
-continued
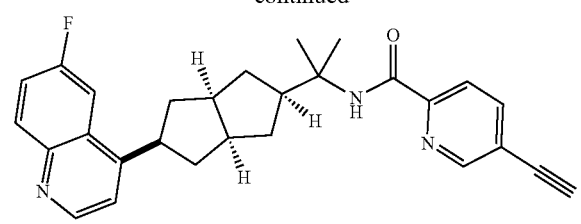
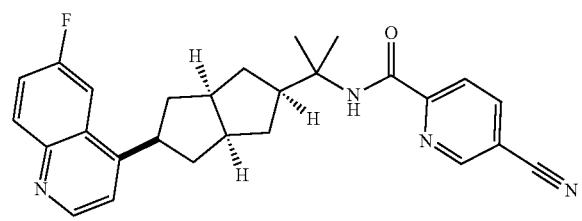
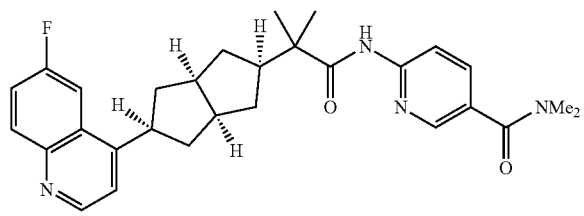
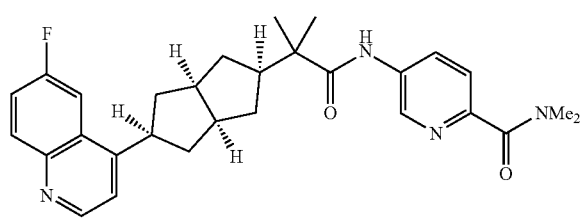
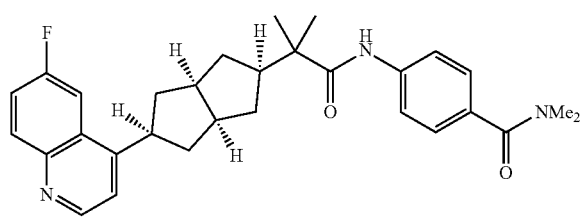
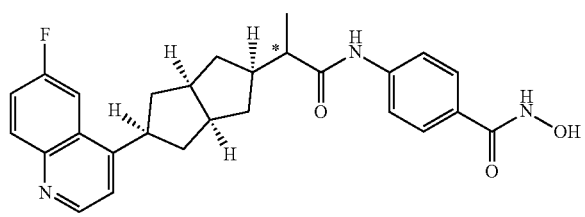
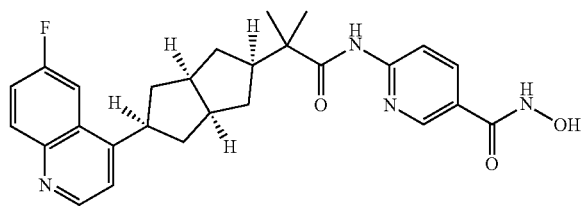
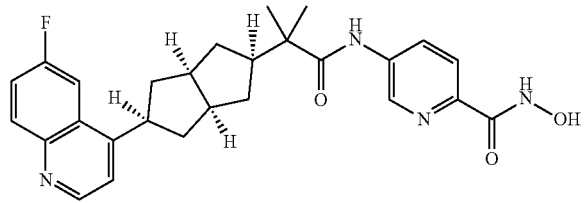
284
-continued
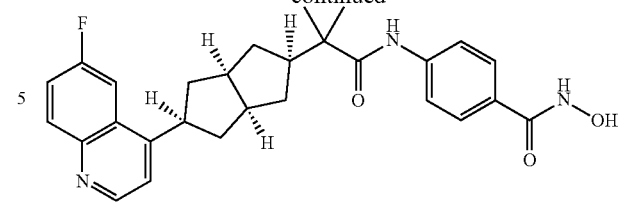
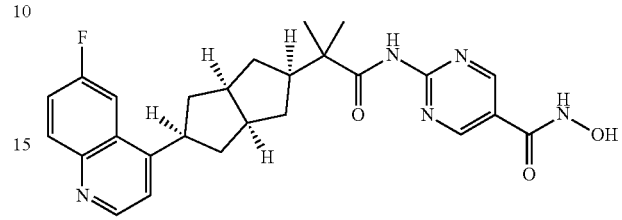
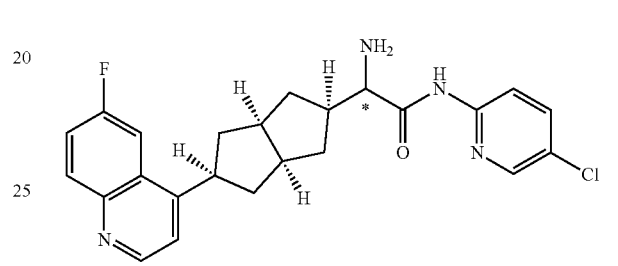
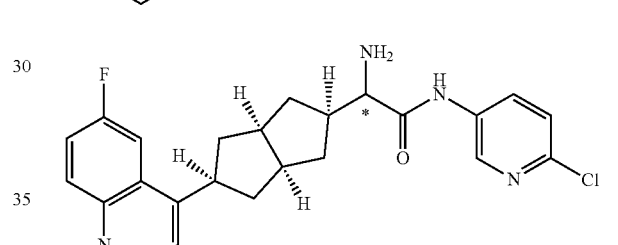
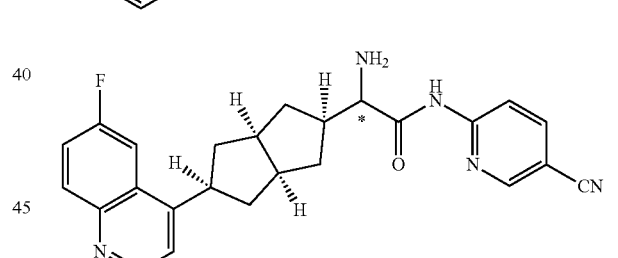
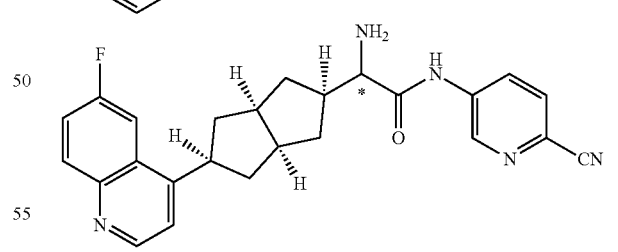
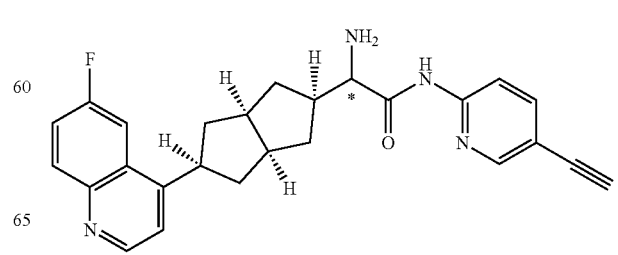

-continued

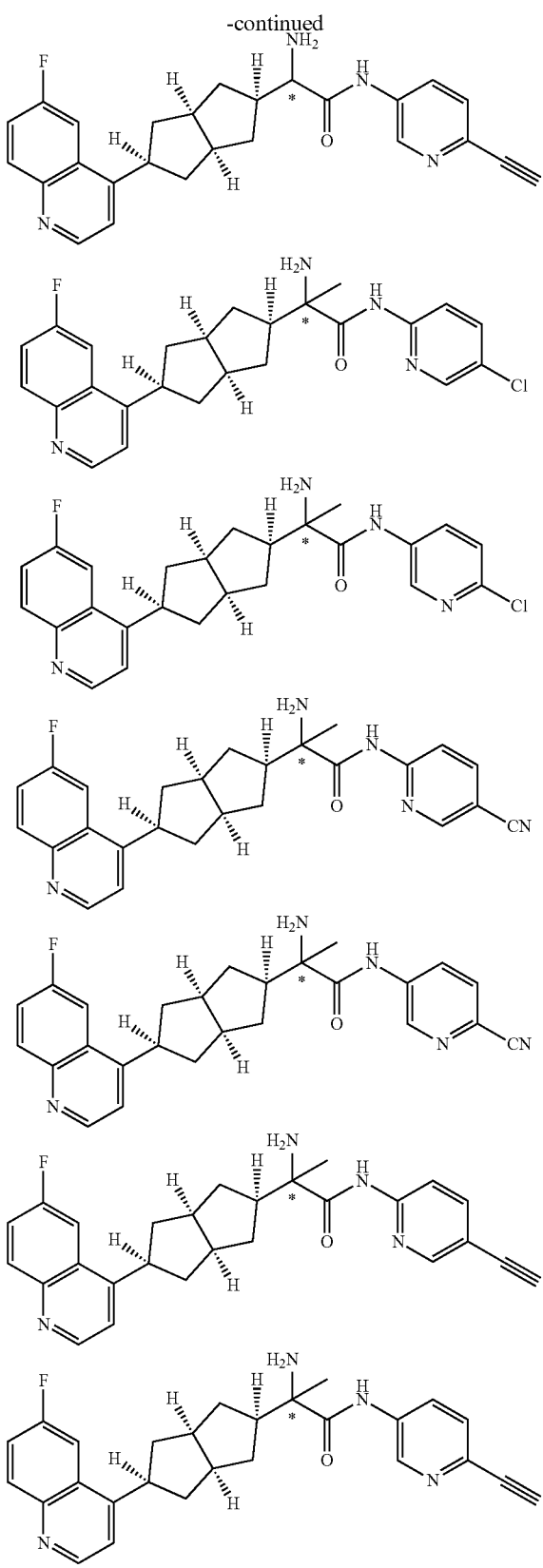

wherein * indicates a chiral center.

21. A pharmaceutical composition, comprising: (i) a therapeutically effective amount of the compound of claim 1, or the pharmaceutically acceptable salt thereof, and (ii) a pharmaceutically acceptable carrier.

22. The pharmaceutical composition of claim 21, wherein the pharmaceutical composition also comprises a second therapeutic agent selected from the following group: antibody PD-1, PD-L1, or CTLA-4.

23. A method of inhibiting IDO activity and/or HDAC activity, comprising: administering an inhibitory effective amount of the compound of claim 1 or a pharmaceutically acceptable salt thereof to a subject in need thereof, or administering an inhibitory effective amount of pharmaceutical composition of claim 21 to a subject in need thereof.

24. A method for preparing the compound of claim 1, wherein the method comprises the following steps:

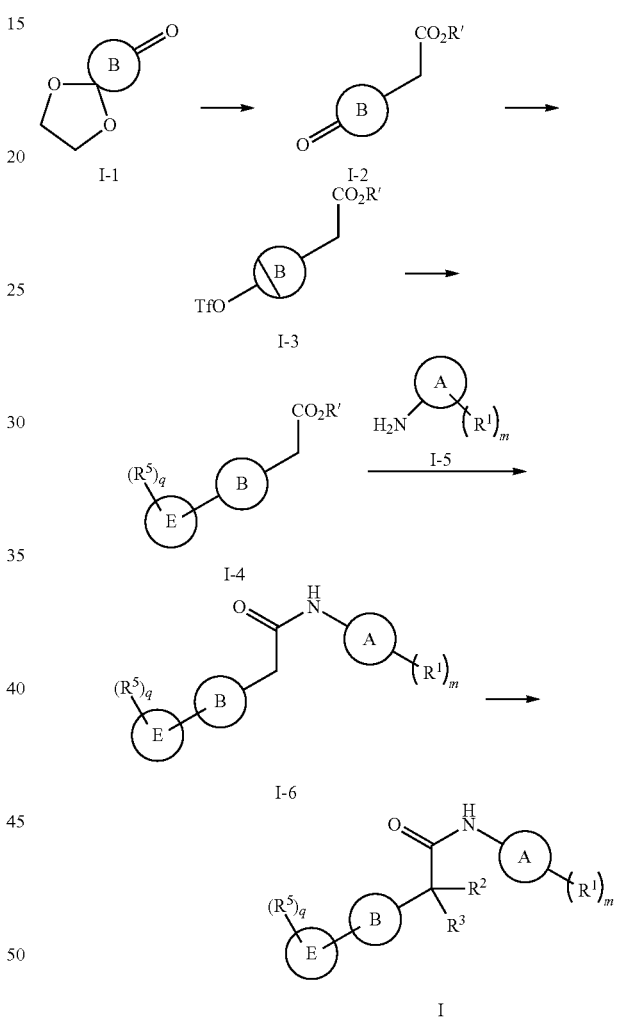

(i) in an inert solvent, converting compound I-1 to I-2 by Wittig reaction followed by Pd—C catalyzed hydrogenation and deprotection of protecting group;
(ii) in an inert solvent, using a base to convert the compound I-2 to I-3, and then reacting compound I-3 with a boron compound of an corresponding aryl or heteroaryl group to obtain the coupling compound containing an ethylenic bond, and catalytically hydrogenated to obtain the compound I-4;
(iii) subjecting compound I-4 to ester hydrolysis to obtain a n acid, and reacting the resulting acid with I-5 to give compound I-6;
(iv) in an inert solvent and under a basic condition, introducing a group into the α-position of the amide in compound I-6 to afford compound I;

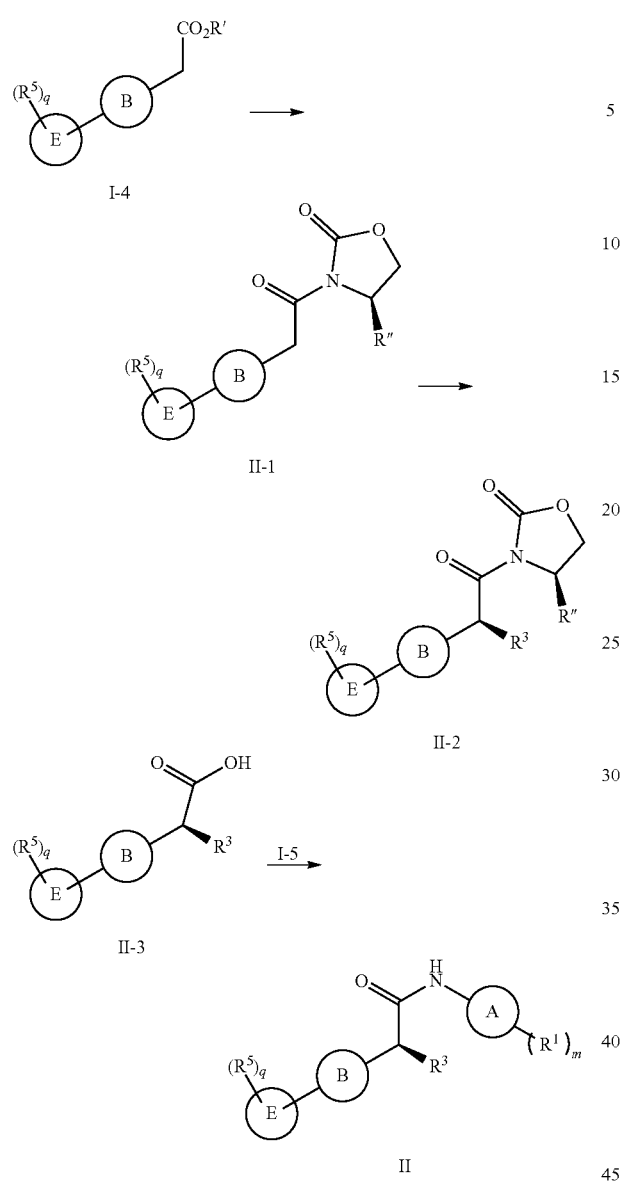

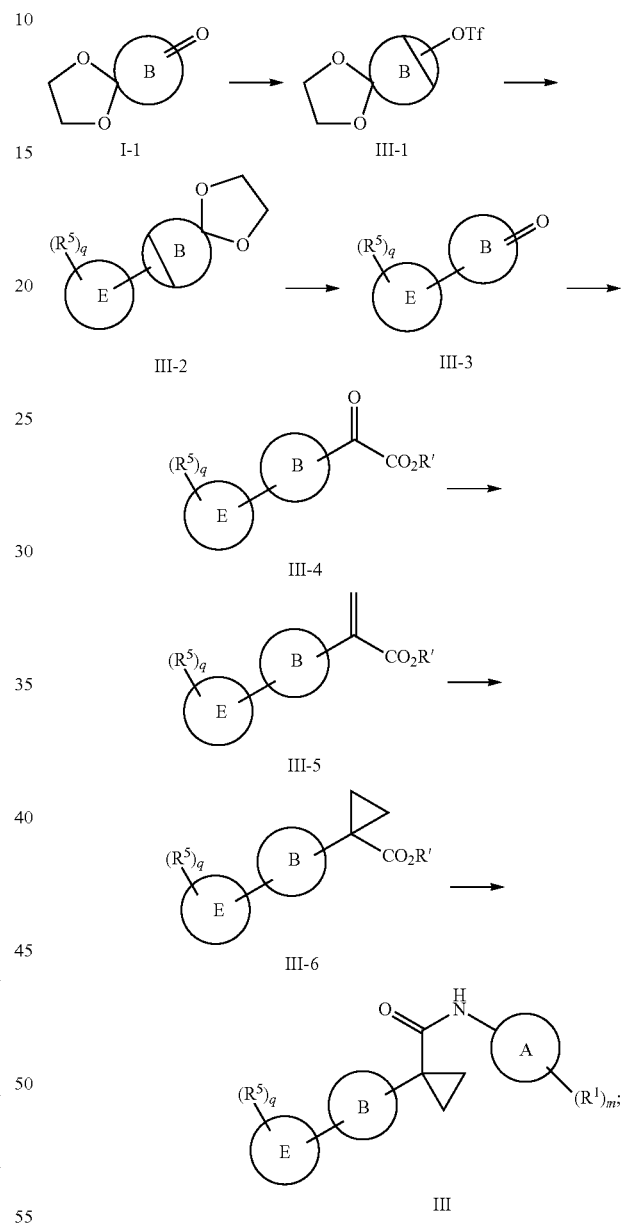

(viii) starting from compound I-1, preparing α-ketoester III-4 via multi-step reaction, then converting compound III-4 to α,β-unsaturated ester III-5 by Wittig reaction, and using the compound III-5 for double bond cyclopropanation reaction to give compound III-6, and subjecting compound III-6 to ester hydrolysis and amidation reaction to give compound III;

(v) subjecting compound I-4 to ester hydrolysis to obtain an acid, and reacting the resulting acid with Evans chiral reagent to obtain compound II-1, which facilitates the introduction of a chiral $R^3$ group at the α-position of the amide, to afford compound II-2;

(vi) hydrolyzing compound II-2 to give acid II-3, and reacting the acid II-3 with compound I-5 to give the compound II;

(vii) when the Evans chiral reagent used in (v) is in opposite configuration, the above (v) and (vi) steps are used to prepare the compound IIa, which is the enantiomer of the compound II;

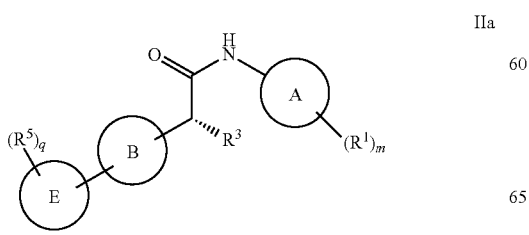

wherein, in

indicates a double bond; and R' is phenyl or benzyl.

* * * * *